US007223556B1

(12) United States Patent
Zhou et al.

(10) Patent No.: US 7,223,556 B1
(45) Date of Patent: *May 29, 2007

(54) TARGETED PROTEOLYSIS BY RECRUITMENT TO UBIQUITIN PROTEIN LIGASES

(75) Inventors: Pengbo Zhou, New York, NY (US); Peter M. Howley, Wellesley, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/415,795

(22) Filed: Oct. 8, 1999

Related U.S. Application Data

(60) Provisional application No. 60/103,787, filed on Oct. 9, 1998.

(51) Int. Cl.
*C12P 21/06* (2006.01)
*C12N 9/00* (2006.01)
*C12N 5/16* (2006.01)
*C12N 5/18* (2006.01)
*C12N 5/22* (2006.01)
*C07H 21/04* (2006.01)

(52) U.S. Cl. .................... 435/68.1; 435/69.7; 435/183; 435/325; 435/354; 435/366; 435/375; 536/23.4

(58) Field of Classification Search ............... 435/68.1, 435/7.1, 183, 69.7, 254.11, 254.21, 325, 366, 435/375, 377; 536/23.4
See application file for complete search history.

(56) References Cited

U.S. PATENT DOCUMENTS 5,252,466 A  10/1993 Cronan, Jr. ................ 435/69.7

FOREIGN PATENT DOCUMENTS

WO    WO 99/18989    4/1999

OTHER PUBLICATIONS

Verma et al., (Sep. 18, 1997) Nature, vol. 389, pp. 239-242.*
Kumar et al. (Mar. 1998) Proc. Natl. Acad. Sci., vol. 95 pp. 2417-2422.*
Cohen et al. (Apr. 16, 2004) BMC Developmental Biology, vol. 4, pp. 1-7.*

Feldman, R.M. et al. "A Complex of Cdc4p, Skp1p, and Cdc53p/Cullin Catalyzes Ubiquitination of the Phosphorylated CDK Inhibitor vSic1p" Cell 91(2):221-230 (1997).
Li, F.N. et al. "GRR1 of Saccharomyces Cerevisiae is Connected To The Ubuitin Proteolysis Machinery Through SKP1: Coupling Glucose Sensing to Gene Expression and The Cell Cycle" EMBO J. 16(18): 5629-5638 (1997).
Patto, E.E. et al. "Combinatorial Control In Ubiquintin-dependent Proteolysis: Don't Skp the F-box Hypothesis" Trends Genet. 14(6): 236-243 (1998).
Skowyra D. et al. "F-box Proteins Are Receptor That Recruits Phosphorylated Subatrates to the SCF Ubiquitin0ligase Complex" Cell 91(2): 209-219, (1997).
Zhou, P et al. "Ubiquitination and Degradation of the Substrate Recognition Subunits of SCF Ubiquitin-protein Ligases" Molecular Cell 2(5): 571-580 (1998).
Sheffner, M et al. (1991), *The State of the p53 and Retinoblastoma Genes in Human Cervical Carcinoma Cell Lines*, Proc. Natl. Acad. Sci. USA 88:5523.
Huitbregtse, J.M. et al. (1995), *A Family of Proteins Structually and Functionally Related to the E6-AP Ubiquitin-Protein Ligase*, Proc. Natl. Acad. Sci. USA 92:2563.
Scheffner, M. et al. (1993), *The HPV-16 E6 and E6-AP Complex Functions as a Ubiquitin-Protein Ligase in the Ubiquitination of p53*, CELL 75(3):495.
Huibregtse, J.M. et al. (1993), *Localization of the E6-AP Regions that Direct Human Papillomarvirus E6 Binding, Association with p53, and Ubiquitination of associated Proteins*, Mol. Cell Biol. 13(8):4918.
Scheffner, M. et al. (1992), *Interaction of the Human Papillomavirus Type 16 E6 Oncoprotein with Wild-Type and Mutant Human p53 Proteins*, J. VIROl. 66(8):5100.
Scheffner, M. et al. (1992), *Targeted Degradation of the Retinoblastoma Protein by Human Papillomavirus E7-E6 Fusion Proteins*, EMBO. J. 11(7):2425.
Munger, K. et al. (1992), *Interactions of HPV E6and E7 Oncoproteins with Tumour Suppressor Gene Products*, Cancer Surv. 12:197.
Huibregtse, J.M. et al. (1991), *A Cellular Protein Mediates Association of p53 with the E6 Oncoprotein of Human Papillomarvirus Types 16 or 18*, EMBO. J. 10(13):4129.

* cited by examiner

Primary Examiner—Elizabeth Slobodyansky
(74) Attorney, Agent, or Firm—Foley Hoag LLP

(57) ABSTRACT

The present invention relates to methods and reagents for targeting proteolysis of a polypeptide by cis or trans association with a ubiquitin protein ligase, and further provides methods and reagents for inhibiting the ubiquitination and proteolysis of cellular proteins which are recognized by a ubiquitin protein ligase.

13 Claims, 12 Drawing Sheets

A

B

*cdc34-2*

*skp1-11*

*cdc28-4*

A

B

A

B

C

A

B

Figure 1:
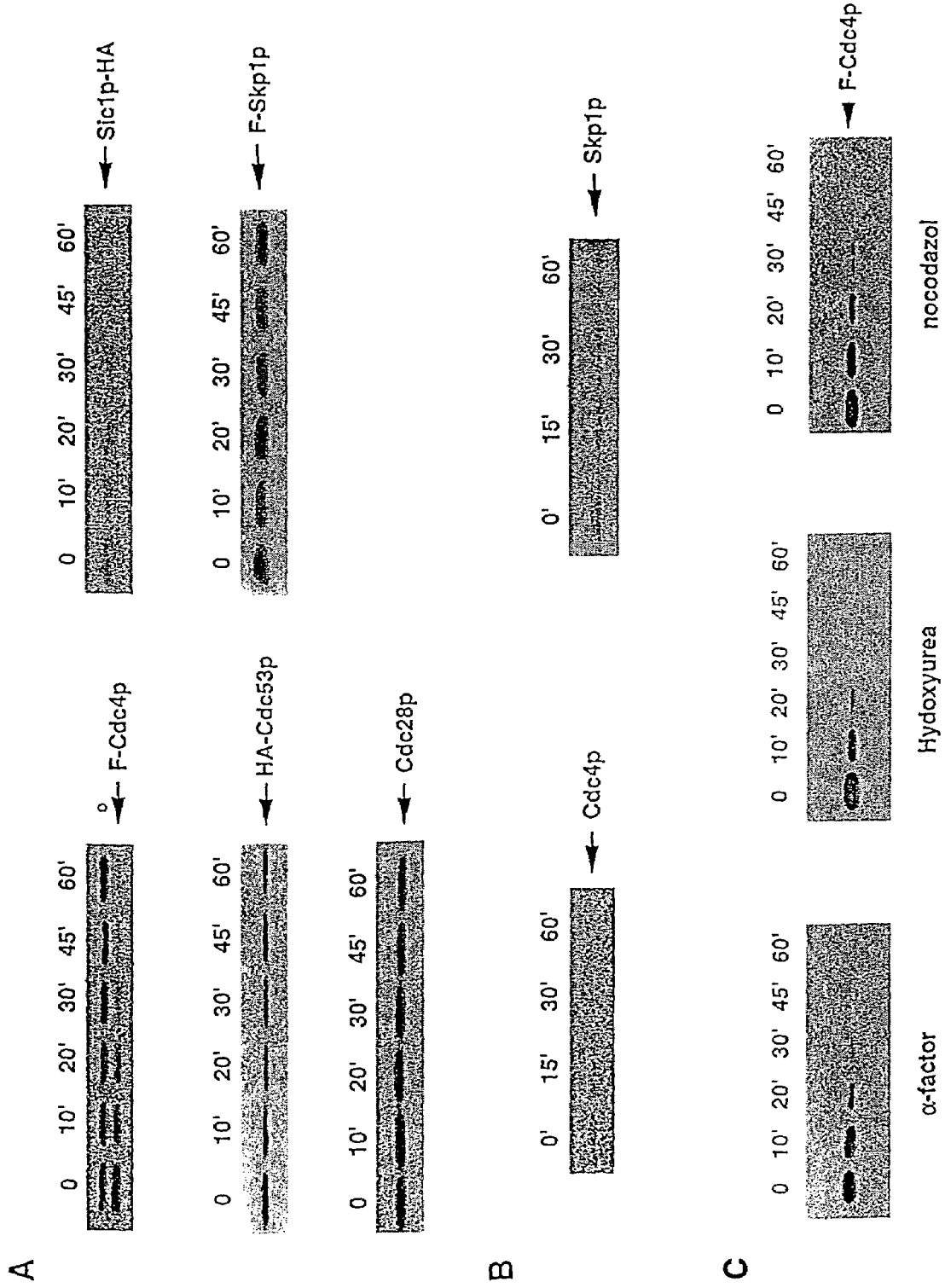

C

TARGETED PROTEOLYSIS BY RECRUITMENT TO UBIQUITIN PROTEIN LIGASES

This application claims the benefit of U.S. Provisional Application No. 60/103,787, filed on Oct. 9, 1998, the contents of which are incorporated herein by reference.

1. BACKGROUND OF THE INVENTION

Many diseases and pathological conditions involve the inappropriate expression or undesirable activity of one or more cellular genes. Examples include cancer, in which one or more cellular oncogenes become activated and results in the unchecked progression of cell cycle processes. Furthermore, many human genetic diseases, such as Huntington's disease and certain prion conditions, result from the inappropriate activity of a polypeptide as opposed to the loss of its function. Drug therapy strategies for these disorders have frequently employed molecular antagonists which target the polypeptide product of the disease gene(s). Additionally, infectious diseases such as HIV have been successfully treated with molecular antagonists targeted to specific essential retroviral gene(s). The discovery or rational design of such disease gene or pathogen gene antagonists is often difficult and time-consuming. Furthermore, such molecular antagonists frequently have unanticipated effects on other cellular activities which were not targeted for therapeutic intervention. Therefore a systematic means for degrading one or more target polypeptides which cause or contribute to a disease or condition would allow the rapid development of suitable antagonist therapeutic agents once a disease-causing polypeptide or pathogen gene function is identified.

The ability to systematically antagonize specific target polypeptide activities would further allow for the general elucidation and control of the essential polypeptide-mediated functions of a host cell. Indeed, the field of genetics is essentially an approach to understanding biological processes through the systematic elimination of cellular polypeptide functions. Historically, the genetic approach has involved the development of "screens" for mutations in genes which affect a specific phenotypic trait of an organism. The great advantage of this approach has been that no prior knowledge of the molecular nature of the genes involved is required because the "screen" identifies the affected genes by marking them with mutations. The mutation involved is frequently a change in the gene's sequence which results in a loss-of-function of the encoded gene product. Unfortunately the genetic approach has many limitations. Indeed the study of essential genes, required for cell viability, is exceedingly difficult using a purely genetic approach. The implementation of "reverse genetics" in yeast (see e.g. Winston et al. (1983) Methods Enzymol 101: 211–28) and, later, in mammals (see e.g. Capecchi (1989) Science 244: 1288–92), has allowed the positive identification of a gene as essential through the inability to recover viable yeast haploid gene "knockout" spores or homozygous recessive "knockout" mice. Nevertheless, the exact biological processes in which the essential gene is involved are difficult to determine due to the inability to isolate and/or study the doomed knockout yeast spore or the inviable homozygous mouse zygote. Thus the downstream effects on specific aspects of cell function following removal of the essential gene product cannot be readily determined using these traditional "knockout" studies. Furthermore, while traditional gene "knockout" experiments may be useful in demonstrating that a given gene is essential for the life of the organism, they provide neither a convenient method for determining how rapidly cellular function ceases nor what cellular processes immediately follow the removal of the gene product, nor further do they allow for the facile determination of the rate at which so-called "second-site suppressing" mutations can arise which restore cell viability following the removal of the essential gene. These considerations are important in the selection of targets for the rational design of, for example, antibiotic or chemotherapeutic pharmaceutical agents.

The functional characterization of a specific cellular protein often relies on experimentally altering the levels of the protein of interest, and studying the biological consequences of this manipulation. Gene knockout, ribozyme, anti-sense or RNA-mediated interference (RNAI) technologies are frequently used in different eukaryotic organisms to either eliminate or reduce the levels of a cellular protein. Antisense oligonucleotides and designer ribozymes provide a means for the systematic removal of a specific gene product without the prior bioengineering of the cellular target. (see, e.g. Hargest and Williamson (1996) Gene Ther. 3: 97–102; Lipkowitz et al. (1996) Am J Kidney Dis 28: 475–92; and Bennett and Schwartz (1995) Circulation 92: 1981–93); however the successful employment of such nucleic acid antagonists has met with many difficulties. Furthermore, where the immediate removal of existing gene product is desired, antisense and ribozyme gene antagonists are relatively inefficient since existing gene products are removed only at the rate of their natural turnover.

A systematic, rational means for antagonizing the function of a specific cellular or pathogen gene would provide a powerful strategy for dealing with certain disease conditions as well as providing a means to determine and control the essential biological functions of a host cell.

A number of methods for the directed inactivation of a specific target polypeptide functions in a host eucaryotic cell have been developed. For example, in an attempt to provide for a systematic means of deriving temperature-sensitive conditional alleles of a given gene target, Dohmen et al. have devised a temperature-sensitive "degron" cassette that can be appended to any gene of interest and used to render it thermosensitive (Dohmen et al. (1994) Science 263: 1273–6). The generality with which this thermosensitive degron can be successfully applied to any target polypeptide has yet to be determined and the necessity of relying upon thermal induction for the resulting system is a major drawback. Indeed, eucaryotic cells experience a transient heat-shock response which can have profound effects on some cellular processes such as transcription. Furthermore, the requirement for induction by heat shock precludes useful application to mammalian transgenic animal systems. Another example of a system for the controlled removal of a specific gene product is the use of the ubiquitin N-end rule proteolytic system to rapidly and inducibly degrade a specific target which has been engineered to carry a predisposing non-methionine amino terminal amino acid (Moqtaderi, et al. (1996) Nature 383: 188–91). This system can be made inducible by engineering the host cell to express a key component(s) of the N-end rule proteolytic system under the control of a suitable promoter, such as a copper-inducible promoter. Still other systems have been developed for the controlled removal of a specific host gene. Notably the Cre/lox system (see e.g. Sauer (1998) Methods 14: 381–92) allows for the inducible deletion of a specific target gene through the action of the Cre site-specific DNA recombinase. Using this system, genetic switches can be designed to ablate a specific target gene in a specific tissue and at a specific time during development. One shortcoming of this method is that, following recombinational deletion of the targeted gene from the chromosome, the remaining mRNA and polypeptide products of the gene may only slowly be titrated out of the host cell through consecutive mitotic cell divisions and/or the eventual turnover of the mRNA and polypeptide by cellular ribonucleases and proteases. Thus it would be desirable to have a more rapid means for directly inactivating specific target genes in a host eucaryotic cell. A principal disadvantage of all of these systems is that they require the specific bioengineering of the target cell or host to potentiate the removal of the targeted gene function. In particular, these methods require the molecular modification of the target polypeptide-encoding gene and so it is difficult to employ them in the alteration of endogenous cellular protein levels. Therefore these techniques, while potentially useful in the identification and study of gene function in a model organism, are unlikely to be applicable to the therapeutic treatment of specific human disease conditions.

The steady state level of a cellular protein is reached when the balance is achieved between the rates of its synthesis and degradation. Altering the amount of a cellular protein has been a fundamental approach in understanding its normal cellular function. Many important technologies have been developed to manipulate cellular protein levels. Gene transfer and transgenic technologies in tissue culture or in animals are frequently used to overproduce proteins, whereas gene knockout, ribozyme or RNAI have been used to either eliminate or reduce expression of specific proteins. Although complete elimination of a cellular protein often allows the determination of the cellular functions of a protein, there are instances where the reduction in the level of a specific gene product may be desirable in order to assess the function of a specific protein in a specific process. Furthermore, complete gene knockout is sometimes not desirable, in situations in which the deletion of a particular gene has pleiotropic effects that may overshadow specific cellular functions.

Ubiquitin dependent proteolysis is a major catabolic pathway utilized by eukaryotic cells for the degradation of cellular proteins. Protein ubiquitination is catalyzed by the concerted actions of three classes of enzymes; the E1 ubiquitin-activating enzymes, the E2 ubiquitin-conjugating enzymes, and the E3 ubiquitin protein ligases (reviewed in Hochstrasser (1996) Annu Rev. Genet 30: 405–39). While E1 and E2 are primarily involved in the activation and transfer of ubiquitin, the substrate specificity of the ubiquitin pathway is conferred by the E3 ubiquitin protein ligases. Recent studies have revealed distinct E3 components and ubiquitination machineries that operate at various cellular processes to target distinct substrates for degradation.

For example, the SCF (Skp1, Cullin and F-box-containing proteins) ubiquitin protein ligases function to promote cell cycle transitions by targeting multiple cell cycle regulators for ubiquitin-dependent proteolysis (reviewed in King et al. (1996) Science 274: 1652–9; Patton et al. (1998) Genes Dev 12: 692–705; Koepp et al. (1999) Cell 97: 431–4; and references therein). Among the subunits of the SCF complexes, Skp1 and cullin are thought to form a stable core complex that is shared by different F-box-containing proteins, and interacts with E2 through the cullin subunit. Multiple F-box proteins exist that serve as receptors for recognition and recruitment of various target polypeptides to the core SCF for ubiquitination. Different F-box proteins share the common F-box domain for Skp1 binding, but utilize additional modular protein—protein interaction domains, such as WD40 or leucine-rich repeats (LRR) for binding distinct classes of substrates. Recently, a fourth subunit of SCFs, Rbx-1/Roc1, was identified that interacts with F-box proteins, and is thought to stimulate interaction between the Cdc34 ubiquitin-conjugating enzyme and SCF ubiquitin-protein ligases (Kamura et al. (1999) Science 284: 657–61; Skowyra (1999) Science 284: 662–5; Ohta et al. (1999) Mol Cell 3: 535–41; Tan et al. (1999) Mol Cell 3: 527–33). Our recent studies indicated that the yeast F-box-containing proteins, such as Cdc4p, is itself a target of the SCF-mediated ubiquitination and degradation (Zhou and Howley (1998) Mol Cell 2: 571–80). This suggests that the intact SCF complexes may be transient in nature, and that the proteolysis of the F-box proteins is essential for maintaining the SCF proteolytic activities by permitting the exchange of the substrate recognition components.

Transit through the G1/S boundary and initiation of DNA synthesis in the yeast *Saccharomyces cerevisiae* require ubiquitin-dependent proteolysis of the CDK inhibitor Sic1p by an SCF ubiquitin ligase (reviewed in (Deshaies (1997) Curr Opin Genet Dev 7: 7–16; King et al. (1996) Science 274: 1652–9; and references therein). Genetic analyses have identified four proteins, Cdc34p, Cdc4p, Cdc53p, and Skp1p, whose functions are required for Sic1p ubiquitination (Bai et al. (1996) Cell 86: 263–74; Mathias et al. (1996) Mol Cell Biol 16: 6634–43; Schwob et al. (1994) Cell 79: 233–44). Recently, the Sic1p ubiquitination pathway was biochemically defined by in vitro reconstitution using recombinant proteins (Feldman et al. (1997) Cell 91: 221–30; Skowyra et al. (1997) Cell 91: 209–19). The E3 activity is conferred by a multiprotein complex, designated $SCF^{Cdc4p}$, consisting of Skp1p, Cdc53p and Cdc4p. In association with the Cdc34p ubiquitin conjugating, enzyme, $SCF^{Cdc4p}$ promotes Sic1p ubiquitination in vitro in the presence of the E1 ubiquitin activating enzyme and ubiquitin. Importantly, phosphorylation of Sic1p by Cdc28p/G1 cyclin dependent kinase is a prerequisite for Sic1p recognition by Cdc4p (Feldman et al. (1997) Cell 91: 221–30; Schneider et al. (1996) Science 272: 560–2; Schwob et al. (1994) Cell 79: 233–44; Skowyra et al. (1997) Cell 91: 209–19; Verma et al. (1997) Science 278: 455–60). Although the in vitro reconstitution experiments have defined the essential ubiquitin enzyme components and the biochemical mechanisms for the Cdc34p/$SCF^{Cdc4p}$ ubiquitination pathway, the question remains as to how the individual components collaborate in vivo to deliver ubiquitin to $SCF^{Cdc4p}$ substrates, and how the activity of the SCFcdc4p ubiquitin protein ligase complex is controlled through the various cell cycle transitions.

Mutations of the Cdc34p/$SCF^{Cdc4p}$ pathway components affect the stability of several regulators of cell growth in addition to Sic1p, including the Cdk inhibitor Far1p (Henchoz et al. (1997) Genes Dev 11: 3046–60; McKinney et al. (1993) Genes Dev7: 833–43), the $p58^{ctF13}$ subunit of the Cbf3 kinetochore assembly complex (Kaplan et al. (1997) Cell 91: 491–500), the DNA replication protein Cdc6p (Drury et al. (1997) EMBO J 16: 5966–76; Piatti et al. (1996) Genes Dev 10: 1516–31), and the GCN4p transcription factor (Kornitzer et al. (1994) EMBO J 13: 6021–30). The Cdc34p/$SCF^{Cdc4p}$ proteolytic activity has also been implicated in phases of cell cycle other than G1/S (King et al. (1996) Science 274: 1652–9), as deletion of SIC1 allows cdc4$^{ts}$, cdc34$^{ts}$, cdc53$^{ts}$ and skp1$^{ts}$ cells to pass through the G1/S boundary, but they become arrested at G2-M (Bai et al. (1996) Cell 86: 263–74; Schwob et al. (1994) Cell 79: 233–44). Therefore, the Cdc34p/$SCF^{Cdc4p}$ pathway must be active at different stages of the cell cycle to mediate the degradation of a variety of substrates (Deshaies (1997) Curr Opin Genet Dev 7: 7–16; King et al. (1996) Science 274: 1652–9).

Two additional SCF complexes, SCF$^{Grr1p}$ and SCF$^{Met30p}$, have also been identified in *S. cerevisiae* and are implicated in the degradation of G1-specific cyclins or regulators of sulfur metabolism, respectively (Patton et al. (1998) Genes Dev 12: 692–705; Skowyra et al. (1997) Cell 91: 209–19). The three SCFs share in common the Cdc53p and Skp1p components, and differ in the F-box-containing subunits, Cdc4p or Grr1p or Met30p. It is these different F-box-containing proteins that serve as the substrate recognition subunits. It is currently unclear whether the individual intact SCFs are somehow regulated within cells, or whether there is an equilibrium involving, the transient assembly of SCFs with the individual F-box subunit recognition component. Here we report that the F-box-containing subunits of SCFs are intrinsically short-lived proteins. The SCF$^{Cdc4p}$ machinery mediates the autoubiquitination and degradation of the F-box-containing Cdc4p, the substrate recognition component of SCF$^{Cdc4p}$. Our studies suggest a novel mechanism for the rapid assembly and disassembly of distinct SCF complexes through auto-ubiquitination of the F-box-containing SCF components, which allows the cell to respond in a timely manner to different cell cycle or environmental signals to target a variety of specific cellular proteins for proteolysis.

The SCF ubiquitin ligases are only one group of known ubiquitin ligases. Other groups of structurally related ubiquitin ligases include the HECT domain ubiquitin ligases which include mammalian E6-AP and Nedd-4, and yeast RSP5 (see Huibegtse et al. (1995) Proc Natl Acad Sci USA 92: 2563–7; Wang et al. (1999) Mol Cell Biol 19: 342–52) as well as the more recently discovered HECT domain ubiquitin ligase proteins such as mammalian Smurfl (Zhu, et al. (1999) Nature 400: 687–93), yeast TOM1 (saleh et al. (1998) J Mol biol 282: 933–46; Utsugi et al. (1999) Gene 234: 285–95), and human EDD (Callaghan et al. (1999) Oncogene 17: 3479–91). The HECT domain ubiquitin ligases effect ubiquitin conjugation, and thereby activate targeted proteolysis, of a number of polypeptide targets such as the *Schizosaccharomyces pombe* mitotic activating tyrosine phosphatase cdc25p (Nefsky and Beach (1996) EMBO J 15: 1301–12) and the SMADs, a group of proteins which control embryonic development and a wide variety of cellular responses to TGF-beta signals (Zhu et al. (1999) Nature 400: 687–93). While many targets of HECT-mediated ubiquitin-dependent proteolysis interact directly with their target protein, others interact through a third "adaptor" polypeptide which itself is not targeted for ubiquitination. For example, Grb10 remains unubiquitinated following its interaction with Nedd4 HECT ubiquitin ligase, and may serve to target other proteins, such as tyrosine kinase receptors, for ubiquitination (Morrione et al. (1999) J Biol Chem 274L 24094–9).

A third group of ubiquitin protein ligases are those involved in the degradation of polypeptides with particular amino-terminal amino acid residues. These include the yeast and mammalian Ubr1p N-end rule ubiquitin ligases which bind to destabilizing target polypeptide N-terminal residues and facilitate ubiquitination of the bound target (Kwon et al. (1998) Proc Natl Acad Sci USA 95: 7893–903; Varshavsky (1996) Proc Natl Acad Sci USA 93: 12142–9). This group of ubiquitin protein ligases likely function to control the intracellular levels of polypeptides which have undergone an endoproteolytic processing event which removes the normal stabilizing amino-terminal methionine residue. Particular classes of amino acid residues such as the basic residues (arginine, lysine and histidine) or the bulky hydrophobic residues (phenylalanine, leucine, tryptophan, tyrosine, and isoleucine), when exposed at the amino-terminus of the resulting processed protein, result in requitment of Ubr1p-type ubiquitin protein ligases which effect ubiquitination of the target, resulting eventually in the proteasome-dependent destruction of the target polypeptide.

It is an object of the instant invention to exploit the ubiquitin protein ligases for experimental and therapeutic purposes by providing modified ubiquitin protein ligase polypeptides which recruit target polypeptides for ubiquitin conjugation and ubiquitin-dependent proteolytic degradation by a cellular proteasome. Such modified ubiquitin protein ligases allow for the specific and regulated destruction of any target polypeptide which is cloned or for which an interaction domain is available. It is a further an object of the invention to provide inhibitors of ubiquitin protein ligases which prevent their interaction and/or ubiquitination of a target protein which is present in a host cell. These ubiquitin protein ligase inhibitors allow for the specific blocking of ubiquitin-mediated degradation of a target protein and thereby stabilize the level of the target protein in the host cell. Therefore, the invention generally provides methods and compositions to stimulate a ubiquitin protein ligase activity on a target polypeptide, or to repress a ubiquitin protein ligase activity on a target polypeptide.

2. SUMMARY OF THE INVENTION

The invention generally provides methods for increasing or decreasing a ubiquitin protein ligase ubiquitination activity on a target polypeptide. In general, increased ubiquitination of a target polypeptide is effected by cis or trans targeting the target polypeptide to a ubiquitin protein ligase while decreased ubiquitination of the target polypeptide is effected by contacting the target polypeptide with a target polypeptide ubiquitination inhibitor of the invention.

In a preferred embodiment, the invention provides a method for targeting degradation of a polypeptide in vivo by providing a ubiquitin protein ligase polypeptide that encodes a ubiquitin conjugation activity, functionally linking the ubiquitin protein ligase polypeptide to a target polypeptide interaction domain that provides a target polypeptide recruitment activity, and expressing the ubiquitin protein ligase polypeptide-target polypeptide interaction domain hybrid in a cell. The hybrid protein recruits the target polypeptide through the target polypeptide interaction domain and ubiquitinates the target polypeptide through the ubiquitin protein ligase domain. The resulting ubiquitinated target polypeptide is typically further subject to ubiquitin-dependent proteolysis by a cellular porteasome.

In certain embodiments, the ubiquitin protein ligase polypeptide is an E3 ubiquitin protein ligase polypeptide, preferably an SCF polypeptide, a HECT polypeptide, or a UBR1 polypeptide. In preferred embodiments, the E3 ubiquitin protein ligase polypeptide is an F-box polypeptide, preferably an F-box polypeptide which further comprises a WD domain. In some embodiments, the F-box polypeptide is Cdc4p, Pop1p, Pop 2p, Grr1p, Met30p, HOSp, beta TrCPp, or FWD1p. In certain embodiments, the F-box polypeptide is a polypeptide which is at least 70% identical to a contiguous polypeptide sequence of a polypeptide selected from the group consisting of SEQ ID Nos. 2, 4, 6, 8, 10, and 12. In preferred embodiments, the F-box polypeptide is encoded by a nucleic acid which is at least 80% identical to a contiguous nucleic acid sequence of SEQ ID Nos. 1, 3, 5, 7, 9, and 11. In still more preferred embodiments, the F-box polypeptide is encoded by a nucleic acid which hybridizes, preferably under conditions of high stringency to a nucleic acid selected from the group consisting of SEQ ID Nos. 1, 3, 5, 7, 9, and 11.

In other embodiments the SCF polypeptide may be any SCF polypeptide subunit, such as a mammalian or a yeast Cdc4 polypeptide, Skp1 polypeptide or cullin polypeptide. In still other embodiments, the ubiquitin protein ligase polypeptide is a HECT polypeptide, preferably an E6-AP, a Nedd-4, an RSP5, a Smurfl, a TOM1 or an EDD HECT polypeptide. In still other embodiments, the ubiquitin protein ligase polypeptide may be a yeast or a mammalian UBR1 polypeptide.

In some embodiments of the invention, the target polypeptide interaction domain is a papillomavirus E7 polypeptide, or an SV40 LTP polypeptide. In preferred embodiments, the target polypeptide is a p107 polypeptide, an IκB polypeptide, a Sic1 polypeptide, a C1n2 polypeptide, an E2 polypeptide or a beta-catenin polypeptide.

In highly preferred embodiments, the invention provides a method for decreasing the level of a target polypeptide by providing an SCF recruitment domain which is operably linked to a target polypeptide interaction domain to form an SCF recruitment domain-target polypeptide interaction domain fusion protein. This SCF recruitment domain-target polypeptide interaction domain fusion protein is expressed and recruits and ubiquitinates the target polypeptide such that the level of said target polypeptide is decreased. In preferred embodiments, the SCF recruitment domain is an F-box polypeptide, preferably further comprising a WD domain, and still more preferably corresponding to a Cdc4 polypeptide, a Grr1 polypeptide, a Pop1 polypeptide, a Pop 2 polypeptide, a Met30 polypeptide, a HOS polypeptide, a betaTrCP polypeptide or a FWD1 polypeptide. In certain preferred embodiments, the F-box polypeptide is at least 70% to a polypeptide of at least 20 contiguous amino acids of a polypeptide selected from the group consisting of SEQ ID Nos. 2, 4, 6, 8, 10, and 12; or is an F-box polypeptide is encoded by a nucleic acid which hybridizes to a nucleic acid selected from the group consisting of 1, 3, 5, 7, 9, and 11.

The invention further provides a method for creating a destabilized polypeptide subject to SCF-mediated proteolysis by operably linking an SCF recruitment domain to target polypeptide. The invention further provides a method for expressing a destabilized target polypeptide subject to SCF-mediated proteolysis comprising: providing an SCF recruitment domain which is operably linked to a target polypeptide and expressing the SCF-target polypeptide fusion, thereby expressing a destabilized target protein.

In preferred embodiments, the invention provides nucleic acids for expressing an SCF recruitment domain-target polypeptide interaction domain comprising: a nucleic acid encoding an SCF recruitment domain; and a nucleic acid encoding a heterologous polypeptide domain. In preferred embodiments, the nucleic acid encoding the SCF recruitment domain and the nucleic acid encoding the heterologous polypeptide domain are operably linked so as to encode an SCF recruitment domain-heterologous polypeptide domain fusion protein. In certain embodiments of this aspect of the invention, the encoded heterologous polypeptide domain is a target polypeptide. In preferred embodiments, the encoded heterologous polypeptide domain is a target polypeptide interaction domain. In other preferred embodiments, the SCT recruitment domain is encoded by a nucleic acid which is at least 90% identical to a nucleic acid of SEQ ID Nos. 1, 3, 5, 7, 9, or 11. In more preferred embodiments, the SCT recruitment domain is encoded by a nucleic acid which hybridizes, preferably under stringent conditions, to nucleic acid of SEQ ID Nos. 1, 3, 5, 7, 9, or 11.

In still more other embodiments, the vector comprises a nucleic acid encoding an SCF recruitment domain and a cloning site for inserting an heterologous polypeptide encoding sequence.

The invention also provides methods of treating a cell to stabilize a target polypeptide of ubiquitin protein ligase by contacting the cell with a preparation containing an effective amount of an organic compound which can competitively inhibit interaction of the target polypeptide with the ubiquitin protein ligase. In preferred embodiments, the organic compound is a peptide or peptidomimetic, preferably one which is a competitive inhibitor of a WD domain, and most preferably one which includes the general chemical structure specified by the formula: G-H-X (3–6)-h-X-X-h-X-r-X-t (2–3)-p-X-h-h-X-X-X-D-X-X-X-X-h-W-D (SEQ ID No. 14).

Other features and advantages of the invention will be apparent from the following detailed description and claims.

3. BRIEF DESCRIPTION OF THE FIGURES

FIG. 1 demonstrates that the F-box containing polypeptide Cdc4p is an unstable component of the $SCF^{Cdc4p}$ ubiquitin protein ligase complex.

Figure 2:
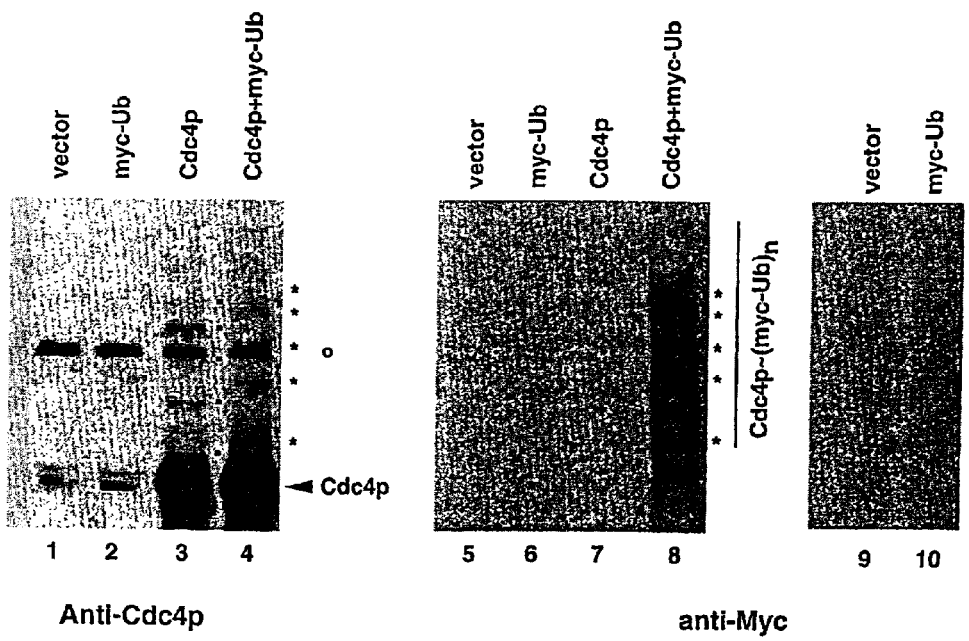
Figure 2:
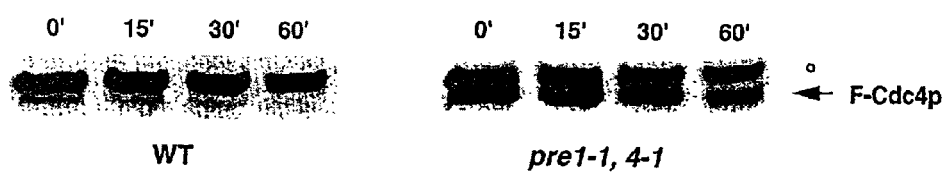

FIG. 2 shows that Cdc4p is ubiquitinated and proteolytically degraded by the proteasome in vivo.

Figure 3:
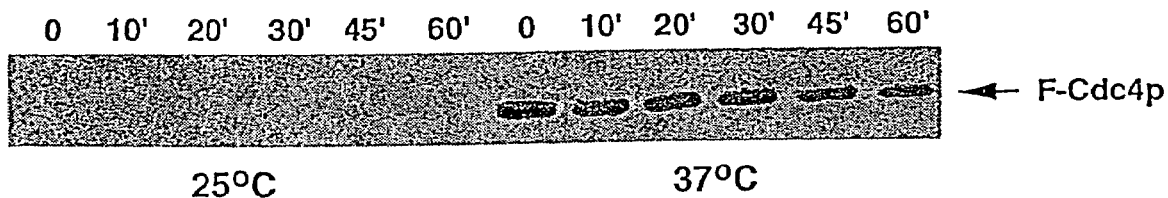
Figure 3:
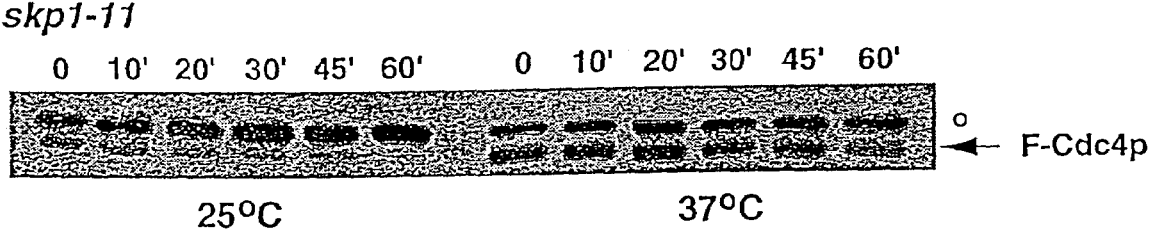
Figure 3:
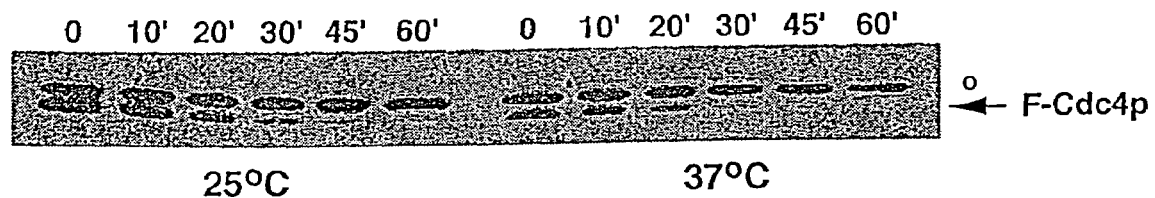

FIG. 3 demonstrates that the $Cdc34p/SCF^{Cdc4p}$ E3 ubiquitin ligase complex is required for proteolysis of the Cdc4p F-box protein.

Figure 4:
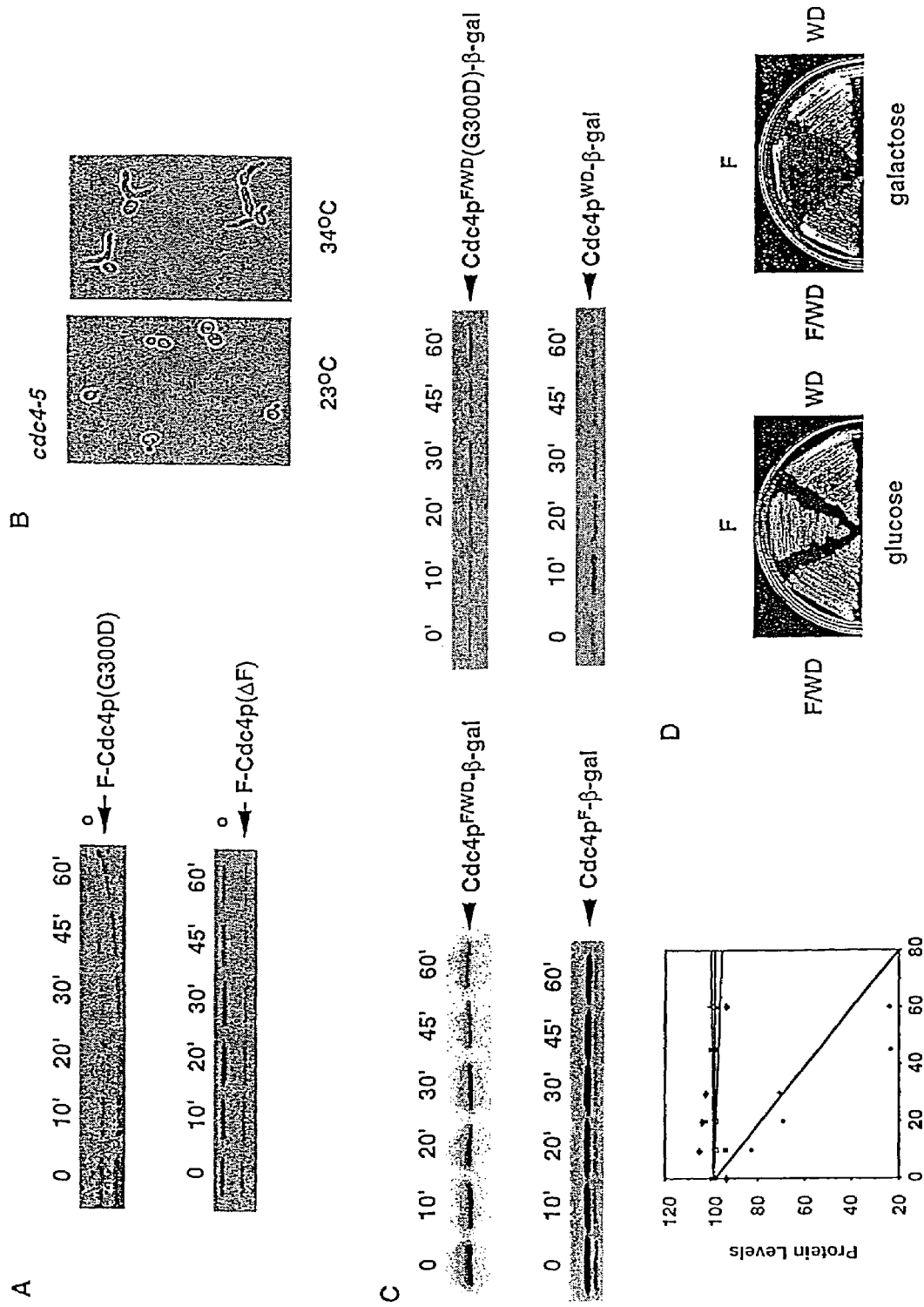

FIG. 4 demonstrates that functional F-box and WD polypeptide domains are necessary and sufficient for proteolysis of Cdc4p as well as an heterologous target polypeptide (β-galactosidase) fused to Cdc4p. FIG. 4D illustrates that an F-box polypeptide-beta-galactosidase fusion protein acts as a dominant negative inhibitor of cell growth.

Figure 5:
Figure 5:
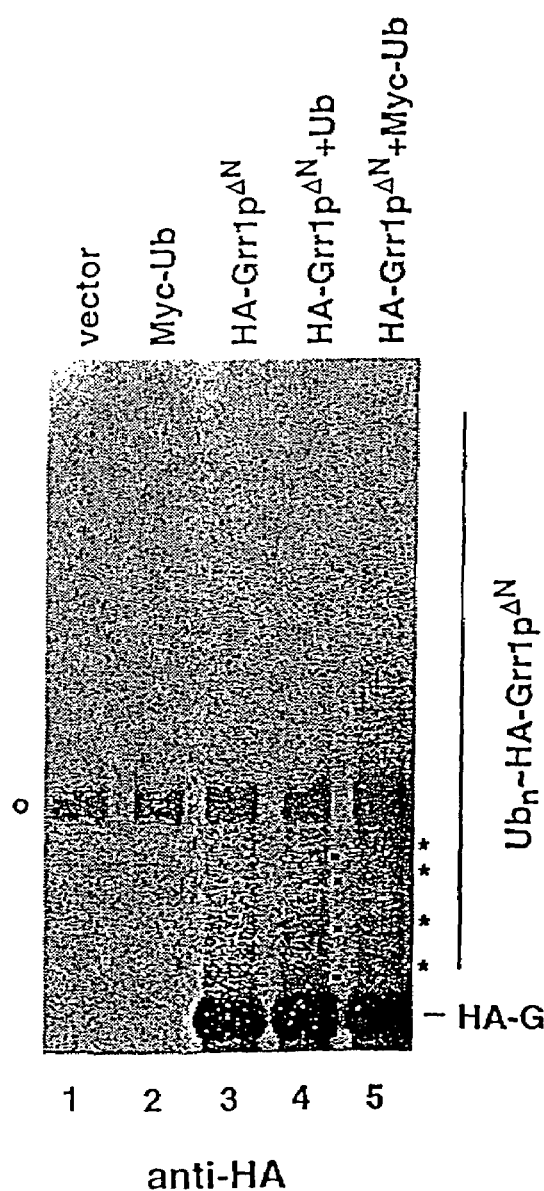

FIG. 5 demonstrates that Grr1p, another F-box containing polypeptide, is also rapidly degraded by a ubiquitin dependent proteolysis.

Figure 6:
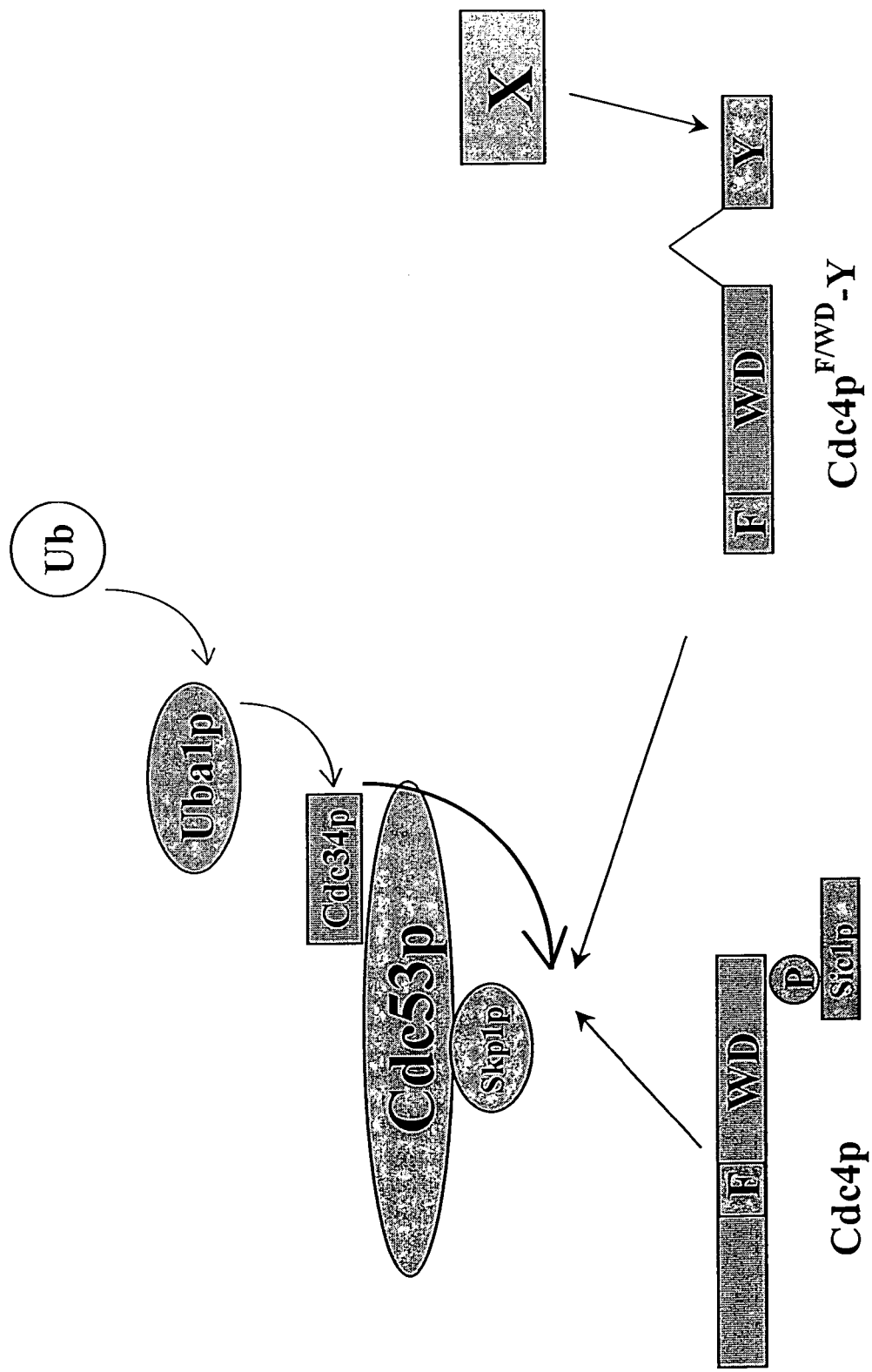

FIG. 6 shows the trans-targeting of a target polypeptide (X) through noncovalent interaction with a target polypeptide interaction domain (Y).

Figure 7:
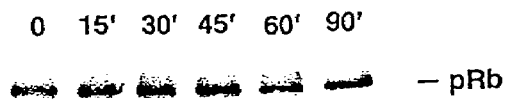
Figure 7:
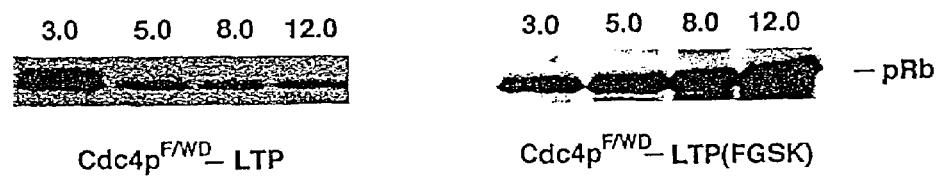
Figure 7:
Figure 7:
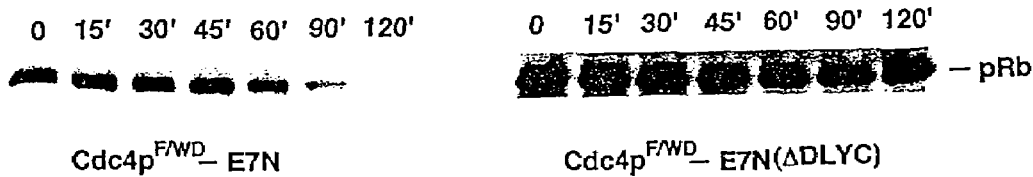

FIG. 7 demonstrates the trans-targeting of tumor-suppressor retinoblastoma (pRB) by either of two retinoblastoma interaction domains: the SV40 Large T antigen polypeptide (LTP) (Panel B); or the poapillomavirus oncoprotein E7 amino-terminus (E7N) (Panel C).

Figure 8:
Figure 8:

FIG. 8 demonstrates the trans-targeting of pappillomavirus E2 protein.

Figure 9:
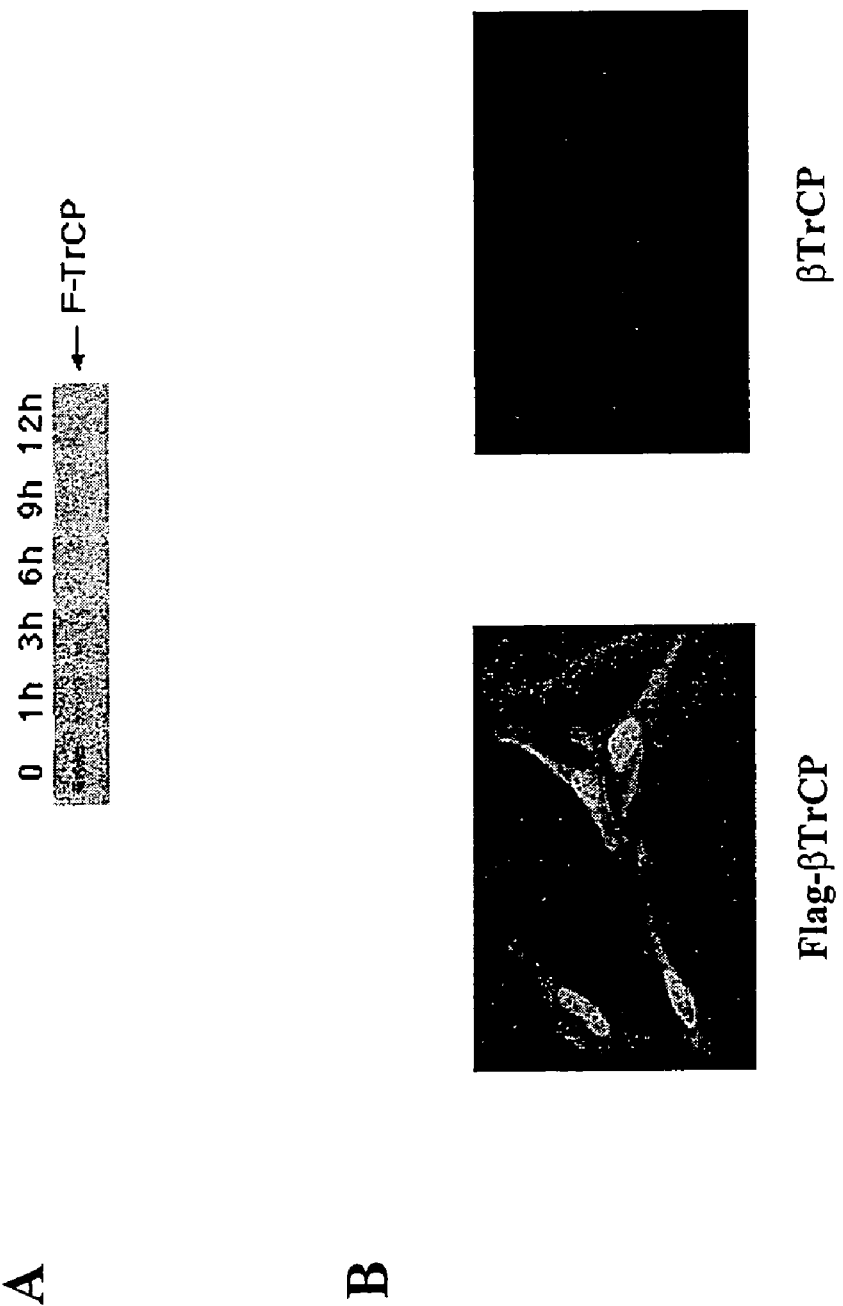

FIG. 9 demonstrates: (A) that βTrCP is a short-lived protein when expressed in a mammalian cell; and (B) that human βTRCP is localized to both the nucleus and cytoplasm of HeLa cells.

Figure 10:
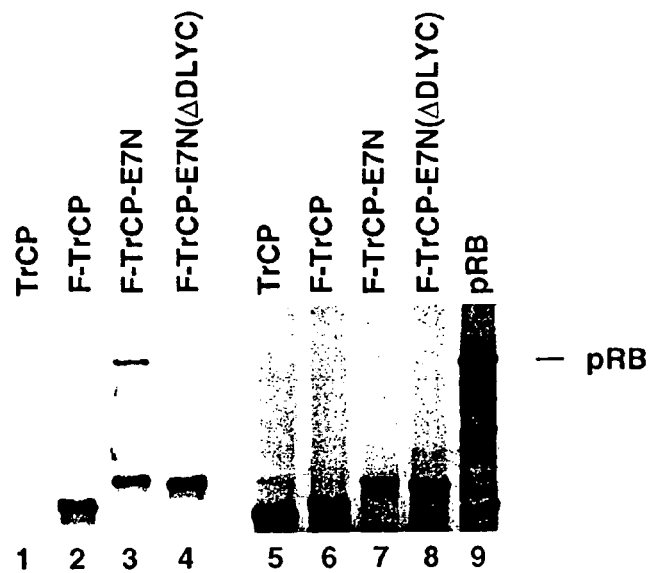
Figure 10:
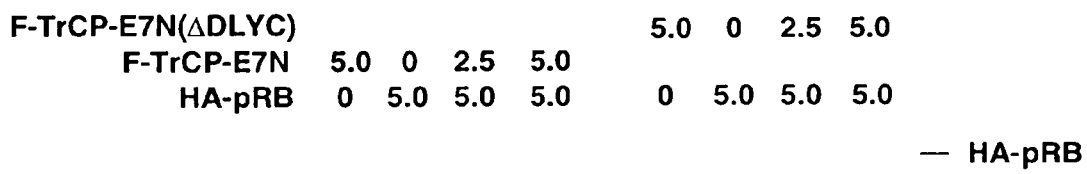
Figure 10:
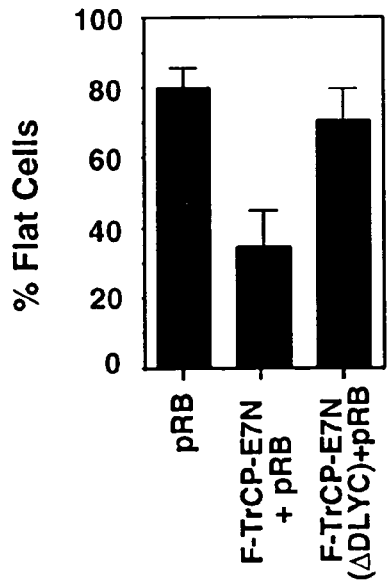

FIG. 10 demonstrates the trans-targeting of retinoblastoma tumor suppressor (pRB) in mammalian cells and the resulting block of pRB induced growth arrest as indicated by cell morphology (panel C).

Figure 11:
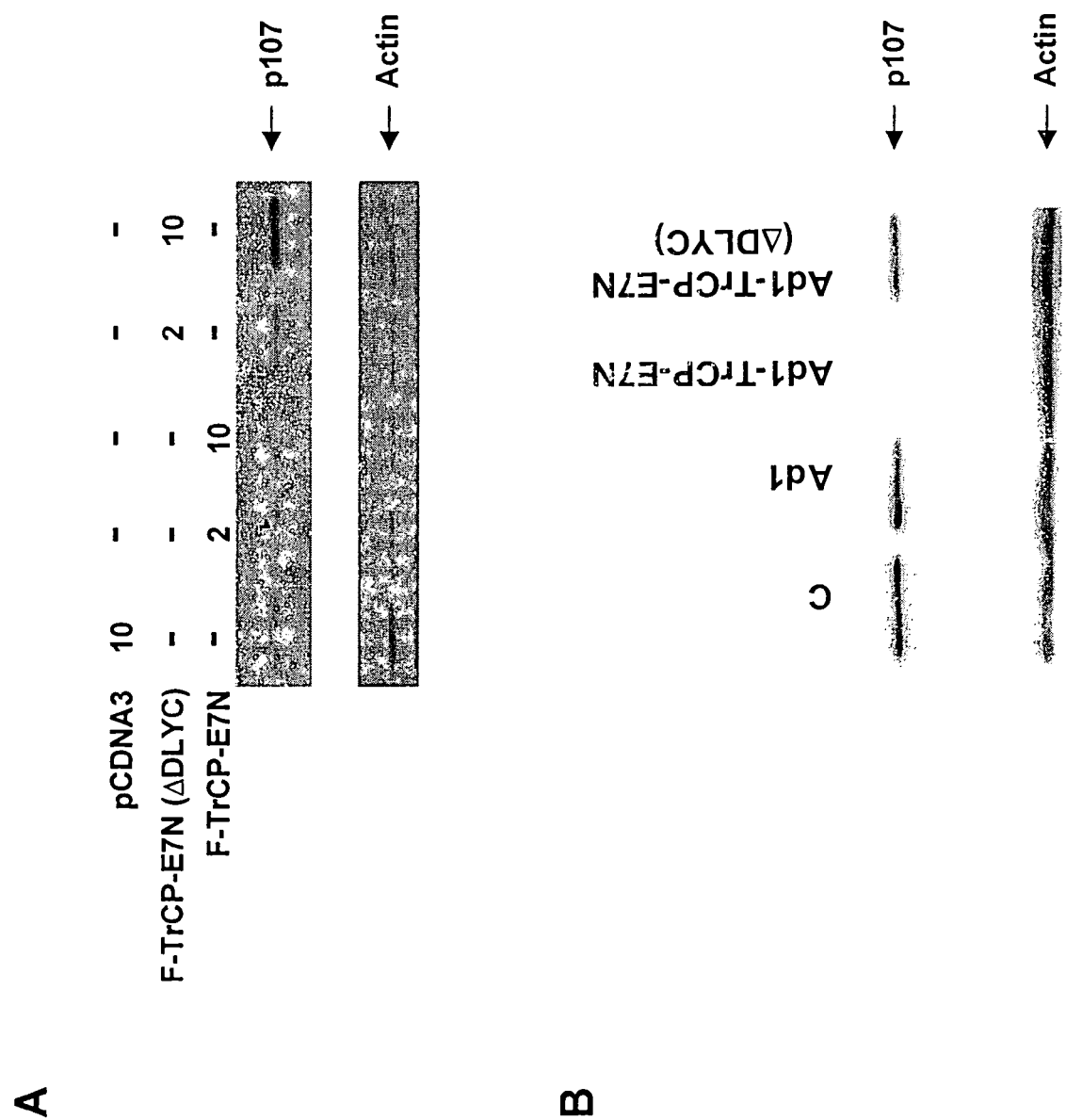

FIG. 11 demonstrates the trans-targeting of endogenous human p107 in mammalian cells.

Figure 12:
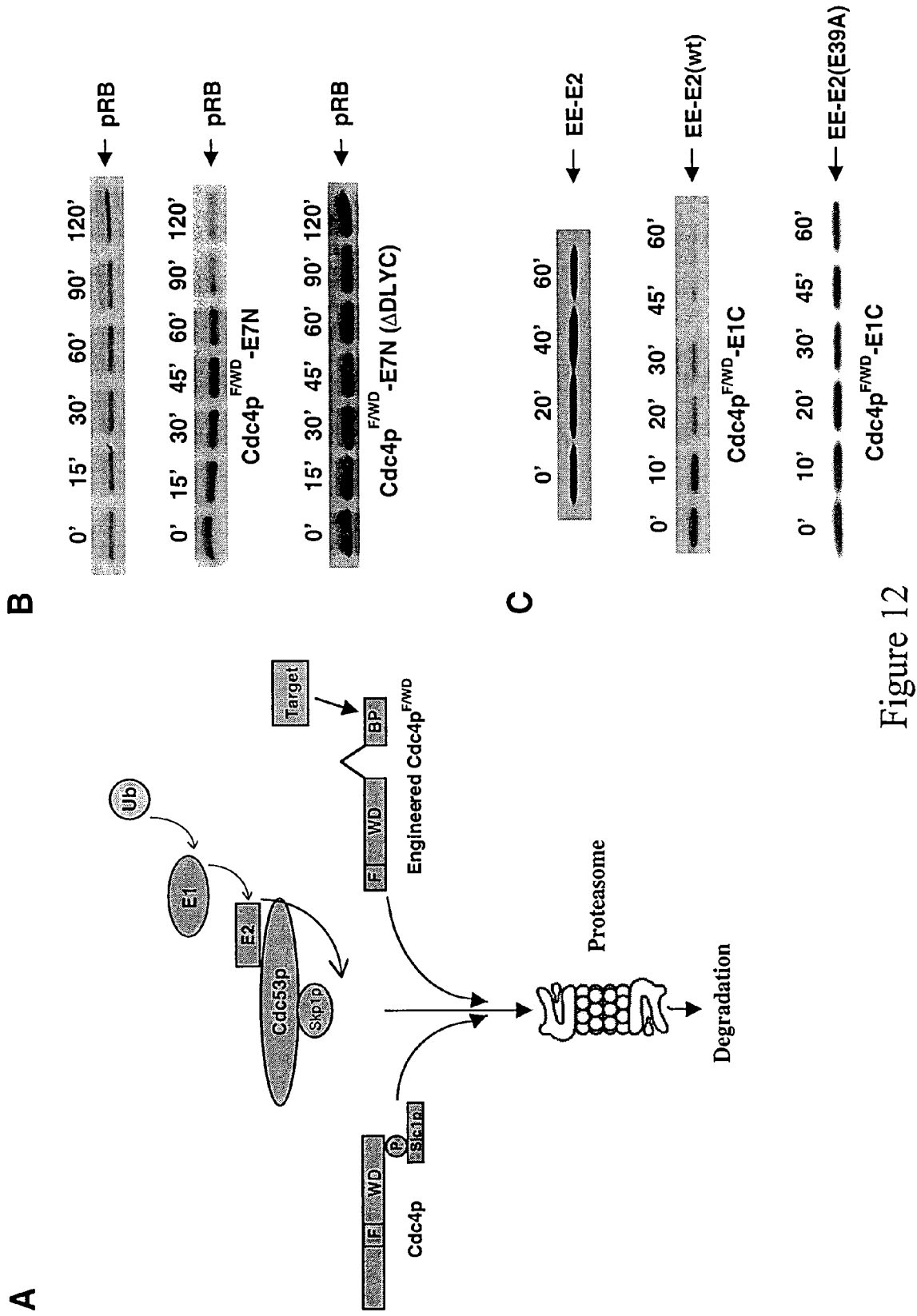

FIG. 12 depicts an exemplary trans-targeting embodiment of the invention. FIG. 12, panel A depicts a method for modifying the F-box protein Cdc4p by fusion to a target polypeptide interaction domain (BP) so as recruit a target polypeptide for ubiquitination and proteasome-dependent degradation. The trans-targeting of Retinoblastoma (panel B) The engineered SCF$^{Cdc4p}$ machinery can efficiently target the degradation of Retinoblastoma (panel B) or the papillomavirus E2 regulatory protein (panel C) in yeast.

4. DETAILED DESCRIPTION OF THE INVENTION

4.1. General

The invention provides compositions and methods for increasing or decreasing the rate of ubiquitin-dependent proteolytic degradation of a target polypeptide in a host cell.

In preferred embodiments, the invention provides methods and reagents for targeted proteolysis through recruitment of the targeted polypeptide to a protein ubiquitin ligase. Preferred protein ubiquitin ligases include E3-type ubiquitin ligases such as the SCF ubiquitin ligases, the HECT ubiquitin ligases or the UBR1 ubiquitin ligases. The targeted polypeptide may be a natural target of ubiquitination by these ubiquitin ligases or may be a polypeptide which is not normally targeted for degradation by ubiquitin conjugation in general or by an E3-type ubiquitin protein ligase of the invention in particular. In preferred embodiments, the target polypeptide is recruited to an E3 ubiquitin ligase complex either by covalent joining of the target polypeptide to a component of the complex (cis targeting) or by noncovalent association of the target polypeptide with a component of the complex (trans targeting). The invention thereby provides for the controlled degradation of any cellular protein for which the encoding gene has been cloned or for which an interacting polypeptide is known or can easily be elucidated by one of skill in the art. The controlled proteolysis of a target protein provides a general method for antagonizing a polypeptide activity for therapeutic, diagnostic or research purposes.

In one aspect of the invention, the invention provides for the cis targeting of a polypeptide. In this aspect of the invention, the targeted polypeptide may be joined to a component of an SCF (Skp1/Cul1 1/F-box protein) which serves as an SCF recruitment domain. In preferred embodiments of this aspect of the invention, the SCF recruitment domain is an F-box protein and the targeted polypeptide is produced as an F-box fusion protein. The F-box polypeptide sequence may be obtained from an F-box-containing protein such as Cdc4p, Grr1p, Met30p, HOS (human homolog of Slimb), beta TrCP (Slimb), or FWD1 (mouse beta TrCP). Alternatively, an F-box containing polypeptide from a related protein may be used, or a synthetic F-box polypeptide sequence, related in structure to Cdc4p, Pop 1, Pop 2, Grr1p, Met30p, HOS, beta TrCP, Pop 1, Pop 2 or FWD1 may be used. In certain embodiments, the F-box polypeptide-target polypeptide fusion protein includes a WD-40 polypeptide region such as provided by the WD repeats of Cdc4p or as can be obtained from a large family of proteins which contain WD repeat sequences (see e.g. van der Voorn and Ploegh (1992) FEBS Lett 307: 131–4).

In preferred embodiments of the invention, the targeted polypeptide is recruited to an SCF E3 ubiquitin ligase complex by trans association with at least one component of the complex. Preferably, such trans targeting of a polypeptide or polypeptides is effected by fusing a "target polypeptide interaction domain" to an F-box polypeptide sequence. The "target polypeptide interaction domains" may be readily obtained by screening a library of naturally-occurring polypeptide sequence such as by using the yeast two-hybrid methodology (Fields and Song (1989) Nature 340:245–6; Gyuris et al. (1993) Cell 75:791–803). Alternatively, synthetic interaction domains may be obtained by any of various peptide display selection methods, such as phage display, which are known in the art.

The invention further provides methods and compositions for the inhibition of a ubiquitin ligase interaction with a target polypeptide. This aspect of the invention provides antagonists of the ubiquitin protein ligase mediated degradation of particular cellular target polypeptides. Such antagonists are useful in stabilizing ubiquitin ligase targeted cellular polypeptides, such as a tumor suppressor proteins or IκB, the protein inhibitor of NF-κB. In certain embodiments, the ubiquitin protein ligase inhibitors of the invention antagonize the interaction of an SCF ubiquitin protein ligase and a cellular target. In preferred embodiments, the inhibitors antagonize the interaction of an SCF F-box protein and a target polypeptide. For example, cellular target polypeptides which interact with an SCF F-box protein include IκB, Sic1p, Cln2p, and beta-catenin. The F-box interaction/target polypeptide inhibitors of the invention are useful in stabilizing such cellular target proteins and they thereby promote a bioactivity supplied by the target polypeptide such as a cell cycle inhibitor activity, a cyclin activity, a tumor suppressor activity, a Wnt signaling activity or an NF-κB signaling activity. The F-box protein/target protein interaction inhibitors of the invention may be, for example, dominant negative forms of F-box polypeptides, or peptidomimetic or other small molecule inhibitors of an F-box protein/target polypeptide interaction.

In a related embodiment of the invention, methods and compositions for the identification of inhibitors of the interaction between an F-box protein and the other subunits of an SCF complex are provided. In this embodiment, inhibitors of SCF complex interaction with F-box proteins such as Cdc4p, Pop 1, Pop 2, Grr1p, Met30p, HOS, beta TrCP, Pop 1, Pop 2 or FWD1 are identified and used. These inhibitors of F-box protein/target protein and F-box protein/SCF complex interaction can be dominant negative forms of F-box polypeptides or peptidomimetic or other small molecule inhibitors of the SCF/F-box protein interaction.

In a preferred embodiment, the method comprises introducing into a host cell a chimeric polypeptide which is capable of triggering the degradation of a target polypeptide. In an even more preferred embodiment, the chimeric polypeptide recruits the target polypeptide into an E3 ubiquitin-protein ligase complex, such that the target polypeptide is ubiquitinated and degraded in the target cell. The target cell can be a eukaryotic cell, such as a mammalian cell, e.g., a human cell.

The invention is based at least on the discovery that the expression in a host cell of a "chimeric" or "hybrid" polypeptide containing: (i) a domain of a substrate binding component of an E3 ubiquitin-protein ligase complex, e.g., yeast cdc4p or the human protein h-βTrCP, which domain provides a ubiquitination activity, e.g. by recruiting target proteins into an SCF ubiquitin protein ligase complex; and (ii) a domain capable of interacting with a pRB retinoblastoma target polypeptide, results in the degradation of the pRb target polypeptide in the host cell.

Accordingly, the invention provides methods and compositions for degrading any polypeptide of interest in a eukaryotic cell and can be used for treating any disease or conditions in which it is beneficial to degrade a particular polypeptide, e.g., a protein that provides for deregulated cellular proliferation

4.2. Definitions

For convenience, the meaning of certain terms and phrases employed in the specification, examples, and appended claims are provided below.

The term "agonist", as used herein, is meant to refer to an agent that mimics or upregulates (e.g. potentiates or supplements) bioactivity of the protein of interest. An agonist can be a wild-type protein or derivative thereof having at least one bioactivity of the wild-type protein. An agonist can also be a compound that upregulates expression of a gene or which increases at least one bioactivity of a protein. An agonist can also be a compound which increases the interaction of a polypeptide of interest with another molecule, e.g, a target peptide or nucleic acid.

"Antagonist" as used herein is meant to refer to an agent that downregulates (e.g. suppresses or inhibits) bioactivity of the protein of interest. An antagonist can be a compound which inhibits or decreases the interaction between a protein and another molecule, e.g., a target peptide, such as interaction between ubiquitin and its substrate. An antagonist can also be a compound that downregulates expression of the gene of interest or which reduces the amount of the wild type protein present.

The term "allele", which is used interchangeably herein with "allelic variant" refers to alternative forms of a gene or portions thereof. Alleles occupy the same locus or position on homologous chromosomes. When a subject has two identical alleles of a gene, the subject is said to be homozygous for that gene or allele. When a subject has two different alleles of a gene, the subject is said to be heterozygous for the gene. Alleles of a specific gene can differ from each other in a single nucleotide, or several nucleotides, and can include substitutions, deletions, and/or insertions of nucleotides. An allele of a gene can also be a form of a gene containing mutations.

The term "cell death" or "necrosis", is a phenomenon when cells die as a result of being killed by a toxic material, or other extrinsically imposed loss of function of a particular essential gene function.

"Biological activity" or "bioactivity" or "activity" or "biological function", which are used interchangeably, for the purposes herein means a catalytic, effector, antigenic or molecular tagging function that is directly or indirectly performed by the polypeptides of this invention (whether in its native or denatured conformation), or by any subsequence thereof.

As used herein the term "bioactive fragment of a polypeptide" refers to a fragment of a full-length polypeptide, wherein the fragment specifically agonizes (mimics) or antagonizes (inhibits) the activity of a wild-type polypeptide. The bioactive fragment preferably is a fragment capable of interacting with at least one other molecule, protein or DNA, with which a full length protein can bind.

"Cells," "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

The term "chimeric polypeptide" refers generally to a polypeptide comprising two subunits which do not occur together in the same polypeptide in nature, or at least, if present within the same polypeptide in nature, wherein the subunits do not occur in the same order in nature as in the chimeric polypeptide. When referring to the chimeric polypeptide of the invention, the term refers to a polypeptide comprising at least two functional subunits, a first functional subunit which recruits the chimeric polypeptide in an E3 ubiquitin-protein ligase complex, and a second functional subunit which binds to a target polypeptide.

The term "degrading" as used herein is meant to include "inducible degradation" and is used to refer to proteolytic degradation as may be facilitated by a component of the ubiquitin proteolytic pathway. Such an "inducible degradation" as referred to herein, is meant to describe the targeted degradation of a specific "target gene polypeptide."

A "delivery complex" shall mean a targeting means (e.g., a molecule that results in higher affinity binding of a gene, protein, polypeptide or peptide to a target cell surface and/or increased cellular or nuclear uptake by a target cell). Examples of targeting means include: sterols (e.g. cholesterol), lipids (e.g. a cationic lipid, virosome or liposome), viruses (e.g., adenovirus, adeno-associated virus, and retrovirus) or target cell specific binding agents (e.g., ligands recognized by target cell specific receptors). Preferred complexes are sufficiently stable in vivo to prevent significant uncoupling prior to internalization by the target cell. However, the complex is cleavable under appropriate conditions within the cell so that the gene, protein, polypeptide or peptide is released in a functional form.

The term "E3 complex" also referred to herein as "E3 ubiquitin protein ligase complex" and "SCF ubiquitin protein ligase complex" ("Skp1-cullin-F-box" protein complex) refers to a complex which plays a role in providing the specificity of substrate recognition for ubiquitin dependent proteolysis. Examples of E3 complexes include the SCF$^{Cdc4p}$ complex, consisting of Skp1p, Cdc53p and Cdc4p, a complex which is required for ubiquitination of Sic1p Other E3 complexes include SCF$^{Grr1p}$ and SCF$^{Met30p}$, complexes which contain the Skl1p and Cdc53p proteins, as well as the Grr1p and Met30p, respectively.

The term "E3 substrate recognition subunit," also referred to as a "target polypeptide recognition domain" refers to the polypeptide of an E3 complex which provides E3 substrate specificity. Examples of E3 substrate recognition subunits include Cdc4p, Grr1p, Met30p and h-βTrCP. E3 substrate recognition subunits typically contain an F-box.

The term "E3 ubiquitin protein ligase recruiting domain" used interchangeably with "E3 recruiting domain" refers to a domain of an E3 substrate recognition subunit which is sufficient for interacting with the other components of an E3 complex to thereby form an E3 complex. In a preferred embodiment, an E3 recruiting domain comprises an F-box and at least one WD repeat.

The terms "epitope" and "epitope tag", as used herein, are meant to refer to any of various convenient molecular markers known in the art, such as hemaglutinin or FLAG, so that the level of a polypeptide can be confirmed in a Western blot using, for example, a suitable anti-flu or anti-FLAG antibody.

The term "equivalent" is understood to include nucleotide sequences encoding functionally equivalent polypeptides of or functionally equivalent peptides having an activity of an—protein such as described herein. Equivalent nucleotide sequences will include sequences that differ by one or more nucleotide substitutions, additions or deletions, such as allelic variants; and will, therefore, include sequences that differ from the nucleotide sequence of the—gene shown in SEQ ID NOs:, due to the degeneracy of the genetic code.

As used herein, the terms "gene", "recombinant gene" and "gene construct" refer to a nucleic acid comprising an open reading frame encoding a polypeptide of the present invention, including both exon and (optionally) intron sequences.

A "recombinant gene" refers to nucleic acid encoding a polypeptide and comprising-encoding exon sequences, though it may optionally include intron sequences which are derived from, for example, a chromosomal gene or from an unrelated chromosomal gene. The term "intron" refers to a DNA sequence present in a given gene which is not translated into protein and is generally found between exons.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are identical at that position. A degree of homology or similarity or identity between nucleic acid sequences is a function of the number of identical or matching nucleotides at positions shared by the nucleic acid sequences. A degree of identity of amino acid sequences is a function of the number of identical amino acids at positions shared by the amino acid sequences. A degree of homology or similarity of amino acid sequences is a function of the number of amino acids, i.e. structurally related, at positions shared by the amino acid sequences. An "unrelated" or "non-homologous" sequence shares less than 40% identity, though preferably less than 25% identity, with one of the sequences of the present invention.

The term "interact" as used herein is meant to include detectable relationships or association (e.g. biochemical interactions) between molecules, such as interaction between protein—protein, protein-nucleic acid, nucleic acid-nucleic acid, and protein-small molecule or nucleic acid-small molecule in nature. An interaction can be direct or indirect, i.e., mediated by another molecule. Two molecules interacting directly are also referred to as binding to each other.

The term "isolated" as used herein with respect to nucleic acids, such as DNA or RNA, refers to molecules separated from other DNAs, or RNAs, respectively, that are present in the natural source of the macromolecule. For example, an isolated nucleic acid encoding one of the subject polypeptides preferably includes no more than 10 kilobases (kb) of nucleic acid sequence which naturally immediately flanks the gene in genomic DNA, more preferably no more than 5 kb of such naturally occurring flanking sequences, and most preferably less than 1.5 kb of such naturally occurring flanking sequence. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides.

The term "modulation" as used herein refers to both upregulation (i.e., activation or stimulation (e.g., by agonizing or potentiating)) and downregulation (i.e. inhibition or suppression (e.g., by antagonizing, decreasing or inhibiting)).

The term "mutated gene" refers to an allelic form of a gene, which is capable of altering the phenotype of a subject having the mutated gene relative to a subject which does not have the mutated gene. If a subject must be homozygous for this mutation to have an altered phenotype, the mutation is said to be recessive. If one copy of the mutated gene is sufficient to alter the genotype of the subject, the mutation is said to be dominant. If a subject has one copy of the mutated gene and has a phenotype that is intermediate between that of a homozygous and that of a heterozygous subject (for that gene), the mutation is said to be co-dominant.

The "non-human animals" of the invention include mammalians such as rodents, non-human primates, sheep, dog, cow, chickens, amphibians, reptiles, etc. Preferred non-human animals are selected from the rodent family including rat and mouse, most preferably mouse, though transgenic amphibians, such as members of the *Xenopus* genus, and transgenic chickens can also provide important tools for understanding and identifying agents which can affect, for example, embryogenesis and tissue formation. The term "chimeric animal" is used herein to refer to animals in which the recombinant gene is found, or in which the recombinant gene is expressed in some but not all cells of the animal. The term "tissue-specific chimeric animal" indicates that one of the recombinant genes, e.g., gene encoding a chimeric polypeptide, is present and/or expressed or disrupted in some tissues but not others.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

The term "nucleotide sequence complementary to the nucleotide sequence set forth in SEQ ID No. x" refers to the nucleotide sequence of the complementary strand of a nucleic acid strand having SEQ ID No. x. The term "complementary strand" is used herein interchangeably with the term "complement". The complement of a nucleic acid strand can be the complement of a coding strand or the complement of a non-coding strand. When referring to double stranded nucleic acids, the complement of a nucleic acid having SEQ ID No. x refers to the complementary strand of the strand having SEQ ID No. x or to any nucleic acid having the nucleotide sequence of the complementary strand of SEQ ID No. x. When referring to a single stranded nucleic acid having the nucleotide sequence SEQ ID No. x, the complement of this nucleic acid is a nucleic acid having a nucleotide sequence which is complementary to that of SEQ ID No. x. The nucleotide sequences and complementary sequences thereof are always given in the 5' to 3' direction.

The term "percent identical" refers to sequence identity between two amino acid sequences or between two nucleotide sequences. Identity can each be determined by comparing a position in each sequence which may be aligned for purposes of comparison. When an equivalent position in the compared sequences is occupied by the same base or amino acid, then the molecules are identical at that position; when the equivalent site occupied by the same or a similar amino acid residue (e.g., similar in steric and/or electronic nature), then the molecules can be referred to as homologous (similar) at that position. Expression as a percentage of homology, similarity, or identity refers to a function of the number of identical or similar amino acids at positions shared by the compared sequences. Expression as a percentage of homology, similarity, or identity refers to a function of the number of identical or similar amino acids at positions shared by the compared sequences. Various alignment algorithms and/or programs may be used, including FASTA, BLAST, or ENTREZ. FASTA and BLAST are available as a part of the GCG sequence analysis package (University of Wisconsin, Madison, Wis.), and can be used with, e.g., default settings. ENTREZ is available through the National Center for Biotechnology Information, National Library of Medicine, National Institutes of Health, Bethesda, Md. In one embodiment, the percent identity of two sequences can be determined by the GCG program with a gap weight of 1, e.g., each amino acid gap is weighted as if it were a single amino acid or nucleotide mismatch between the two sequences.

Other techniques for alignment are described in *Methods in Enzymology*, vol. 266: Computer Methods for Macromolecular Sequence Analysis (1996), ed. Doolittle, Academic Press, Inc., a division of Harcourt Brace & Co., San Diego, Calif., USA. Preferably, an alignment program that permits gaps in the sequence is utilized to align the sequences. The Smith-Waterman is one type of algorithm that permits gaps in sequence alignments. See *Meth. Mol. Biol.* 70: 173–187 (1997). Also, the GAP program using the Needleman and Wunsch alignment method can be utilized to align sequences. An alternative search strategy uses MPSRCH software, which runs on a MASPAR computer. MPSRCH uses a Smith-Waterman algorithm to score sequences on a massively parallel computer. This approach improves ability to pick up distantly related matches, and is especially tolerant of small gaps and nucleotide sequence errors. Nucleic acid-encoded amino acid sequences can be used to search both protein and DNA databases.

Databases with individual sequences are described in *Methods in Enzymology*, ed. Doolittle, supra. Databases include Genbank, EMBL, and DNA Database of Japan (DDBJ).

Preferred homologous nucleic acids have a sequence at least 70%, and more preferably 80% identical and more preferably 90% and even more preferably at least 95% identical to an nucleic acid sequence of a sequence shown in one of the sequence listings. Nucleic acids at least 90%, more preferably 95%, and most preferably at least about 98–99% identical with a nucleic sequence represented in one of the sequence listings are of course also within the scope of the invention. In preferred embodiments, the nucleic acid is mammalian. In comparing a new nucleic acid with known sequences, several alignment tools are available. Examples include PileUp, which creates a multiple sequence alignment, and is described in Feng et al., J. Mol. Evol. (1987) 25:351–360. Another method, GAP, uses the alignment method of Needleman et al., J. Mol. Biol. (1970) 48: 443–453. GAP is best suited for global alignment of sequences. A third method, BestFit, functions by inserting gaps to maximize the number of matches using the local homology.

As used herein, the term "promoter" means a DNA sequence that regulates expression of a selected DNA sequence operably linked to the promoter, and which effects expression of the selected DNA sequence in cells. The term encompasses "tissue specific" promoters, i.e. promoters, which effect expression of the selected DNA sequence only in specific cells (e.g. cells of a specific tissue). The term also covers so-called "leaky" promoters, which regulate expression of a selected DNA primarily in one tissue, but cause expression in other tissues as well. The term also encompasses non-tissue specific promoters and promoters that constitutively express or that are inducible (i.e. expression levels can be controlled).

The terms "protein", "polypeptide" and "peptide" are used interchangeably herein when referring to a gene product. The term polypeptide includes peptidomimetics.

The term "recombinant protein" refers to a polypeptide of the present invention which is produced by recombinant DNA techniques, wherein generally, DNA encoding a polypeptide is inserted into a suitable expression vector which is in turn used to transform a host cell to produce the heterologous protein. Moreover, the phrase "derived from", with respect to a recombinant gene, is meant to include within the meaning of "recombinant protein" those proteins having an amino acid sequence of a native polypeptide, or an amino acid sequence similar thereto which is generated by mutations including substitutions and deletions (including truncation) of a naturally occurring form of the polypeptide.

The term "repression" as used herein is meant to include "inducible repression" and is used to refer to transcriptional repression as by a transcriptional repressor such as a DNA binding transcriptional repressor which binds a target promoter (a "repressible" promoter) to be repressed.

"Small molecule" as used herein, is meant to refer to a composition, which has a molecular weight of less than about 5 kD and most preferably less than about 4 kD. Small molecules can be nucleic acids, peptides, polypeptides, peptidomimetics, carbohydrates, lipids or other organic (carbon containing) or inorganic molecules. Many pharmaceutical companies have extensive libraries of chemical and/or biological mixtures, often fungal, bacterial, or algal extracts, which can be screened with any of the assays of the invention, e.g., to identify compounds that modulate the interaction between two polypeptides.

As used herein, the term "specifically hybridizes" or "specifically detects" refers to the ability of a nucleic acid molecule to hybridize to at least approximately 6, 12, 20, 30, 50, 100, 150, 200, 300, 350, 400 or 425 consecutive nucleotides of a nucleic acid.

The term "target cell" refers to a cell comprising a target polypeptide, the degradation or proteolytic stabilization of which is desired.

The term "target polypeptide" refers to a polypeptide, the degradation of which is desired in a cell.

A "target polypeptide interaction domain" refers to a polypeptide or peptidomimetic that is capable of binding to a target polypeptide.

As used herein, the term "target gene" refers to the nucleic acid which encodes a gene of interest. The target gene can be an "essential" gene, required for continued cell viability whose function is to be shut-off by the method of the invention. The term "target gene" is used to refer to any cellular gene which may targeted for inhibition by proteolytic degradation of its encoded polypeptide. The target gene may be modified directly to effect controlled proteolysis (such as by the fusing the coding sequence to an E3/SCF-recruitment domain. The term "target polypeptide" is used interchangeably with the term "target gene polypeptide" and refers to the polypeptide gene product of the target gene as described above.

"Transcriptional regulatory sequence" is a generic term used throughout the specification to refer to DNA sequences, such as initiation signals, enhancers, and promoters, which induce or control transcription of protein coding sequences with which they are operably linked. In preferred embodiments, transcription of a nucleic acid encoding a chimeric polypeptide of the invention is under the control of a promoter sequence (or other transcriptional regulatory sequence) which controls the expression of the recombinant gene in a cell-type in which expression is intended.

As used herein, the term "transfection" means the introduction of a nucleic acid, e.g., via an expression vector, into a recipient cell by nucleic acid-mediated gene transfer.

As used herein, the term "transgene" means a nucleic acid sequence (encoding, e.g., a chimeric polypeptide of the invention) which has been introduced into a cell. A transgene could be partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can also be present in a cell in the form of an episome. A transgene can include one or more transcriptional regulatory sequences and any other nucleic acid, such as introns, that may be necessary for optimal expression of a selected nucleic acid.

A "transgenic animal" refers to any animal, preferably a non-human mammal, bird or an amphibian, in which one or more of the cells of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. In the typical transgenic animals described herein, the transgene causes cells to express a chimeric polypeptide or other polypeptide of interest. However, transgenic animals in which the recombinant chimeric gene is silent are also contemplated, as for example, the FLP or CRE recombinase dependent constructs. Moreover, "transgenic animal" also includes those recombinant animals in which gene disruption of one or more genes is caused by human intervention, including both recombination and antisense techniques.

The term "treating" as used herein is intended to encompass curing as well as ameliorating at least one symptom of the condition or disease.

The term "wild-type allele" refers to an allele of a gene which, when present in two copies in a subject results in a wild-type phenotype. There can be several different wild-type alleles of a specific gene, since certain nucleotide changes in a gene may not affect the phenotype of a subject having two copies of the gene with the nucleotide changes.

The term "ubiquitin" as used herein refers to an abundant 76 amino acid residue polypeptide that is found in all eukaryotic cells. The ubiquitin polypeptide is characterized by a carboxy-terminal glycine residue that is activated by ATP to a high-energy thiol-ester intermediate in a reaction catalyzed by a ubiquitin-activating enzyme (E1). The activated ubiquitin is transferred to a substrate polypeptide via an isopeptide bond between the activated carboxy-terminus of ubiquitin and the epsilon-amino group of a lysine residue(s) in the protein substrate. This transfer requires the action of ubiquitin conjugating enzymes such as E2 and, in some instances, E3 activities. The ubiquitin modified substrate is thereby altered in biological function, and, in some instances, becomes a substrate for components of the ubiquitin-dependent proteolytic machinery which includes both ubiquitin isopeptidase enzymes as well as proteolytic proteins which are subunits of the proteasome. As used herein, the term "ubiquitin" includes within its scope all known as well as unidentified eukaryotic ubiquitin homologs of vertebrate or invertebrate origin. Examples of ubiquitin polypeptides as referred to herein include the human ubiquitin polypeptide which is encoded by the human ubiquitin encoding nucleic acid sequence (GenBank Accession Numbers: U49869, X04803) as well as all equivalents. Another example of a ubiquitin polypeptide as referred to herein is murine ubiquitin which is encoded by the murine ubiquitin encoding nucleic acid sequence (GenBank Accession Number: X51730).

The term "ubiquitin conjugation machinery" as used herein refers to a group of proteins which function in the ATP-dependent activation and transfer of ubiquitin to substrate proteins. The term thus encompasses: E1 enzymes, which transform the carboxy-terminal glycine of ubiquitin into a high energy thiol intermediate by an ATP-dependent reaction; E2 enzymes (the UBC genes), which transform the E1-S~Ubiquitin activated conjugate into an E2-S~Ubiquitin intermediate which acts as a ubiquitin donor to a substrate, another ubiquitin moiety (in a poly-ubiquitination reaction), or an E3; and the E3 enzymes (or ubiquitin ligases) which facilitate the transfer of an activated ubiquitin molecule from an E2 to a substrate molecule or to another ubiquitin moiety as part of a polyubiquitin chain. The term "ubiquitin conjugation machinery", as used herein, is further meant to include all known members of these groups as well as those members which have yet to be discovered or characterized but which are sufficiently related by homology to known ubiquitin conjugation enzymes so as to allow an individual skilled in the art to readily identify it as a member of this group. The term as used herein is meant to include novel ubiquitin activating enzymes which have yet to be discovered as well as those which function in the activation and conjugation of ubiquitin-like or ubiquitin-related polypeptides to their substrates and to poly-ubiquitin-like or poly-ubiquitin-related protein chains.

The term "ubiquitin-dependent proteolytic machinery" as used herein refers to proteolytic enzymes which function in the biochemical pathways of ubiquitin, ubiquitin-like, and ubiquitin-related proteins. Such proteolytic enzymes include the ubiquitin C-terminal hydrolases, which hydrolyze the linkage between the carboxy-terminal glycine residue of ubiquitin and various adducts; ubiquitin isopeptidases, which hyrolyze the glycine76-lysine48 linkage between cross-linked ubiquitin moieties in poly-ubiquitin conjugates; as well as other enzymes which function in the removal of ubiquitin conjugates from ubiquitinated substrates (generally termed "deubiquitinating enzymes"). The aforementioned protease activities function in the removal of ubiquitin units from a ubiquitinated substrate following or during ubiquitin-dependent degradation as well as in certain proofreading functions in which free ubiquitin polypeptides are removed from incorrectly ubiquitinated proteins. The term "ubiquitin-dependent proteolytic machinery" as used herein is also meant to encompass the proteolytic subunits of the proteasome (including human proteasome subunits C2, C3, C5, C8, and C9). The term "ubiquitin-dependent proteolytic machinery" as used herein thus encompasses two classes of proteases: the deubiquitinating enzymes and the proteasome subunits. The protease functions of the proteasome subunits are not known to occur outside the context of the assembled proteasome, however independent functioning of these polypeptides has not been excluded.

The term "ubiquitin system" as referred to herein is meant to describe all of the aforementioned components of the ubiquitin biochemical pathways including ubiquitin, ubiquitin conjugation machinery, ubiquitin-dependent proteolytic machinery, or any of the substrates which these ubiquitin system components act upon.

The term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

4.3. Polypeptides and Nucleic Acids of the Present Invention

A chimeric polypeptide of the invention comprises two functional subunits. The first functional subunit comprises a polypeptide which allows the chimeric (or "hybrid) polypeptide to be targeted into the ubiquitin-dependent proteolysis pathway. This subunit is referred to generally as a "ubiquitin protein ligase polypeptide" and is also referred to herein as "E3 ubiquitin-protein ligase complex recruitment domain" or also as "E3 recruitment domain", or, more specifically as an "SCF recruitment domain" or, still more specifically, as an "F-box polypeptide" or "F-box/WD40 domain". The second functional subunit comprises a polypeptide which binds the target polypeptide and thereby recruits the target polypeptide for degradation by the ubiquitin-dependent proteolysis pathway. This second subunit is also referred to herein as the "target polypeptide interaction domain". The subunits may be derived from naturally-occurring polypeptides or may be non-naturally occurring homologs thereof.

It will be generally appreciated that, under certain circumstances, it may be advantageous to provide homologs of an E3 substrate recognition subunit and/or target polypeptide binding domain for preparing a chimeric polypeptide of the invention. For example, such homologs may be useful when, e.g., a target peptide binding domain also comprises an undesirable biological activity. Thus, a chimeric polypeptide of interest derived from non-naturally occurring homologs of one or both subunits may induce degradation of a target polypeptide with fewer side effects relative to a chimeric polypeptide in which the two functional subunits derive from naturally occurring polypeptides.

Homologs of each of the subject subunit polypeptides can be generated by mutagenesis, such as by discrete point mutation(s), or by truncation. For instance, mutation can give rise to homologs which retain substantially the same, or merely a subset, of the biological activity of the polypeptide from which it was derived. Preferred homologs for use in the invention include those which are resistant to proteolytic cleavage, as for example, due to mutations which alter enzymatic targeting of the protein. Other preferred homologs may have post-translational modifications (e.g., to alter phosphorylation pattern of protein). Modification of the structure of the subject polypeptides can be for such purposes as enhancing therapeutic or prophylactic efficacy, stability (e.g., ex vivo shelf life).

Chimeric polypeptides or subunits thereof may also be chemically modified to create derivatives by forming covalent or aggregate conjugates with other chemical moieties, such as glycosyl groups, lipids, phosphate, acetyl groups and the like. Covalent derivatives of can be prepared by linking the chemical moieties to functional groups on amino acid sidechains of the protein or at the N-terminus or at the C-terminus of the polypeptide.

Modified peptides can be produced, for instance, by amino acid substitution, deletion, or addition. The substitutional variant may be a substituted conserved amino acid or a substituted non-conserved amino acid. For example, it is reasonable to expect that an isolated replacement of a leucine with an isoleucine or valine, an aspartate with a glutamate, a threonine with a serine, or a similar replacement of an amino acid with a structurally related amino acid (i.e. isosteric and/or isoelectric mutations) will not have a major effect on the biological activity of the resulting molecule. Conservative replacements are those that take place within a family of amino acids that are related in their side chains. Genetically encoded amino acids can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur-containing=cysteine and methionine. (see, for example, Biochemistry, $2^{nd}$ ed., Ed. by L. Stryer, WH Freeman and Co.: 1981). Whether a change in the amino acid sequence of a peptide results in a functional homolog (e.g., functional in the sense that it has the specific biological activity required for the particular subunit, i.e., capability to form an E3 complex or capability to bind to a target polypeptide) can be readily determined by assessing the ability of the variant peptide to perform these biological activities, as further described herein. Polypeptides in which more than one replacement has taken place can readily be tested in the same manner.

This invention further contemplates a method for generating sets of combinatorial mutants of the subject chimeric polypeptides or functional subunits thereof, as well as truncation mutants, is especially useful for identifying potential variant sequences (e.g., homologs). Combinatorially-derived homologs can be generated to have an increased potency relative to a naturally occurring form of the protein.

In one embodiment, the variegated library of variants is generated by combinatorial mutagenesis at the nucleic acid level, and is encoded by a variegated gene library. For instance, a mixture of synthetic oligonucleotides can be enzymatically ligated into gene sequences such that the degenerate set of potential sequences are expressible as individual polypeptides, or alternatively, as a set of larger fusion proteins (e.g., for phage display) containing the set of sequences therein.

There are many ways by which such libraries of potential homologs can be generated from a degenerate oligonucleotide sequence. Chemical synthesis of a degenerate gene sequence can be carried out in an automatic DNA synthesizer, and the synthetic genes then ligated into an appropriate expression vector. The purpose of a degenerate set of genes is to provide, in one mixture, all of the sequences encoding the desired set of potential sequences. The synthesis of degenerate oligonucleotides is well known in the art (see for example, Narang, S A (1983) Tetrahedron 39:3; Itakura et al. (1981) Recombinant DNA, Proc 3$^{rd}$ Cleveland Sympos. Macromolecules, ed. A G Walton, Amsterdam: Elsevier pp 273–289; Itakura et al. (1984) Annu. Rev. Biochem. 53:323; Itakura et al. (1984) Science 198:1056; Ike et al. (1983) Nucleic Acid Res. 11:477. Such techniques have been employed in the directed evolution of other proteins (see, for example, Scott et al. (1990) Science 249:386–390; Roberts et al. (1992) PNAS 89:2429–2433; Devlin et al. (1990) Science 249: 404–406; Cwirla et al. (1990) PNAS 87: 6378–6382; as well as U.S. Pat. Nos. 5,223,409, 5,198,346, and 5,096,815).

Likewise, a library of coding sequence fragments can be provided in order to generate a variegated population of polypeptide fragments for screening and subsequent selection of bioactive (i.e., having the desired biological activity, such as the capability to form an E3 complex or the capability to bind to a target polypeptide) fragments. A variety of techniques are known in the art for generating such libraries, including chemical synthesis. In one embodiment, a library of coding sequence fragments can be generated by (i) treating a double stranded PCR fragment of a coding sequence of interest with a nuclease under conditions wherein nicking occurs only about once per molecule; (ii) denaturing the double stranded DNA; (iii) renaturing the DNA to form double stranded DNA which can include sense/antisense pairs from different nicked products; (iv) removing single stranded portions from reformed duplexes by treatment with S1 nuclease; and (v) ligating the resulting fragment library into an expression vector. By this exemplary method, an expression library can be derived which codes for N-terminal, C-terminal and internal fragments of various sizes.

A wide range of techniques are known in the art for screening gene products of combinatorial libraries made by point mutations or truncation, and for screening cDNA libraries for gene products having a certain property. Such techniques will be generally adaptable for rapid screening of the gene libraries generated by the combinatorial mutagenesis of homologs of chimeric polypeptides or subunits thereof. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate sequences created by combinatorial mutagenesis techniques.

Combinatorial mutagenesis has a potential to generate very large libraries of mutant proteins, e.g., in the order of $10^{26}$ molecules. Combinatorial libraries of this size may be technically challenging to screen even with high throughput screening assays. To overcome this problem, a new technique has been developed recently, recursive ensemble mutagenesis (REM), which allows one to avoid the very high proportion of non-functional proteins in a random library and simply enhances the frequency of functional proteins, thus decreasing the complexity required to achieve a useful sampling of sequence space. REM is an algorithm which enhances the frequency of functional mutants in a library when an appropriate selection or screening method is employed (Arkin and Yourvan, 1992, PNAS USA 89:7811–7815; Yourvan et al., 1992, Parallel Problem Solving from Nature, 2., In Maenner and Manderick, eds., Elsevir Publishing Co., Amsterdam, pp. 401–410; Delgrave et al., 1993, Protein Engineering 6(3):327–331).

The invention provides for the isolation of additional nucleic acids of the invention by means of cross-hybridization with at least one nucleic acid provided by the invention. For example, high and low stringency methodologies as described in Sanbrook et al. (1989) Molecular Cloning; Cold Spring Harbor Press) are generally useful for isolating nucleic acids which encode polypeptides for use in the instant invention, e.g. ubiquitin protein ligase encoding nucleic acids. For example, related nucleic acids can be obtained by screening a genomic or cDNA library by stringent hybridization methodology. Appropriate stringency conditions which promote DNA hybridization, for example, 6.0× sodium chloride/sodium citrate (SSC) at about 45° C., followed by a wash of 2.0×SSC at 50° C., are known to those skilled in the art or can be found in *Current Protocols in Molecular Biology*, John Wiley & Sons, N.Y. (1989), 6.3.1–6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C.

The invention also provides for reduction of the chimeric polypeptides or subunits thereof to generate mimetics, e.g., peptide or non-peptide agents, such as small molecules, which are able to trigger ubiquitination and degradation of a target polypeptide. Thus, such mutagenic techniques as described above are also useful to map the determinants of the functional proteins which participate in protein—protein interactions involved in, for example, binding of the subject target binding domain to a target peptide.

4.4. Ubiquitin Protein Ligase/E3 Recruitment Polypeptides

In a preferred embodiment, the first functional unit, i.e., the E3 recruiting domain", of the chimeric protein is derived from a polypeptide component of an E3 ubiquitin-protein ligase complex. In a even more preferred embodiment, the first functional subunit of the chimeric protein is from a component of the complex which interacts with the substrate to be degraded, e.g., the cdc4p, Grr1p, Met30p, h-βTrCP subunits and homologs thereof. Accordingly, in an illustrative embodiment, the first functional subunit of a chimeric protein of the invention is a domain of a substrate recognition component of an E3 ubiquitin-protein ligase complex, which domain is sufficient for recruiting the component into the complex. This domain is also referred to herein as "E3 substrate recognition domain".

In a preferred embodiment, the first functional subunit of the chimeric polypeptide of the invention comprises an F-box or portion thereof sufficient for interaction with at least one other E3 component. In an exemplary embodiment, the first functional subunit comprises at least the F-box from the human protein h-βTrCP (corresponding to the polypeptide of SEQ ID NO: 4 which is encoded by the nucleic acid of SEQ ID No. 3), or homolog thereof or a portion thereof. This human protein is further described in Margottin et al. (1998) *Mol. Cell* 1: 565 and can be found in GenBank (Accession No. Y14153). The F-box of this protein corresponds to amino acid 148–192 (SEQ ID NO: 49, which is encoded by SEQ ID NO: 48) of the sequence shown in Margottin et al., supra, or SEQ ID No. 4. Another preferred first functional subunit comprises a polypeptide or homolog or portion thereof selected from the group consisting of Cdc4p, Grr1p, and Met30p. Yet other F-box containing proteins of which the F-box can be included in a chimeric polypeptide of the invention include Cyclin F; Skp2p; Pop1; C02F5.7; F48E8.7; MD6; YJL149w; N0376; 9934.4; 8039.5; N1161; SconB; Scon-2; fim; UFO; C02F5.7; C14B1.3; C17C3.6; C26E6.5; F43C9/1; F48E8.7; K10B2.1; T01E8.4; ZK328.7; Ro3D7; MD6; p110SIII; E3012.9K; and _TrCP (see, e.g., Margottin et al., supra; Bai et al. (1996) *Cell* 86:263; Kominami et al. (1997), *Genes Dev.* 11: 1548; Li et al. (1997) *EMBO J.* 16:5629). The amino acid sequence of WD repeats of the *S. cerevisiae* Met30p, *Neurospora crassa* Scon2p and the *Xenopus levi* proteins can be found in Margollis et al., supra. Yet other F-box proteins from which portions can be used in the invention include any of the F-box containing proteins described in Bai et al., supra, or F-box containing proteins that have not been isolated yet. Such proteins can be isolated based on the sequence homology between the F-boxes, using methods known in the art and further described herein, e.g., PCR. An alignment of the F-boxes indicates the position of conserved residues (see, e.g., Bai et al., supra).

In another preferred embodiment, the first functional subunit comprises at least one WD repeat, or at least a portion thereof sufficient for interaction with at least one other E3 component. The E3 recruiting domain may also contain at least two, at least three, at least four, at least five, at least six or any higher number of WD repeats from an E3 substrate binding component. For example, a Cdc4 polypeptide which lacks the three C-terminal WD repeats out of the seven WD repeats present in the protein, is capable of forming an E3 complex (Skowyra et al. (1997) *Cell* 91:209). The number of WD repeats that must be included in a chimeric protein of the invention, as well as which portion of the repeats must be included, can be determined as described in Skowyra or as further described herein). Preferred WD repeats for use in the invention are included in the h-βTrCP protein having SEQ ID No. 4. As described in Margollin et al., supra, the first WD repeat corresponds to amino acids 260–293, the second WD repeat corresponds to amino acids 305–333, the third WD repeat corresponds to amino acids 345–373, the fourth WD repeat corresponds to amino acids 388–416; the fifth WD repeat corresponds to amino acids 428–456, the sixth WD repeat corresponds to amino acids 468–497; and the seventh WD repeat corresponds to amino acids 518–546 of the amino acid sequence of the h-βTrCP protein. The amino acid sequence of WD repeats of the *S. cerevisiae* Met30p, *Neurospora crassa* Scon2p and the *Xenopus levi* proteins can also be found in Margollis et al., supra.

In an even more preferred embodiment, the first functional subunit comprises both an F-box and at least one WD repeat, or portions thereof, sufficient for recruitment into an E3 ubiquitin-protein ligase complex.

The portion of a substrate recognition component of an E3 ubiquitin-protein ligase complex that is necessary and sufficient for recruitment into the E3 ubiquitin-protein ligase complex can be determined by several methods well known in the art which do not require undue experimentations For example, portions of E3 substrate recognition components can be contacted with at least one other component of an E3 ubiquitin-protein ligase complex and their level of interaction can be determined and compared to that of the wild-type substrate recognition component (as described, e.g, in Margottin et al.) The in vitro assay can be performed with purified, semipurified proteins, proteins expressed in a reticulocyte lysate, or expressed in a prokaryotic or eukaryotic expression system. Other assays that can be used include cellular assays, in which a portion of a substrate recognition unit, e.g., h-βTrCP, is expressed in a cell in the form of a fusion protein by being fused to a "marker protein" (e.g., by transfection into the cell of an expression construct encoding the fusion protein). The half-life of the fusion protein in the cell is then determined. A longer half-life of the fusion protein, relative to a fusion protein comprising an essentially full-length h-βTrCP fused to the marker protein, indicates that the portion of h-βTrCP is not sufficient for recruitment into an E3 ubiquitin-protein ligase complex. These and other assays are further described herein, in particular in the experimental section.

Homologs of known substrate recognition subunits can be identified using methods known in the art. For example, homologs can be cloned by hybridization at moderate or high stringency. Homologs can also be cloned by PCR using a low annealing temperature of the primers, allowing for hybridization of the primers to nucleic acids allowing for mismatches.

It is likely that substrate binding components of E3 complexes are localized in different cellular compartments. In this case, it may be advantageous for practicing the method of the invention, to use an E3 recruiting domain from an E3 substrate binding component that is naturally localized in the same cellular compartment as the target protein. Some E3 substrate recognition components are also capable of acting in several compartments. For example, h-βTrCP is able to target both cytoplasmic (e.g., CD4, as described in the Examples), as well as nuclear (e.g., pRb, as described in the Examples) proteins for degradation by the ubiquitin proteolytic pathway. Alternatively, it is possible to modify an E3 recruiting domain or the chimeric polypeptide itself to target it to the same cellular compartment as that in which the target polypeptide is located. For example, a nuclear localization signal can be added to a chimeric polypeptide. A chimeric polypeptide can also be targeted to a specific cellular compartment by deleting certain cellular localization sequences that might be present in either or both of the E3 recruiting subunit or the target polypeptide binding subunit of the chimeric polypeptide. Cellular localization sequences are well known in the art and can be identified in a polypeptide by, e.g., using computer programs. Cellular localization sequences which can be added to a particular polypeptide to alter the cellular localization of the polypeptide are also known in the art. Cellular localization sequences are typically short polypeptides.

Alternatively, new E3 substrate recognition components can be identified, such as by assays allowing for the isolation of proteins interacting with other known components of E3 complexes. For example, two hybrid assays or phage display techniques can be used to isolate such polypeptides (these techniques are further described below).

4.5. Target Polypeptide Interaction Domains

The second functional subunit of the chimeric protein of the invention is a domain allowing the recruitment of a target polypeptide to an E3 complex in a cell, to thereby degrade the target polypeptide by the ubiquitin proteolytic pathway. Accordingly, the only requirement for the second functional subunit is that is binds to the target polypeptide with sufficient affinity that it recruits the target polypeptide into an E3 complex and thereby causes the target polypeptide to be degraded.

The target polypeptide interaction domain can be, for example, a portion of a polypeptide that is known to interact with the desired target polypeptide, or it can be a natural or synthetic polypeptide that has been identified by its ability to interact with the desired target polypeptide.

Methods for identifying polypeptides that interact with a specific target polypeptide include yeast and mammalian two hybrid assays, as well as phage display methods. These methods present the advantage that the nucleic acid encoding the interacting peptides is simultaneously identified, as opposed to other methods.

Yeast two-hybrid systems may be used to screen a mammalian (typically human) cDNA expression library, wherein a cDNA is fused to a GAL4 DNA binding domain or activator domain, and a nucleic acid encoding a polypeptide of interest, such as a target polypeptide, is fused to a GAL4 activator domain or DNA binding domain, respectively. Such a yeast two-hybrid system can screen for cDNAs encoding proteins which bind to polypeptides of interest. For example, a cDNA library can be produced from mRNA from a cell line that expresses the target polypeptide. Such a cDNA library cloned in a yeast two-hybrid expression system (Chien et al. (1991) *Proc. Natl. Acad. Sci.* (*U.S.A*) 88: 9578 or *Cell* 72: 233) can be used to identify cDNAs which encode proteins that interact with the target polypeptide and thereby produce expression of the GAL4-dependent reporter gene.

Polypeptides which interact with the target polypeptide can also be identified by immunoprecipitation of target polypeptide with antibody and identification of co-precipitating species. Further, polypeptides that bind the target polypeptide can be identified by screening a peptide library (e.g., a bacteriophage peptide display library, a spatially defined VLSIPS peptide array, and the like) with a NF-AT$_c$ polypeptide. Accessory proteins may also be identified by cross-linking in vivo with bifunctional cross-linking reagents (e.g., dimethylsuberimidate, glutaraldehyde, etc.) and subsequent isolation of cross-linked products that include a target polypeptide. For a general discussion of cross-linking, see Kunkel et al. (1981) *Mol. Cell. Biochem.* 34: 3, which is incorporated herein by reference. Preferably, the bifunctional cross-linking reagent will produce cross-links which may be reversed under specific conditions after isolation of the cross-linked complex so as to facilitate isolation of the target polypeptide binding protein from the target polypeptide. Isolation of cross-linked complexes that include a target polypeptide is preferably accomplished by binding an antibody that binds a target polypeptide with an affinity of at least $1 \times 10^7$ M$^{-1}$ to a population of cross-linked complexes and recovering only those complexes that bind to the antibody with an affinity of at least $1 \times 10^7$ M$^{-1}$. Identification of polypeptides that are cross-linked to the target polypeptide will then allow the newly identified polypeptides to be used as target polypeptide binding domains in the method of the invention.

The method of the invention includes various methods for isolating a target polypeptide interaction domain with any selected target polypeptide by using techniques which are known in the art. Such techniques include the yeast two-hybrid interaction trap and related methods, yeast cytoplasmic two-hybrid methods, mammalian two-hybrid methods, Far Western protocol methods, phage display technology-based methods, protein trap plus nucleic acid "snag" methods, surface plasmon resonance-based biomolecular interaction analysis methods, and polypeptide matrix display technologies. Preferred embodiments of the method, including yeast and mammalian two-hybrid, protein snag, Far Western and phage display technologies, have the distinct advantage of providing for both the rapid identification of a target polypeptide and the facile isolation of a corresponding a target polypeptide-encoding nucleic acid. Some of the embodiments of the ubiquitin trap method are summarized below in Table 1. As this table illustrates, each embodiment of the ubiquitin trap method employs distinct preferred forms of the TAG molecule, which is operably linked to the a target polypeptide, and the optional molecular marker which is operably attached to the a target polypeptide.

As summarized in Table I these general methods of cloning interacting proteins by virtue of their affinity for a target protein are all understood to be aspects of the immediate invention.

TABLE I

| METHOD | TAG molecule- [target poplypeptide] | Marker molecule- [target interaction domain] | Reference |
| --- | --- | --- | --- |
| 1. Yeast Two-Hybrid or Interaction Trap | GAL 4 or lex A Polypeptide [DNA Binding Domains] | B42, VP16, or GAL4 Polypeptide [Transcriptional Activation Domains] | (Gyuris et al. (1993) Cell 75: 791–803) & (Fields et al. (1994) Trends in Gen. 10: 286–92) |
| 2. Yeast Cytoplasmic Two-Hybrid [SRS, SOS Recruitment System] | Src Polypeptide [myristoylation signal] | hSos Polypeptide [GEF, mammalian guanyl nucleotide exchange factor] | (Aronheim et al. (1997) Mol. Cell. Biol. 17: 3094–3102) |
| 3. Mammalian Two-Hybrid or Interaction Trap | GAL 4 or lex A Polypeptide [DNA Binding Domains] | VP16 Polypeptide [herpes simplex virus transcriptional activator] | (Luo et al. (1997) BioTechniq. 22: 350–2) |
| 4. Far-Western [related to Western except detection is by interaction with a protein other than an antibody] | Radioactive atoms, Epitope Tags, Affinity Tags [e.g. $^{35}$S-met, $^{32}$P, or $^{125}$I; HA or FLAG; or biotin or polyHis] | None, or Expression Vector Fusion Polypeptide | (see e.g. Bonardi, et al. (1995) Bioch. Biophys. Res. Comm. 206: 260–5) |
| 5. Phage Display | Affinity Tags [e.g. biotin, polyHIS to facilitate immobilization to a solid support matrix] | bacteriophage coat protein [e.g. filamentous phage gIII or gVIII coat protein] | (see e.g. Smith (1985) Science 228: 1315–17 & Johnson et al. (1993) Curr. Opin. Struc. Bio. 3: 564) |

TABLE I-continued

| METHOD | TAG molecule- [target poplypeptide] | Marker molecule- [target interaction domain] | Reference |
| --- | --- | --- | --- |
| 6. Protein Trap + Nucleic Acid Snag [Affymax Peptide Library & Screening Method] | Affinity Tags [e.g. biotin, polyHIS to facilitate immobilization to a solid support matrix] | lac repressor protein [lacI; with lac operator incorporated into the expression vector] | (U.S. Pat. Nos. 5,270,170; 5,338,665; & 5,498,530) |
| 7. Biomolecular Interaction Analysis [e.g. Pharmacia BIAcore surface plasmon resonance detection] | Affinity Tags [e.g. polyHIS to directly link to a Ni-based chip or a DNA binding domain to link to a detection chip via a DNA oligo] | None, Affinity Tag [isolated proteins may be used w/o prior modification; method of producing protein may, in some instances introduce an affinity purification tag] | (see e.g. Fivash et al. (1998) Curr. Opin. Biotechnol. 9: 97–101 & Schuck (1997) Annu. Re. Biophys. Biomol. Struct. 26: 541–66) |
| 8. Peptide Matrix Arrays [e.g. Affymax combinatorial peptide matrix arrays] | None; or modified to support detection [e.g. fluorsescently tagged] | Solid Support Matrix [in situ synthesis of random polypeptides an associated identification tag address] | (e.g. U.S. Pat. Nos. 5,653,939; 5,679,773; 5,690,894; 5,708,153; & 5,744,305) |

The various embodiments of the various target polypeptide interaction domain isolation methods as summarized in Table I and discussed in general above, are described in detail below.

In a preferred method, a target polypeptide interaction domain is obtained using the yeast "two-hybrid" or "interaction trap" method. Specific protein—protein interactions are essential to the function of important cellular processes. The yeast two-hybrid or interaction trap assay has been developed as a means of detecting specific protein—protein interactions thereby allowing for the assessment of such interactions between known components of a biochemical pathway or macromolecular assemblage as well as allowing for the cloning of novel components of such pathways and assemblages. One aspect of the present invention pertains to the use of target polypeptide to clone other target polypeptide system proteins including proteins of the target polypeptide conjugation machinery and proteins of the target polypeptide proteolytic machinery as well as the substrates thereof. In a preferred embodiment of the invention, mammalian target polypeptide is used as the "bait" in a two hybrid or interaction trap cloning procedure. Briefly, the yeast two-hybrid assay relies upon the detection of a transcriptional activation signal delivered to a reporter gene. This transcriptional activation signal is generated by the reconstitution of a reporter gene-specific transcriptional activator from covalently separate DNA binding and transcriptional activation domains via a specific protein—protein interaction. The yeast two-hybrid assay has been applied to the analysis of a number of important cellular processes, including the proteins responsible for the regulation of the cell cycle (see e.g. U.S. Pat. Nos. 5,580,736 & 5,695,941 (Brent)) and proteins involved in a macromolecular complex which controls the binding of transcriptional activators to chromatin (see e.g. the Example section of U.S. Pat. No. 5,667,973 (Fields and Song)).

Two-hybrid or Interaction trap systems are based on the finding that most eukaryotic transcription activators are modular and can be divided into two distinct domains, a DNA binding domains and a transcriptional activation domain. Furthermore, it has been shown that the DNA binding domain does not have to be covalently linked to the activation domain, so long as the two separate polypeptides interact with one another, for the complex to function as a transcriptional activator, (Ma et al. (1988) *Cell* 55:443–446).

The interaction trap system relies upon this fact to clone proteins which interact with one another by virtue of their ability to noncovalently reconstitute a transcriptional activator when they are independently fused to the two distinct domains of a "third party" synthetic transcriptional activator. In particular, the method makes use of two chimeric genes which independently express a DNA binding domain hybrid protein and a transcriptional activation domain hybrid protein.

To illustrate, a first hybrid gene comprises the coding sequence for a DNA-binding protein, such as the bacterial repressor protein lexA, fused in frame to the coding sequence for a target polypeptide polypeptide, such as the polypeptide target polypeptide itself as a particular example of the method. The second hybrid gene comprises the coding sequence for a transcriptional activation domain, such as the transcriptional activator sequence B42 (Ma and Ptashne (1987) *Cell* 51:113–119), fused in frame to a sample gene from a cDNA library which encodes a selection of test polypeptides representing various target polypeptide interaction domain candidates. The target polypeptide of the first hybrid gene is commonly referred to as the "bait" while the polypeptide product of the sample gene component of the second hybrid gene is commonly referred to as the "prey". The first hybrid gene can also be thought of as expressing a specific form of the "target polypeptide trap" of the present invention as it generally conforms to the above stated definition of a target polypeptide trap (ie. target polypeptide-TAG, wherein the target polypeptide moiety is target polypeptide and the TAG entity is the lexA DNA binding domain). Both the first hybrid gene and the second hybrid gene are expressed simultaneously in a yeast cell. If the bait and prey hybrid proteins are able to interact, e.g., form a target polypeptide/target polypeptide-interacting protein complex, they bring into close proximity the lexA DNA binding domain and the B42 synthetic activation domain, thereby reconstituting a transcriptional activator protein with the DNA recognition specificity of lexA. A third hybrid gene contained in the same yeast cell is then used to detect the presence of this "noncovalently" reconstituted transcriptional activator. The third hybrid gene comprises a reporter gene which is operably linked to a DNA sequence comprising a binding site for the DNA-binding domain of the first hybrid gene, in this case the lexA operator. The "noncovalently" formed transcriptional activator (in this case lexA//

B42) recognizes this lexA DNA binding sequence linked to the reporter and causes the expression of this third hybrid reporter gene which can be detected and used to score for the interaction of the GLC1A and sample proteins.

In a preferred embodiment of the invention, two or more reporter genes, each operably linked to the same DNA binding recognition sequence, are present in the same yeast cell in the presence of the first and second hybrid genes. As an example, one of the reporters could encode an easily assayed heterologous enzyme activity, such as the bacterial lacZ gene which encodes a beta-galactosidase enzyme activity capable of being detected and measured using a chromogenic substrate such as X-gal which is converted to a blue chromophore in the presence of beta-galactosidase enzyme activity. Further, the same cell could contain a second reporter gene comprising the coding sequence for the yeast LEU2 gene. The same haploid yeast cell would also preferably contain a deleted or otherwise mutant allele of the naturally occurring chromosomal copy of the LEU2 gene, thereby making growth on leucine deficient media solely dependent upon expression of the LEU2 hybrid reporter gene. If the product of a first hybrid gene, lexA-target polypeptide for example, interacts with the product of a second hybrid gene, the synthetic activator B42 fused to a target polypeptide conjugating enzyme (UBC or E2activity) for example, then the resulting reconstituted third party transcriptional activator lexA//B42, would bind to and activate both of the third hybrid gene reporters resulting in both the complementation of this yeast strain's leucine auxotrophic phenotype, due to activation of the LEU2 reporter, and blue colony color on X-GAL containing media, due to activation of the LacZ reporter.

In another embodiment of this two hybrid or interaction trap screen, one of the two third hybrid gene reporters is the yeast HIS3 gene and the haploid yeast cell also contains a deleted or otherwise mutant allele of the naturally occurring chromosomal copy of the HIS3 gene, thereby making growth on histidine deficient media solely dependent upon expression of the HIS3 hybrid reporter gene. In this instance, the protocol can be adapted for use either with first hybrid genes which otherwise independently (i.e. cryptically) weakly activate transcription on their own in the absence of the second hybrid gene product or in the specific identification and isolation of proteins that interact with the product of the first hybrid gene to such a degree that the resulting expression of the third hybrid gene reporters is of a sufficient strength so as to surpass a predetermined threshold. These applications are made possible by the addition of Aminotriazole (3-amino-1,2,4-triazole or 3-ATZ) to the media used in the screen. 3-Aminotriazole is a competitive inhibitor of the histidine anabolic enzyme activity encoded by the *Saccharomyces cerevisiae* HIS3 gene product (see e.g. Erickson and Hannig (1995) Yeast 11: 157–67). The addition of 3-ATZ to media lacking histidine results in a condition where the abovementioned yeast strain must evince sufficiently strong interaction between the first and second hybrid gene products so as to create a sufficiently high steady state level of the reconstituted third party transcriptional activator, thereby stimulating HIS3 reporter expression sufficiently so as to overcome the competitive inhibition of the HIS3 gene product by 6-ATZ. As stated above, this technique is also adaptable to instances wherein the abovementioned target polypeptide-TAG first hybrid gene product is sufficient to cause activation of the third hybrid gene reporters on its own, in the absence of a second hybrid or "prey" gene product. In this instance where the "bait" is found to cryptically activate transcription on its own, or is known to function naturally as a transcriptional activator, 3-ATZ can be added to suitable media lacking histidine until the appropriate level of 3-ATZ sufficient to block the level of activity of the product of the HIS3 reporter expressed in the presence of the first hybrid gene alone. This level of 3-ATZ can then be added to the media on which the two hybrid screen is performed so that complementation for growth on histidine deficient media now depends upon the higher levels of expression of the HIS 3 reporter obtained when the product of the first hybrid gene interacts with the product of the second hybrid gene as compared to the level of expression obtained from the HIS 3 reporter in the presence of the first hybrid gene alone.

In other embodiments of this two hybrid or interaction trap version of the target polypeptide trap method, any of a number of the elements of the system can be modified. For example, Fields and his coworkers (see e.g. U.S. Pat. No. 5,667,973) devised one version of the interaction trap in which the DNA binding entity of the first hybrid gene product is the DNA binding domain of the yeast transcriptional activator GAL4, but can otherwise be the DNA binding domain of any transcriptional activator having separate DNA-binding and transcriptional activation domains such as those of the yeast GCN4 and ADR1 proteins, and the transcriptional activation domain of the second hybrid gene product is the GAL4 transcriptional activation domain. In this case, a yeast strain which is null or deficient for its normal chromosomal copy of the GAL4 gene and which contains first and second hybrid gene clones encoding bait and prey products that interact, can be selected for directly on media containing galactose as the sole carbon source because the reconstituted third party transcriptional activator (GAL4 DNA BIND//GAL4 TSX ACT) will drive expression of the necessary galactose catabolic enzyme activities including the products of the GAL1 and GAL10 genes. If the same yeast strain also contains a GAL1-lacZ third hybrid gene reporter, then these same transformants can also be screened for blue color on X-gal/galactose media where the intensity of blue color detected will be directly related to the strength of the interaction between the products of the first and the second hybrid gene. In some instances, it may be preferable that the yeast contain another hybrid gene, such as GAL1-HIS3, in which the GAL1 transcriptional regulatory sequences are fused to the structural gene of HIS3. This third hybrid gene allows for direct selection of target polypeptide-interacting target polypeptide interaction domain prey second hybrid genes by growing the yeast strain on galactose media in the absence of exogenous histidine. In this particular example, the use of 3-ATZ in the growth media, as described above, can be applied in situations where the first hybrid gene alone serves as a weak transcriptional activator or where only very strong target polypeptide-interacting target polypeptide interaction domains are desired.

The method of the present invention allows for the use of any of a number of different reporter genes whose expression is driven by the physical association of the first and second hybrid genes. The choice of reporter gene will depend upon the particular circumstances such as the ease of selection or assay of such genes. Such genes include, without limitation, lacZ, amino acid biosynthetic genes (e.g. the yeast LEU2, HIS3, TRP1, or URA3 genes, nucleic acid biosynthetic genes, the mammalian chloramphenicol acetyltransferase (CAT) gene or GUS gene, or any surface antigen gene for which specific antibodies are available. Reporter genes may encode any enzyme that provides a phenotypic marker, for example, a protein that is necessary for cell growth or a toxic protein leading to cell death, or one encoding a protein detectable by color assay or one whose expression leads to an absence of color. Particularly preferred reporter genes are those encoding fluorescent markers, such as the GFP gene (Green Fluorescent Protein gene and variants thereof). Reporter genes may facilitate either a selection or a screen for reporter gene expression, and quantitative differences in reporter gene expression may be measured as an indication of interaction affinities.

It is understood that the method of the present invention allows for the use of any of a number of DNA binding domains in the construction of the first hybrid gene. Thus, in addition to lexA and GAL4 DNA binding domains, other DNA binding domains that are well known in the art include the DNA binding portions of the proteins ACE1, (CUP1), lambda cI, lac repressor, jun, fos, or GCN4. The method provides for the use of these alternative DNA binding domains by way of additionally altering the third hybrid or reporter gene construct (or constructs) such that it contains a fragment of DNA encompassing the binding site of the alternative DNA binding domain, and wherein said binding site is operably linked to the reporter gene(s).

The molecular marker of the test polypeptide is meant to facilitate identification of a target polypeptide interaction domain and isolation of its encoding nucleic acid. In the yeast two-hybrid embodiment of the target polypeptide trap invention, the molecular marker is typically a transcriptional activation domain which functions in yeast and which is a component of the second hybrid gene. It is understood that the second hybrid gene of the present invention can encode any of a number of alternative transcriptional activation domains including the GAL4 transcriptional activation domain region II, the strong transcriptional activator VP16, the weak synthetic transcriptional activators B17 and B112, or the amphipathic helix domain described in Giniger and Ptashne ((1987) Nature 330:670). Modifications of the transcriptional activation can be particularly useful when attempting to either increase or decrease the sensitivity of the target polypeptide trap screen. In the method of the present invention the second hybrid gene may further contain, in addition to a transcriptional activation domain, an optional nuclear localization sequence, such as that of the SV40 Large T antigen encoded by the amino acid sequence PPKKKRKVA (SEQ ID No. 13), which allows for the requisite partitioning of the product of the second hybrid gene in cases where the prey moiety is normally exclusively cytoplasmic. The second hybrid gene may additionally contain an epitope tag, such as hemaglutinin or FLAG, so that production of full length second hybrid gene prey products can be confirmed in a Western blot. Furthermore, as explained below, the prey epitope tag provides a convenient means of testing for covalent linkage of the bait and prey moieties as is anticipated in some applications of the method of this invention. This determination is conveniently made by means of a Western blot analysis and provides a biochemical means of classifying the clones obtained from a target polypeptide trap screen.

It is further understood that in the method of the present invention the nature of the sample gene cDNA used in constructing the second hybrid gene can be tailored to various applications of the target polypeptide trap cloning method. In particular, cDNAs may be constructed from any mRNA population and inserted into an equivalent vector for the expression of the second hybrid gene. Such a library of choice may be constructed de novo using commercially available kits (e.g., from Stratagene, LaJolla, Calif.) or using well established preparative methods. Alternatively, a number of cDNA libraries (from a number of different organisms) are publicly and commercially available; sources of libraries include, e.g. Clontech (Palo Alto, Calif.) and Stratagene (La Jolla, Calif.) as well as publicly available libraries such as those described and summarized on the internet (see www.fccc.edu/research/labs/golemis/IT_libraries.html).

It is worth noting that many commercially available yeast two-hybrid systems have been created, many of which have particular advantages and all of which are understood to be adaptable to, and therefore aspects of, the present invention. For example, the Invitrogen (Carlsbad, Calif.) Hybrid Hunter™ System makes use of the drug Zeocin and a drug resistance marker ($Zeo^R$) to maintain selection for the first hybrid gene encoding vector. This modification of the method allows greater compatibility with other yeast two-hybrid libraries (i.e. prey or second hybrid gene encoding vector systems) as well freeing a useful selectable prototrophy marker for use in modifications of the standard two hybrid protocol. Such modifications of the standard two hybrid protocol may involve, for example, the introduction of a library of test polypeptides to identify proteins capable of potentiating a target polypeptide interaction with another protein it would not normally directly interact with (see e.g. the "three hybrid" system described in SenGupta et al. (1996) Proc. Natl. Acad. Sci. USA 93: 8496–8501). This modification of the system may be useful in identifying polypeptide agonists of the target polypeptide system. Alternatively, a library of test polypeptides may be introduced into a yeast strain already expressing a target polypeptide/target polypeptide interaction domain first hybrid gene/second hybrid gene interaction pair and polypeptides capable of disrupting this interaction may be selected (see e.g. the "split hybrid" system described in Shih et al. (1996) Proc. Natl. Acad. Sci. USA 93: 13896–901). This modification of the system may be useful in identifying polypeptide antagonists of the target polypeptide system. Still other methods for identifying molecular agonists and antagonists of the target polypeptide system are described in further detail in the diagnostic and therapeutic applications section. These alternative approaches to the development of therapeutic applications are herein incorporated into those sections.

It is further noted that the prey proteins do not need to be naturally occurring full-length polypeptides. For example, a prey protein may be encoded by a "domain" library of small partial cDNA sequences which can be obtained by internal priming of cDNA synthesis with random (non-polyT) primers and selection of appropriate sized partial cDNA fragments (e.g. <1 kb). Alternatively the prey entity encoded by the second hybrid gene may correspond to a synthetic sequence or may be the product of a randomly generated open reading frame or a portion thereof. This particular embodiment is also usefully employed in the development of therapeutics which modulate the activity of the target polypeptide trap moiety. This particular embodiment of the target polypeptide trap method, in which a purely synthetic target polypeptide system interacting protein is sought, is also readily adapted to the phage display and peptide matrix display embodiments of the present invention.

In still other applications of the yeast two-hybrid system, the first and second hybrid genes are independently expressed in haploid yeast strains of opposite mating type. For example, a single homogeneous strain expressing a first hybrid gene (target polypeptide-TAG) "bait" can be established by transforming a yeast strain having the appropriate two-hybrid driven (e.g. $GAL4_{OP}$ or $lexA_{op}$-driven) third hybrid gene selectable markers and/or reporters with the first hybrid gene encoding vector. A heterogeneous population of second hybrid gene expressing yeast cells is then created by means of high efficiency transformation of a second haploid yeast strain of opposite mating type. This heterogeneous population is then mated to the yeast strain of opposite mating carrying the first hybrid gene. Test polypeptides encoded by the second hybrid gene population which constitute target polypeptide-interacting target polypeptide interaction domain's can be selected for by requiring expression of the third hybrid gene selectable marker. This can be achieved by plating on the appropriate selective media. This "mass mating" protocol obviates repetition of the most difficult step (i.e. high-efficiency transformation of a yeast strain with a second hybrid gene encoding "prey" library) when performing repeated screen with different target polypeptide first hybrid gene "baits". Thus many different target polypeptide trap targets can be screened simultaneously or in rapid progression. This configuration thus facilitates many embodiments of the target polypeptide trap method—such as the use of a target polypeptide interaction domain, obtained in a first round of screening with the target polypeptide trap method, as a target polypeptide in a subsequent round of screening. This technique also facilitates the assembly of a "global grid" analysis of the entire target polypeptide system where the potential interaction of every target polypeptide system protein is tested against every other target polypeptide system protein revealing every point of interaction in the target polypeptide biochemical pathway network. Indeed, it is a goal of the yeast two-hybrid analysis of the target polypeptide system described here to develop a hierarchy of systematic matings assays. This "Global Grid" would provide a first-step functional characterization of each component as it is identified. Specific examples of this analysis are described in the Examples section of this application.

Since other eukaryotic cells use a mechanism similar to that of yeast for transcription, such cells, including mammalian cells such as HeLa, can be used instead of yeast to test for protein—protein interactions with the target polypeptide trap invention. In particular, the method of the present invention can be employed in a mammalian two-hybrid assay (Luo et al., (1997) Biotechniques 22:350–352). In this adaptation of the yeast two-hybrid system, the proteins of the first and second hybrid genes are expressed from mammalian promoters in a mammalian cell. As in the yeast nuclear two-hybrid method described above, the target polypeptide-TAG is encoded by a first hybrid gene, in which the TAG moiety is a polypeptide DNA binding domain, and a library of test polypeptides is expressed by a population of second hybrid genes comprising a collection of cDNA sequences fused to a polypeptide transcriptional activation domain. In one example of a preferred embodiment, interaction of the prey tagged with a VP16 transcriptional activation domain with a bait fused to a GAL4 DNA binding domain drives expression of reporters that direct the synthesis of Hygromycin B phosphotransferase, Chloramphenicol acetyltransferase, or CD4 cell surface antigen (Fearon et al. (1992) PNAS 89:7958–62). In another, interaction of these first and second hybrid gene products drives the synthesis of SV40 T antigen, which in turn promotes the replication of the prey plasmid, which carries an SV40 origin (Vasavada et al. (1991) PNAS 88:10686–90). Suitable promoters for expression of the first hybrid gene bait and the second hybrid gene prey in mammalian cells include strong viral promoters such as those from CMV and SV40 (refs.?????) or weaker cellular promoters such as that from the tk (thymidine kinase) gene. The vectors that express these hybrid gene products are cotransfected with a third hybrid gene encoding a reporter such as chloramphenicol acetyltransferase (CAT) or beta-galactosidase into a mammalian cell line. The reporter of the third hybrid gene, which contains upstream DNA binding sites specific for the DNA binding domain of the first hybrid gene, can alternatively be integrated into the mammalian genome by prior transfection, selection, and clonal isolation and characterization. If the two hybrid gene products interact, there will be a significant increase in the expression of the reporter gene which can be detected and assayed using the appropriate reagents. This technique, by using small tissue culture samples, can be adapted for use in high throughput screens. The mammalian two-hybrid has two main advantages: assay results can be obtained within 48 hours of transfection and protein interactions in mammalian cells may better mimic actual in vivo interactions, particularly in the case where the relevant interaction is dependent upon mammalian post-translational modifications (including phosphorylations and glycosylations) of the first and/or second hybrid gene product or in instances where the products of the first and second hybrid gene interact indirectly through joint contact with a third molecule (such as a protein) which is endogenous to mammalian cells but not to yeast cells.

The conventional two-hybrid system, as described above, is based on a transcriptional readout and may not be suitable for either identifying transcriptional repressors or analyzing the binding partners of a transcriptional activator. A transcriptional repressor may, for example, prevent transcriptional activation resulting from recruitment of the second hybrid gene product's polypeptide transcriptional activation domain, while a target polypeptide which functions as a transcriptional activator may mask transcriptional activation resulting from productive recruitment of a second hybrid gene's target polypeptide interaction domain-polypeptide transcriptional activation domain. A novel screen for detecting protein—protein interactions that is not based directly on the formation of a hybrid transcriptional activator has been developed by Michael Karin and his colleagues and termed the SRS or SOS recruitment system (Aronheim et al. (1997) Mol. Cell. Biol. 17:3094–3102). As summarized in Table I, in this embodiment of the target polypeptide trap, the polypeptide TAG is typically a Src derived polypeptide myristoylation signal, which when expressed in vivo is joined to a membrane lipid and directed to the cell membrane; while the target polypeptide interaction domain molecular marker is typically a guanyl nucleotide exchange factor such as mammalian hSos. This cytoplasmic two hybrid assay system involves the use of a defective ras/raf cytoplasmic signaling pathway in yeast. (White, et al. (1995) Cell 80:433–541). In this system, the mammalian guanyl nucleotide exchange factor (GEF) hSos is recruited to the plasma membrane in a *Saccharomyces cerevisiae* strain harboring a temperature-sensitive Ras GEF. At nonpermissive temperatures, the Cdc25–2 allele of Ras GEF is inactive and thus growth becomes dependent on the ability of a heterologous protein/protein interaction to facilitate recruitment of hSos to the plasma membrane, resulting in the stimulation of the Ras-dependent signaling cascade. The two hybrid genes necessary to utilize this system are analogous to the first and second hybrid genes of the yeast two-hybrid method described above, except a membrane localization signal, as opposed to a transcriptional activation signal, is reconstituted from these two components as detailed below. In the SRS system the first hybrid gene corresponds to a DNA encoding a myristoylation signal, such as that from Src, which is fused in frame to the coding sequence of a known protein of interest (or "bait"). In a preferred embodiment of the present invention, the bait is target polypeptide and the first hybrid gene is a Src myristoylation signal-target polypeptide fusion. The second hybrid gene of the SRS technique is comprised of the coding sequence for hSos fused in-frame to the coding sequence of a sample gene from a cDNA library (or "prey"). Because the interaction of bait and prey is assayed by reconstitution of a cytoplasmic signal transduction pathway necessary for growth and not a nuclear transcriptional activation activity, this embodiment is particularly well suited to the use of target polypeptide polypeptides which have transcriptional activator or transcriptional repressor properties which interfere with a conventional two-hybrid assay readout. This technique also has the advantage of avoiding problems occurring with second hybrid gene products which otherwise independently cause activation of third hybrid gene reporters. In particular, although the problem of "cryptic" activation by the bait is avoidable when using HIS3 as a reporter in the presence of aminotriazole as described above, there is otherwise no way of completely avoiding a nonspecific background of positive prey clones of a type which further test nonspecific for the original bait. Detection of an interaction of such a prey clone with the target polypeptide-TRAP product of the first hybrid gene using the cytoplasmic two hybrid detection method avoids "false negatives" from this class of proteins which appears to nonspecifically activate reporter genes when allowed to localize to the nucleus.

There exist a number of techniques, known in the art, for cloning genes from conventional lambda cDNA expression libraries (such as lambda gt11) by virtue of the ability of their encoded gene product to interact with a protein or proteins of interest. These assays are essentially modifications of a traditional "Western" protocol (see e.g. Sambrook et al. *Molecular Cloning: A Laboratory Manual* CSH Press) except a non-antibody protein is substituted for the antibody used in the detection phase of the assay. It is understood that the method of the present invention includes such screening and cloning techniques as applied to screens employing a target polypeptide trap target probe. As summarized in Table I, such "Far-Western" embodiments of the target polypeptide trap method employ radioactive atoms, epitope tags or affinity tags to serve as target polypeptide "TAG" entities, and require no specific molecular marker moiety to mark the target polypeptide interaction domain candidate polypeptides. In many cases, however, the target polypeptide interaction domain polypeptides are from phage cloning vectors (e.g. λgt11) as fusions to expression vector polypeptide-encoding sequences such as LacZ or LacZ fragments. Traditional "Far-Western" screening techniques typically employ phage lambda cDNA libraries produced from various sources of cellular mRNA, depending upon the application. These libraries are then plated at a low m.o.i. (multiplicity of infection) on a suitable bacterial host (e.g. *E. coli* XL-1 blue or BL21 (DE3) pLysE) so as to produce a high density of plaques. Typically about 1 million such plaques must be obtained for a fully representative sampling of cDNA species. The cDNA insert in such cloning vectors is typically under the control of a Lac I (Lac operon repressor) repressible promoter (e.g. that provided by the lac operator). Following the formation of lytic plaques (e.g. typically requiring incubation for 8 hours at 37 degrees Celcius (C)), nitrocellulose filters which have been pre-soaked in 10 mM IPTG are overlayed on the plates. The IPTG induces expression of the cDNA species encoded by the phage lambda under the control of the lac promoter. The resulting plates are then incubated an additional 12–16 hours at 37 degrees C., and the nitrocellulose filters are removed and blocked in 5% nonfat dry mild in TTBS (Blotto) for 2–16 hours at room temperature (r.t.) with gentle shaking. The blocked filters are then exposed to the target polypeptide trap probe.

A number of methods for labeling the material of the target polypeptide trap for use in Far-Western screening techniques exist in the art. Suitable TAGS for labeling the target polypeptide trap target molecule for use in the target polypeptide trap cloning procedure include: $^{35}$S-met, $^{32}$P, $^{125}$I, antibody epitope tags (e.g. HA, FLAG, etc.), and biotin. Some of the alternative TAGS and methods for operably linking them to a target polypeptide are described in Section 4.3 above.

In a preferred embodiment, target polypeptide is used as the probe and the target polypeptide trap probe is synthesized by in vitro transcription and translation techniques which are well known in the art and available as kits from a number of sources (e.g. Promega Biotech, Madison, Wis.). Synthesis of the target polypeptide molecule from a suitable target polypeptide encoding vector in the presence of $^{35}$S-met results in the synthesis of a $^{35}$S labeled target polypeptide probe. The blocked filters produced as described above are then incubated in the presence of the $^{35}$S labeled target polypeptide probe in fresh Blotto (typically 2 ml/150 mm filter) with gentle agitation overnight at room temperature or 4 degrees Celcius. The filters are then washed extensively with large volumes of TTBS several times to remove unbound target polypeptide probe and then dried and exposed to X-ray film overnight. Plaques which appear to be labeled by the target polypeptide probe by virtue of an affinity between the gene product encoded by the cDNA and the target polypeptide probe, are picked and subjected to several rounds of plaque purification which involves the use of the above described procedure at increasingly low plating densities so as to facilitate the removal of contaminating non target polypeptide reactive plaques.

In a preferred embodiment of this target polypeptide trap Far-Western protocol, lysates are prepared from these pure clones and phage from these are used to infect a fresh culture of *E. coli* which are then incubated in the presence of 1 mM IPTG for 2 hours at 37 degrees Celcius. The cells are then lysed in SDS loading buffer, and the resulting lysate is run on a denaturing (e.g. SDS PAGE) protein gel along with dye labelled protein markers. The gel is transferred to nitrocellulose and probed with either the $^{35}$S labeled target polypeptide probe or a negative control probe. The results of this type of Far-Western analysis thus reveal both the specificity of the interaction between the target polypeptide probe and the lambda cDNA encoded target polypeptide interaction domain protein (i.e. whether the interaction occurs only with the target polypeptide probe and not the negative control probe) and the molecular weight of the target polypeptide interaction domain. The latter information is useful in the classification of clones obtained in a target polypeptide trap screen, while the former information is necessary to determine the significance of the target polypeptide trap interaction.

The target polypeptide trap method of the invention provides for yet another configuration of the target polypeptide trap screen employing "phage display" technology. As summarized in Table I, this embodiment of the target polypeptide trap method employs an affinity tag, or other means of immobilizing a target polypeptide to a solid support matrix, as a TAG to mark the target polypeptide; and a bacteriophage coat protein, such as filamentous phage coat protein gIII, which serves as a molecular marker of the population of test polypeptides representing target polypeptide interaction domain candidates. A phage-display library is a protein expression library, constructed in a bacteriophage derived vector, that expresses a collection of cloned protein sequences as fusions with a phage coat protein. This arrangement results in the expression of fusion proteins on the exterior of the phage particle. This disposition advantageously allows contact and binding between the recombinant binding protein and an immobilized ligand. In the method of the present invention phage clones expressing binding proteins are substantially enriched for target polypeptide trap specific binding activities by means of serial passage of phage populations which bind to an immobilized target polypeptide trap target (target polypeptide-TAG) ligand.

Phage display can be performed in a variety of formats; for their review see e.g., Smith ((1985) Science 228:1315–1317) and Johnson, et al. ((1993) Current Opinion in Structural Biology 3:564). The group of almost identical E. coli filamentous phages M13, fd, and fl are most often used in phage display libraries, as either of the phage gIII or gVIII coat proteins can be used to generate fusion proteins without disrupting the ultimate packaging of the viral particle (Ladner et al. PCT publication WO 90/02909; Garrad et al., PCT publication WO 92/09690; Marks et al. (1992) J. Biol. Chem. 267:16007–16010; Griffiths et al. (1993) EMBO J 12:725–734; Clackson et al. (1991) Nature 352:624–628; and Barbas et al. (1992) PNAS 89:4457–4461). In addition, there are many U.S. patents which describe this and closely related technologies in great detail (see e.g. U.S. Pat. No. 5,571,698; U.S. Pat. No. 5,580,717; U.S. Pat. No. 5,627,024).

In brief, this procedure involves the immobilization of the target protein (the target polypeptide trap in the method of the present invention) by, e.g., treating it with a biotinylating agent which is commercially available (Promega Biotech, Madison, Wis.). Treatment under the appropriate conditions results in the introduction of 1–6 biotin moieties per molecule of target protein. The biotinylated protein (e.g. target polypeptide-biotin) can then be bound essentially irreversibly to a solid support (e.g. a polystyrene dish) that is coated with streptavidin. After blocking non-specific protein absorption sites with bovine serum albumin, the streptavidin-coated plates are treated with the biotinylated protein (e.g. the target polypeptide trap), blocked with biotin, and rinsed. Alternative affinity tag systems suitable for immobilizing the target polypeptide to a solid support matrix are described in Section 4.3. The phage library can be added to the plates which are now coated with the target protein bound to streptavidin via the biotin linker. Phage display clones which do not bind to the target polypeptide trap are then washed away under non-denaturing conditions. The remaining phage which are bound to the target polypeptide trap are eluted with an elution wash (e.g. pH 2.2 buffer). Following this initial round of selection, the "trapped" and eluted population of phage enriched for clones expressing a target polypeptide trap interacting species is then amplified by growth in a bacterial host. The entire procedure is then repeated with the resulting phage population, resulting in the further enrichment for recombinant phage expressing high-affinity target polypeptide trap interacting clones.

Just as in the two hybrid embodiment of the target polypeptide trap method, it is understood that any person of reasonable skill in the art will recognize that there are many alternative embodiments of the composition of the phage display population and the choice of the target population to be trapped will depend in part on the particular goals of the investigation. In particular the test polypeptide target polypeptide interaction domain candidates may be encoded by any of a number of natural or synthetic nucleic acid sequences, such as partial cDNA "domain" libraries or synthetic "randomized oligonucleotide" libraries, as discussed for the varied application of the yeast two-hybrid method (Section 4.3.1). For example, there are many examples of phage display libraries in which the short random polypeptides are displayed on the outer surface of the phage population. Smith and coworkers (Smith (1985) Science 228:1315–1317 and Parmley and Smith (1985) Gene 73:305–318) have demonstrated that small protein fragments (10–50 amino acids) can be displayed efficiently on the surface of filamentous phage by inserting short gene fragments into gene III of the fd phage. Such random sequences can also be created through the use of randomly synthesized oligonucleotides of an appropriate size in the creation of the phage coat protein fusion library. In several instances, such random peptide phage display libraries have been used successfully to identify small peptide inhibitors of a particular protein activity. For example, random peptide phage display libraries have been used to elucidate peptide inhibitors of Human T-Cell Leukemia Virus-I (HTLV-I) (see U.S. Pat. No. 5,717,058). Thus, in a preferred embodiment of the present invention, a target polypeptide conjugating protein or a target polypeptide isopeptidase is immobilized on a solid matrix and subjected to biopanning with a phage display library of random peptides (peptide fusion phage). After one or, more preferably, two, or, still more preferably, three or more rounds of selection for phage expressing polypeptide sequences which bind to the target polypeptide trap polypeptide, the resulting phage collection is isolated and the sequences encoding the binding polypeptides is determined by sequencing the particular oligonucleotide sequences fused to the DNA sequence of the bacteriophage coat protein. The polypeptides encoded by these sequences can then be tested for the ability to affect the activity of the target polypeptide trap conjugating or isopeptidase activity in a particular binding or enzymatic assay, many of which are known in the art.

A second application of the phage display embodiment of the target polypeptide trap method is in the creation of target polypeptide system proteins with altered binding properties. This technique has been applied, for example, in the isolation of growth hormone variants with altered binding properties (U.S. Pat. No. 5,688,666). Thus, in a preferred embodiment of the present invention, a nucleic acid sequence encoding target polypeptide or a target polypeptide-like protein is fused to the carboxyl terminal domain of M13 gene III. The resulting vector is then mutated at one or more selected positions within the sequence encoding, in a preferred example, target polypeptide by either chemical or enzymatic techniques which are well known in the art thereby forming a family of related phage display vectors. The resulting collection of the target polypeptide mutant proteins displayed in phage display format is used a first round of selection by contact the phagemid particles with a target molecule such as, in a preferred embodiment, a target polypeptide conjugating enzyme or a mutant thereof. The phagemid particles that bind are then separated from those that don't by washing, followed by elution of the specifically bound phagemids. The washing step can be adjusted to increase the stringency so that only the very highest affinity mutant polypeptides are selected. The specifically bound phagemids are then eluted using an appropriate elution buffer and the resulting selected phagemids are amplified and used in one or more additional rounds of selection (i.e.

the above steps are repeated starting at the step where the phagemid particle mix is contacted with the target polypeptide conjugating enzyme). The resulting target polypeptide mutants are potentially useful in designing therapeutic inhibitors of specific target polypeptide conjugating enzymes or discovering target polypeptide sequence variants with altered specificities (i.e. increased binding specificity for a target polypeptide conjugating enzyme or a variant thereof).

In another variation of the phage display method, immunoglobulin polypeptides are displayed on the outer surface of the phage capsid and antibody molecules specific to target polypeptide trap polypeptides are thereby identified. The preparation of combinatorial antibody libraries on phagemids is described by Kang et al., (1991) PNAS, U.S.A., 88:4363–4366; Barbas et al. (1991) PNAS, U.S.A. 88:7978–7982; Kang et al. (1991) PNAS, U.S.A. 88:11120–11123; Barbas et al. (1992) PNAS, USA, 89; 4457–4461; and Gram et al., PNAS, U.S.A. (1992) 89:3576–3580, the disclosures of which are hereby incorporated by reference. U.S. Pat. No. 5,702,892 also describes phage-display of immunoglobulin heavy chain libraries. Such immunoglobulin expressing phage display libraries are commercially available (RPAS, Pharmacia Catalog number 27-9400-01, for example).

Another aspect of the invention concerns the use of the target polypeptide trap to screen peptide and cDNA vector libraries in which the candidate target polypeptide interaction domains are expressed as fusions to a DNA binding protein from a recombinant DNA expression vector wherein the vector itself contains a binding site for the DNA binding protein of the fusion library. The screening method results in the formation of a complex comprising the fusion protein (target polypeptide interaction domain candidate fused to a DNA binding domain, e.g. lacI) bound to both: an immobilized target polypeptide trap molecule (target polypeptide-TAG) through the peptide encoded by vector target polypeptide interaction domain cDNA, and to the recombinant DNA vector through the DNA binding domain of said fusion protein. Thus affinity purification of the target polypeptide interaction domain provides a means of simultaneously identifying a target polypeptide interaction domain and isolating the target polypeptide interaction domain's encoding cDNA vector. This method allows for an "in vitro" screen since the entire procedure can be conducted with an extract obtained from a lysed population of, e.g. an E. coli strain carrying a suitable library of target polypeptide interaction domain candidate test polypeptides expressed as fusions to a DNA binding protein such as the lac repressor (product of the lacI gene). Optimal results are obtained from bacterial libraries carried by bacterial strains which do not themselves produce a lac repressor protein (e.g lacI deletion strains, which are readily available). As summarized in Table I, in this particular embodiment of the target polypeptide trap method, the TAG entity used to mark the target polypeptide is typically an affinity tag which, as in the phage display embodiment, serves to facilitate immobilization of the target polypeptide to a solid support matrix such as a petri plate or a column resin; while the molecular marker, which identifies the target polypeptide interaction domain test polypeptide, is a DNA binding polypeptide with affinity for a nucleic acid sequence present in the test-polypeptide encoding vector. Immobilization of the target polypeptide interaction domain to the immobilized target polypeptide by protein/protein interaction therefore simultaneously results in the immobilization of the target polypeptide interaction domain-encoding vector via a protein/nucleic acid "snag" interaction which facilitates the in vitro identification of target polypeptide interaction domain encoding vector clones.

This methodology has been described elsewhere in greater detail (see U.S. Pat. Nos. 5,270,170, 5,338,665, and 5,498,530, incorporated herein by reference). Briefly, the method makes use of the stable binding of a DNA binding protein, such as that of the lac operon repressor, the product of the lacI gene, to its recognition sequence in the lac operator (lacO). In a preferred embodiment, a synthetic derivative of the lacI gene consisting to two lac headpieces joined by a linker (Kaptein et al. (1990) Bioch. Pharmacol. 40:89–96) is operably linked to a DNA encoding a random polypeptide or a ligand fragment comprising a portion of a target polypeptide interaction domain-encoded gene product which possesses affinity for a target polypeptide. The vector encoding this fusion protein is constructed so as to additionally contain a lac operator sequence (lacO) or a derivative lacO binding site such as that of the symmetric variant of lacO called lacO S which has an approximately ten-fold higher affinity for repressor than the wild-type sequence (Sadler et al. (1983) Proc. Natl. Acad. Sci. USA 80:6785–9; Simons et al. (1984) Proc. Natl. Acad. Sci. USA 81:1624–8). The resultant library is transformed into a host cell such that about at least 1 million transformants are created, and the resultant transformed host cells are cultured under conditions such that the vector encoded fusion protein is produced and binds to a binding site, e.g. a lacO sequence, located in a vector that encodes the fusion protein. The resultant population of cells is then lysed under conditions such that the fusion protein remains bound to the vector that encodes the fusion protein (e.g. lysis by lysozyme in a suitable buffer such as 35 mM HEPES [pH 7.5 with KOH], 0.1 mM EDTA, 100 mM Na glutamate, 5% glycerol, 0.3 mg/ml BSA, 1 mM DTT and 0.1 mM PMSF). The long half-life of certain DNA/DNA binding protein complexes such as that of the lac repressor bound to lacO (dissociation constant of $10^{-13}$M, and a half-life of about 30 minutes) is therefore preferred in the method of the present invention. The resulting cell lysate is contacted with a target polypeptide trap (target polypeptide-TAG) molecule under conditions such that the fusion protein remains bound to the vector that encodes the fusion protein. In a preferred embodiment, the target polypeptide trap molecule is immobilized to a column matrix and the cell lysate is passed through the column under conditions which preserve both the target polypeptide/target polypeptide interaction domain-lacI interaction and the target polypeptide interaction domain-lacI/lacO interaction. In an alternative embodiment allowing smaller "batch screens" for candidate target polypeptide interaction domain molecules, the target polypeptide trap molecule is immobilized to a suitable bead matrix (e.g. agarose or sepharose) and incubated with the cell lysate so as to allow the formation of bead-target polypeptide trap/target polypeptide interaction domain-lacI/ lacO-vector DNA complexes which are then isolated by centrifugation. Nonspecifically associated lacI/lacO-vector DNA complexes are removed by washing the column or beads with a suitable wash buffer (e.g. HEG buffer containing 35 mM HEPES/KOH pH 7.5, 0.1 mM EDTA, 100 mM Na Glutamate). The specifically bound vectors encoding the target polypeptide interaction domain-lacI fusion protein, are then eluted from the column or matrix under either native conditions (e.g. using IPTG [isopropylthiogalactoside] which is known to decrease the affinity of lacI for lacO binding sites) or denaturing conditions (e.g. using phenol or SDS—containing buffers which will interfere with the target polypeptide/target polypeptide interaction domain protein—protein interaction). The nucleic acid of the eluted target polypeptide interaction domain fusion protein encoding vector is then recovered using standard techniques of extraction and precipitation which are well known in the art. If desired, the recovered target polypeptide interaction domain-encoding vector DNA can be put through an additional round(s) of selection by retransforming this eluted vector nucleic acid into a suitable host cell (e.g. the host cell strain used in the previous "round" of screening) and then repeating the steps recited above. Repeated application of this "molecular snag" technique can be expected to produce vectors which encode target polypeptide interaction domain's with increasingly strong affinities for the target polypeptide of the target polypeptide trap.

Those skilled in the art will appreciate that there are a wide variety of other DNA binding proteins, including polypeptides derived from naturally occurring DNA binding proteins, as well as polypeptides derived from proteins artificially engineered to interact with specific DNA, which can be used in the immediate application of the present invention.

Another method for studying biomolecular interactions which can be readily adapted for use in the subject invention is real-time Biomolecular Interaction Analysis (BIA). As summarized in Table I, in this embodiment of the target polypeptide trap method, the TAG entity used to mark the target polypeptide is typically an affinity tag which serves to immobilize the target polypeptide to a specialized detector surface. In this embodiment, there is no need for a molecular marker to identify the target polypeptide interaction domain, since a productive target polypeptide/target polypeptide interaction domain interaction can be directly detected through altered properties of the surface to which the target polypeptide is immobilized. In some embodiments of this method, an affinity tag molecular marker may be associated with the target polypeptide interaction domain, and may have facilitated purification of the target polypeptide interaction domain to obtain the homogeneous population of test polypeptides which is preferred in the BIA embodiment of the target polypeptide trap method.

This technique allows biospecific interactions to be studied in real time without labeling any of the interactants. Detection depends on changes in the mass concentration of macromolecules at the biospecific interface. BIA uses the optical phenomenon surface plasmon resonance to monitor biomolecular interactions. Surface plasmon resonance is an optical phenomenon arising in thin metal films under conditions of total internal refection which relies on changes in the intensity of reflected light which occur at the resonance angle. By keeping other factors constant, surface plasmon resonance provides a measure of changes in the concentration of molecules in a surface layer of solution in contact with the sensor surface. Briefly, the system is composed of three essential elements: a sensor chip, an optical detection system, and an integrated micro-fluidic cartridge (IFC) for controlled transport of samples to the sensor surface. The sensor chip is modified to the application so that one interactant is immobilized on the sensor surface (the target polypeptide), which forms one wall of a micro-flow cell. In some applications, the ligand is attached indirectly to the surface through binding to another immobilized molecule (a technique referred to as capturing). Solution containing the other interactant(s) is streamed continuously over the sensor surface by the IFC. As molecules from solution bind to the immobilized interactant, the resonance angle changes and a response is registered. Following association of the subject free interactant molecule analyte test polypeptide target polypeptide interaction domain candidate, the target polypeptide/target polypeptide interaction domain complex dissociates at a rate proportional to the dissociation constant for this reaction. Dissociation of the target polypeptide/target polypeptide interaction domain complex can be monitored in real time by monitoring the signal obtained from the sensor surface resonance angle detector. The signal level will eventually return to that measured prior to introduction of the target polypeptide interaction domain moiety when all of the target polypeptide/target polypeptide interaction domain complex has decomposed and he target polypeptide interaction domain has diffused away. Detailed descriptions of surface resonance-based detection methods for biomolecular analysis applications may be obtained from commercial suppliers of these systems such as Pharmacia (Piscataway, N.J.) which produces the Pharmacia Biosensor AB system.

The basic advantages of this embodiment of the target polypeptide trap method include real-time and label-free monitoring of target polypeptide/target polypeptide interaction domain interactions. Furthermore, reusable sensor chip technology allows multiple target polypeptide target polypeptide trap targets to be analyzed; and flexible experimental design, rapid analysis, exact sample handling technology and integrated systems analysis facilitate high throughput screening for target polypeptide interaction domain polypeptides. These features also facilitate screening for small molecules which enhance or inhibit particular target polypeptide/target polypeptide interaction domain interactions. This method is thus well suited to screens for therapeutic target polypeptide system agonist and antagonist compounds.

The utility of the BIAcore biomolecular analysis method has been demonstrated in a number of studies (summarized in, e.g., Fivash et al. (1998) Curr. Opin. Biotechnol. 9: 97–101; Salamon et al. (1997) Biochim. Biophys. Acta. 1331: 131–52 & 117–29; Schuck (1997) Curr. Opin. Biotechnol. 8: 498–502; Schuck (1997) Annu. Rev. Biophys. Biomol. Struct. 26: 541–66; Van Regenmortel et al. (1997) Immunol. Invest. 26: 67–82; O'Shannessy and Winzor (1996) Anal. Biochem. 236: 275–83; and Szabo et al. (1995) Curr. Opin. Struct. Biol. 5: 699–705). These studies further provide the skilled artisan with additional information useful in guiding the application of this technique to the target polypeptide trap method described by the present invention.

In yet another embodiment, the present invention allows for the instantaneous screening of large collections of polypeptides that are synthesized on, and remain covalently bound to, the surface of a support matrix. As summarized in Table I, in this embodiment of the target polypeptide trap method the TAG moiety may be dispensable in certain detection schemes or it may be a fluorescent label or another energy transfer system which facilitates identification of a target polypeptide interaction domain-immobilized target polypeptide and its assignment to a specific matrix "address" which serves to reveal the identity of the interacting target polypeptide interaction domain. The molecular marker in this embodiment is typically a solid support matrix on which the target polypeptide interaction domain polypeptide has been synthesized and which facilitates the creation of the target polypeptide interaction domain identifying "address". Methods of producing such "protein chips" using photosensitive substrates and a precisely delivered source of light have been described (see e.g. U.S. Pat. Nos. 5,679,773, 5,744,305 and WO 90/15070). To screen for biological activity, the substrate protein chip, representing a collection of potential target polypeptide system interacting polypeptides (target polypeptide interaction domains), is exposed to one or more target polypeptide trap polypeptides. The target polypeptide trap polypeptide is tagged, preferably with a fluorescent marker, a radioactive marker, or an antibody epitope. In still other embodiments the detection system employed obviates the need to TAG the target polypeptide employed. Examples include a electrical detection based systems (U.S. Pat. Nos. 5,653,939 and 5,670,322), as well as an optical fiber-based detection system (U.S. Pat. No. 5,690,894). The location of the marker on the substrate is detected with, for example, photon detection or through the altered optical or electrical properties resulting from interaction of the immobilized target polypeptide interaction domain with the target polypeptide at a specific "address". Through knowledge of the sequence of the material at the location where binding is detected, it is possible to quickly determine which target polypeptide interaction domain sequence binds with the target polypeptide probe and, therefore, the technique can be used to screen very large numbers of polypeptides for target polypeptide interaction domain activity. For example, in a preferred embodiment of this protein chip technology, a fluorescently labeled target polypeptide trap polypeptide is exposed to a peptide chip matrix substrate. Nonspecifically bound target polypeptide trap polypeptides are removed and the peptide chip matrix substrate is placed in a microscope detection apparatus for identification of locations where binding takes place. The microscope detection apparatus includes, in a preferred embodiment, a monochromatic or polychromatic light source for directing light at the substrate, and means for detecting fluoresced light from the substrate, as well as means for determining a location of the fluoresced light. The means for detecting light fluoresced on the substrate may in some embodiments include a photon counter. The means for determining a location of the fluoresced light may include an x/y translation table for the substrate. Translation of the slide and data collection are recorded and managed by an appropriately programmed digital computer. Analysis of the collected data allows immediate identification of polypeptide sequences representing target polypeptide interaction domains that interact with the specified target polypeptide trap polypeptide.

The resulting identified target polypeptide interaction domain polypeptide sequences are of utility in several aspects. These synthetic sequences can be reasonably assumed, in some instances, to mimic the structures of naturally-occurring target polypeptide interaction domain ligand interaction domains. Comparison of the thus identified synthetic target polypeptide interaction domain polypeptide sequences with the existing protein databases (e.g. GenBank and SWISS-PROT.) as well as EST databases (Boguski, M. (1995) TIBS 20:295–6) therefore allows the identification of naturally-occurring candidate target polypeptide interaction domains which can then be easily obtained for further analysis. In addition, we note here that the synthetically derived target polypeptide interaction domain polypeptides identified by analysis of peptide display matrices represent potentially therapeutic compounds for use in the prevention and treatment of diseases and conditions involving components of the biochemical pathways of the target polypeptide system. In this and other applications of the target polypeptide trap method the identification of a synthetic target polypeptide interaction domain polypeptide sequence has immediated utility independent of its application to the discovery of additional naturally-occurring target polypeptide interaction domain polypeptides.

Indeed, as it applies to the identification of compounds of utility in the alteration of target polypeptide system processes, the present invention is not limited in scope to the identification of polypeptide interactors. We note here that methods for the synthesis of diverse collections of tagged compounds attached to solid supports have been described (U.S. Pat. No. 5,708,153). This technology is not limited to polypeptides but rather allows the synthesis of diverse collections of tagged compounds of random oligomeric structure. Furthermore, in preferred embodiments, these oligomeric compounds carry specific identifying tags (e.g. oligonucleotide tags) which allow amplification of the tags and identification of the monomer therewith associated. It is understood that the present invention makes available the application of this technology to the method of the target polypeptide trap, thereby allowing the identification of compounds of chemically diverse structure for use in the prevention and treatment of diseases and disorders involving the target polypeptide system.

4.6. Ubiquitin Protein Ligase Inhibitors

The invention demonstrates that recruitment to a ubiquitin protein ligase is sufficient to target a polypeptide for ubiquitin conjugation and subsequent ubiquitin dependent proteolytic degradation. Accordingly, the invention also makes available methods and reagents to block or antagonize the recruitment of certain cellular proteins to ubiquitin protein ligases in vivo. The invention thereby provides means by which a target of a ubiquitin protein ligase can be stabilized in vivo by preventing recruitment to, and subsequent ubiquitination by, the ubiquitin protein ligase. In preferred embodiments, the inhibitors of the invention prevent the interaction of a ubiquitin ligase with a target polypeptide and the inhibitor is a small molecule, polypeptide, or peptidomimetic; the mechanism of inhibition may be competitive or noncompetitive; and the target polypeptide may be a cellular polypeptide, a pathogen-encoded polypeptide or a target polypeptide employed in trans-targeting embodiments of the invention.

For example, effective competitive inhibitors of the invention may be designed based upon the polypeptide structures which comprise the interaction complex between the ubiquitin protein ligase and the target polypeptide. A minimal target polypeptide/ubiquitin protein ligase interaction complex may be characterized by deletion analysis employing protein—protein interaction assays known in the art and described in detail above for the elucidation of target polypeptide interaction domains. Additional methodologies, such as alanine-scanning mutagenesis provide further refined information regarding the structure of the protein/ protein interaction domain interface. In certain situations, the crystal structure of one or both of the binding partners may be available to provide still further guidance to the skilled artisan in designing the competitive inhibitor.

Exemplary noncompetitive inhibitors of the invention include, for example, compounds which bind to a region of the target polypeptide other than the ubiquitin protein ligase interaction region, and allosterically alter the structure of the ubiquitin protein ligase interaction region. Such noncompetitive allosteric target polypeptide inhibitors may have certain advantages—for example they may provide a high degree of specificity to the inhibition as they will fail to recognize and bind to other target polypeptides of the ubiquitin protein ligase. In certain instances, preferred noncompetitive inhibitors of the invention may be elucidated based upon known or readily determined binding partners of the target polypeptide. For example, the structure of a substrate or substrate analog of a target polypeptide enzyme may be used to design appropriate enzyme active site binding noncompetitive inhibitors. Exemplary enzyme active site binding noncompetitive inhibitors include substrate transition state analogs which bind tightly to a target enzyme active site with a high degree of specificity and allosterically alter the structure of the ubiquitin protein ligase interaction region of the target enzyme polypeptide. In another example, the structure of a target polypeptide binding partner protein is used to design the noncompetitive inhibitor of the invention. In this example, the binding partner protein interacts with a region of the target polypeptide which is different from the region recognized by the ubiquitin protein ligase. For example, the structure of the NFκB binding partner of IκB can be used to design preferred noncompetitive inhibitors of the interaction of IκB with a βTrCP containing SCF ubiquitin protein ligase.

The ubiquitin protein ligase competitive inhibitors of the invention can be designed to mimic the polypeptide structure of either the ubiquitin protein ligase component of the interaction region or the target polypeptide component of the interaction region. Such competitive inhibitors thereby prevent the recruitment of the target polypeptide to the ubiquitin protein ligase by blocking the recruitment function of the ubiquitin protein ligase. Depending upon the structure of the inhibitor, the inhibition of recruitment may be very specific to the target polypeptide, or may be affect the recruitment of other polypeptides which are targeted by the ubiquitin protein ligase. For example, preferred target polypeptide-specific inhibitors mimic the structure of a WD repeat polypeptide sequence which interacts with a target polypeptide. These "WD repeat" competitive inhibitors are designed to bind to the target polypeptide and prevent its interaction with a WD repeat of a WD repeat containing F-box polypeptide of an SCF ubiquitin ligase. The invention thereby provides a class of competitive inhibitors which antagonize the ubiquitination of the target polypeptide and only those other targets which share a similar WD repeat interaction pocket.

In certain embodiments, the inhibitor has a molecular weight of less than 10,000 atomic mass units (amu), more preferably less than 7500 amu, 5000 amu, and even more preferably less than 3000 amu. For instance, the ubiquitin ligase/target polypeptide inhibitor can be either a peptide or peptidomimetic, preferably corresponding in length to a 3–25 mer, e.g., and in certain preferred embodiments, containing a core sequence corresponding to a WD repeat conserved sequence of G-H-X$^{(3-6)}$-h-X-X-h-X-r-X-t$^{(2-3)}$-p-X-h-h-X-X-X-X-D-X-X-X-X-h-W-D (SEQ ID No. 14); wherein "X" indicates any amino acid residue, the number ranges indicated in superscript indicate a variable number of the indicated residue type at that position, "h" indicates a hydrophobic residue, "r" indicates an aromatic amino acid residue, "t" indicates an amino acid residue which stabilizes a tight polypeptide backbone turn such as glycine, proline, aspartic acid or asparagine, and p indicates a polar amino acid residue. In other embodiments the WD repeat competitive inhibitor is provided as a gene construct for expressing the WD repeat peptide. The WD repeat peptide, peptidomimetic or gene construct is formulated in the pharmaceutical preparation for delivery to an animal to be treated.

The invention further provides certain broad-specificity ubiquitin protein ligase inhibitors. For example, the production of a beta-galactosidase fusion to a mutant Cdc4p F-box protein lacking the WD repeat-containing domain resulted in an inhibition of cell growth in yeast (see FIG. 4, panel D). This general inhibition of growth was accompanied by the stabilization of the beta-galactosidase-F-box fusion polypeptide which was otherwise targeted for cis-mediated ubiquitination and proteolytic degradation when expressed as a fusion to intact Cdc4p containing the WD repeat domain (see FIG. 4, panel C). Accordingly, the invention provides a beta-galactosidase-F-box fusion protein and other inhibitors which antagonize one or more ubiquitin protein ligase activities. Such broad-range inhibitors are particularly useful for the purpose of blocking ubiquitin-conjugation and proteolytic degradation of all cellular protein targets of a particular class of SCF ubiquitin ligase—e.g. an SCF$^{Cdc4p}$, an SCF$^{Grr1p}$, an SCF$^{Met3p}$, or an SCF$^{hbTrtCp}$.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I–IV (D. M. Weir and C. C. Blackwell, eds., 1986); Manipulating the Mouse Embryo, (Cold Spring Harbor Laboratory Press, Cold Spring Harbor, N.Y., 1986).

It is understood that the inhibitors of the invention can be competitive or noncompetitive, and can be general to a class of ubiquitin protein ligase or specific to a particular cellular target protein or somewhat broader in specificity to include multiple cellular protein targets. In preferred embodiments, the present invention provides a peptide, or peptidomimetic that inhibits the ubiquitin-dependent degradation of the target polypeptide. The peptide/peptidomimetic can, in certain preferred embodiments, range in size from 3–25 amino acid residues. In certain embodiments, a WD repeat inhibitor of the present invention includes a WD repeat core structure having the formula: G-H-X$^{(3-16)}$-h-X-X-h-X-r-X-t$^{(2-3)}$-p-X-h-h-X-X-X-X-D-X-X-X-X-h-W-D (SEQ ID No. 14), wherein:

G represents a glycine residue, or an analog thereof;

H represents a histidine residue, or an analog thereof;

D represents an aspartic acid residue, or an analog thereof;

W represents a tryptophan residue, or an analog thereof;

and "X" indicates any amino acid residue, "h" indicates a hydrophobic residue, "r" indicates an aromatic amino acid residue, "t" indicates an amino acid residue which stabilizes a tight polypeptide backbone turn such as glycine, proline, aspartic acid or asparagine, and p indicates a polar amino acid residue. While the invention includes all of the groups of inhibitors set forth above, the following descriptions are illustrative of an exemplary WD repeat ubiquitin protein ligase competitive inhibitor of the invention. It is understood that chemical design and other methods described for the WD repeat inhibitor apply broadly to all classes of inhibitor discussed herein.

The following definitions and explanations are provided in support of the description of the exemplary WD repeat and other ubiquitin protein ligase inhibitors of the invention.

The term "heteroatom" as used herein means an atom of any element other than carbon or hydrogen. Preferred heteroatoms are boron, nitrogen, oxygen, phosphorus, sulfur and selenium.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., C1–C30 for straight chain, C3–C30 for branched chain), and more preferably 20 or fewer. Likewise, preferred cycloalkyls have from 3–10 carbon atoms in their ring structure, and more preferably have 5, 6 or 7 carbons in the ring structure.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), -CF3, —CN and the like. Exemplary substituted alkyls are described below. Cycloalkyls can be further substituted with alkyls, alkenyls, alkoxys, alkylthios, aminoalkyls, carbonyl-substituted alkyls, -CF3, —CN, and the like.

The term "aralkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls. In preferred embodiments, a substituent designated herein as alkyl is a lower alkyl.

The term "aryl" as used herein includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, -CF3, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, -CF3, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, -CF3, —CN, or the like.

The term "carbocycle", as used herein, refers to an aromatic or non-aromatic ring in which each atom of the ring is carbon.

As used herein, the term "nitro" means -NO2; the term "halogen" designates —F, —Cl, —Br or —I; the term "sulfhydryl" means —SH; the term "hydroxyl" means —OH; and the term "sulfonyl" means -SO2-.

As used herein, the definition of each expression, e.g. alkyl, m, n, etc., when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. Protective Groups in Organic Synthesis, 2nd ed.; Wiley: New York, 1991).

The term "amino acid residue" is known in the art. In general the abbreviations used herein for designating the amino acids and the protective groups are based on recommendations of the IUPAC-IUB Commission on Biochemical Nomenclature (see Biochemistry (1972) 11:1726–1732). In certain embodiments, the amino acids used in the application of this invention are those naturally occurring amino acids found in proteins, or the naturally occurring anabolic or catabolic products of such amino acids which contain amino and carboxyl groups. Particularly suitable amino acid side chains include side chains selected from those of the following amino acids: glycine, alanine, valine, cysteine, leucine, isoleucine, serine, threonine, methionine, glutamic acid, aspartic acid, glutamine, asparagine, lysine, arginine, proline, histidine, phenylalanine, tyrosine, and tryptophan.

The term "amino acid residue" further includes analogs, derivatives and congeners of any specific amino acid referred to herein, as well as C-terminal or N-terminal protected amino acid derivatives (e.g. modified with an N-terminal or C-terminal protecting group). For example, the present invention contemplates the use of amino acid analogs wherein a side chain is lengthened or shortened while still providing a carboxyl, amino or other reactive precursor functional group for cyclization, as well as amino acid analogs having variant side chains with appropriate functional groups). For instance, the subject compound can include an amino acid analog such as, for example, cyanoalanine, canavanine, djenkolic acid, norleucine, 3-phosphoserine, homoserine, dihydroxy-phenylalanine, 5-hydroxytryptophan, 1-methylhistidine, 3-methylhistidine, diaminopimelic acid, ornithine, or diaminobutyric acid. Other naturally occurring amino acid metabolites or precursors having side chains which are suitable herein will be recognized by those skilled in the art and are included in the scope of the present invention.

Also included are the (D) and (L) stereoisomers of such amino acids when the structure of the amino acid admits of stereoisomeric forms. The configuration of the amino acids and amino acid residues herein are designated by the appropriate symbols (D), (L) or (DL), furthermore when the configuration is not designated the amino acid or residue can have the configuration (D), (L) or (DL). It will be noted that the structure of some of the compounds of this invention includes asymmetric carbon atoms. It is to be understood accordingly that the isomers arising from such asymmetry are included within the scope of this invention. Such isomers can be obtained in substantially pure form by classical separation techniques and by sterically controlled synthesis. For the purposes of this application, unless expressly noted to the contrary, a named amino acid shall be construed to include both the (D) or (L) stereoisomers. D- and L-a-Amino acids are represented by the following Fischer projections and wedge-and-dash drawings. In the majority of cases, D- and L-amino acids have R- and S-absolute configurations, respectively.

A "reversed" or "retro" peptide sequence as disclosed herein refers to that part of an overall sequence of covalently-bonded amino acid residues (or analogs or mimetics thereof) wherein the normal carboxyl-to amino direction of peptide bond formation in the amino acid backbone has been reversed such that, reading in the conventional left-to-right direction, the amino portion of the peptide bond precedes (rather than follows) the carbonyl portion. See, generally, Goodman, M. and Chorev, M. Accounts of Chem. Res. 1979, 12, 423.

The reversed orientation peptides described herein include (a) those wherein one or more amino-terminal residues are converted to a reversed ("rev") orientation (thus yielding a second "carboxyl terminus" at the left-most portion of the molecule), and (b) those wherein one or more carboxyl-terminal residues are converted to a reversed ("rev") orientation (yielding a second "amino terminus" at the right-most portion of the molecule). A peptide (amide) bond cannot be formed at the interface between a normal orientation residue and a reverse orientation residue.

Therefore, certain reversed peptide compounds of the invention can be formed by utilizing an appropriate amino acid mimetic moiety to link the two adjacent portions of the sequences depicted above utilizing a reversed peptide (reversed amide) bond. In case (a) above, a central residue of a diketo compound may conveniently be utilized to link structures with two amide bonds to achieve a peptidomimetic structure. In case (b) above, a central residue of a diamino compound will likewise be useful to link structures with two amide bonds to form a peptidomimetic structure.

The reversed direction of bonding in such compounds will generally, in addition, require inversion of the enantiomeric configuration of the reversed amino acid residues in order to maintain a spatial orientation of side chains that is similar to that of the non-reversed peptide. The configuration of amino acids in the reversed portion of the peptides is preferably (D), and the configuration of the non-reversed portion is preferably (L). Opposite or mixed configurations are acceptable when appropriate to optimize a binding activity.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Contemplated equivalents of the compounds described above include compounds which otherwise correspond thereto, and which have the same general properties thereof (e.g. the ability to bind to opioid receptors), wherein one or more simple variations of substituents are made which do not adversely affect the efficacy of the compound in binding to opioid receptors. In general, the compounds of the present invention may be prepared by the methods illustrated in the general reaction schemes as, for example, described below, or by modifications thereof, using readily available starting materials, reagents and conventional synthesis procedures.

For purposes of this invention, the chemical elements are identified in accordance with the Periodic Table of the Elements, CAS version, Handbook of Chemistry and Physics, 67th Ed., 1986–87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

As used herein, the term "transfection" means the introduction of a nucleic acid, e.g., an expression vector, into a recipient cell by nucleic acid-mediated gene transfer.

"Transcriptional regulatory sequence" is a generic term used throughout the specification to refer to DNA sequences, such as initiation signals, enhancers, and promoters, which induce or control transcription of protein coding sequences with which they are operably linked.

Operably linked is intended to mean that the nucleotide sequence is linked to a regulatory sequence in a manner which allows expression of the nucleotide sequence. Regulatory sequences are art-recognized and are selected to direct expression of the subject peptide. Accordingly, the term transcriptional regulatory sequence includes promoters, enhancers and other expression control elements. Such regulatory sequences are described in Goeddel; Gene Expression Technology: Methods in Enzymology 185, Academic Press, San Diego, Calif. (1990).

The term "gene construct" refers to a vector, plasmid, viral genome or the like which includes a coding sequence, can transfect cells, preferably mammalian cells, and can cause expression of e.g., the ubiquitin protein ligase-target polypeptide interaction domain hybrid of the cells transfected with the construct. The term "gene construct" does not include a wild-type papillomavirus genome, and preferably does not include expressible coding sequences for one or more of the polypeptides of the invention.

As used herein, the term "pharmaceutically acceptable" refers to a carrier medium which does not interfere with the effectiveness of the biological activity of the active ingredients and which is not excessively toxic to the hosts of which it is administered. The administration(s) may take place by any suitable technique, including subcutaneous and parenteral administration, preferably parenteral. Examples of parenteral administration include intravenous, intraarterial, intramuscular, and intraperitoneal, with intravenous being preferred.

A variety of drug screening techniques can be readily adapted to the ubiquitin protein ligase/target polypeptide interaction in order to provide high throughput screening of peptide, peptidomimetic or other small molecule libraries. Such assays can be used to optimize a lead compound, or to assess the potential inhibitory effect of a test compound.

In one embodiment, simple competition assays can be used to assess the ability of a test compound to disrupt the interaction of the ubiquitin protein ligase/target polypeptide complex. In other embodiments, cell-based assays which detect a target polypeptide activity or a ubiquitin protein ligase activity can be used to assess the biological activity of a test compound.

In certain embodiments of the present invention, such as for topical administration to the epidermis, the subject inhibitor pharmaceutical can be a peptide, e.g., having a naturally occurring peptide backbone and amino acid side chains, though it may be N-terminally and/or C-terminally protected.

In preferred embodiments, the peptidyl component of the subject compounds includes, in addition to the core WD repeat sequences, as described herein, no more than about 25 amino acid residues of a protein in which a WD repeat motif naturally exists, more preferably no more than 10–15, and even more preferably 6 or less. With the exception of certain chimeric WD repeat compositions described herein, such as fusion proteins, a preferred composition (especially for ectopic application) includes a peptide comprising a WD repeat core motif and having a molecular weight in the range of about 1500 to 7500 daltons, more preferably from about 2000 to 5000 daltons, and even more preferably in the range of about 2000 to 2750 daltons. The peptide, in addition to the WD repeat core motif, may include other amino acid residues, such as a transcytosis peptide, and may be derivatized at one or more backbone or sidechain points with, e.g. peptides, nucleic acids, carbohydrates, etc. In certain embodiments, the peptide is derivatized with one or more functional groups that enhance cellular uptake and/or alter the half-life of the WD repeat core motif.

This invention further contemplates a method of generating sets of combinatorial libraries of the subject WD repeat peptides which is especially useful for identifying potential variant sequences (e.g. homologs) that are functional in inhibiting WD repeat mediated interactions with target polypeptides.

Combinatorially-derived homologs can be generated which have, e.g., greater affinity, a enhanced potency relative to native peptide sequences, or intracellular half-lives different than the corresponding wild-type polypeptide. For example, the altered peptide can be rendered either more stable or less stable to proteolytic degradation or other cellular process which result in destruction of, or otherwise inactivation of, the peptide. Such homologs can be utilized to alter the envelope of therapeutic application by modulating the half-life of the peptide. For instance, a short half-life can give rise to more transient biological effects and can allow tighter control of peptide levels within the cell.

In a representative embodiment of this method, the amino acid sequences for a population of WD motifs are aligned, preferably to promote the highest homology possible. Amino acids which appear at each position of the aligned sequences are selected to create a degenerate set of combinatorial sequences. To illustrate, multiple WD repeat containing proteins are aligned and, based on these alignments, combinatorial libraries can be generated representing WD repeat peptides which have an amino acid sequence that includes a WD core sequence represented by the formula:

G-H-X$^{(3-6)}$-h-X-X-h-X-r-X-t$^{(2-3)}$-p-X-h-h-X-X-X-X-D-X-X-X-X-h-W-D (SEQ ID No. 14).

Peptides larger than the 15-mer core are, of course, also contemplated. Further expansion of the combinatorial library can be made, for example, by including amino acids which would represent conservative mutations at one or more of the degenerate positions. Inclusion of such conservative mutations can give rise to a library of potential WD peptide sequences represented by the above formula, but wherein Xaa(1) can be an amino acid residue having a polar sidechain, such as arg, asn, asp, cys, glu, gln, his, lys, ser, thr or tyr, as set out by the core structures above. Alternatively, amino acid replacement at degenerate positions can be based on steric criteria, e.g. isosteric replacement, without regard for polarity or charge of amino acid sidechains. Similarly, completely random mutagenesis of one or more of the variant positions (Xaa) can be carried out, e.g., each of Xaa(1)–(11) can be any of the 20 amino acids (or other analogs thereof).

In one embodiment the WD peptide library can be derived by combinatorial chemistry, such as by techniques which are available in the art for generating combinatorial libraries of small organic/peptide libraries. See, for example, Blondelle et al. (1995) Trends Anal. Chem. 14:83; the Affymax U.S. Pat. Nos. 5,359,115 and 5,362,899; the Ellman U.S. Pat. No. 5,288,514; the Still et al. PCT publication WO 94/08051; Chen et al. (1994) JACS 116:2661; Kerr et al. (1993) JACS 115:252; PCT publications WO92/10092, WO93/09668 and WO91/07087; and the Lerner et al. PCT publication WO93/20242).

In a preferred embodiment, the combinatorial peptide library is produced by way of a degenerate library of genes encoding a library of polypeptides which each include at least a portion of potential WD sequences. For instance, a mixture of synthetic oligonucleotides can be enzymatically ligated into gene sequences such that the degenerate set of potential WD nucleotide sequences are expressible as individual polypeptides, or alternatively, as a set of larger fusion proteins (e.g. for phage display) containing the set of WD peptide sequences therein.

There are many ways by which the gene library of potential WD homologs can be generated from a degenerate oligonucleotide sequence. Chemical synthesis of a degenerate gene sequence can be carried out in an automatic DNA synthesizer, and the synthetic genes then be ligated into an appropriate gene for expression. The purpose of a degenerate set of genes is to provide, in one mixture, all of the sequences encoding the desired set of potential WD sequences. The synthesis of degenerate oligonucleotides is well known in the art (see for example, Narang, S A (1983) Tetrahedron 39:3; Itakura et al. (1981) Recombinant DNA, Proc 3rd Cleveland Sympos. Macromolecules, ed. A G Walton, Amsterdam: Elsevier pp. 273–289; Itakura et al. (1984) Annu. Rev. Biochem. 53:323; Itakura et al. (1984) Science 198:1056; Ike et al. (1983) Nucleic Acid Res. 11:477. Such techniques have been employed in the directed evolution of other proteins (see, for example, Scott et al. (1990) Science 249:386–390; Roberts et al. (1992) PNAS 89:2429–2433; Devlin et al. (1990) Science 249: 404–406; Cwirla et al. (1990) PNAS 87: 6378–6382; as well as U.S. Pat. Nos. 5,223,409, 5,198,346, and 5,096,815).

A wide range of techniques are known in the art for screening gene products of combinatorial libraries made by point mutations. Such techniques will be generally adaptable for rapid screening of the gene libraries generated by the combinatorial mutagenesis of WD sequences. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Such illustrative assays are amenable to high throughput analysis as necessary to screen large numbers of degenerate sequences created by combinatorial mutagenesis techniques.

In an illustrative embodiment of a screening assay, the WD gene library can be expressed as a fusion protein on the surface of a viral particle. For instance, in the filamentous phage system, foreign peptide sequences can be expressed on the surface of infectious phage, thereby conferring two significant benefits. First, since these phage can be applied to affinity matrices at very high concentrations, a large number of phage can be screened at one time. Second, since each infectious phage displays the combinatorial gene product on its surface, if a particular phage is recovered from an affinity matrix in low yield, the phage can be amplified by another round of infection. The group of almost identical E. coli filamentous phages M13, fd, and f1 are most often used in phage display libraries, as either of the phage gIII or gVIII coat proteins can be used to generate fusion proteins without disrupting the ultimate packaging of the viral particle (Ladner et al. PCT publication WO 90/02909; Garrard et al., PCT publication WO 92/09690; Marks et al. (1992) J. Biol. Chem. 267:16007–16010; Griffths et al. (1993) EMBO J 12:725–734; Clackson et al. (1991) Nature 352:624–628; and Barbas et al. (1992) PNAS 89:4457–4461).

For example, the recombinant phage antibody system (RPAS, Pharmacia Catalog number 27-9400-01) can be easily modified for use in expressing and screening E2 motif combinatorial libraries of the present invention. For instance, the pCANTAB 5 phagemid of the RPAS kit contains the gene which encodes the phage gIII coat protein. The E2 combinatorial gene library can be cloned into the phagemid adjacent to the gIII signal sequence such that it will be expressed as a gIII fusion protein. After ligation, the phagemid is used to transform competent E. coli TG1 cells. Transformed cells are subsequently infected with M13KO7 helper phage to rescue the phagemid and its candidate E2 gene insert. The resulting recombinant phage contain phagemid DNA encoding a specific candidate E2 peptide, and display one or more copies of the corresponding fusion coat protein. The phage-displayed candidate proteins which are capable of, for example, binding an E1 protein, are selected or enriched by panning. For instance, the phage library can be panned on glutathione immobilized E1-GST fusion proteins, and unbound phage washed away from the cells. The bound phage is then isolated, and if the recombinant phage express at least one copy of the wild type gIII coat protein, they will retain their ability to infect *E. coli*. Thus, successive rounds of reinfection of *E. coli*, and panning will greatly enrich for E2 homologs which can then be screened for further PV inhibitory activities. Subsequent selection, e.g. of a reduced set of variants from the library, may then be based upon more meaningful criteria rather than simple E1-binding ability. For instance, intracellular half-life or selectivity can become selection criteria in secondary screens.

Combined with certain formulations, such peptides can be effective intracellular agents for, e.g., inhibiting PV infection of epithelial cells. However, in order to increase the efficacy of such peptides, the WD peptide can be provided a fusion peptide along with a second peptide which promotes "transcytosis", e.g., uptake of the peptide by epithelial cells. To illustrate, the WD peptide of the present invention can be provided as part of a fusion polypeptide with all or a fragment of the N-terminal domain of the HIV protein Tat, e.g., residues 1–72 of Tat or a smaller fragment thereof which can promote transcytosis. In other embodiments, the WD peptide can be provided a fusion polypeptide with all or a portion of the antenopedia III protein.

To further illustrate, the WD peptide (or peptidomimetic) can be provided as a chimeric peptide which includes a heterologous peptide sequence ("internalizing peptide") which drives the translocation of an extracellular form of a WD peptide sequence across a cell membrane in order to facilitate intracellular localization of the WD peptide. In this regard, the therapeutic WD sequence is one which is active intracellularly. The internalizing peptide, by itself, is capable of crossing a cellular membrane by, e.g., transcytosis, at a relatively high rate. The internalizing peptide is conjugated, e.g., as a fusion protein, to the WD peptide. The resulting chimeric peptide is transported into cells at a higher rate relative to the activator polypeptide alone to thereby provide an means for enhancing its introduction into cells to which it is applied, e.g., to enhance topical applications of the WD peptide.

In one embodiment, the internalizing peptide is derived from the *Drosophila antennapedia* protein, or homologs thereof. The 60 amino acid long homeodomain of the homeo-protein antennapedia has been demonstrated to translocate through biological membranes and can facilitate the translocation of heterologous polypeptides to which it is couples. See for example Derossi et al. (1994) J Biol Chem 269:10444–10450; and Perez et al. (1992) J Cell Sci 102: 717–722. Recently, it has been demonstrated that fragments as small as 16 amino acids long of this protein are sufficient to drive internalization. See Derossi et al. (1996) J Biol Chem 271:18188–18193.

The present invention contemplates a WD peptide or peptidomimetic sequence as described herein, and at least a portion of the Antennapedia protein (or homolog thereof) sufficient to increase the transmembrane transport of the chimeric protein, relative to the WD peptide or peptidomimetic, by a statistically significant amount.

Another example of an internalizing peptide is the HIV transactivator (TAT) protein. This protein appears to be divided into four domains (Kuppuswamy et al. (1989) Nucl. Acids Res. 17:3551–3561). Purified TAT protein is taken up by cells in tissue culture (Frankel and Pabo, (1989) Cell 55:1189–1193), and peptides, such as the fragment corresponding to residues 37–62 of TAT, are rapidly taken up by cell in vitro (Green and Loewenstein, (1989) Cell 55:1179–1188). The highly basic region mediates internalization and targeting of the internalizing moiety to the nucleus (Ruben et al., (1989) J. Virol. 63:1–8).

Another exemplary transcellular polypeptide can be generated to include a sufficient portion of mastoparan (T. Higashijima et al., (1990) J. Biol. Chem. 265:14176) to increase the transmembrane transport of the chimeric protein.

While not wishing to be bound by any particular theory, it is noted that hydrophilic polypeptides may be also be physiologically transported across the membrane barriers by coupling or conjugating the polypeptide to a transportable peptide which is capable of crossing the membrane by receptor-mediated transcytosis. Suitable internalizing peptides of this type can be generated using all or a portion of, e.g., a histone, insulin, transferrin, basic albumin, prolactin and insulin-like growth factor I (IGF-I), insulin-like growth factor II (IGF-II) or other growth factors. For instance, it has been found that an insulin fragment, showing affinity for the insulin receptor on capillary cells, and being less effective than insulin in blood sugar reduction, is capable of transmembrane transport by receptor-mediated transcytosis and can therefor serve as an internalizing peptide for the subject transcellular peptides and peptidomimetics. Preferred growth factor-derived internalizing peptides include EGF (epidermal growth factor)-derived peptides, such as CMHIESLDSYTC (SEQ ID No. 15) and CMYIEALD-KYAC (SEQ ID No. 16); TGF-beta (transforming growth factor beta)-derived peptides; peptides derived from PDGF (platelet-derived growth factor) or PDGF-2; peptides derived from IGF-I (insulin-like growth factor) or IGF-II; and FGF (fibroblast growth factor)-derived peptides.

Another class of translocating/internalizing peptides exhibits pH-dependent membrane binding. For an internalizing peptide that assumes a helical conformation at an acidic pH, the internalizing peptide acquires the property of amphiphilicity, e.g., it has both hydrophobic and hydrophilic interfaces. More specifically, within a pH range of approximately 5.0–5.5, an internalizing peptide forms an alpha-helical, amphiphilic structure that facilitates insertion of the moiety into a target membrane. An alpha-helix-inducing acidic pH environment may be found, for example, in the low pH environment present within cellular endosomes. Such internalizing peptides can be used to facilitate transport of WD peptides and peptidomimetics, taken up by an endocytic mechanism, from endosomal compartments to the cytoplasm.

A preferred pH-dependent membrane-binding internalizing peptide includes a high percentage of helix-forming residues, such as glutamate, methionine, alanine and leucine. In addition, a preferred internalizing peptide sequence includes ionizable residues having pKa's within the range of pH 5–7, so that a sufficient uncharged membrane-binding domain will be present within the peptide at pH 5 to allow insertion into the target cell membrane.

A particularly preferred pH-dependent membrane-binding internalizing peptide in this regard is aa1-aa2-aa3-EAALA(EALA)4-EALEALAA-amide (SEQ ID No. 17), which represents a modification of the peptide sequence of Subbarao et al. (Biochemistry 26:2964, 1987). Within this peptide sequence, the first amino acid residue (aa1) is preferably a unique residue, such as cysteine or lysine, that facilitates chemical conjugation of the internalizing peptide to a targeting protein conjugate. Amino acid residues 2–3 may be selected to modulate the affinity of the internalizing peptide for different membranes. For instance, if both residues 2 and 3 are lys or arg, the internalizing peptide will have the capacity to bind to membranes or patches of lipids having a negative surface charge. If residues 2–3 are neutral amino acids, the internalizing peptide will insert into neutral membranes.

Yet other preferred internalizing peptides include peptides of apo-lipoprotein A-1 and B; peptide toxins, such as melittin, bombolittin, delta hemolysin and the pardaxins; antibiotic peptides, such as alamethicin; peptide hormones, such as calcitonin, corticotrophin releasing factor, beta endorphin, glucagon, parathyroid hormone, pancreatic polypeptide; and peptides corresponding to signal sequences of numerous secreted proteins. In addition, exemplary internalizing peptides may be modified through attachment of substituents that enhance the alpha-helical character of the internalizing peptide at acidic pH.

Yet another class of internalizing peptides suitable for use within the present invention include hydrophobic domains that are "hidden" at physiological pH, but are exposed in the low pH environment of the target cell endosome. Upon pH-induced unfolding and exposure of the hydrophobic domain, the moiety binds to lipid bilayers and effects translocation of the covalently linked polypeptide into the cell cytoplasm. Such internalizing peptides may be modeled after sequences identified in, e.g., *Pseudomonas* exotoxin A, clathrin, or Diphtheria toxin.

Pore-forming proteins or peptides may also serve as internalizing peptides herein. Pore-forming proteins or peptides may be obtained or derived from, for example, C9 complement protein, cytolytic T-cell molecules or NK-cell molecules. These moieties are capable of forming ring-like structures in membranes, thereby allowing transport of attached polypeptide through the membrane and into the cell interior.

Mere membrane intercalation of an internalizing peptide may be sufficient for translocation of the WD peptide or peptidomimetic, across cell membranes. However, translocation may be improved by attaching to the internalizing peptide a substrate for intracellular enzymes (i.e., an "accessory peptide"). It is preferred that an accessory peptide be attached to a portion(s) of the internalizing peptide that protrudes through the cell membrane to the cytoplasmic face. The accessory peptide may be advantageously attached to one terminus of a translocating/internalizing moiety or anchoring peptide. An accessory moiety of the present invention may contain one or more amino acid residues. In one embodiment, an accessory moiety may provide a substrate for cellular phosphorylation (for instance, the accessory peptide may contain a tyrosine residue).

An exemplary accessory moiety in this regard would be a peptide substrate for N-myristoyl transferase, such as GNAAAARR (SEQ ID No. 18) (Eubanks et al., in: Peptides. Chemistry and Biology, Garland Marshall (ed.), ESCOM, Leiden, 1988, pp. 566–69) In this construct, an internalizing peptide would be attached to the C-terminus of the accessory peptide, since the N-terminal glycine is critical for the accessory moiety's activity. This hybrid peptide, upon attachment to a WD peptide or peptidomimetic at its C-terminus, is N-myristylated and further anchored to the target cell membrane, e.g., it serves to increase the local concentration of the peptide at the cell membrane.

To further illustrate use of an accessory peptide, a phosphorylatable accessory peptide is first covalently attached to the C-terminus of an internalizing peptide and then incorporated into a fusion protein with a WD peptide or peptidomimetic. The peptide component of the fusion protein intercalates into the target cell plasma membrane and, as a result, the accessory peptide is translocated across the membrane and protrudes into the cytoplasm of the target cell. On the cytoplasmic side of the plasma membrane, the accessory peptide is phosphorylated by cellular kinases at neutral pH. Once phosphorylated, the accessory peptide acts to irreversibly anchor the fusion protein into the membrane. Localization to the cell surface membrane can enhance the translocation of the polypeptide into the cell cytoplasm.

Suitable accessory peptides include peptides that are kinase substrates, peptides that possess a single positive charge, and peptides that contain sequences which are glycosylated by membrane-bound glycotransferases. Accessory peptides that are glycosylated by membrane-bound glycotransferases may include the sequence x-NLT-x, where "x" may be another peptide, an amino acid, coupling agent or hydrophobic molecule, for example. When this hydrophobic tripeptide is incubated with microsomal vesicles, it crosses vesicular membranes, is glycosylated on the luminal side, and is entrapped within the vesicles due to its hydrophilicity (C. Hirschberg et al., (1987) Ann. Rev. Biochem. 56:63–87). Accessory peptides that contain the sequence x-NLT-x thus will enhance target cell retention of corresponding polypeptide.

In another embodiment of this aspect of the invention, an accessory peptide can be used to enhance interaction of the WD peptide or peptidomimetic with the target cell. Exemplary accessory peptides in this regard include peptides derived from cell adhesion proteins containing the sequence "RGD", or peptides derived from laminin containing the sequence CDPGYIGSRC (SEQ ID No. 19). Extracellular matrix glycoproteins, such as fibronectin and laminin, bind to cell surfaces through receptor-mediated processes. A tripeptide sequence, RGD, has been identified as necessary for binding to cell surface receptors. This sequence is present in fibronectin, vitronectin, C3bi of complement, von-Willebrand factor, EGF receptor, transforming growth factor beta, collagen type I, lambda receptor of *E. Coli*, fibrinogen and Sindbis coat protein (E. Ruoslahti, Ann. Rev. Biochem. 57:375–413, 1988). Cell surface receptors that recognize RGD sequences have been grouped into a superfamily of related proteins designated "integrins". Binding of "RGD peptides" to cell surface integrins will promote cell-surface retention, and ultimately translocation, of the polypeptide.

As described above, the internalizing and accessory peptides can each, independently, be added to WD peptide or peptidomimetic by either chemical cross-linking or in the form of a fusion protein. In the instance of fusion proteins, unstructured polypeptide linkers can be included between each of the peptide moieties.

In general, the internalization peptide will be sufficient to also direct export of the polypeptide. However, where an accessory peptide is provided, such as an RGD sequence, it may be necessary to include a secretion signal sequence to direct export of the fusion protein from its host cell. In preferred embodiments, the secretion signal sequence is located at the extreme N-terminus, and is (optionally) flanked by a proteolytic site between the secretion signal and the rest of the fusion protein.

In an exemplary embodiment, a WD peptide or peptidomimetic is engineered to include an integrin-binding RGD peptide/SV40 nuclear localization signal (see, for example Hart S L et al., 1994; J. Biol. Chem., 269:12468–12474), such as encoded by the nucleotide sequence provided in the Nde1-EcoR1 fragment:

catatgggtggctgccgtggcgatatgt-
tcggttgcggtgctcctccaaaaaagaagagaaag-gtagctggattc (SEQ ID No. 20), which encodes the RGD/SV40 nucleotide sequence:

MGGCRGDMFGCGAPP-KKKRKVAGF (SEQ ID No. 21). In another embodiment, the protein can be engineered with the HIV-1 tat(1–72) polypeptide, e.g., as provided by the Nde1-EcoR1 fragment: catatggagccagtagatcctagactagagccc-tggaagcatc-caggaagtcagcctaaaactgcttgtaccaattgtattg taaaaagtgttgctttcat-tgccaagtttgtttcataacaaaagc-
ccttggcatctcctatggcaggaagaagcggagacagcgacgaagacc
tcctcaaggcagtcagactcatcaagtttctctaagtaagcaaggattc (SEQ ID No. 22), which encodes the HIV-1 tat(1–72) peptide sequence:

MEPVDPRLEPWKHPGSQPKT-ACTNCYCKKCCFHC-QVCFITKALGISYGRKKRRQRRRP PQGSQTHQVSL-SKQ (SEQ ID No. 23). In still another embodiment, the fusion protein includes the HSV-1 VP22 polypeptide (Elliott G., O'Hare P (1997) Cell, 88:223–233) provided by the Nde1-EcoR1 fragment:

cat atg acc tct cgc cgc tcc gtg aag tcg ggt ccg cgg gag gtt ccg cgc gat gag tac gag gat ctg tac tac acc ccg tct tca ggt atg gcg agt ccc gat agt ccg cct gac acc tcc cgc cgt ggc gcc cta cag aca cgc tcg cgc cag agg ggc gag gtc cgt ttc gtc cag tac gac gag tcg gat tat gcc ctc tac ggg ggc tcg tca tcc gaa gac gac gaa cac ccg gag gtc ccc cgg acg cgg cgt ccc gtt tcc ggg gcg gtt ttg tcc ggc ccg ggg cct gcg cgg gcg cct ccg cca ccc gct ggg tcc gga ggg gcc gga cgc aca ccc acc acc gcc ccc cgg gcc ccc cga acc cag cgg gtg gcg act aag gcc ccc gcg gcc ccg gcg gcg gag acc acc cgc ggc agg aaa tcg gcc cag cca gaa tcc gcc gca ctc cca gac gcc ccc gcg tcg acg gcg cca acc cga tcc aag aca ccc gcg cag ggg ctg gcc aga aag ctg cac ttt agc acc gcc ccc cca aac ccc gac gcg cca tgg acc ccc cgg gtg gcc ggc ttt aac aag cgc gtc ttc tgc gcc gcg gtc ggg cgc ctg gcg gcc atg cat gcc cgg atg gcg gcg gtc cag ctc tgg gac atg tcg cgt ccg cgc aca gac gaa gac ctc aac gaa ctc ctt ggc atc acc acc atc cgc gtg acg gtc tgc gag ggc aaa aac ctg ctt cag cgc gcc aac gag ttg gtg aat cca gac gtg gtg cag gac gtc gac gcg gcc acg gcg act cga ggg cgt tct gcg gcg tcg cgc ccc acc gag cga cct cga gcc cca gcc cgc tcc gct tct cgc ccc aga cgg ccc gtc gag gaa ttc (SEQ ID No. 24)

which encodes the HSV-1 VP22 peptide having the sequence:

MTSRRSVKSGPREVPRDEYEDLYYTPSS-GMASPDSPPDTSRRGALQTRSRQRGEVRFVQ YDES-DYALYGGSSSEDDEHPEVPRTRRPVS-GAVLSGPGPARAPPPPAGSGGAGRTPTTAP RAPRTGRVATKAPAAPAAETTRGRK-SAQPESAALPDAPASTAPTRSKTPAQGLARKLHF STAPPNPDAPWTPRVAGFNKRVF-CAAVGRLAAMHARMAAVQLWDMSRPRTDEDLNE LLGITTIRVTVCEGKNLLQRANELVNPD-VVQDVDAATATRGRSAASRPTERPRAPARSA SRPRRPVE (SEQ ID No. 25).

In still another embodiment, the fusion protein includes the C-terminal domain of the VP22 protein from, e.g., the nucleotide sequence (Nde1-EcoR1 fragment):

cat atg gac gtc gac gcg gcc acg gcg act cga ggg cgt tct gcg gcg tcg cgc ccc acc gag cga cct cga gcc cca gcc cgc tcc gct tct cgc ccc aga cgg ccc gtc gag gaa ttc (SEQ ID No. 26)

which encodes the VP22 (C-terminal domain) peptide sequence:

MDVDAATATRGRSA-ASRPTERPRAPARSASR-PRRPVE (SEQ ID No. 27)

In certain instances, it may also be desirable to include a nuclear localization signal as part of the WD peptide.

In the generation of fusion polypeptides including the subject WD peptides, it may be necessary to include unstructured linkers in order to ensure proper folding of the various peptide domains, and prevent steric or other interference of the heterologous domains with the PV inhibitory activity of the WD peptide. Many synthetic and natural linkers are known in the art and can be adapted for use in the present invention, including the $(Gly3Ser)_4$ (SEQ ID No. 28) linker.

In other embodiments, the subject WD therapeutics are peptidomimetics of the WD peptide. Peptidomimetics are compounds based on, or derived from, peptides and proteins. The WD peptidomimetics of the present invention typically can be obtained by structural modification of a known WD peptide sequence using unnatural amino acids, conformational restraints, isosteric replacement, and the like. The subject peptidomimetics constitute the continum of structural space between peptides and non-peptide synthetic structures; WD peptidomimetics may be useful, therefore, in delineating pharmacophores and in helping to translate peptides into nonpeptide compounds with the activity of the parent WD peptides. Moreover, as is apparent from the present disclosure, mimetopes of the subject WD peptides can be provided. Such peptidomimetics can have such attributes as being non-hydrolyzable (e.g., increased stability against proteases or other physiological conditions which degrade the corresponding peptide), increased specificity and/or potency for inhibition of PV replication, and increased cell permeability for intracellular localization of the peptidomimetic. For illustrative purposes, peptide analogs of the present invention can be generated using, for example, benzodiazepines (e.g., see Freidinger et al. in Peptides: Chemistry and Biology, G. R. Marshall ed., ESCOM Publisher: Leiden, Netherlands, 1988), substituted gama lactam rings (Garvey et al. in Peptides: Chemistry and Biology, G. R. Marshall ed., ESCOM Publisher: Leiden, Netherlands, 1988, p123), C-7 mimics (Huffman et al. in Peptides: Chemistry and Biology, G. R. Marshall ed., ESCOM Publisher: Leiden, Netherlands, 1988, p. 105), keto-methylene pseudopeptides (Ewenson et al. (1986) J Med Chem 29:295; and Ewenson et al. in Peptides: Structure and Function (Proceedings of the 9th American Peptide Symposium) Pierce Chemical Co. Rockland, Ill., 1985), b-turn dipeptide cores (Nagai et al. (1985) Tetrahedron Lett 26:647; and Sato et al. (1986) J Chem Soc Perkin Trans 1:1231), b-aminoalcohols (Gordon et al. (1985) Biochem Biophys Res Commun126:419; and Dann et al. (1986) Biochem Biophys Res Commun 134:71), diaminoketones (Natarajan et al. (1984) Biochem Biophys Res Commun 124:141), and methyleneamino-modified (Roark et al. in Peptides: Chemistry and Biology, G. R. Marshall ed., ESCOM Publisher: Leiden, Netherlands, 1988, p134). Also, see generally, Session III: Analytic and synthetic methods, in Peptides: Chemistry and Biology, G. R. Marshall ed., ESCOM Publisher: Leiden, Netherlands, 1988)

In addition to a variety of sidechain replacements which can be carried out to generate the subject WD peptidomimetics, the present invention specifically contemplates the use of conformationally restrained mimics of peptide secondary structure. Numerous surrogates have been developed for the amide bond of peptides. Frequently exploited surrogates for the amide bond include the following groups (i) trans-olefins, (ii) fluoroalkene, (iii) methyleneamino, (iv) phosphonamides, and (v) sulfonamides.

Additionally, peptidomimetics based on more substantial modifications of the backbone of the WD peptide can be used. Peptidomimetics which fall in this category include (i) retro-inverso analogs, and (ii) N-alkyl glycine analogs (so-called peptoids).

Furthermore, the methods of combinatorial chemistry are being brought to bear, e,g, by G. L. Verdine at Harvard University, on the development of new peptidomimetics. For example, one embodiment of a so-called "peptide morphing" strategy focuses on the random generation of a library of peptide analogs that comprise a wide range of peptide bond substitutes.

Such retro-inverso analogs can be made according to the methods known in the art, such as that described by the Sisto et al. U.S. Pat. No. 4,522,752. For example, the illustrated retro-inverso analog can be generated as follows. The geminal diamine corresponding to the N-terminal tryptophan is synthesized by treating a protected tryptophan analog with ammonia under HOBT-DCC coupling conditions to yield the N-Boc amide, and then effecting a Hofmann-type rearrangement with I,I-bis-(trifluoroacetoxy)iodobenzene (TIB), as described in Radhakrishna et al. (1979) J. Org. Chem. 44:1746. The product amine salt is then coupled to a side-chain protected (e.g., as the benzyl ester) N-Fmoc D-lys residue under standard conditions to yield the pseudodipeptide. The Fmoc (fluorenylmethoxycarbonyl) group is removed with piperidine in dimethylformamide, and the resulting amine is trimethylsilylated with bistrimethylsilylacetamide (BSA) before condensation with suitably alkylated, side-chain protected derivative of Meldrum's acid, as described in U.S. Pat. No. 5,061,811 to Pinori et al., to yield the retro-inverso tripeptide analog WKH. The pseudotripeptide is then coupled with an L-methionine analog under standard conditions to give the protected tetrapeptide analog. The protecting groups are removed to release the product, and the steps repeated to enlogate the tetrapeptide to the full length peptidomimetic. It will be understood that a mixed peptide, e.g. including some normal peptide linkages, will be generated. As a general guide, sites which are most susceptible to proteolysis are typically altered, with less susceptible amide linkages being optional for mimetic switching The final product, or intermediates thereof, can be purified by HPLC.

Retro-enantio analogs such as this can be synthesized commercially available D-amino acids (or analogs thereof) and standard solid- or solution-phase peptide-synthesis techniques. For example, in a preferred solid-phase synthesis method, a suitably amino-protected (t-butyloxycarbonyl, Boc) D-trp residue (or analog thereof) is covalently bound to a solid support such as chloromethyl resin. The resin is washed with dichloromethane (DCM), and the BOC protecting group removed by treatment with TFA in DCM. The resin is washed and neutralized, and the next Boc-protected D-amino acid (D-lys) is introduced by coupling with diisopropylcarbodiimide. The resin is again washed, and the cycle repeated for each of the remaining amino acids in turn (D-his, D-met, etc). When synthesis of the protected retro-enantio peptide is complete, the protecting groups are removed and the peptide cleaved from the solid support by treatment with hydrofluoric acid/anisole/dimethyl sulfide/thioanisole. The final product is purified by HPLC to yield the pure retro-enantio analog.

The trans olefin analog of a WD peptide can be synthesized according to the method of Y. K. Shue et al. (1987) Tetrahedron Letters 28:3225. Referring to the illustrated example, Boc-amino L-Ile is converted to the corresponding a-amino aldehyde, which is treated with a vinylcuprate to yield a diastereomeric mixture of alcohols, which are carried on together. The allylic alcohol is acetylated with acetic anhydride in pyridine, and the olefin is cleaved with osmium tetroxide/sodium periodate to yield the aldehyde, which is condensed with the Wittig reagent derived from a protected tyrosine precursor, to yield the allylic acetate. The allylic acetate is selectively hydrolyzed with sodium carbonate in methanol, and the allylic alcohol is treated with triphenylphosphine and carbon tetrabromide to yield the allylic bromide. This compound is reduced with zinc in acetic acid to give the transposed trans olefin as a mixture of diastereomers at the newly-formed center. The diastereomers are separated and the pseudodipeptide is obtained by selective transfer hydrogenolysis to unveil the free carboxylic acid.

The pseudodipeptide is then coupled at the C-terminus, according to the above example, with a suitably protected tyrosine residue, and at the N-terminus with a protected alanine residue, by standard techniques, to yield the protected tetrapeptide isostere A-I-Y-Y (SEQ ID No. 29). The terapeptide is then further condensed with the olefinic tripeptide analog derived by similar means for Lys-Ala-Arg, and so forth to build up the full WD peptide. The protecting groups are then removed with strong acid to yield the desired peptide analog, which can be further purified by HPLC.

Other pseudodipeptides can be made by the method set forth above merely by substitution of the appropriate starting Boc amino acid and Wittig reagent. Variations in the procedure may be necessary according to the nature of the reagents used, but any such variations will be purely routine and will be obvious to one of skill in the art.

It is further possible couple the pseudodipeptides synthesized by the above method to other pseudodipeptides, to make peptide analogs with several olefinic functionalities in place of amide functionalities. For example, pseudodipeptides corresponding to Met-Arg or Tyr-Lys, etc. could be made and then coupled together by standard techniques to yield an analog of the WD peptide which has alternating olefinic bonds between residues.

The synthesis of such phosphonate derivatives can be adapted from known synthesis schemes. See, for example, Loots et al. in Peptides: Chemistry and Biology, (Escom Science Publishers, Leiden, 1988, p. 118); Petrillo et al. in Peptides: Structure and Function (Proceedings of the 9th American Peptide Symposium, Pierce Chemical Co. Rockland, Ill., 1985).

Many other peptidomimetic structures are known in the art and can be readily adapted for use in the subject WD peptidomimetics. To illustrate, the WD peptidomimetic may incorporate the 1-azabicyclo[4.3.0]nonane surrogate (see Kim et al. (1997) J. Org. Chem. 62:2847), or an N-acyl piperazic acid (see Xi et al. (1998) J. Am. Chem. Soc. 120:80), or a 2-substituted piperazine moiety as a constrained amino acid analogue (see Williams et al. (1996) J. Med. Chem. 39:1345–1348). In still other embodiments, certain amino acid residues can be replaced with aryl and bi-aryl moieties, e.g., monocyclic or bicyclic aromatic or heteroaromatic nucleus, or a biaromatic, aromatic-heteroaromatic, or biheteroaromatic nucleus.

The subject WD peptidomimetics can be optimized by, e.g., combinatorial synthesis techniques combined with such high throughput screening as described herein.

Moreover, other examples of mimetopes include, but are not limited to, protein-based compounds, carbohydrate-based compounds, lipid-based compounds, nucleic acid-based compounds, natural organic compounds, synthetically derived organic compounds, anti-idiotypic antibodies and/or catalytic antibodies, or fragments thereof. A mimetope can be obtained by, for example, screening libraries of natural and synthetic compounds for compounds capable of inhibiting E1-WD interaction. A mimetope can also be obtained, for example, from libraries of natural and synthetic compounds, in particular, chemical or combinatorial libraries (i.e., libraries of compounds that differ in sequence or size but that have the same building blocks). A mimetope can also be obtained by, for example, rational drug design. In a rational drug design procedure, the three-dimensional structure of a compound of the present invention can be analyzed by, for example, nuclear magnetic resonance (NMR) or x-ray crystallography. The three-dimensional structure can then be used to predict structures of potential mimetopes by, for example, computer modelling. the predicted mimetope structures can then be produced by, for example, chemical synthesis, recombinant DNA technology, or by isolating a mimetope from a natural source (e.g., plants, animals, bacteria and fungi).

According to another aspect of this invention, WD peptides and peptidomimetics may be administered directly to PV infected cells. Direct delivery of such WD therapeutics may be facilitated by formulation of the peptidyl compound in any pharmaceutically acceptable dosage form, e.g., for delivery orally, intratumorally, peritumorally, interlesionally, intravenously, intramuscularly, subcutaneously, periolesionally, or (preferably) topical routes, to exert local therapeutic effects.

Topical administration of the therapeutic is advantageous since it allows localized concentration at the site of administration with minimal systemic adsorption. This simplifies the delivery strategy of the agent to the disease site and reduces the extent of toxicological characterization. Furthermore, the amount of material to be applied is far less than that required for other administration routes. Effective delivery requires the agent to diffuse into the affected cells. Successful intracellular delivery of agents not naturally taken up by cells has been achieved by exploiting the natural process of intracellular membrane fusion, or by direct access of the cell's natural transport mechanisms which include endocytosis and pinocytosis (Duzgunes (1985) Subcellular Biochemistry 11:195–286). Such processes are also useful in the direct delivery and uptake of the subject WD peptides and peptidomimetic by papillomavirus-infected cells.

In one embodiment, the membrane barrier can be overcome by associating the WD protein in complexes with lipid formulations closely resembling the lipid composition of natural cell membranes. In particular, the subject WD peptidomimetics are encapsulated in liposomes to form pharmaceutical preparations suitable for administration to living cells and, in particular, suitable for topical administration to human skin. The Yarosh U.S. Pat. No. 5,190,762 demonstrates that proteins can be delivered across the outer skin layer and into living cells, without receptor binding, by liposome encapsulation.

These lipids are able to fuse with the cell membranes on contact, and in the process, the associated WD peptidomimetic is delivered intracellularly. Lipid complexes can not only facilitate intracellular transfers by fusing with cell membranes but also by overcoming charge repulsions between the cell membrane and the molecule to be inserted. The lipids of the formulations comprise an amphipathic lipid, such as the phospholipids of cell membranes, and form hollow lipid vesicles, or liposomes, in aqueous systems. This property can be used to entrap the WD peptidomimetic within the liposomes.

Liposomes offer several advantages: They are non-toxic and biodegradable in composition; they display long circulation half-lives; and recognition molecules can be readily attached to their surface for targeting to tissues. Finally, cost effective manufacture of liposome-based pharmaceuticals, either in a liquid suspension or lyophilized product, has demonstrated the viability of this technology as an acceptable drug delivery system.

Liposomes have been described in the art as in vivo delivery vehicles. The structure of various types of lipid aggregates varies, depending on composition and method of forming the aggregate. Such aggregates include liposomes, unilamellar vesicles, multilamellar vesicles, micelles and the like, having particle sizes in the nanometer to micrometer range. Methods of making lipid aggregates are by now well-known in the art. For example, the liposomes may be made from natural and synthetic phospholipids, glycolipids, and other lipids and lipid congeners; cholesterol, cholesterol derivatives and other cholesterol congeners; charged species which impart a net charge to the membrane; reactive species which can react after liposome formation to link additional molecules to the liposome membrane; and other lipid soluble compounds which have chemical or biological activity.

In one embodiment, pH sensitive liposomes are a preferred type of liposome for use with the present invention. One pathway for the entry of liposomes into cellular cytoplasm is by endocytosis into lysozymes of low pH. Accordingly, liposomes which are stable at neutral pH but release their contents at acidic pH can be used to deliver enzymes into the lysozymes of the cytoplasm, whereupon the contents are released.

Liposomes can be made sensitive to the low pH of the lysozymes by the lipid composition. In particular, pH sensitive liposomes can be prepared by using phospholipids which form lipid bilayers when charged but fail to stack in an ordered fashion when neutralized. An example of such a phospholipid is phosphatidylethanolamine, which is negatively charged above pH 9. The net charge of a phospholipid can be maintained at a pH which would otherwise neutralize the head groups by including charged molecules in the lipid bilayer which themselves can become neutralized. Examples of these charged molecules are oleic acid and cholesteryl hemisuccinate, which are negatively charged at neutral pH but become neutralized at pH 5. The effect of combining these together in a lipid bilayer is that at pH 9 μl molecules are charged; at pH 7 the net negative charge of the oleic acid and cholesteryl hemisuccinate maintains the stability of the phosphatidylethanolamine, and at pH 5 all components are protonated and the lipid membrane is destabilized. Additional neutral molecules, such as phosphatidylcholine, can be added to the liposomes as long as they do not interfere with stabilization of the pH sensitive phospholipid by the charged molecules.

In another embodiment, the WD peptidomimetic is formulated with a positively charged synthetic (cationic) lipid N-[1-(2,3-dioleyloxy)propyl]-N,N,N-trimethylammonium chloride (DOTMA), in the form of liposomes, or small vesicles, which can fuse with the negatively charged lipids of the cell membranes of mammalian cells, resulting in uptake of the contents of the liposome (see, for example, Felgner et al. (1987) PNAS 84:7413–7417; and U.S. Pat. No. 4,897,355 to Eppstein, D. et al.). Another cationic lipid which can be used to generate WD peptidomimetic containing liposomes is the DOTMA analogue, 1,2-bis(oleoyloxy)-3-(trimethyl-ammonio)propane (DOTAP) in combination with a phospholipid to form delivery vesicles.

Lipofectin™ (Bethesda Research Laboratories, Gaithersburg, Md.) and/or LipofectAMINE™, commercially available reagents, can be used to deliver the WD peptidomimetic directly into cells. Positively charged complexes prepared in this way spontaneously attach to negatively charged cell surfaces, fuse with the plasma membrane, and can efficiently deliver functional WD peptidomimetic into, for example, keratinocytes. Sells et al. (1995) Biotechniques 19:72–76 describe a procedure for delivery of purified proteins into a variety of cells using such polycationic lipid preparations.

A significant body of information is emerging regarding the use of other cationic lipids for the delivery of macromolecules into cells. Other suitable lipid vesicles for direct delivery of the WD peptidomimetic include vesicles containing a quaternary ammonium surfactant (Ballas et al. (1988) Biochim. Biophys Acta 939:8–18); lipophilic derivatives of spermine (Behr et al. (1989) PNAS 86:6982–6986).

The lipid formulations of the subject WD peptidomimetic can be used in pharmaceutical formulations to deliver the WD peptidomimetic by various routes and to various sites in the animal body to achieve the desired therapeutic effect. Local or systemic delivery of the therapeutic agent can be achieved by administration comprising application or insertion of the formulation into body cavities, inhalation or insufflation of an aerosol, or by parenteral introduction, comprising intramuscular, intravenous, intradermal, peritoneal, subcutaneous and topical administration.

Topical formulations are those advantageously applied to the skin or mucosa. Target mucosa can be that of the vaginal, cervical, vulvar, penal or anorectal mucosa, or target mucosa can be that of the gastrointestinal tract, comprising the mouth, larynx, esophagus and stomach. Lipids present in topical formulations can act to facilitate introduction of therapeutic WD peptidomimetic into the target tissue, such as the stratum or corneum of the skin, by perturbing the barrier properties of the protective membrane, or by introducing perturbing agents or penetration enhancers such as DMSO, Azone™ or by promoting the activity of these penetration enhancers.

Other pharmaceutical formulations comprising the cationic lipids of the invention are topical preparations containing an anesthetic or cytostatic agent, immunomodulators, bioactive peptides or oligonucleotides, sunscreens or cosmetics. Preparations for topical use are conveniently prepared with hydrophilic and hydrophobic bases in the form of creams, lotions, ointments or gels; alternatively, the preparation may be in the form of a liquid that is sprayed on the skin. The effect of the cationic lipids is to facilitate the penetration of the active antiviral agent through the stratum corneum of the dermis.

The composition and form of pharmaceutical preparations comprising the liposome, in combination with the WD peptidomimetic, can vary according to the intended route of administration.

Also, by suitable modifications of the liposome membranes, the liposomes can be made to bind to specific sub-populations of cells.

In still another embodiment, the therapeutic WD peptidomimetic can be delivered by way of an artificial viral envelope (AVE). The art as described a number of viral envelopes which exploit molecular recognition of cell surface receptors by viral surface proteins as a means for selective intracellular delivery of macromolecules, including proteins. According to the method of Schreier, et. al., U.S. Pat. No. 5,252,348, a virtually unlimited number of artificial viral envelopes can be prepared and applied using recombinant or isolated surface determinants. For example, the AVEs be generated as viral mimetics of a number of human viruses including arboviruses; flaviviridae; bunyaviridae; hepatitis viruses; Epstein-Barr viruses; herpes viruses; paramyxoviruses; respiratory syncytical virus; retroviruses including human T-lymphotrophic virus type I and II (HTLV-I/II) and human immunodeficiency virus type 1 and 2 (HIV-1/2); rhinoviruses; orthopoxviruses; and human papilloma viruses (particularly those engineered not to express E6 and/or E7).

In another embodiment, direct delivery of a therapeutic WD peptidomimetic may be facilitated by chemical modification of the polypeptide itself. One such modification involves increasing the lipophilicity of the WD peptidomimetic in order to increase binding to the cell surface, in turn, stimulating non-specific endocytosis of the protein. Lipophilicity may be increased by adding a lipophilic moiety (e.g., one or more fatty acid molecules) to the WD peptidomimetic. A wide variety of fatty acids may be employed. For example, the protein may be palmitoylated. Alternatively, a lipopeptide may be produced by fusion or cross-linking, to permit the WD peptidomimetic to resemble the natural lipopeptide from E. coli, tripalmitoyl-5-glycerylcysteil-seryl-serine, at its amino terminus. This lipopeptide has been shown to increase the uptake of fused peptides (P. Hoffmann et al., (1988) Immunobiol. 177:158–70). Lipophilicity may also be increased by esterification of the protein at tyrosine residues or other amino acid residues. And uptake of the WD peptidomimetic may be increased by addition of a basic polymer such as polyarginine or polylysine (Shen et al. (1978) PNAS 75:1872–76).

Direct delivery of WD peptidomimetics according to this invention may also be effected by the use of transport moieties, such as protein carriers known to cross cell membranes. For example, a WD peptide may be fused to a carrier protein, preferably by a genetic fusion which may be expressed in a system such as E. coli, barulovirus or yeast. According to one embodiment of this invention, the amino terminus of the WD peptide may be fused to the carboxy terminus of a transport moiety using standard techniques.

Nucleotide sequences encoding such carrier-WD peptide fusion proteins, operatively linked to regulatory sequences, may be constructed and introduced into appropriate expression systems using conventional recombinant DNA procedures. The resulting fusion protein may then be purified and tested for its capacity to (1) enter intact eukaryotic cells and (2) inhibit viral DNA replication once inside the intact eukaryotic cells.

Useful carrier proteins include, for example, bacterial hemolysins or "blending agents", such as alamethicin or sulfhydryl activated lysins. Other carrier moieties which may be used include cell entry components of bacterial toxins, such as Pseudomonas exotoxin, tetanus toxin, ricin toxin, and diphtheria toxin. Also useful is melittin, from bee venom. Other useful carrier proteins include proteins which are viral receptors, cell receptors or cell ligands for specific receptors that are internalized, i.e., those which cross mammalian cell membranes via specific interaction with cell surface receptors, recognized and taken into the cell by cell surface receptors. Such cell ligands include, for example, epidermal growth factor, fibroblast growth factor, transferrin and platelet-derived growth factor. Alternatively, the ligand may be a non-peptide, such as mannose-6-phosphate, which permits internalization by the mannose-6-phosphate receptor. The transport moiety may also be selected from bacterial immunogens, parasitic immunogens, viral immunogens, immunoglobulins or fragments thereof that bind to target molecules, cytokines, growth factors, colony stimulating factors and hormones. A transport moiety may also be derived from the tat protein of HIV-1.

As an alternative or addition to the above-described chemical modifications and protein carriers, which may be employed alone or in combination, other agents which allow penetration of the keratinized cell layer may be employed to facilitate delivery of the WD peptidomimetics of this invention to papillomavirus-infected cells. In topical applications, for example, the WD peptidomimetic may be administered in combination with dimethylsulfoxide, an agent which promotes penetration of cell membranes by substances mixed with it. Useful keratinolytic agents include, for example, salicylic acid, urea, and alpha-hydroxyacids. For such applications, the WD peptidomimetic and any other agent may be administered topically, in cream or gel form.

According to an alternate embodiment of this invention, the therapeutic WD peptidomimetic may be administered serially or in combination with other therapeutics used in the treatment of papillomavirus infections or diseases caused by them. Such therapeutics include interferons, such as IFN-g, IFN-a and IFN-b derived from natural sources or produced by recombinant techniques, other cell mediators formed by leukocytes or produced by recombinant techniques such as for example, interleukin-1, interleukin-2, tumor necrosis factor, macrophage colony stimulating factor, macrophage migration inhibitory factor, macrophage activation factor, lymphotoxin and fibroblast growth factor. Alternatively, the WD peptidomimetic may be administered serially or in combination with conventional therapeutic agents or regimens such as, for example, salicylic acid, podophyllotoxin, retinoic acid, surgery, laser therapy and cryotherapy. Such combination therapies may advantageously utilize less than conventional dosages of those agents, or involve less radical regimens, thus avoiding any potential toxicity or risks associated with those therapies.

It will also be understood by those skilled in the art that any of the above enumerated delivery methods may be augmented, where topical application is being carried out, by the use of ultrasound or iontophoretic delivery devises which facilitate transdermal delivery of proteins. See, for example, Banga et al. (1993) Pharm Res 10:697–702; and Mitragotri et al. (1995) Science 269:850–853.

In another aspect, the present invention relates to gene therapy constructs containing a nucleic acid encoding, for example in an exemplary method, a WD peptide of the present invention, operably linked to at least one transcriptional regulatory sequence. The gene constructs of the present invention are formulated to be used as a part of a gene therapy protocol to deliver the subject therapeutic protein to an animal to be treated.

Any of the methods known to the art for the insertion of DNA fragments into a vector may be used to construct expression vectors consisting of appropriate transcriptional/translational control signals and the desired WD peptide-encoding nucleotide sequence. See, for example, Maniatis T., Fritsch E. F., and Sambrook J. (1989): Molecular Cloning (A Laboratory Manual), Cold Spring Harbor Laboratory, Cold Spring Harbor, N.Y.; and Ausubel F. M., Brent R., Kingston R. E., Moore, D. D., Seidman J. G., Smith J. A., and Struhl K. (1992): Current Protocols in Molecular Biology, John Wiley & Sons, New York. These methods may include in vitro DNA recombinant and synthetic techniques and in vivo genetic recombination. Expression of a nucleic acid sequence encoding a WD peptide may be regulated by a second nucleic acid sequence so that the peptide is expressed in a host infected or transfected with the recombinant DNA molecule. For example, expression of a WD peptide may be controlled by any promoter/enhancer element known in the art. The promoter activation may be tissue specific or inducible by a metabolic product or administered substance.

Promoters/enhancers which may be used to control the expression of the WD peptide in vivo include, but are not limited to, the native WD promoter, the cytomegalovirus (CMV) promoter/enhancer (Karasuyama et al., 1989, J. Exp. Med., 169:13), the human b-actin promoter (Gunning et al. (1987) PNAS 84:4831–4835), the glucocorticoid-inducible promoter present in the mouse mammary tumor virus long terminal repeat (MMTV LTR) (Klessig et al. (1984) Mol. Cell Biol. 4:1354–1362), the long terminal repeat sequences of Moloney murine leukemia virus (MuLV LTR) (Weiss et al. (1985) RNA Tumor Viruses, Cold Spring Harbor Laboratory, Cold Spring Harbor, N.Y.), the SV40 early or late region promoter (Bernoist et al. (1981) Nature 290:304–310; Templeton et al. (1984) Mol. Cell Biol., 4:817; and Sprague et al. (1983) J. Virol., 45:773), the promoter contained in the 3' long terminal repeat of Rous sarcoma virus (RSV) (Yamamoto et al., 1980, Cell, 22:787–797), the herpes simplex virus (HSV) thymidine kinase promoter/enhancer (Wagner et al. (1981) PNAS 82:3567–71), and the herpes simplex virus LAT promoter (Wolfe et al. (1992) Nature Genetics, 1:379–384), and Keratin gene promoters, such as Keratin 14.

Expression constructs of the subject WD peptides may be administered in any biologically effective carrier, e.g. any formulation or composition capable of effectively delivering the recombinant gene to cells in vivo. Approaches include insertion of the WD peptide coding sequence in viral vectors including recombinant retroviruses, adenovirus, adeno-associated virus, and herpes simplex virus-1, or recombinant eukaryotic plasmids. Viral vectors transfect cells directly; plasmid DNA can be delivered with the help of, for example, cationic liposomes (lipofectin) or derivatized (e.g. antibody conjugated), polylysine conjugates, gramacidin S, artificial viral envelopes or other such intracellular carriers, as well as direct injection of the gene construct or CaPO4 precipitation carried out in vivo. It will be appreciated that because transduction of appropriate target cells represents the critical first step in gene therapy, choice of the particular gene delivery system will depend on such factors as the phenotype of the intended target and the route of administration, e.g. locally or systemically.

A preferred approach for in vivo introduction of nucleic acid into a cell is by use of a viral vector containing nucleic acid encoding the particular WD peptide desired. Infection of cells with a viral vector has the advantage that a large proportion of the targeted cells can receive the nucleic acid. Additionally, molecules encoded within the viral vector, e.g., the recombinant WD peptide, are expressed efficiently in cells which have taken up viral vector nucleic acid.

In addition to viral transfer methods, such as those illustrated above, non-viral methods can also be employed to cause expression of a WD peptide in the tissue of an animal. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the WD peptide-encoding gene by the targeted cell. Exemplary gene delivery systems of this type include liposomal derived systems, poly-lysine conjugates, and artificial viral envelopes.

In clinical settings, the gene delivery systems for the therapeutic WD peptide coding sequence can be introduced into a patient by any of a number of methods, each of which is familiar in the art. For instance, a pharmaceutical preparation of the gene delivery system can be introduced systemically, e.g. by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or "gene gun" techniques. In preferred embodiments, the gene therapy construct of the present invention is applied topically to an infected or transformed cells of the skin or mucusal tissue. A WD peptide gene construct can, in one embodiment, be delivered in a gene therapy construct by electroporation using techniques described, for example, by Dev et al. ((1994) Cancer Treat Rev 20:105–115).

The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced intact from recombinant cells, e.g. retroviral vectors, the pharmaceutical preparation can comprise one or more cells which produce the gene delivery system.

4.7. Expression Vectors and Nucleic Acid Compositions

In another aspect of the invention, the proteins described herein are provided in expression vectors. For instance, expression vectors are contemplated which include a nucleotide sequence encoding a polypeptide containing a composite activator of the present invention, which coding sequence is operably linked to at least one transcriptional regulatory sequence. Regulatory sequences for directing expression of the instant fusion proteins are art-recognized and are selected by a number of well understood criteria. Exemplary regulatory sequences are described in Goeddel; Gene Expression Technology: Methods in Enzymology, Academic Press, San Diego, Calif. (1990). For instance, any of a wide variety of expression control sequences that control the expression of a DNA sequence when operatively linked to it may be used in these vectors to express DNA sequences encoding the fusion proteins of this invention. Such useful expression control sequences, include, for example, the early and late promoters of SV40, adenovirus or cytomegalovirus immediate early promoter, the lac system, the trp system, the TAC or TRC system, T7 promoter whose expression is directed by T7 RNA polymerase, the promoter for 3-phosphoglycerate kinase or other glycolytic enzymes, the promoters of acid phosphatase, e.g., Pho5, and the promoters of the yeast y-mating factors and other sequences known to control the expression of genes of prokaryotic or eukaryotic cells or their viruses, and various combinations thereof. It should be understood that the design of the expression vector may depend on such factors as the choice of the host cell to be transformed. Moreover, the vector's copy number, the ability to control that copy number and the expression of any other protein encoded by the vector, such as antibiotic markers, should also be considered.

As will be apparent, the subject gene constructs can be used to cause expression of the subject fusion proteins in cells propagated in culture, e.g. to produce proteins or polypeptides, including fusion proteins, for purification.

This invention also pertains to a host cell transfected with a recombinant gene in order to express one of the subject polypeptides. The host cell may be any prokaryotic or eukaryotic cell. For example, a fusion proteins of the present invention may be expressed in bacterial cells such as E. coli, insect cells (baculovirus), yeast, or mammalian cells. Other suitable host cells are known to those skilled in the art.

Accordingly, the present invention further pertains to methods of producing the subject fusion proteins—e.g., the target polypeptide:F-box protein chimeric polypeptides described herein. For example, a host cell transfected with an expression vector encoding a protein of interest can be cultured under appropriate conditions to allow expression of the protein to occur. The protein may be secreted, by inclusion of a secretion signal sequence, and isolated from a mixture of cells and medium containing the protein. Alternatively, the protein may be retained cytoplasmically and the cells harvested, lysed and the protein isolated. A cell culture includes host cells, media and other byproducts. Suitable media for cell culture are well known in the art. The proteins can be isolated from cell culture medium, host cells, or both using techniques known in the art for purifying proteins, including ion-exchange chromatography, gel filtration chromatography, ultrafiltration, electrophoresis, and immunoaffinity purification with antibodies specific for particular epitopes of the protein.

Thus, a coding sequence for a fusion protein of the present invention can be used to produce a recombinant form of the protein via microbial or eukaryotic cellular processes. Ligating the polynucleotide sequence into a gene construct, such as an expression vector, and transforming or transfecting into hosts, either eukaryotic (yeast, avian, insect or mammalian) or prokaryotic (bacterial cells), are standard procedures.

Expression vehicles for production of a recombinant protein include plasmids and other vectors. For instance, suitable vectors for the expression of the instant fusion proteins include plasmids of the types: pBR322-derived plasmids, pEMBL-derived plasmids, pEX-derived plasmids, pBTac-derived plasmids and pUC-derived plasmids for expression in prokaryotic cells, such as E. coli.

A number of vectors exist for the expression of recombinant proteins in yeast. For instance, YEP24, YIP5, YEP51, YEP52, pYES2, and YRP17 are cloning and expression vehicles useful in the introduction of genetic constructs into S. cerevisiae (see, for example, Broach et al., (1983) in Experimental Manipulation of Gene Expression, ed. M. Inouye Academic Press, p. 83, incorporated by reference herein). These vectors can replicate in E. coli due the presence of the pBR322 ori, and in S. cerevisiae due to the replication determinant of the yeast 2 micron plasmid. In addition, drug resistance markers such as ampicillin can be used.

The preferred mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. Examples of other viral (including retroviral) expression systems can be found below in the description of gene therapy delivery systems. The various methods employed in the preparation of the plasmids and transformation of host organisms are well known in the art. For other suitable expression systems for both prokaryotic and eukaryotic cells, as well as general recombinant procedures, see Molecular Cloning: A Laboratory Manual, 2nd Ed., ed. by Sambrook, Fritsch and Maniatis (Cold Spring Harbor Laboratory Press, 1989) Chapters 16 and 17. In some instances, it may be desirable to express the recombinant fusion proteins by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

In yet other embodiments, the subject expression constructs are derived by insertion of the subject gene into viral vectors including recombinant retroviruses, adenovirus, adeno-associated virus, and herpes simplex virus-1, or recombinant bacterial or eukaryotic plasmids. As described in greater detail below, such embodiments of the subject expression constructs are specifically contemplated for use in various in vivo and ex vivo gene therapy protocols.

Retrovirus vectors and adeno-associated virus vectors are generally understood to be the recombinant gene delivery system of choice for the transfer of exogenous genes in vivo, particularly into humans. These vectors provide efficient delivery of genes into cells, and the transferred nucleic acids are stably integrated into the chromosomal DNA of the host. A major prerequisite for the use of retroviruses is to ensure the safety of their use, particularly with regard to the possibility of the spread of wild-type virus in the cell population. The development of specialized cell lines (termed "packaging cells") which produce only replication-defective retroviruses has increased the utility of retroviruses for gene therapy, and defective retroviruses are well characterized for use in gene transfer for gene therapy purposes (for a review see Miller, A. D. (1990) Blood 76:271). Thus, recombinant retrovirus can be constructed in which part of the retroviral coding sequence (gag, pol, env) has been replaced by nucleic acid encoding a fusion protein of the present invention, e.g., a composite activator, rendering the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in Current Protocols in Molecular Biology, Ausubel, F. M. et al., (eds.) Greene Publishing Associates, (1989), Sections 9.10–9.14 and other standard laboratory manuals. Examples of suitable retroviruses include pLJ, pZIP, pWE and pEM which are well known to those skilled in the art. Examples of suitable packaging virus lines for preparing both ecotropic and amphotropic retroviral systems include ÿCrip, ÿCre, ÿ2 and ÿAm. Retroviruses have been used to introduce a variety of genes into many different cell types, including neural cells, epithelial cells, endothelial cells, lymphocytes, myoblasts, hepatocytes, bone marrow cells, in vitro and/or in vivo (see for example Eglitis et al., (1985) Science 230:1395–1398; Danos and Mulligan, (1988) PNAS USA 85:6460–6464; Wilson et al., (1988) PNAS USA 85:3014–3018; Armentano et al., (1990) PNAS USA 87:6141–6145; Huber et al., (1991) PNAS USA 88:8039–8043; Ferry et al., (1991) PNAS USA 88:8377–8381; Chowdhury et al., (1991) Science 254:1802–1805; van Beusechem et al., (1992) PNAS USA 89:7640–7644; Kay et al., (1992) Human Gene Therapy 3:641–647; Dai et al., (1992) PNAS USA 89:10892–10895; Hwu et al., (1993) J. Immunol. 150:4104–4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

Furthermore, it has been shown that it is possible to limit the infection spectrum of retroviruses and consequently of retroviral-based vectors, by modifying the viral packaging proteins on the surface of the viral particle (see, for example PCT publications WO93/25234, WO94/06920, and WO94/11524). For instance, strategies for the modification of the infection spectrum of retroviral vectors include: coupling antibodies specific for cell surface antigens to the viral env protein (Roux et al., (1989) PNAS USA 86:9079–9083; Julan et al., (1992) J. Gen Virol 73:3251–3255; and Goud et al., (1983) Virology 163:251–254); or coupling cell surface ligands to the viral env proteins (Neda et al., (1991) J. Biol. Chem. 266:14143–14146). Coupling can be in the form of the chemical cross-linking with a protein or other variety (e.g. lactose to convert the env protein to an asialoglycoprotein), as well as by generating fusion proteins (e.g. single-chain antibody/env fusion proteins). This technique, while useful to limit or otherwise direct the infection to certain tissue types, and can also be used to convert an ecotropic vector in to an amphotropic vector.

Another viral gene delivery system useful in the present invention utilizes adenovirus-derived vectors. The genome of an adenovirus can be manipulated such that it encodes a gene product of interest, but is inactivate in terms of its ability to replicate in a normal lytic viral life cycle (see, for example, Berkner et al., (1988) BioTechniques 6:616; Rosenfeld et al., (1991) Science 252:431–434; and Rosenfeld et al., (1992) Cell 68:143–155). Suitable adenoviral vectors derived from the adenovirus strain Ad type 5 d1324 or other strains of adenovirus (e.g., Ad2, Ad3, Ad7 etc.) are well known to those skilled in the art. Recombinant adenoviruses can be advantageous in certain circumstances in that they are not capable of infecting nondividing cells and can be used to infect a wide variety of cell types, including airway epithelium (Rosenfeld et al., (1992) cited supra), endothelial cells (Lemarchand et al., (1992) PNAS USA 89:6482–6486), hepatocytes (Herz and Gerard, (1993) PNAS USA 90:2812–2816) and muscle cells (Quantin et al., (1992) PNAS USA 89:2581–2584). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al., supra; Haj-Ahmand and Graham (1986) J. Virol. 57:267). Most replication-defective adenoviral vectors currently in use and therefore favored by the present invention are deleted for all or parts of the viral E1 and E3 genes but retain as much as 80% of the adenoviral genetic material (see, e.g., Jones et al., (1979) Cell 16:683; Berkner et al., supra; and Graham et al., in Methods in Molecular Biology, E. J. Murray, Ed. (Humana, Clifton, N.J., 1991) vol. 7. pp. 109–127). Expression of the inserted chimeric gene can be under control of, for example, the E1A promoter, the major late promoter (MLP) and associated leader sequences, the viral E3 promoter, or exogenously added promoter sequences.

Yet another viral vector system useful for delivery of the subject chimeric genes is the adeno-associated virus (AAV). Adeno-associated virus is a naturally occurring defective virus that requires another virus, such as an adenovirus or a herpes virus, as a helper virus for efficient replication and a productive life cycle. (For a review, see Muzyczka et al., Curr. Topics in Micro. and Immunol. (1992) 158:97–129). It is also one of the few viruses that may integrate its DNA into non-dividing cells, and exhibits a high frequency of stable integration (see for example Flotte et al., (1992) Am. J. Respir. Cell. Mol. Biol. 7:349–356; Samulskio et al., (1989) J. Virol. 63:3822–3828; and McLaughlin et al., (1989) J. Virol. 62:1963–1973). Vectors containing as little as 300 base pairs of AAV can be packaged and can integrate. Space for exogenous DNA is limited to about 4.5 kb. An AAV vector such as that described in Tratschin et al., (1985) Mol.

Cell. Biol. 5:3251–3260 can be used to introduce DNA into cells. A variety of nucleic acids have been introduced into different cell types using AAV vectors (see for example Hermonat et al., (1984) PNAS USA 81:6466–6470; Tratschin et al., (1985) Mol. Cell. Biol. 4:2072–2081; Wondisford et al., (1988) Mol. Endocrinol. 2:32–39; Tratschin et al., (1984) J. Virol. 51:611–619; and Flotte et al., (1993) J. Biol. Chem. 268:3781–3790).

Other viral vector systems that may have application in gene therapy have been derived from herpes virus, vaccinia virus, and several RNA viruses. In particular, herpes virus vectors may provide a unique strategy for persistence of the recombinant gene in cells of the central nervous system and ocular tissue (Pepose et al., (1994) Invest Ophthalmol Vis Sci 35:2662–2666)

In addition to viral transfer methods, such as those illustrated above, non-viral methods can also be employed to cause expression of a protein in the tissue of an animal. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the gene by the targeted cell. Exemplary gene delivery systems of this type include liposomal derived systems, poly-lysine conjugates, and artificial viral envelopes.

In a representative embodiment, a gene encoding a composite activator can be entrapped in liposomes bearing positive charges on their surface (e.g., lipofectins) and (optionally) which are tagged with antibodies against cell surface antigens of the target tissue (Mizuno et al., (1992) No Shinkei Geka 20:547–551; PCT publication WO91/06309; Japanese patent application 1047381; and European patent publication EP-A-43075). For example, lipofection of neuroglioma cells can be carried out using liposomes tagged with monoclonal antibodies against glioma-associated antigen (Mizuno et al., (1992) Neurol. Med. Chir. 32:873–876).

In yet another illustrative embodiment, the gene delivery system comprises an antibody or cell surface ligand which is cross-linked with a gene binding agent such as poly-lysine (see, for example, PCT publications WO93/04701, WO92/22635, WO92/20316, WO92/19749, and WO92/06180). For example, any of the subject gene constructs can be used to transfect specific cells in vivo using a soluble polynucleotide carrier comprising an antibody conjugated to a polycation, e.g. poly-lysine (see U.S. Pat. No. 5,166,320). It will also be appreciated that effective delivery of the subject nucleic acid constructs via-mediated endocytosis can be improved using agents which enhance escape of the gene from the endosomal structures. For instance, whole adenovirus or fusogenic peptides of the influenza HA gene product can be used as part of the delivery system to induce efficient disruption of DNA-containing endosomes (Mulligan et al., (1993) Science 260–926; Wagner et al., (1992) PNAS USA 89:7934; and Christiano et al., (1993) PNAS USA 90:2122).

In clinical settings, the gene delivery systems can be introduced into a patient by any of a number of methods, each of which is familiar in the art.

For instance, a pharmaceutical preparation of the gene delivery system can be introduced systemically, e.g. by intravenous injection, and specific transduction of the construct in the target cells occurs predominantly from specificity of transfection provided by the gene delivery vehicle, cell-type or tissue-type expression due to the transcriptional regulatory sequences controlling expression of the gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g. Chen et al., (1994) PNAS USA 91: 3054–3057).

In some embodiments of the invention, the target gene to be regulated by the regulatable F-box protein is an endogenous gene, which contains an exogenous regulatable F-box protein sequence. The exogenous regulatable F-box protein sequence can be inserted into the endogenous gene's coding sequence. In certain embodiments, the endogenous target gene is a DNA binding protein, capable of binding with high affinity and specificity to a target sequence. In a preferred embodiment, the DNA binding protein is human. However, the DNA binding protein can be from any other species. For example, the DNA binding protein can be from the yeast GAL4 protein.

In other embodiments, the target gene to be regulated by the regulatable F-box protein is an exogenous gene. In some embodiments, the exogenous gene is integrated into the chromosomal DNA of a cell. The exogenous gene can be inserted into the chromosomal DNA, or the exogenous gene can substitute for at least a portion of an endogenous gene. Alternatively, the exogenous gene can be present on an extrachromosomal DNA element, such as a plasmid or a viral vector. The target gene can be present in a single copy or in multiple copies. In view of the experimental results described herein, it is not necessary that the target gene be present in more than one copy. However, if even higher levels of protein encoded by the target gene is desired, multiple copies of the gene can be used.

A wide variety of genes can be employed as the target gene, including genes that encode a therapeutic protein. The target gene can be any sequence of interest which provides a desired phenotype. It can encode a surface membrane protein, a secreted protein, a cytoplasmic protein, or there can be a plurality of target genes encoding different products. The proteins which are expressed, singly or in combination, can involve homing, cytotoxicity, proliferation, immune response, inflammatory response, clotting or dissolving of clots, hormonal regulation, etc. The proteins expressed may be naturally-occurring proteins, mutants of naturally-occurring proteins, unique sequences, or combinations thereof.

Various secreted products include hormones, such as insulin, human growth hormone, glucagon, pituitary releasing factor, ACTH, melanotropin, relaxin, etc.; growth factors, such as EGF, IGF-1, TGF-ÿ, -ÿ, PDGF, G-CSF, M-CSF, GM-CSF, FGF, erythropoietin, thrombopoietin, megakaryocytic stimulating and growth factors, etc.; interleukins, such as IL-1 to -13; TNF-ÿ and -ÿ, etc.; and enzymes and other factors, such as tissue plasminogen activator, members of the complement cascade, perforins, superoxide dismutase, coagulation factors, antithrombin-III, Factor VIIIc, Factor VIIIvW, Factor IX, ÿ-antitrypsin, proteinC, proteinS, endorphins, dynorphin, bone morphogenetic protein, CFTR, etc.

The gene can encode a naturally-occurring surface membrane protein or a protein made so by introduction of an appropriate signal peptide and transmembrane sequence. Various such proteins include homing receptors, e.g. L-selectin (Mel-14), blood-related proteins, particularly having a kringle structure, e.g. Factor VIIIc, Factor VIIIvW, hematopoietic cell markers, e.g. CD3, CD4, CD8, Bcell receptor, TCR subunits ÿ, ÿ, ÿ, ÿ, CD10, CD19, CD28, CD33, CD38, CD41, etc., receptors, such as the interleukin receptors IL-2R, IL-4R, etc., channel proteins, for influx or efflux of ions, e.g. H+, Ca+2, K+, Na+, Cl−, etc., and the like; CFTR, tyrosine activation motif, zap-70, etc.

Proteins may be modified for transport to a vesicle for exocytosis. By adding the sequence from a protein which is directed to vesicles, where the sequence is modified proximal to one or the other terminus, or situated in an analogous position to the protein source, the modified protein will be directed to the Golgi apparatus for packaging in a vesicle. This process in conjunction with the presence of the chimeric proteins for exocytosis allows for rapid transfer of the proteins to the extracellular medium and a relatively high localized concentration.

Also, intracellular proteins can be of interest, such as proteins in metabolic pathways, regulatory proteins, steroid receptors, transcription factors, etc., depending upon the nature of the host cell. Some of the proteins indicated above can also serve as intracellular proteins.

By way of further illustration, in T-cells, one may wish to introduce genes encoding one or both chains of a T-cell receptor. For B-cells, one could provide the heavy and light chains for an immunoglobulin for secretion. For cutaneous cells, e.g. keratinocytes, particularly stem cells keratinocytes, one could provide for protection against infection, by secreting ÿ-, ÿ- or ÿ-interferon, antichemotactic factors, proteases specific for bacterial cell wall proteins, etc.

In addition to providing for expression of a gene having therapeutic value, there will be many situations where one may wish to direct a cell to a particular site. The site can include anatomical sites, such as lymph nodes, mucosal tissue, skin, synovium, lung or other internal organs or functional sites, such as clots, injured sites, sites of surgical manipulation, inflammation, infection, etc. By providing for expression of surface membrane proteins which will direct the host cell to the particular site by providing for binding at the host target site to a naturally-occurring epitope, localized concentrations of a secreted product can be achieved. Proteins of interest include homing receptors, e.g. L-selectin, GMP140, CLAM-1, etc., or addressing, e.g. ELAM-1, PNAd, LNAd, etc., clot binding proteins, or cell surface proteins that respond to localized gradients of chemotactic factors. There are numerous situations where one would wish to direct cells to a particular site, where release of a therapeutic product could be of great value.

For use in gene therapy, the target gene can encode any gene product that is beneficial to a subject. The gene product can be a secreted protein, a membraneous protein, or a cytoplasmic protein. Preferred secreted proteins include growth factors, differentiation factors, cytokines, interleukins, tPA, and erythropoietin. Preferred membraneous proteins include receptors, e.g, growth factor or cytokine receptors or proteins mediating apoptosis, e.g., Fas receptor. Other candidate therapeutic genes are disclosed in PCT/ US93/01617.

In yet another embodiment, a "gene activation" construct which, by homologous recombination with a genomic DNA, alters the transcriptional regulatory sequences of an endogenous gene, can be used to introduce recognition elements for a DNA binding activity of one of the subject engineered proteins. A variety of different formats for the gene activation constructs are available. See, for example, the Transkaryotic Therapies, Inc PCT publications WO93/09222, WO95/31560, WO96/29411, WO95/31560 and WO94/ 12650.

4.8. Kits

This invention further provides kits useful for the foregoing applications. One such kit contains one or more nucleic acids encoding a chimeric polypeptide comprising a target polypeptide which encodes a bioactivity and a regulatable F-box protein, which is inserted into the target polypeptide. The kit may further comprise an additional nucleic acids such as specialized vectors which contain a cloning site for insertion of a desired target gene by the practitioner. For example, a preferred kit would contain a cloning site comprising at least one restriction site for insertion of an N-Target polypeptide of a target polypeptide, which is supplied by the user of the kit. In preferred embodiments, the cloning site is a polylinker. In preferred embodiments, this N-Target polypeptide cloning site is followed by a regulatable F-box protein sequence. In particularly preferred embodiments, the N-Target polypeptide cloning site of the vector is made available to the user in all three possible reading frames by supplying three different versions of the vector corresponding to single nucleotide insertions at the cloning site so that an in-frame fusion of the N-Target polypeptide to the regulatable F-box protein occurs. In preferred embodiments, the regulatable F-box protein sequence is further followed by a cloning site for a C-Target polypeptide element of the target sequence, which target may be supplied by the user. In still more preferred embodiments, versions of the vector corresponding to all three possible reading frames between the regulatable F-box protein and the C-target polypeptide are made available to the user. For regulatable applications, i.e., in cases in which the recombinant protein contains a ligand binding domain or inducible domain, the kit may further contain an oligomerizing agent, such as the macrolide dimerizers discussed above. Such kits may for example contain a sample of a dimerizing agent capable of dimerizing the two recombinant proteins and activating transcription of the target.

Constructs may be designed in accordance with the principles, illustrative examples and materials and methods disclosed in the patent documents and scientific literature cited herein, each of which is incorporated herein by reference, with modifications and further exemplification as described herein. Components of the constructs can be prepared in conventional ways, where the coding sequences and regulatory regions may be isolated, as appropriate, ligated, cloned in an appropriate cloning host, analyzed by restriction or sequencing, or other convenient means. Particularly, using PCR, individual fragments including all or portions of a functional unit may be isolated, where one or more mutations may be introduced using "primer repair", ligation, in vitro mutagenesis, etc. as appropriate. In the case of DNA constructs encoding chimeric proteins, DNA sequences encoding individual domains and sub-domains are joined such that they constitute a single open reading frame encoding a chimeric protein capable of being translated in cells or cell lysates into a single polypeptide harboring all component domains. The DNA construct encoding the chimeric protein may then be placed into a vector that directs the expression of the protein in the appropriate cell type(s). For biochemical analysis of the encoded chimera, it may be desirable to construct plasmids that direct the expression of the protein in bacteria or in reticulocyte-lysate systems. For use in the production of proteins in mammalian cells, the protein-encoding sequence is introduced into an expression vector that directs expression in these cells. Expression vectors suitable for such uses are well known in the art. Various sorts of such vectors are commercially available.

4.9. Transgenic Organisms

The invention provides transgenic plants and animals which carry one or more F-box protein modified target genes which can be regulated. These transgenic organisms can be generated with the nucleic acid target gene:F-box protein hybrids of the invention. For example, the invention further provides for transgenic animals, which can be used for a variety of purposes, e.g., to study the function of a target gene. The transgenic animals of the invention can be animals expressing a transgene encoding a target:F-box protein hybrid protein or fragment thereof or variants thereof, including mutants and polymorphic variants thereof. These animals can be used to determine the effect of expression of a target gene protein in a specific site or in a specific temporal window. In one aspect, the invention features a cell or cell line, which contains a knock-in of an F-box protein which has been inserted into a particular target gene. In a preferred embodiment, the cell or cell line is an undifferentiated cell, for example, a stem cell, embryonic stem cell, oocyte or embryonic cell.

Yet in a further aspect, the invention features a method of producing a non-human mammal with a targeted disruption in an interleukin-1 gene. For example, a target gene knock-in construct can be created with a portion of the target gene having an internal portion of said target gene replaced by a marker. The knock-out construct can then be transfected into a population of embryonic stem m(ES) cells. Transfected cells can then be selected as expressing the marker. The transfected ES cells can then be introduced into an embryo of an ancestor of said mammal. The embryo can be allowed to develop to term to produce a chimeric mammal with the knock-out construct in its germline. Breeding said chimeric mammal will produce a heterozygous mammal with a targeted disruption in the target gene. Homozygotes can be generated by crossing heterozygotes.

In another aspect, the invention features target knock-out constructs, which can be used to generate the animals described above. In one embodiment, the target construct can comprise a portion of the target gene, wherein an internal portion of said target gene is replaced by a selectable marker. Preferably, the marker is the neo gene and the portion of the target gene is at least 2.5 kb long or 7.0 or 9.5 kb long (including the replaced portion and any target flanking sequences). The internal portion preferably covers at least a portion of an exon and in some embodiments it covers all of the exons which encode an target polypeptide.

Yet other non-human animals within the scope of the invention include those in which the expression of the endogenous Target gene has been mutated or "knocked out". A "knock out" animal is one carrying a homozygous or heterozygous deletion of a particular gene or genes. These animals could be useful to determine whether the absence of the target polypeptide will result in a specific phenotype, in particular whether these mice have or are likely to develop a specific disease, such as high susceptibility to heart disease or cancer. Furthermore these animals are useful in screens for drugs which alleviate or attenuate the disease condition resulting from the mutation of the target gene as outlined below. These animals are also useful for determining the effect of a specific amino acid difference, or allelic variation, in a target gene.

In a preferred embodiment of this aspect of the invention, a transgenic target gene knock-in mouse, carrying the mutated target locus on one or both of its chromosomes, is used as a model system for transgenic or drug treatment of the condition resulting from loss of target gene expression.

Methods for obtaining transgenic and knockout non-human animals are well known in the art. Knock out mice are generated by homologous integration of a "knock out" construct into a mouse embryonic stem cell chromosome which encodes the gene to be knocked out. In one embodiment, gene targeting, which is a method of using homologous recombination to modify an animal's genome, can be used to introduce changes into cultured embryonic stem cells. By targeting a specific gene of interest in ES cells, these changes can be introduced into the germlines of animals to generate chimeras. The gene targeting procedure is accomplished by introducing into tissue culture cells a DNA targeting construct that includes a segment homologous to a target locus, and which also includes an intended sequence modification to the target genomic sequence (e.g., insertion, deletion, point mutation). The treated cells are then screened for accurate targeting to identify and isolate those which have been properly targeted.

Gene targeting in embryonic stem cells is in fact a scheme contemplated by the present invention as a means for disrupting a target gene function through the use of a targeting transgene construct designed to undergo homologous recombination with one or more target genomic sequences. The targeting construct can be arranged so that, upon recombination with an element of at gene, a positive selection marker is inserted into (or replaces) coding sequences of the gene. The inserted sequence functionally disrupts the target gene, while also providing a positive selection trait. Exemplary targeting constructs are described in more detail below.

Generally, the embryonic stem cells (ES cells) used to produce the knockout animals will be of the same species as the knockout animal to be generated. Thus for example, mouse embryonic stem cells will usually be used for generation of knockout mice.

Embryonic stem cells are generated and maintained using methods well known to the skilled artisan such as those described by Doetschman et al. (1985) J. Embryol. Exp. MoIBRhol. 87:27–45). Any line of ES cells can be used, however, the line chosen is typically selected for the ability of the cells to integrate into and become part of the germ line of a developing embryo so as to create germ line transmission of the knockout construct. Thus, any ES cell line that is believed to have this capability is suitable for use herein. One mouse strain that is typically used for production of ES cells, is the 129J strain. Another ES cell line is murine cell line D3 (American Type Culture Collection, catalog no. CKL 1934) Still another preferred ES cell line is the WW6 cell line (Ioffe et al. (1995) PNAS 92:7357–7361). The cells are cultured and prepared for knockout construct insertion using methods well known to the skilled artisan, such as those set forth by Robertson in: Teratocarcinomas and Embryonic Stem Cells: A Practical Approach, E. J. Robertson, ed. IRL Press, Washington, D.C. [1987]); by Bradley et al. (1986) Current Topics in Devel. Biol. 20:357–371); and by Hogan et al. (Manipulating the Mouse Embryo: A Laboratory Manual, Cold Spring Harbor Laboratory Press, Cold Spring Harbor, N.Y. [1986]).

A knock out construct refers to a uniquely configured fragment of nucleic acid which is introduced into a stem cell line and allowed to recombine with the genome at the chromosomal locus of the gene of interest to be mutated. Thus a given knock out construct is specific for a given gene to be targeted for disruption. Nonetheless, many common elements exist among these constructs and these elements are well known in the art. A typical knock out construct contains nucleic acid fragments of not less than about 0.5 kb nor more than about 10.0 kb from both the 5' and the 3' ends of the genomic locus which encodes the gene to be mutated. These two fragments are separated by an intervening fragment of nucleic acid which encodes a positive selectable marker, such as the neomycin resistance gene ($neo^R$). The resulting nucleic acid fragment, consisting of a nucleic acid from the extreme 5' end of the genomic locus linked to a nucleic acid encoding a positive selectable marker which is in turn linked to a nucleic acid from the extreme 3' end of the genomic locus of interest, omits most of the coding sequence for target or other gene of interest to be knocked out. When the resulting construct recombines homologously with the chromosome at this locus, it results in the loss of the omitted coding sequence, otherwise known as the structural gene, from the genomic locus. A stem cell in which such a rare homologous recombination event has taken place can be selected for by virtue of the stable integration into the genome of the nucleic acid of the gene encoding the positive selectable marker and subsequent selection for cells expressing this marker gene in the presence of an appropriate drug (neomycin in this example).

Variations on this basic technique also exist and are well known in the art. For example, a "knock-in" construct refers to the same basic arrangement of a nucleic acid encoding a 5' genomic locus fragment linked to nucleic acid encoding a positive selectable marker which in turn is linked to a nucleic acid encoding a 3' genomic locus fragment, but which differs in that none of the coding sequence is omitted and thus the 5' and the 3' genomic fragments used were initially contiguous before being disrupted by the introduction of the nucleic acid encoding the positive selectable marker gene. This "knock-in" type of construct is thus very useful for the construction of mutant transgenic animals when only a limited region of the genomic locus of the gene to be mutated, such as a single exon, is available for cloning and genetic manipulation. Alternatively, the "knock-in" construct can be used to specifically eliminate a single functional domain of the targeted gene, resulting in a transgenic animal which expresses a polypeptide of the targeted gene which is defective in one function, while retaining the function of other domains of the encoded polypeptide. This type of "knock-in" mutant frequently has the characteristic of a so-called "dominant negative" mutant because, especially in the case of proteins which homomultimerize, it can specifically block the action of (or "poison") the polypeptide product of the wild-type gene from which it was derived. In a variation of the knock-in technique, a marker gene is integrated at the genomic locus of interest such that expression of the marker gene comes under the control of the transcriptional regulatory elements of the targeted gene. A marker gene is one that encodes an enzyme whose activity can be detected (e.g., b-galactosidase), the enzyme substrate can be added to the cells under suitable conditions, and the enzymatic activity can be analyzed. One skilled in the art will be familiar with other useful markers and the means for detecting their presence in a given cell. All such markers are contemplated as being included within the scope of the teaching of this invention.

As mentioned above, the homologous recombination of the above described "knock out" and "knock in" constructs is very rare and frequently such a construct inserts nonhomologously into a random region of the genome where it has no effect on the gene which has been targeted for deletion, and where it can potentially recombine so as to disrupt another gene which was otherwise not intended to be altered. Such nonhomologous recombination events can be selected against by modifying the abovementioned knock out and knock in constructs so that they are flanked by negative selectable markers at either end (particularly through the use of two allelic variants of the thymidine kinase gene, the polypeptide product of which can be selected against in expressing cell lines in an appropriate tissue culture medium well known in the art—i.e. one containing a drug such as 5-bromodeoxyuridine). Thus a preferred embodiment of such a knock out or knock in construct of the invention consist of a nucleic acid encoding a negative selectable marker linked to a nucleic acid encoding a 5' end of a genomic locus linked to a nucleic acid of a positive selectable marker which in turn is linked to a nucleic acid encoding a 3' end of the same genomic locus which in turn is linked to a second nucleic acid encoding a negative selectable marker Nonhomologous recombination between the resulting knock out construct and the genome will usually result in the stable integration of one or both of these negative selectable marker genes and hence cells which have undergone nonhomologous recombination can be selected against by growth in the appropriate selective media (e.g. media containing a drug such as 5-bromodeoxyuridine for example). Simultaneous selection for the positive selectable marker and against the negative selectable marker will result in a vast enrichment for clones in which the knock out construct has recombined homologously at the locus of the gene intended to be mutated. The presence of the predicted chromosomal alteration at the targeted gene locus in the resulting knock out stem cell line can be confirmed by means of Southern blot analytical techniques which are well known to those familiar in the art. Alternatively, PCR can be used.

Each knockout construct to be inserted into the cell must first be in the linear form. Therefore, if the knockout construct has been inserted into a vector (described infra), linearization is accomplished by digesting the DNA with a suitable restriction endonuclease selected to cut only within the vector sequence and not within the knockout construct sequence.

For insertion, the knockout construct is added to the ES cells under appropriate conditions for the insertion method chosen, as is known to the skilled artisan. For example, if the ES cells are to be electroporated, the ES cells and knockout construct DNA are exposed to an electric pulse using an electroporation machine and following the manufacturer's guidelines for use. After electroporation, the ES cells are typically allowed to recover under suitable incubation conditions. The cells are then screened for the presence of the knock out construct as explained above. Where more than one construct is to be introduced into the ES cell, each knockout construct can be introduced simultaneously or one at a time.

After suitable ES cells containing the knockout construct in the proper location have been identified by the selection techniques outlined above, the cells can be inserted into an embryo. Insertion may be accomplished in a variety of ways known to the skilled artisan, however a preferred method is by microinjection. For microinjection, about 10–30 cells are collected into a micropipet and injected into embryos that are at the proper stage of development to permit integration of the foreign ES cell containing the knockout construct into the developing embryo. For instance, the transformed ES cells can be microinjected into blastocytes. The suitable stage of development for the embryo used for insertion of ES cells is very species dependent, however for mice it is about 3.5 days. The embryos are obtained by perfusing the uterus of pregnant females. Suitable methods for accomplishing this are known to the skilled artisan, and are set forth by, e.g., Bradley et al. (supra).

While any embryo of the right stage of development is suitable for use, preferred embryos are male. In mice, the preferred embryos also have genes coding for a coat color that is different from the coat color encoded by the ES cell genes. In this way, the offspring can be screened easily for the presence of the knockout construct by looking for mosaic coat color (indicating that the ES cell was incorporated into the developing embryo). Thus, for example, if the ES cell line carries the genes for white fur, the embryo selected will carry genes for black or brown fur.

After the ES cell has been introduced into the embryo, the embryo may be implanted into the uterus of a pseudopregnant foster mother for gestation. While any foster mother may be used, the foster mother is typically selected for her ability to breed and reproduce well, and for her ability to care for the young. Such foster mothers are typically prepared by mating with vasectomized males of the same species. The stage of the pseudopregnant foster mother is important for successful implantation, and it is species dependent. For mice, this stage is about 2–3 days pseudopregnant.

Offspring that are born to the foster mother may be screened initially for mosaic coat color where the coat color selection strategy (as described above, and in the appended examples) has been employed. In addition, or as an alternative, DNA from tail tissue of the offspring may be screened for the presence of the knockout construct using Southern blots and/or PCR as described above. Offspring that appear to be mosaics may then be crossed to each other, if they are believed to carry the knockout construct in their germ line, in order to generate homozygous knockout animals. Homozygotes may be identified by Southern blotting of equivalent amounts of genomic DNA from mice that are the product of this cross, as well as mice that are known heterozygotes and wild type mice.

Other means of identifying and characterizing the knockout offspring are available. For example, Northern blots can be used to probe the mRNA for the presence or absence of transcripts encoding either the gene knocked out, the marker gene, or both. In addition, Western blots can be used to assess the level of expression of the target gene knocked out in various tissues of the offspring by probing the Western blot with an antibody against the particular target protein, or an antibody against the marker gene product, where this gene is expressed. Finally, in situ analysis (such as fixing the cells and labeling with antibody) and/or FACS (fluorescence activated cell sorting) analysis of various cells from the offspring can be conducted using suitable antibodies to look for the presence or absence of the knockout construct gene product.

Yet other methods of making knock-out or disruption transgenic animals are also generally known. See, for example, Manipulating the Mouse Embryo, (Cold Spring Harbor Laboratory Press, Cold Spring Harbor, N.Y., 1986). Recombinase dependent knockouts can also be generated, e.g. by homologous recombination to insert target sequences, such that tissue specific and/or temporal control of inactivation of a Target-gene can be controlled by recombinase sequences (described infra).

Animals containing more than one knockout construct and/or more than one transgene expression construct are prepared in any of several ways. The preferred manner of preparation is to generate a series of mammals, each containing one of the desired transgenic phenotypes. Such animals are bred together through a series of crosses, backcrosses and selections, to ultimately generate a single animal containing all desired knockout constructs and/or expression constructs, where the animal is otherwise congenic (genetically identical) to the wild type except for the presence of the knockout construct(s) and/or transgene(s).

A targeted transgene can encode the wild-type form of the protein, or can encode homologs thereof, including both agonists and antagonists, as well as antisense constructs. In preferred embodiments, the expression of the transgene is restricted to specific subsets of cells, tissues or developmental stages utilizing, for example, cis-acting sequences that control expression in the desired pattern. In the present invention, such mosaic expression of a target protein can be essential for many forms of lineage analysis and can additionally provide a means to assess the effects of, for example, lack of target gene expression which might grossly alter development in small patches of tissue within an otherwise normal embryo. Toward this and, tissue-specific regulatory sequences and conditional regulatory sequences can be used to control expression of the transgene in certain spatial patterns. Moreover, temporal patterns of expression can be provided by, for example, conditional recombination systems or prokaryotic transcriptional regulatory sequences.

Genetic techniques, which allow for the expression of transgenes can be regulated via site-specific genetic manipulation in vivo, are known to those skilled in the art. For instance, genetic systems are available which allow for the regulated expression of a recombinase that catalyzes the genetic recombination of a target sequence. As used herein, the phrase "target sequence" refers to a nucleotide sequence that is genetically recombined by a recombinase. The target sequence is flanked by recombinase recognition sequences and is generally either excised or inverted in cells expressing recombinase activity. Recombinase catalyzed recombination events can be designed such that recombination of the target sequence results in either the activation or repression of expression of one of the subject target proteins. For example, excision of a target sequence which interferes with the expression of a recombinant target gene, such as one which encodes an antagonistic homolog or an antisense transcript, can be designed to activate expression of that gene. This interference with expression of the protein can result from a variety of mechanisms, such as spatial separation of the target gene from the promoter element or an internal stop codon. Moreover, the transgene can be made wherein the coding sequence of the gene is flanked by recombinase recognition sequences and is initially transfected into cells in a 3' to 5' orientation with respect to the promoter element. In such an instance, inversion of the target sequence will reorient the subject gene by placing the 5' end of the coding sequence in an orientation with respect to the promoter element which allow for promoter driven transcriptional activation.

The transgenic animals of the present invention all include within a plurality of their cells a transgene of the present invention, which transgene alters the phenotype of the "host cell" with respect to regulation of cell growth, death and/or differentiation. Since it is possible to produce transgenic organisms of the invention utilizing one or more of the transgene constructs described herein, a general description will be given of the production of transgenic organisms by referring generally to exogenous genetic material. This general description can be adapted by those skilled in the art in order to incorporate specific transgene sequences into organisms utilizing the methods and materials described below.

In an illustrative embodiment, either the cre/loxP recombinase system of bacteriophage P1 (Lakso et al. (1992) PNAS 89:6232–6236; Orban et al. (1992) PNAS 89:6861–6865) or the FLP recombinase system of Saccharomyces cerevisiae (O'Gorman et al. (1991) Science 251: 1351–1355; PCT publication WO 92/15694) can be used to generate in vivo site-specific genetic recombination systems. Cre recombinase catalyzes the site-specific recombination of an intervening target sequence located between loxP sequences. loxP sequences are 34 base pair nucleotide repeat sequences to which the Cre recombinase binds and are required for Cre recombinase mediated genetic recombination. The orientation of loxP sequences determines whether the intervening target sequence is excised or inverted when Cre recombinase is present (Abremski et al. (1984) J. Biol. Chem. 259:1509–1514); catalyzing the excision of the target sequence when the loxP sequences are oriented as direct repeats and catalyzes inversion of the target sequence when loxP sequences are oriented as inverted repeats.

Accordingly, genetic recombination of the target sequence is dependent on expression of the Cre recombinase. Expression of the recombinase can be regulated by promoter elements which are subject to regulatory control, e.g., tissue-specific, developmental stage-specific, inducible or repressible by externally added agents. This regulated control will result in genetic recombination of the target sequence only in cells where recombinase expression is mediated by the promoter element. Thus, the activation expression of a recombinant target protein can be regulated via control of recombinase expression.

Use of the cre/loxP recombinase system to regulate expression of a recombinant target protein requires the construction of a transgenic animal containing transgenes encoding both the Cre recombinase and the subject protein. Animals containing both the Cre recombinase and a recombinant target gene can be provided through the construction of "double" transgenic animals. A convenient method for providing such animals is to mate two transgenic animals each containing a transgene, e.g., a target gene and recombinase gene.

One advantage derived from initially constructing transgenic animals containing a target transgene in a recombinase-mediated expressible format derives from the likelihood that the subject protein, whether agonistic or antagonistic, can be deleterious upon expression in the transgenic animal. In such an instance, a founder population, in which the subject transgene is silent in all tissues, can be propagated and maintained. Individuals of this founder population can be crossed with animals expressing the recombinase in, for example, one or more tissues and/or a desired temporal pattern. Thus, the creation of a founder population in which, for example, an antagonistic target transgene is silent will allow the study of progeny from that founder in which disruption of target mediated induction in a particular tissue or at certain developmental stages would result in, for example, a lethal phenotype.

Similar conditional transgenes can be provided using prokaryotic promoter sequences which require prokaryotic proteins to be simultaneous expressed in order to facilitate expression of the target transgene. Exemplary promoters and the corresponding trans-activating prokaryotic proteins are given in U.S. Pat. No. 4,833,080.

Moreover, expression of the conditional transgenes can be induced by gene therapy-like methods wherein a gene encoding the trans-activating protein, e.g. a recombinase or a prokaryotic protein, is delivered to the tissue and caused to be expressed, such as in a cell-type specific manner. By this method, a target gene:F-box protein transgene could remain silent into adulthood until "turned on" by the introduction of the trans-activator.

In an exemplary embodiment, the "transgenic non-human animals" of the invention are produced by introducing transgenes into the germline of the non-human animal. Embryonal target cells at various developmental stages can be used to introduce transgenes. Different methods are used depending on the stage of development of the embryonal target cell. The specific line(s) of any animal used to practice this invention are selected for general good health, good embryo yields, good pronuclear visibility in the embryo, and good reproductive fitness. In addition, the haplotype is a significant factor. For example, when transgenic mice are to be produced, strains such as C57BL/6 or FVB lines are often used (Jackson Laboratory, Bar Harbor, Me.). Preferred strains are those with $H-2^b$, $H-2^d$ or $H-2^q$ haplotypes such as C57BL/6 or DBA/1. The line(s) used to practice this invention may themselves be transgenics, and/or may be knockouts (i.e., obtained from animals which have one or more genes partially or completely suppressed). In one embodiment, the transgene construct is introduced into a single stage embryo. The zygote is the best target for microinjection. In the mouse, the male pronucleus reaches the size of approximately 20 micrometers in diameter which allows reproducible injection of 1–2 pl of DNA solution. The use of zygotes as a target for gene transfer has a major advantage in that in most cases the injected DNA will be incorporated into the host gene before the first cleavage (Brinster et al. (1985) PNAS 82:4438–4442). As a consequence, all cells of the transgenic animal will carry the incorporated transgene. This will in general also be reflected in the efficient transmission of the transgene to offspring of the founder since 50% of the germ cells will harbor the transgene.

Normally, fertilized embryos are incubated in suitable media until the pronuclei appear. At about this time, the nucleotide sequence comprising the transgene is introduced into the female or male pronucleus as described below. In some species such as mice, the male pronucleus is preferred. It is most preferred that the exogenous genetic material be added to the male DNA complement of the zygote prior to its being processed by the ovum nucleus or the zygote female pronucleus. It is thought that the ovum nucleus or female pronucleus release molecules which affect the male DNA complement, perhaps by replacing the protamines of the male DNA with histones, thereby facilitating the combination of the female and male DNA complements to form the diploid zygote.

Thus, it is preferred that the exogenous genetic material be added to the male complement of DNA or any other complement of DNA prior to its being affected by the female pronucleus. For example, the exogenous genetic material is added to the early male pronucleus, as soon as possible after the formation of the male pronucleus, which is when the male and female pronuclei are well separated and both are located close to the cell membrane. Alternatively, the exogenous genetic material could be added to the nucleus of the sperm after it has been induced to undergo decondensation. Sperm containing the exogenous genetic material can then be added to the ovum or the decondensed sperm could be added to the ovum with the transgene constructs being added as soon as possible thereafter.

Introduction of the transgene nucleotide sequence into the embryo may be accomplished by any means known in the art such as, for example, microinjection, electroporation, or lipofection. Following introduction of the transgene nucleotide sequence into the embryo, the embryo may be incubated in vitro for varying amounts of time, or reimplanted into the surrogate host, or both. In vitro incubation to maturity is within the scope of this invention. One common method in to incubate the embryos in vitro for about 1–7 days, depending on the species, and then reimplant them into the surrogate host.

For the purposes of this invention a zygote is essentially the formation of a diploid cell which is capable of developing into a complete organism. Generally, the zygote will be comprised of an egg containing a nucleus formed, either naturally or artificially, by the fusion of two haploid nuclei from a gamete or gametes. Thus, the gamete nuclei must be ones which are naturally compatible, i.e., ones which result in a viable zygote capable of undergoing differentiation and developing into a functioning organism. Generally, a euploid zygote is preferred. If an aneuploid zygote is obtained, then the number of chromosomes should not vary by more than one with respect to the euploid number of the organism from which either gamete originated.

In addition to similar biological considerations, physical ones also govern the amount (e.g., volume) of exogenous genetic material which can be added to the nucleus of the zygote or to the genetic material which forms a part of the zygote nucleus. If no genetic material is removed, then the amount of exogenous genetic material which can be added is limited by the amount which will be absorbed without being physically disruptive. Generally, the volume of exogenous genetic material inserted will not exceed about 10 picoliters. The physical effects of addition must not be so great as to physically destroy the viability of the zygote. The biological limit of the number and variety of DNA sequences will vary depending upon the particular zygote and functions of the exogenous genetic material and will be readily apparent to one skilled in the art, because the genetic material, including the exogenous genetic material, of the resulting zygote must be biologically capable of initiating and maintaining the differentiation and development of the zygote into a functional organism.

The number of copies of the transgene constructs which are added to the zygote is dependent upon the total amount of exogenous genetic material added and will be the amount which enables the genetic transformation to occur. Theoretically only one copy is required; however, generally, numerous copies are utilized, for example, 1,000–20,000 copies of the transgene construct, in order to insure that one copy is functional. As regards the present invention, there will often be an advantage to having more than one functioning copy of each of the inserted exogenous DNA sequences to enhance the phenotypic expression of the exogenous DNA sequences.

Any technique which allows for the addition of the exogenous genetic material into nucleic genetic material can be utilized so long as it is not destructive to the cell, nuclear membrane or other existing cellular or genetic structures. The exogenous genetic material is preferentially inserted into the nucleic genetic material by microinjection. Microinjection of cells and cellular structures is known and is used in the art.

Reimplantation is accomplished using standard methods. Usually, the surrogate host is anesthetized, and the embryos are inserted into the oviduct. The number of embryos implanted into a particular host will vary by species, but will usually be comparable to the number of off spring the species naturally produces.

Transgenic offspring of the surrogate host may be screened for the presence and/or expression of the transgene by any suitable method. Screening is often accomplished by Southern blot or Northern blot analysis, using a probe that is complementary to at least a portion of the transgene. Western blot analysis using an antibody against the protein encoded by the transgene may be employed as an alternative or additional method for screening for the presence of the transgene product. Typically, DNA is prepared from tail tissue and analyzed by Southern analysis or PCR for the transgene. Alternatively, the tissues or cells believed to express the transgene at the highest levels are tested for the presence and expression of the transgene using Southern analysis or PCR, although any tissues or cell types may be used for this analysis.

Alternative or additional methods for evaluating the presence of the transgene include, without limitation, suitable biochemical assays such as enzyme and/or immunological assays, histological stains for particular marker or enzyme activities, flow cytometric analysis, and the like. Analysis of the blood may also be useful to detect the presence of the transgene product in the blood, as well as to evaluate the effect of the transgene on the levels of various types of blood cells and other blood constituents.

Progeny of the transgenic animals may be obtained by mating the transgenic animal with a suitable partner, or by in vitro fertilization of eggs and/or sperm obtained from the transgenic animal. Where mating with a partner is to be performed, the partner may or may not be transgenic and/or a knockout; where it is transgenic, it may contain the same or a different transgene, or both. Alternatively, the partner may be a parental line. Where in vitro fertilization is used, the fertilized embryo may be implanted into a surrogate host or incubated in vitro, or both. Using either method, the progeny may be evaluated for the presence of the transgene using methods described above, or other appropriate methods.

The transgenic animals produced in accordance with the present invention will include exogenous genetic material. As set out above, the exogenous genetic material will, in certain embodiments, be a DNA sequence which results in the production of a target protein (either agonistic or antagonistic), and antisense transcript, or a target mutant. Further, in such embodiments the sequence will be attached to a transcriptional control element, e.g., a promoter, which preferably allows the expression of the transgene product in a specific type of cell.

Retroviral infection can also be used to introduce transgene into a non-human animal. The developing non-human embryo can be cultured in vitro to the blastocyst stage. During this time, the blastomeres can be targets for retroviral infection (Jaenich, R. (1976) PNAS 73:1260–1264). Efficient infection of the blastomeres is obtained by enzymatic treatment to remove the zona pellucida (Manipulating the Mouse Embryo, Hogan eds. (Cold Spring Harbor Laboratory Press, Cold Spring Harbor, 1986). The viral vector system used to introduce the transgene is typically a replication-defective retrovirus carrying the transgene (Jahner et al. (1985) PNAS 82:6927–6931; Van der Putten et al. (1985) PNAS 82:6148–6152). Transfection is easily and efficiently obtained by culturing the blastomeres on a monolayer of virus-producing cells (Van der Putten, supra; Stewart et al. (1987) EMBO J. 6:383–388). Alternatively, infection can be performed at a later stage. Virus or virus-producing cells can be injected into the blastocoele (Jahner et al. (1982) Nature 298:623–628). Most of the founders will be mosaic for the transgene since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line by intrauterine retroviral infection of the midgestation embryo (Jahner et al. (1982) supra).

A third type of target cell for transgene introduction is the embryonal stem cell (ES). ES cells are obtained from pre-implantation embryos cultured in vitro and fused with embryos (Evans et al. (1981) Nature 292:154–156; Bradley et al. (1984) Nature 309:255–258; Gossler et al. (1986) PNAS 83: 9065–9069; and Robertson et al. (1986) Nature 322:445–448). Transgenes can be efficiently introduced into the ES cells by DNA transfection or by retrovirus-mediated transduction. Such transformed ES cells can thereafter be combined with blastocysts from a non-human animal. The ES cells thereafter colonize the embryo and contribute to the germ line of the resulting chimeric animal. For review see Jaenisch, R. (1988) Science 240:1468–1474.

4.11. Cell-Free Assays

Cell-free assays can be used to identify compounds which are capable of interacting with an F-box protein protein or binding partner, to thereby modify the activity of the F-box protein protein or binding partner. Such a compound can, e.g., modify the structure of an F-box protein protein or binding partner and thereby affect its activity. Cell-free assays can also be used to identify compounds which modulate the interaction between an F-box protein protein and an F-box protein binding partner, such as a target peptide. In a preferred embodiment, cell-free assays for identifying such compounds consist essentially in a reaction mixture containing an F-box protein protein and a test compound or a library of test compounds in the presence or absence of a binding partner. A test compound can be, e.g., a derivative of an F-box protein binding partner, e.g., a biologically inactive target peptide, or a small molecule.

Accordingly, one exemplary screening assay of the present invention includes the steps of contacting an F-box protein protein or functional fragment thereof or an F-box protein binding partner with a test compound or library of test compounds and detecting the formation of complexes. For detection purposes, the molecule can be labeled with a specific marker and the test compound or library of test compounds labeled with a different marker. Interaction of a test compound with an F-box protein protein or fragment thereof or F-box protein binding partner can then be detected by determining the level of the two labels after an incubation step and a washing step. The presence of two labels after the washing step is indicative of an interaction.

An interaction between molecules can also be identified by using real-time BIA Biomolecular Interaction Analysis, Pharmacia Biosensor AB) which detects surface plasmon resonance (SPR), an optical phenomenon. Detection depends on changes in the mass concentration of macromolecules at the biospecific interface, and does not require any labeling of interactants. In one embodiment, a library of test compounds can be immobilized on a sensor surface, e.g., which forms one wall of a micro-flow cell. A solution containing the F-box protein protein, functional fragment thereof, F-box protein analog or F-box protein binding partner is then flown continuously over the sensor surface. A change in the resonance angle as shown on a signal recording, indicates that an interaction has occurred. This technique is further described, e.g., in BIAtechnology Handbook by Pharmacia.

Another exemplary screening assay of the present invention includes the steps of (a) forming a reaction mixture including: (i) an F-box protein polypeptide, (ii) an F-box protein binding partner, and (iii) a test compound; and (b) detecting interaction of the F-box protein and the F-box protein binding protein. The F-box protein polypeptide and F-box protein binding partner can be produced recombinantly, purified from a source, e.g., plasma, or chemically synthesized, as described herein. A statistically significant change (potentiation or inhibition) in the interaction of the F-box protein and F-box protein binding protein in the presence of the test compound, relative to the interaction in the absence of the test compound, indicates a potential agonist (mimetic or potentiator) or antagonist (inhibitor) of F-box protein self-excision bioactivity for the test compound. The compounds of this assay can be contacted simultaneously. Alternatively, an F-box protein protein can first be contacted with a test compound for an appropriate amount of time, following which the F-box protein binding partner is added to the reaction mixture. The efficacy of the compound can be assessed by generating dose response curves from data obtained using various concentrations of the test compound. Moreover, a control assay can also be performed to provide a baseline for comparison. In the control assay, isolated and purified F-box protein polypeptide or binding partner is added to a composition containing the F-box protein binding partner or F-box protein polypeptide, and the formation of a complex is quantitated in the absence of the test compound.

Complex formation between an F-box protein protein and an F-box protein binding partner may be detected by a variety of techniques. Modulation of the formation of complexes can be quantitated using, for example, detectably labeled proteins such as radiolabeled, fluorescently labeled, or enzymatically labeled F-box protein proteins or F-box protein binding partners, by immunoassay, or by chromatographic detection.

Typically, it will be desirable to immobilize either the F-box protein or its binding partner to facilitate separation of complexes from uncomplexed forms of one or both of the proteins, as well as to accommodate automation of the assay. Binding of an F-box protein to an F-box protein binding partner, can be accomplished in any vessel suitable for containing the reactants. Examples include microtitre plates, test tubes, and micro-centrifuge tubes. In one embodiment, a fusion protein can be provided which adds a domain that allows the protein to be bound to a matrix. For example, glutathione-S-transferase/F-box protein (GST/F-box protein) fusion proteins can be adsorbed onto glutathione sepharose beads (Sigma Chemical, St. Louis, Mo.) or glutathione derivatized microtitre plates, which are then combined with the F-box protein binding partner, e.g. an $^{35}$S-labeled F-box protein binding partner, and the test compound, and the mixture incubated under conditions conducive to complex formation, e.g. at physiological conditions for salt and pH, though slightly more stringent conditions may be desired. Following incubation, the beads are washed to remove any unbound label, and the matrix immobilized and radiolabel determined directly (e.g. beads placed in scintilant), or in the supernatant after the complexes are subsequently dissociated. Alternatively, the complexes can be dissociated from the matrix, separated by SDS-PAGE, and the level of F-box protein protein or F-box protein binding partner found in the bead fraction quantitated from the gel using standard electrophoretic techniques.

Other techniques for immobilizing proteins on matrices are also available for use in the subject assay. For instance, either the F-box protein or its cognate binding partner can be immobilized utilizing conjugation of biotin and streptavidin. For instance, biotinylated F-box protein molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with an F-box protein can be derivatized to the wells of the plate, and F-box protein trapped in the wells by antibody conjugation. As above, preparations of an F-box protein binding protein and a test compound are incubated in the F-box protein presenting wells of the plate, and the amount of complex trapped in the well can be quantitated. Exemplary methods for detecting such complexes, in addition to those described above for the GST-immobilized complexes, include immunodetection of complexes using antibodies reactive with the F-box protein binding partner, or which are reactive with F-box protein protein and compete with the binding partner; as well as enzyme-linked assays which rely on detecting an enzymatic activity associated with the binding partner, either intrinsic or extrinsic activity. In the instance of the latter, the enzyme can be chemically conjugated or provided as a fusion protein with the F-box protein binding partner. To illustrate, the F-box protein binding partner can be chemically cross-linked or genetically fused with horseradish peroxidase, and the amount of polypeptide trapped in the complex can be assessed with a chromogenic substrate of the enzyme, e.g. 3,3'-diamino-benzadine terahydrochloride or 4-chloro-1-napthol. Likewise, a fusion protein comprising the polypeptide and glutathione-S-transferase can be provided, and complex formation quantitated by detecting the GST activity using 1-chloro-2,4-dinitrobenzene (Habig et al (1974) J Biol Chem 249:7130).

For processes which rely on immunodetection for quantitating one of the proteins trapped in the complex, antibodies against the protein, such as anti-F-box protein antibodies, can be used. Alternatively, the protein to be detected in the complex can be "epitope tagged" in the form of a fusion protein which includes, in addition to the F-box protein sequence, a second polypeptide for which antibodies are readily available (e.g. from commercial sources). For instance, the GST fusion proteins described above can also be used for quantification of binding using antibodies against the GST moiety. Other useful epitope tags include myc-epitopes (e.g., see Ellison et al. (1991) J Biol Chem 266:21150–21157) which includes a 10-residue sequence from c-myc, as well as the pFLAG system (International Biotechnologies, Inc.) or the pEZZ-protein A system (Pharmacia, N.J.).

Cell-free assays can also be used to identify compounds which interact with an F-box protein protein and modulate an activity of an F-box protein protein. Accordingly, in one embodiment, an F-box protein protein is contacted with a test compound and the catalytic activity of F-box protein is monitored. In one embodiment, the ability of the F-box protein to bind a target molecule is determined. The binding affinity of the F-box protein to a target molecule can be determined according to methods known in the art.

4.12. Cell Based Assays

The invention further provides certain cell-based assays for the identification of F-box protein modulating agents which agonize or antagonize the self-excision activity of a wild type or conditional mutant F-box protein. In one embodiment, the effect of a test compound on the expression of an F-box protein-containing gene is determined by transfection experiments using a reporter gene comprising a conveniently assayed marker into which has been inserted the subject F-box protein polypeptide sequence. The reporter gene can be any gene encoding a protein which is readily quantifiable, e.g. the luciferase or CAT gene. Such reporter gene are well known in the art. The test compound is contacted with the reporter gene expressing cell line and the amount of reporter (e.g. CAT) activity produced in the presence of a test compound is compared to the amount of activity produced in the absence of the test compound.

In preferred embodiments, the cell-based assays of the present invention make of use of the genetic complementation of a particular biological phenotype by the target:F-box protein polypeptide for the purpose of identifying F-box protein self-excision agonist and antagonist compounds. For example, the complementation of a yeast gal4 mutant phenotype, characterized by an inability to grow on a media containing galactose as the sole carbon source, by a GAL4: F-box protein hybrid protein is dependent upon F-box protein self-excision from the hybrid protein. Screening for F-box protein self-excision agonist and antagonist compounds may thus be effected by contacting the gal4 GAL4: F-box protein yeast strain with a test compound and measuring a galactose growth characteristic in the presence and in the absence of the compound. Suitable galactose growth characteristics include colony size and doubling time on galactose media. An F-box protein self-excision to may be used to identify agonist and antagonists which affect this galactose growth phenotype.

Another generally-applicable cell based assays useful for the identification of F-box protein self-excision agonists and antagonists is the yeast two-hybrid assay (Gyuris et al. (1993) Cell 75: 791–803) which is readily adaptable to isolating natural (e.g from a cDNA expression library) or synthetic (detected from a library of random open reading frames) polypeptides which interact with an F-box protein polypeptide of the invention. This F-box protein polypeptide/F-box protein polypeptide binding partner interaction can be further adapted to screens which increase or decrease this F-box protein polypeptide/F-box protein polypeptide binding partner interaction, thereby allowing detection of F-box protein self-excision agonists and antagonists.

In a preferred embodiment of the invention, the chimeric polypeptide is introduced into a target cell by introducing and expressing in the target cell a nucleic acid encoding the chimeric polypeptide. In another embodiment of the invention, the chimeric polypeptide, or peptidomimetic thereof is introduced directly into the target cell. The method of administration of a chimeric polypeptide to a target cell may depend on various factors, including but not limited to whether the target cell is in a subject or ex vivo, whether prolonged or temporally limited presence of the chimeric polypeptide is desired and which method of administration may be more effective for a particular type of cell.

The target cell can be any cell which contains the necessary components of the ubiquitin proteolytic pathway and a target polypeptide. In a preferred embodiment, the cell is a eukaryotic cell, preferably a mammalian cell and even more preferably a human cell. However, the target cell can also be a murine, rat, canine, feline, bovine, ovine, porcine, goat, equine, or a primate cell. A target cell can also be a yeast cell, e.g., *Saccharomyces Cerevisiae* cell.

The target cell can be any type of cell, present in a subject or outside of a subject. For example, the cell in which a target polypeptide is to be degraded can be in a subject and the chimeric polypeptide or nucleic acid encoding such is administered to the subject. Alternatively, the target cell can be obtained from a subject, the chimeric polypeptide or nucleic acid encoding such is introduced into the target cell and the target cell is optionally administered to the same or another subject. In yet another embodiment, the target cell is not obtained directly from a subject, but is a cell from a cell culture and the chimeric polypeptide or nucleic acid encoding such is introduced in vitro into the target cell. Accordingly, the target cell can be a cell from any established cell line, which can be obtained, e.g., from the American Type Culture Collection (12301 Parklawn Drive, Rockville, Md.).

The target cell can be a cell in suspension or can be part of a tissue or organ. The cell can be an undifferentiated cell, e.g., a blast cell, or the cell can be a differentiated or partially differentiated cell. The cell can be a somatic cell or a germ cell. The cell can be a normal cell or a cell from a tumor, e.g., malignant or benign tumor. The cell can be a blood cell, such as a lymphocyte, a granulocyte, an eosinophil, a basophil, an erythrocyte. In other embodiments, the cell can be a muscle cell, a renal cell, a liver cell, a epithelial cell, a bone cell (e.g., osteoblast or osteocyte), a cartilage cell, mesenchymal cell, endothelial cell, brain cell, or any other cell type, so long as the cell contains the necessary elements of the ubiquitin proteolysis pathway, or can be modified to contain these components.

A nucleic acid encoding a chimeric polypeptide of the invention is preferably included in a vector, e.g., a eukaryotic expression vector. The vector preferably comprises a promoter and may contain enhancer and other regulatory elements. The promoter can be cell-type specific, or the promoter can be expressible in different types of cells. The promoter can also be constitutive. Alternatively, the promoter can be inducible. An inducible promoter is useful in embodiments in which the target polypeptide is to be degraded only at certain times, in a controllable manner.

Ligating nucleic acid fragments into a gene construct, such as an expression vector, and transforming or transfecting into hosts, either eukaryotic (yeast, avian, insect or mammalian) or prokaryotic (bacterial) cells, are standard procedures well known in the art, and described in references cited herein.

Vectors that allow expression of a nucleic acid in a cell are referred to as expression vectors. Typically, expression vectors used for expressing a chimeric polypeptide contain a nucleic acid encoding a chimeric polypeptide, operably linked to at least one transcriptional regulatory sequence. Regulatory sequences are art-recognized and are selected to direct expression of the subject chimeric proteins. Transcriptional regulatory sequences are described in Goeddel; *Gene Expression Technology: Methods in Enzymology* 185, Academic Press, San Diego, Calif. (1990).

Suitable vectors for the expression of a chimeric polypeptide include plasmids of the types: pBR322-derived plasmids, pEMBL-derived plasmids, pEX-derived plasmids, pBTac-derived plasmids and pUC-derived plasmids for expression in prokaryotic cells, such as *E. coli*.

A number of vectors exist for the expression of recombinant proteins in yeast. For instance, YEP24, YIP5, YEP51, YEP52, pYES2, and YRP17 are cloning and expression vehicles useful in the introduction of genetic constructs into *S. cerevisiae* (see, for example, Broach et al. (1983) in Experimental Manipulation of Gene Expression, ed. M. Inouye Academic Press, p. 83, incorporated by reference herein). These vectors can replicate in *E. coli* due the presence of the pBR322 ori, and in *S. cerevisiae* due to the replication determinant of the yeast 2 micron plasmid. In addition, drug resistance markers such as ampicillin can be used.

The preferred mammalian expression vectors contain both prokaryotic sequences, to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papillomavirus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see Molecular Cloning A Laboratory Manual, $2^{nd}$ Ed., ed. by Sambrook, Fritsch and Maniatis (Cold Spring Harbor Laboratory Press: 1989) Chapters 16 and 17.

A vector for use in the invention may also contain additional regulatory elements, such as elements which regulate the stability of the mRNA encoding the chimeric polypeptide or elements which regulate the level of transduction of the mRNA or the stability of the chimeric polypeptide. Such elements are well known in the art.

The invention also provides nucleic acids, and vectors comprising such, which encode an E3 recruiting domain. In a preferred embodiment, the nucleic acid further comprises the nucleotide sequence of at least one restriction enzyme recognition site, which allows in frame insertion of a nucleic acid encoding a target protein binding domain, such that expression of the nucleic acid produces a chimeric polypeptide. The restriction enzyme site can be located upstream or downstream of the nucleotide sequence encoding the E3 recruiting domain.

Vectors encoding chimeric polypeptides can be introduced into target cells by various methods. The choice of the method may depend on the type of target cell and whether the vector is to be introduced into cells in a host, i.e., in vivo, or ex vivo.

In certain embodiments, it may be preferable to directly introduce a chimeric polypeptide or peptidomimetic thereof into a target cell, as opposed to inserting a nucleic acid encoding such.

The polypeptides can be synthesized in vitro or alternatively, the polypeptides of the invention can be produced in a cell, isolated and introduced into the target cell. For example, a host cell transfected with a nucleic acid vector directing expression of a nucleotide sequence encoding the subject polypeptides can be cultured under appropriate conditions to allow expression of the peptide to occur. Suitable media for cell culture are well known in the art. The recombinant polypeptide can be isolated from cell culture medium, host cells, or both using techniques known in the art for purifying proteins including ion-exchange chromatography, gel filtration chromatography, ultrafiltration, electrophoresis, and immunoaffinity purification with antibodies specific for such peptide. In a preferred embodiment, the recombinant polypeptide is a fusion protein containing a domain which facilitates its purification, such as GST fusion protein or a Histidine tagged protein.

In some instances, it may be desirable to express a recombinant polypeptide by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

Methods for introducing polypeptides or peptidomimetics into cells are well known in the art and include, e.g., use of liposomes.

The methods and compositions of the invention provide a means for degradating any desired protein in a cell, so long as the target polypeptide can be recruited to an E3 complex and thereby be degraded. Accordingly, the invention provides methods and compositions for treating or preventing any disease or condition in a subject, which is caused by or contributed to by the presence of an abnormal amount of a specific polypeptide. The invention can be used to reduce the amount of a target protein to various extends as well as to eliminate essentially all of the target polypeptide from the target cell.

The target polypeptide can be a cytoplasmic polypeptide, a nuclear polypeptide or a membranous polypeptide, e.g., a polypeptide attached to the cytoplasmic membrane.

In one embodiment, the target polypeptide is involved in regulating the growth and/or differentiation and/or death of a cell. For example, the target polypeptide can be an oncoprotein, the presence of which contributes to the immortalization of a cell. Accordingly, the invention provides methods and compositions for treating cancer and other proliferative disorders.

In another embodiment, the target polypeptide is that of a microorganism, e.g., a virus or intracellular bacteria. Preferred polypeptides are those which are necessary for the survival and/or reproduction of the microorganism. Thus, methods involving degradation of such polypeptides can be used for treating and/or preventing infections by microorganisms.

Also within the scope of the invention are methods for specifically eliminating cells in a subject, by targeting and degrading polypeptides which are essential for the survival of the target cell. Thus, controlling expression of the chimeric polypeptide with an inducible promoter provides a method for controlled cell death. Such a method is particularly useful in gene therapy methods, by providing a safety mechanism, by which genetically engineered can be destroyed upon administration of a compound inducing expression of the chimeric polypeptide.

Pharmaceutical compositions for use in accordance with the present invention may be formulated in conventional manner using one or more physiologically acceptable carriers or excipients. As used herein "pharmaceutical compositions" include any compositions that may be administered to treat a subject according to the method of the invention, and may comprise a chimeric polypeptide, peptidometic, nucleic acid encoding a chimeric polypeptide and/or other desirable compounds. Thus, the compounds and their physiologically acceptable salts and solvates may be formulated for administration by, for example, injection, inhalation or insufflation (either through the mouth or the nose) or oral, buccal, parenteral or rectal administration.

For such therapy, the pharmaceutical compositions of the invention can be formulated for a variety of loads of administration, including systemic and topical or localized administration. Techniques and formulations generally may be found in Remmington's Pharmaceutical Sciences, Meade Publishing Co., Easton, Pa. For systemic administration, injection is preferred, including intramuscular, intravenous, intraperitoneal, and subcutaneous. For injection, the pharmaceutical compositions of the invention can be formulated in liquid solutions, preferably in physiologically compatible buffers such as Hank's solution or Ringer's solution. In addition, the pharmaceutical compositions may be formulated in solid form and redissolved or suspended immediately prior to use. Lyophilized forms are also included.

For oral administration, the pharmaceutical compositions may take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., ationd oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound. For buccal administration the compositions may take the form of tablets or lozenges formulated in conventional manner. For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the pharmaceutical compositions may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays or using suppositories. For topical administration, the pharmaceutical compositions of the invention are formulated into ointments, salves, gels, or creams as generally known in the art. A wash solution can be used locally to treat an injury or inflammation to accelerate healing.

In clinical settings, a gene delivery system of the chimeric polypeptide encoding nucleic acid can be introduced into a patient by any of a number of methods, each of which is familiar in the art. For instance, a pharmaceutical preparation of the gene delivery system can be introduced systemically, e.g., by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g., Chen et al. (1994) *PNAS* 91: 3054–3057). A nucleic acid encoding a chimeric polypeptide can be delivered in a gene therapy construct by electroporation using techniques described, for example, by Dev et al. ((1994) *Cancer Treat Rev* 20:105–115).

The pharmaceutical preparation of the gene therapy construct or compound of the invention can consist essentially of the gene delivery system in an acceptable diluent, or can comprise a slow release matrix in which the gene delivery vehicle or compound is imbedded. Alternatively, where the complete gene delivery system can be produced intact from recombinant cells, e.g., retroviral vectors, the pharmaceutical preparation can comprise one or more cells which produce the gene delivery system.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

The invention provides a quick, easy, and economic alternative to the gene knock-out technology to eliminate any cellular protein in tissue culture or in animals. For example, a chimeric polypeptide or nucleic acid encoding such can be introduced into embryonic stem cells or in a blastocyst (for preparing transgenic animals), but also at any later stage of development of the embryo or animal, or even in an adult animal. Thus, the target polypeptide can be degraded from the early developmental stages on, or it can be degraded only at specific developmental stages or in a mature animal. This allows the study of the function of a specific target polypeptide, by specifically eliminating the polypeptide in the desired cell or in all the cells of an animal.

The method of the invention will be useful, e.g., in drug discovery. For example, specific degradation of a protein of interest can be used to determine the effect of a drug that would eliminate or inhibit the activity of the protein of interest, and thus whether this protein is an ideal target for drug intervention.

In another embodiment, the invention provides a screening method for identifying compounds which modulate, i.e., inhibit or stimulate, the interaction between two molecules. In a preferred embodiment, the invention provides a method for identifying compounds which inhibit the binding of two polypeptides to each other. For example, a method for identifying a compound which inhibits the interaction between polypeptide X and polypeptide Y comprises expressing in a cell a chimeric polypeptide comprising (i) an E3 recruiting domain, e.g., an F-box and WD repeats of the human h-βTrCP protein and (ii) a portion of polypeptide X, sufficient for binding to polypeptide Y. Optionally, a nucleic acid encoding polypeptide Y, or a portion thereof sufficient for binding to polypeptide X, can also be introduced and expressed in the cell. Polypeptide Y (the target polypeptide) can also be linked to a marker peptide which can easily be detected, e.g., by using an antibody to the marker peptide. For example, a marker peptide can be a myc tag or a peptide of the Influenza virus, for which highly specific antibodies are commercially available. The cell can then be contacted with a test compound and the presence and/or amount of polypeptide Y is determined. Any of a variety of techniques for detecting the presence and/or amount of polypeptide Y can be used. For example, methods including the use of an antibody directed to polypeptide Y or to a marker peptide linked to polypeptide Y can be used, and include methods such as immunoprecipitations and Western Blots, immunohistochemistry. Alternatively, polypeptide Y can be labeled, e.g., radioactively labeled, and the presence of the presence and/or amount of polypeptide Y is determined, e.g., by measuring the amount of radioactivity that is precipitated with an antibody that binds specifically to polypeptide Y. The presence of a higher level of polypeptide Y in a cell contacted with a test compound relative to the level of polypeptide Y present in an identical cell which was not contacted with the test compound indicates that the test compound inhibits the interaction between polypeptide X and polypeptide Y.

In another embodiment of the above-described screening assay, the polypeptide comprising a portion of polypeptide Y sufficient for binding to X, further comprises a cell death inducing domain, e.g., from the Fas or Apo-1 protein, such that the presence of a sufficient amount of Y in a cell induces the cell to undergo cell death. In this case, contacting the cell with a compound which inhibits the interaction between the polypeptides X and Y will result in cell death, whereas contacting the cell with a compound which does not inhibit binding of the two polypeptides to each other will not result in cell death since the death inducing polypeptide will be degraded in the cell by the ubiquitin proteolytic pathway. In this embodiment it may be preferable to control the presence of Y in a cell by, e.g., operably linking the nucleic acid encoding Y to an inducible promoter.

Thus, the method of the invention provides an easy and reliable screening assay for identifying compounds which inhibit or stimulate the interaction between two polypeptides in a cell, in particular a mammalian cell.

The method of the invention also provides a powerful technology for the functional genomic studies to analyze the functions of novel genes identified by the human genome project.

Furthermore, the function of proteins interacting with a specific protein of interest can be determined by specifically targeting the degradation of one or more of these interacting proteins. In addition, through systematic elimination of multiple interacting proteins and comparison of the phenotypes generated from each targeted proteolysis, an overall picture of the entire pathway of these proteins can be obtained. Thus, in addition to the numerous therapeutic uses for the method of the invention, the method is a useful experimental tool that can be used for elucidating the biological activity of any protein of interest. The information derived from this research can then be used for diagnostic, prognostic and therapeutic purposes.

The present invention is further illustrated by the following examples which should not be construed as limiting in any way. The contents of all cited references (including literature references, issued patents, published patent applications as cited throughout this application are hereby expressly incorporated by reference. The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, $2^{nd}$ Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I–IV (D. M. Weir and C. C. Blackwell, eds., 1986); Manipulating the Mouse Embryo, (Cold Spring Harbor Laboratory Press, Cold Spring Harbor, N.Y., 1986).

5. EXAMPLES

Cdc4p is an Unstable Component of the $SCF^{Cdc4p}$ Complex

The $Cdc34p/SCF^{Cdc4p}$ pathway appears to operate at cell cycle stages other than the G1/S transition (King et al. (1996) Science 274: 1652–9), suggesting that the components involved in the $Cdc34p/SCF^{Cdc4p}$ pathway must be physically present throughout the cell cycle. Indeed, the steady-state level of Cdc34p does not fluctuate during the cell cycle (Goebl et al. (1994) Mol Cell Biol 14: 3022–9). To test whether the components comprising the $SCF^{Cdc4p}$ complex are stable and available throughout the cell cycle, we examined the half life of individual $SCF^{Cdc4p}$ components in exponentially growing yeast cells. Expression of epitope-tagged Cdc4p, Cdc53p and Skp1p under the control of the galactose-inducible GAL1-10 promoter was induced for 1 hour in exponentially growing KY130 cells, and the stability of the proteins was determined following promoter shut-off by switching cells into glucose media containing cycloheximide (Visintin et al. (1997) Science 278: 460–3). As shown in FIG. 1A, Cdc53p and Skp1p were stable (T1/2>60'), whereas Cdc4p was short-lived, with a half life of 15 minutes, similar to that of Sic1p (Verma et al. (1997) Science 278: 455–60). To examine whether the observed instability of Cdc4p was an intrinsic property and not due to heterologous expression of epitop tagged Cdc4p, we examined the half life of endogenous Cdc4p, which is expressed at very low levels in wild type cells. By pulse chase, we found that endogenous Cdc4p was also unstable, with a t1/2 comparable to what was observed for the transfected Cdc4p (FIG. 1B). This experiment also independently confirmed the stability of the endogenous Skp1p (FIG. 1B). Since Cdc34p/$SCF^{Cdc4p}$ proteolytic activity has been implicated in multiple cell cycle stages (Bai et al. (1996) Cell 86: 263–74; Schwob et al. (1994) Cell 79: 233–44), we next analyzed the half life of Cdc4p in cells synchronized at specific stages of the cell cycle. As shown in FIG. 1C, Cdc4p was rapidly degraded in synchronized cells upon release from alpha-factor mediated arrest in G1 phase, from hydroxyurea arrest in S phase, or from nocodazole arrest in M phase, demonstrating that Cdc4p is degraded throughout the cell cycle. These data indicated that Cdc4p was the only short-lived component of the $Cdc34p/SCF^{Cdc4p}$ complex, and that intact $SCF^{Cdc4p}$ existed as a transient complex in vivo.

FIG. 1 shows that Cdc4p is the only unstable component of the $SCF^{Cdc4p}$ ubiquitin protein ligase complex. (A) Exponentially growing KY130 cells carrying either Flag-Cdc4p, HA-Cdc53p, Flag-Skp1p or Sic1p-HA under the control of the GAL1-10 promoter, were induced to express the individually tagged proteins for 1 hour by 2% galactose, and their half-lives were determined by promoter shut-off and immunoblotting using anti-Flag (M2) or HA.11 monoclonal antibodies to detect F-Cdc4p, Sic1p-HA, HA-Cdc53p and F-Skp1p, respectively. As a loading control, endogenous Cdc28p was visualized by immunoblotting using an anti-Cdc28p antibody. "o" is an unknown species in yeast extracts which cross-reacts with the anti-Flag M2 monoclonal antibody. (B) The endogenous Cdc4p is short-lived. Pulse-chase analysis was carried out in exponentially growing KY130 cells, and the decay of the endogenous Cdc4p or Skp1p over time were determined by immunoprecipitation with an affinity purified anti-Cdc4p polyclonal antibody or an anti-Skp1p antibody. $^{35}$S-labeled Cdc4p or Skp1p immunoprecipitates were subjected to SDS-PAGE and were visualized after 4 days of exposure. (C) KY130 cells carrying GAL-F-Cdc4p were first arrested by α-factor in G1 phase, hydroxyurea in S phase or nocodazole in M phase (Visintin et al., 1997). Following the release from growth arrest, the levels of F-Cdc4p over the indicated time periods upon promoter shut-off was determined by immunoprecipitation and visualized by immunoblotting using the anti-Flag M2 antibody. The M2 cross-reacting species in (A) was not present in the immunoprecipitates.

Cdc4p is Degraded by the Ubiquitin-Proteasome Pathway

We next examined whether Cdc4p proteolysis was ubiquitin dependent by testing directly whether Cdc4p was ubiquitinated in vivo. Since endogenous Cdc4p is present at very low levels and because multiubiquitinated species are quickly degraded by the 26S proteasome, high copy number plasmids expressing Cdc4p either alone or together with Myc-tagged ubiquitin were introduced into wild type yeast cells to facilitate detection of ubiquitin-conjugated Cdc4p intermediates. Myc-tagged ubiquitin can be efficiently conjugated to proteins to form multi-ubiquitinated chains (Ellison and Hochstrasser (1991) J Biol Chem 266: 21150–7). Furthermore, addition of the Myc-epitope on ubiquitin results in a distinct electrophoretic pattern of slower migrating species on SDS PAGE when compared to that of the protein conjugated to native ubiquitin, thus serving as a specific indicator of ubiquitinated intermediates (Ellison and Hochstrasser (1991) J Biol Chem 266: 21150–7). Cdc4p was immunoprecipitated from extracts of exponentially growing cells using an anti-Cdc4p polyclonal antibody, blotted and probed with the 9E10 monoclonal antibody for Myc-Ub, and with the Cdc4p-specific antibody. In Cdc4p and Myc-Ub expressing cells, a ladder of slower migrating species was detected by the Cdc4p specific antibody as well as the Myc antibody that recognizes Myc-Ub conjugated proteins (FIG. 2A, lanes 4 and 8). In cells expressing Cdc4p alone, a similar spectrum of bands was observed with the Cdc4p specific antibody, but not the Myc antibody (FIG. 2A, lanes 3 and 7). However, slower migrating species of Cdc4p could be detected using the anti-ubiquitin antibody (data not shown), identifying the slow migrating species in Cdc4p expressing cells (FIG. 2A, lane 3) as ubiquitinated conjugates. Furthermore, Myc-ubiquitin conjugates of endogenous Cdc4p could be observed upon longer exposure of lane 6 (FIG. 2A, lanes 10). The Cdc4p-Myc-Ub$_n$ species had slower electrophoretic mobility compared to the Cdc4p-Ub$_n$ species due to the addition of the Myc-tag on the ubiquitin (FIG. 2A, compare lanes 3 and 4). These data provide unambiguous evidence that the slow migrating species of Cdc4p are ubiquitinated. Furthermore, Cdc4p degradation was inhibited in yeast cells carrying the temperature sensitive pre1-1, pre-4-1 double mutations of the 20S proteasome subunits at 37° C. (FIG. 2B) (Hilt et al. (1993) J Biol Chem 268: 3479–86), indicating that Cdc4p is subjected to proteasome mediated proteolysis. Taken together with the rapid turnover rate of Cdc4p, these experiments indicate that the F-box-containing component of SCF$^{Cdc4p}$ is itself subject to degradation by the ubiquitin-proteasome pathway.

FIG. 2 shows that Cdc4p is ubiquitinated and degraded by the proteasome in vivo. (A) INVSc1 cells expressing Myc-Ub alone (lanes 2 and 6), or Cdc4p alone (lanes 3 and 7), or Myc-Ub and Cdc4p (lanes 4 and 8) were immunoprecipitated with the anti-Cdc4p polyclonal antibody, and were immunoblotted with either anti-Cdc4p antibody or the 9E10 anti-Myc antibody which recognized Myc-tagged ubiquitin. INVSc1 cells carrying expression vectors alone (lanes 1, 5 and 9) were used as a negative control. The arrowhead indicates the endogenous Cdc4p (lanes 1 and 2) or ectopically expressed Cdc4p (lanes 3 and 4). Upon 5× prolonged exposure, the endogenous Cdc4p was shown to be modified by the Myc-Ub (lane 10). "." and "*" represents Cdc4p modified by endogenous ubiquitin or Myc-Ub, respectively. "o" indicates a cellular protein cross-reactive with the Cdc4p antibody. (B) The stability of the F-Cdc4p in YY371 and YY374 cells was assessed by promoter shut-off at 37° C. "o" is an unknown protein cross-reacting with the anti-Flag M2 monoclonal antibody.

The F-Box-Containing Grr1p of the SCF$^{Grr1p}$ is Also Ubiquitinated and Rapidly Degraded.

To investigate whether the rapid turnover of Cdc4p is a specific feature of that protein, or whether it is a characteristic shared by other F-box-containing ubiquitin protein ligases, we examined the stability of the F-box-containing Grr1p of SCF$^{Grr1p}$ (Barral et al. (1995) Genes Dev 9: 399–409; Li and Johnston (1997) EMBO J 16: 5629–38; Skowyra et al. (1997) Cell 91: 209–19). HA-tagged Grr1p, lacking, the N-terminal 280 amino acids (HA-Grr1p$^{\Delta N}$), has previously been shown to be fully functional since it can complement a grr1 null allele (Li and Johnston (1997) EMBO J 5629–38). The half life of HA-Grr1p$^{\Delta N}$ was determined in wild type cells constitutively expressing HA-Grr1p$^{\Delta N}$. In a pulse chase analysis shown in FIG. 5A, HA-Grr1p$^{\Delta N}$ was rapidly degraded, with a t1/2 of 30 minutes. Ubiquitin conjugates of HA-Grr1p$^{\Delta N}$ were demonstrated by the marked enhancement of a HA-Grr1p$^{\Delta N}$ ubiquitin ladder when exogenous ubiquitin was also overexpressed (FIG. 5B, compare lanes 3 and 4). Furthermore, the spectrum of the HAGrr1p$^{\Delta N}$~Myc-Ub species exhibited the characteristic shift of the electrophoretic mobility compared to ubiquitinated HA-Grr1p$^{\Delta N}$ proteins conjugated with the native ubiquitin (FIG. 5B, lanes 3, 4 and 5) (Ellison and Hochstrasser (1991) J Biol Chem 266: 21150–7). In Myc-Ub expressing cells, the slower migrating HA-Grr1p$^{\Delta N}$ conjugates were immunoreactive with anti-Myc antibody (data not shown). These results indicate that HA-Grr1p$^{\Delta N}$ is indeed ubiquitinated inside the cell. An analogous SCF$^{Skp2}$ complex was recently described in human cells (Lisztwan et al. (1998) EMBO J 17: 368–83). Interestingly, the protein level of the human homolog of Grr1p, p45$^{Skp2}$, decreases during the M phase of the cell cycle. Although the abundance of the SKP2 mRNA is cell cycle regulated (Zhang et al. (1995) Cell 58: 1085–95), ubiquitin-dependent proteolysis may also play a role since addition of the proteasome inhibitor LLnL prevents the decrease of Skp2 protein levels in M phase (Lisztwan et al. (1998) EMBO J 17: 368–83). Therefore, we propose that ubiquitin-dependent proteolysis of F-box-containing substrate recognition component in SCFs is likely a general scheme for the function of the SCF ubiquitin-protein ligases.

FIG. 5 shows that Grr1p is also a short-lived protein and is ubiquitinated in vivo. (A) Wild type Y81 cells constitutively expressing HA-GRR1$^{\Delta N}$ were grown to mid-log phase, and the half-life of HA-Grr1p$^{\Delta N}$ was determined by pulse-chase analysis and immunoprecipitation with the HA.11 anti-HA polyclonal antibody (Babco) as in FIG. 1B. (B) Y81 cells expressing Myc-Ub alone (lanes 2), or HA-Grr1p$^{\Delta N}$ alone (lanes 3), Ub and HA-Grr1p$^{\Delta N}$ (lanes 4 or Myc-Ub and HA-Grr1p$^{\Delta N}$ (lanes 5) were immunoprecipitated with the HA.11 anti-HA polyclonal antibody (Babco) and immunoblotted with the HA.11 monoclonal antibody (Babco) for HA-Grr1p$^{\Delta N}$. "." and "*" are examples of HA-Grr1p$^{\Delta N}$ conjugated to ubiquitin or Myc-Ub, respectively. The slower migrating HA-Grr1p$^{\Delta N}$ conjugates marked by "*" were also detected by anti-Myc monoclonal antibody (not shown). "o" indicates unknown species in Y81 extracts that cross-react with HA.11 monoclonal antibody.

Cdc4p Proteolysis is Mediated by the Cdc34p/SCF$^{Cdc4p}$ Machinery

The fact that one of the SCF components is also degraded by the ubiquitin-proteasome pathway raised the question of whether the Cdc34p/SCF$^{Cdc4p}$ machinery that degrades phosphorylated substrates is the same machinery that promotes ubiquitination of Cdc4p, or whether a separate pathway exists for ubiquitin dependent proteolysis of Cdc4p. We therefore analyzed Cdc4p stability in cdc34-2 and skp1-11 temperature sensitive cells. It has been shown that the Cdc4p substrate, Sic1p, is stable in cdc34-2 and skp1-11 cells at the non-permissive temperature due to the inactivation of the Cdc34p ubiquitin-conjugating enzyme and the Skp1p component of SCF$^{Cdc4p}$, respectively (Bai et al. (1996) Cell 86: 263–74; Schwob et al. (1994) Cell 79: 233–44). In both cdc34-2 and skp1-11 mutants, Cdc4p accumulated to a high steady state level, and its degradation was dramatically inhibited at the non-permissive temperature with t1/2>60 minutes (FIG. 3). As a control, we showed that when the temperature was raised from 25° C. to 37° C., F-Cdc4p was degraded at a slightly higher rate in the respective isogenic wild type cells (data not shown). Since Cdc28p dependent phosphorylation is a prerequisite for Sic1p recognition by Cdc4p and its subsequent ubiquitination by the Cdc34p/SCF$^{Cdc4p}$ pathway (Feldman et al. (1997) Cell 91: 221–30; Schneider et al. (1996); Schwob et al. (1994) Cell 79: 233–44; Skowyra et al. (1997) Cell 91: 209–19; Verma et al. (1997) Science 278: 455–60), we next examined whether the Cdc28p kinase also plays a role in the degradation of Cdc4p itself. In cdc28-4 temperature sensitive ells, Sic1p degradation is impaired at the non-permissive temperature (37° C.) and the cells are arrested at the G1/S boundary (Schwob et al. (1994). However, Cdc4p was still rapidly degraded at 37°

C. (FIG. 3), indicating that the inhibition of Cdc4p turnover in cdc34-2 and skpl-11 was not due to a general cell cycle arrest, but rather resulted from the specific inactivation of Cdc34p and Skp1p, respectively. Thus, we conclude that Cdc4p is auto-ubiquitinated by the Cdc34p/SCF$^{Cdc4p}$ machinery. Whereas Sic1p degradation is triggered by Cdc28p-dependent phosphorylation at a specific stage of cell cycle, our results indicate that Cdc4p proteolysis is constitutive and not subject to regulation by the Cdc28p kinase (FIG. 1C, FIG. 3).

FIG. 3 shows that Cdc4p is stabilized in cdc34-2 and skpl-11, but not cdc28-4 temperature sensitive mutant cells. The half-life of the galactose inducible F-Cdc4p in cdc34-2 (KY203), skpl-11 (Y553) or cdc28-4 cells was determined by promoter shut-off at the non-restrictive (25° C.) or restrictive temperatures (37° C.). The decay of the F-Cdc4p protein over time was measured by immunoblotting (skpl-11 and cdc28-4) or immunoprecipitation followed by immunoblotting (cdc34-2) using the anti-Flag antibody. "o" is an unknown species cross-reacting with the anti-Flag M2 monoclonal antibody.

Functional Association of Cdc4p with the Core SCF is Necessary for its Destruction The Cdc4p F-box has been shown to directly interact with Skp1p in the assembly of the SCF$^{Cdc4p}$ complex (Bai et al. (1996) Cell 86: 263–74; Skowyra et al. (1997) Cell 91: 209–19). Since efficient transfer of ubiquitin to Sic1p requires the direct interaction of Sic1p with the Cdc34p/SCF$^{Cdc4p}$ machinery, mutant Cdc4p defective in its binding to Skp1p should be resistant to degradation. To test this hypothesis, we engineered two mutant forms of Cdc4p, containing either a Gly 300 to Asp substitution in the F-box corresponding to the cdc4-5$^{ts}$ allele (Cdc4p(G300D)), or a deletion of the entire F-Box (Cdc4p(ΔF)) (Bai et al. (1996) Cell 86: 263–74). The binding of these mutant proteins to Skp1p was reduced 10 to 15 fold compared to wild type Cdc4p protein in the in vitro binding assays (data not shown). These two mutant Cdc4p proteins were transiently expressed in KY130 cells under the control of the GAL1-10 promoter at 30° C., and their half lives-were examined after promoter shut-off. As shown in FIG. 4A, the Cdc4p(G300D) and Cdc4p(ΔF) proteins were both stable, with half lives greater than 60 minutes. In addition, cells expressing the stable Cdc4p(G300D) mutant exhibited severe growth defects. The cdc4-5 allele bearing the G300D mutation at the chromosomal CDC4 locus (Bai et al., 1996), could only grow at the low permissive temperature (23° C.), and was completely arrested in G1 at 34° C. with large and multiply budded cells (FIG. 4B). This is likely due to the inability of the Cdc4p(G300D) mutant to target its substrates to the SCF machinery for destruction. A similar partial phenotype was observed in KY130 cells ectopically expressing Cdc4p(ΔF). These cells displayed a 2- to 3-fold reduced growth rate compared to cells expressing wild type Cdc4p. Microscopic examination revealed an increased population of large, multiply budded cells, morphologically similar to the G1 arrested cdc4$^{ts}$ cells grown at the non-permissive temperature (Johnson (1991) Thesis in Genetics, Univ. of WA, Seattle; Schwob et al., (1994) Cell 79: 233–44) (FIG. 4B). However, complete growth arrest was not observed since high level expression of the Cdc4p(ΔF) mutant protein could not be sustained in actively dividing KY130 cells for reasons yet to be determined (data not shown). In any case, these observations indicate that binding of Cdc4p with the core SCF is necessary for its proteolysis, and that non-degradable Cdc4p mutant proteins may negatively affect cell growth.

FIG. 4, panels A and B show that the F-box and WD40 domains of Cdc4p target Cdc4p for rapid proteolysis, and that Cdc4p function is required for cell cycle progression from G1 to S. (A) Flag-tagged Cdc4p mutants carrying either a Gly300 to Asp substitution, or an internal deletion of the entire F-box were induced to express in KY130 cells for 1 hour. The half life of the mutant Cdc4p proteins were determined by promoter shut-off as in FIG. 1A. "o" represents the M2 cross-reacting species. (B) Morphology of SJ1012-4 (cdc4-5) cells in YEPD medium at 23° C. (left) or kept at 34° C. for 6 hours (right).

Targeted Degradation of a Polypeptide by Fusion to Cdc4p F-Box and WD40 Repeats

Since Cdc4p is targeted for auto-ubiquitination within the SCF$^{Cdc4p}$ complex, we predicted that any proteins, either covalently linked or in association with Cdc4p, would also be targeted within SCF$^{Cdc4p}$ for rapid degradation. As an initial test of this hypothesis, a Cdc4p segment containing the F-box and the WD40 repeats (Cdc4p$^{F/WD}$) was fused to the stable β-galactosidase protein (t1/2>20 hr) (Bachmair et al. (1986) Science 234: 179–86), and introduced into KY130 cells under the control of the GAL1-10 promoter. This fusion protein is functional since it can complement the temperature sensitivity of a cdc4$^{ts}$ allele (Johnson (1991) Thesis in Genetics, Univ. of WA, Seattle). As shown in FIG. 4C, the Cdc4p$^{F/WD}$-βgal fusion was indeed highly unstable, being degraded with a half life of 35 minutes. However, the same Cdc4p$^{F/WD}$-βgal fusion protein containing the Gly 300->Asp F-box mutation was stable, further suggesting that Cdc4p dependent proteolysis requires a functional interaction with Skp1p (FIG. 4C). Furthermore, Cdc4p segments that lacked either the F-Box or the WD40 repeats (Cdc4p$^{WD}$ or Cdc4p$^{F}$) failed to target degradation of the fused β-galactosidase (FIG. 4C), indicating that both the F-box and the WD40 domains are required for the SCF$^{Cdc4p}$ dependent degradation of the Cdc4p fusion proteins. Deletion of the last three WD repeats of Cdc4p has no effect on Cdc4p/Skp1p/Cdc53p complex formation (Skowyra et al. (1997) Cell 91: 209–19). However, this truncated Cdc4p fails to interact with phosphorylated Sic1p (Skowyra et al. (1997) Cell 91: 209–19). Collectively, these data suggest that the F-box and the WD40 repeat components of Cdc4p are both required for the assembly of a macromoleculer Cdc34p/SCF$^{Cdc4p}$/substrate complex optimal for ubiquitin transfer to Cdc4p and its substrates.

The F-box of Cdc4p contains 42 amino acids and has been biochemically defined as the Skp1p interaction domain (Bai et al. (1996) Cell 86: 263–74). To further analyze the role of F-box for SCF functions, the F-box of Cdc4p was overexpressed in the wild type KY130 cells as a β-galactosidase fusion and cell growth was examined after 2 days. As shown in FIG. 4D, overexpression of the non-degradable Cdc4p$^{F/WD}$-βgal strongly inhibited cell growth, whereas neither the short-lived Cdc4p$^{F/WD}$-βgal, nor the stable Cdc4p$^{WD}$-βgal fusion proteins caused growth inhibition (FIG. 4D). We further showed that the Cdc4p$^{F}$-βgal could enter the core SCF as Skp1p and Cdc53p could be readily detected in the Cdc4p$^{F}$-βgal immunoprecipitates (P. Zhou and P. Howley, unpublished result). This suggested that the F-box alone, when present at high intracellular levels, might exert dominant negative effects through blocking the access of the core SCF by the F-box proteins, therefore interfering with SCF-mediated degradation of substrates or auto-ubiquitination of the F-box-containing SCF components. Interestingly, the entire coding regions of the adenovirus E3-12.9K or the Baculovirus ORF11 are exclusively composed of F-box-like sequences (Bai et al. (1996) Cell 86: 263–74). Given that overexpression of the Cdc4p F-box alone inhibited cell growth, it would be important to investigate whether these viral proteins might similarly perturb cell cycle regulation through interfering with the SCF functions.

FIG. 4, panels C and D show that the F-box and WD40 domains of Cdc4p target proteins connected to Cdc4p for rapid proteolysis. (C) The stable *E. coli* β-galactosidase, when fused to Cdc4p$^{F/WD}$, was rapidly degraded. Segments of Cdc4p including (1) F-box and WD40 repeats (Cdc4p$^{F/WD}$), "●", (2) Cdc4p$^{F/WD}$(G300D) "Δ", (3) F-box (Cdc4p$^F$), "■" or (4) WD40 repeats (Cdc4p$^{WD}$) "♦" were fused to *E. coli* βgal and under the control of the GAL1-10 promoter. The decay of each βgal fusion over time was assessed in KY130 cells by promoter shut-off and immunoblotting using an anti-βgal monoclonal antibody, and was quantitated by densitometer scanning. Logarithmic values were assigned to densitometry-determined protein levels and the percentage of protein remaining was plotted against time (minutes). (D) Overexpression of the F-box as a β-galactosidase fusion inhibits cell growth. KY130 cells carrying Cdc4p$^{F/WD}$-β-Gal (F/WD), Cdc4p$^F$-β-Gal (F) or Cdc4p$^{WD}$-β-Gal (WD) expression plasmids were streaked on medium containing glucose (left) or galactose (right) and incubated at 30° C. for 2 days.

Targeted Degradation of the Retinoblastoma Tumor Suppressor in Yeast

To demonstrate that a selected target polypeptide could be degraded by recruitment to an F-box-containing SCF complex, the retinoblastoma tumor suppressor protein (pRB) was expressed in yeast and targeted for degradation using F-box-pRB interaction domain fusion proteins. We chose the retinoblastoma protein pRB as a proteolysis target, since pRB was known to express at high steady state levels in yeast without interfering with normal growth (Hatakeyama et al., (1994) Genes Dev 8: 1759–71). In addition, the interactions between pRB and viral oncoproteins have been extensively characterized. The pRB expression plasmid p2202TRB under the control of the GALI-10 promoter was introduced into wild type Y81 cells, and the half life of pRB was determined by promoter shut-off following transient induction of pRB by galactose. As shown in FIG. 7A, pRB was highly stable and no degradation was observed within 90 minutes upon promoter shut-off. This result also indicates that although cell cycle dependent phosphorylation of pRB in mammalian cells is faithfully mimicked in *S. cerevisiae* (Hatakeyama et al., (1994) Genes Dev 8: 1759–71), the Cdc34p/SCF$^{Cdc4p}$ machinery that degrades phosphorylated Sic 1p during G1/S transition can not recognize either hyper- or hypo-phosphorylated pRB.

We next engineered two Cdc4p derivatives that were capable of interacting with pRB. These engineered F-box-containing hybrid proteins were composed of two functional entities: the F-box and WD repeat domains of Cdc4p (Cdc4p$^{F/WD}$) sufficient for binding to Skp1p and targeting to the core SCF, and the pRB binding domains of either the simian virus 40 Large T antigen (residues 103–115), designated LTP (for Large T antigen Peptide), or the papillomavirus oncoprotein E7 (residues 2–35), designated E7N (Munger et al. (1989) EMBO J 8: 4099–105). As negative controls, the same domains of each viral oncoprotein carrying point mutations LTP(FGSK) or internal deletions E7N(ΔDLYC) within the conserved LXCXE pRB binding motif, thus abolishing their interactions with pRB, were also covalently attached to Cdc4p$^{F/WD}$ (DeCaprio et al. (1989) Cell 58:1085–95; Dyson et al. (1989) Science 243: 934–7; Figge et al. (1993) Protein Sci 2: 155–64; Munger et al. (1989) EMBO J 8: 40999–105; Yang et al. (1995) Nucleic Acids Res 23: 1152–6). These engineered F-box proteins allowed us to address two questions: 1) whether a stable protein (pRB) can now be degraded by an engineered Cdc4p derivative specifically designed to target pRB proteolysis; 2) whether the core SCF is in dynamic equilibrium with distinct F-box-containing substrate recognition components, and therefore allows the engineered Cdc4p derivatives to target non-SCF substrates to the core SCF for ubiquitination. As shown in FIG. 7B, the steady state levels of pRB in cells expressing Cdc4p$^{F/WD}$-LTP was significantly lower than that in cells expressing Cdc4p$^{F/WD}$-LTP(FGSK) incapable of interacting with pRB (FIG. 7B). To further demonstrate that the decrease of pRB levels was a result of stimulated proteolysis by the engineered pRB-specific ubiquitin-protein ligase (Cdc4p$^{F/WD}$-LTP), but not due to expression of the pRB binding domain of TAg that affects pRB synthesis, the half life of pRB was determined by promoter shut-off in Y81 cells expressing a second version of engineered Cdc4p with Cdc4p$^{F/WD}$ fused to the pRB binding domain of the papillomavirus E7 (aa 2–35) (Cdc4p$^{F/WD}$-E7N). As a control, the turn over rate of pRB was assessed in Y81 cells constitutively expressing Cdc4p$^{F/WD}$-E7N(ΔDLYC), in which Cdc4p$^{F/WD}$ was fused to the same domain of E7 internally deleted of four residues (ΔDLYC), and therefore lost the pRB binding capability (Munger et al. (1989) EMBO J 8: 40999–105). As shown in FIG. 7C, pRB was rapidly degraded in Cdc4p$^{F/WD}$-E7N expressing cells, with a half life of 70 minutes. In Y81 cells expressing Cdc4p$^{F/WD}$-E7N (ΔDLYC) defective for pRB binding, pRB was highly stable within 2 hours following promoter shut-off. These results indicate that by engineering a pRb binding peptide (LTP or E7N) on Cdc4p, the SCF$^{Cdc4p}$ machinery can be directed towards degradation of a non-SCF substrate such as pRb.

FIG. 6 shows a generic scheme for the genetic engineering of the SCF ubiquitin-proteolytic machinery to target degradation of non-SCF substrates (X). Y represents the interaction peptide of protein X that is covalently attached to the F-box-containing SCF subunit to create a "X"-specific ubiquitin-protein ligase.

FIG. 7 demonstrates the trans-targeting of the retinoblastoma tumor suppressor protein. The stable pRB is rapidly degraded by the engineered Cdc4p-derived ubiquitin-protein ligase. (A) pRB is a stable protein in *S. cerevisiae*. Exponentially growing Y81 cells carrying PGAL-RB expressing plasmid p2202TRB was induced for 1 hour with 2% galactose. Promoter shut-off was subsequently carried out, and the remaining pRB levels over time were determined from 100 ug of extracts by immunoblotting using the Ab-5 anti-pRB monoclonal antibody (CALBIOCHEM). (B) The steady state level of pRB is significantly lower in Y81 cells expressing Cdc4p$^{F/WD}$-LTP than those expressing a mutant Cdc4p$^{F/WD}$-LTP(FGSK) hybrid incapable of binding to pRB. Y81 cells containing pRB and the engineered Cdc4p derivatives, Cdc4p$^{F/WD}$-LTP, or Cdc4p$^{F/WD}$-LTP(FGSK) also under the control of the GALI, 10 promoter, were induced for the indicated hours. Cell extracts were prepared and 100 ug of each extracts were subjected to immunoblotting to detect the steady-state levels of pRB following galactose induction. (C) pRB is rapidly degraded in Y81 cells expressing Cdc4p$^{F/WD}$-E7N, but remains highly stable in cell expressing Cdc4p$^{F/WD}$-E7N(ΔDLYC), which is incapable of binding pRB. The turn over rate of pRB was assessed by promoter shut-off in Y81 cells constitutively expressing Cdc4p$^{F/WD}$-E7N or Cdc4p$^{F/WD}$-E7N(ΔDLYC), respectively. The decay of pRB over time was determined by immunoblotting using the Ab-5 anti-pRB monoclonal antibody (CALBIOCHEM).

Targeted Degradation of the HPV E2 Transcription Factor in Yeast

As a further proof the concept of engineering the SCF$^{Cdc4p}$ System, we tested whether Cdc4p could be modified to target degradation of the normally stable E2 transcription factor from the oncogenic human papiuomavirus type 16 (HPV16) using the yeast model system. Besides serving as a regulator of viral transcription, E2 also functions as an auxiliary factor that associates with the HPV16 E1 protein directly involved in viral DNA replication (reviewed in Howley (1996) Virology 3rd ed.; New York: Lippincott-Raven Press). The E2 binding domain on HPV16-E1 was mapped to the carboxyl terminal 424–669 amino acids, designated EIC (Yasugi et al. (1997) Virol 71: 891–9). Furthermore, a Glu39->Ala mutation within the amino terminus of E2 (E2(E39A)) completely abolished E1-E2 association, as determined by the yeast two-hybrid system and in vitro binding assays (Sakai et al. (1996); J Virol 70: 1602–11; Yasugi et al. (1997) Virol 71: 891–9). An E2-specific ubiquitin-protein ligase was engineered with the Cdc4p$^{F/WD}$ segment in-frame fused to E1C and was expressed under the control of the constitutive alcohol dehydrogenase (ADH) promoter in yeast. EE-tagged HPV16-E2 or E2(E39A), which were expressed under the control of the tetracycline-repressible promoter (tetO$^R$), were introduced into the wild type INVSC 1 cells together with Cdc4p$^{F/WD}$-E1C respectively, and the half lives of E2 or E2(E39A) were determined by promoter shut-off. As shown in FIG. 8, EE-E2 was rapidly degraded, with a t1/2 of 16 minutes. However, EE-E2(E39A), which was incapable of binding to Cdc4p$^{F/WD}$-E1C, remained stable following addition of the deoxycycline (FIG. 8). Therefore, we conclude that the SCF ubiquitination system can be directed towards degradation of specific cellular proteins by covalently attaching their interaction peptides onto Cdc4p. These results provide in vivo evidence for a direct role of Cdc4p in substrate recruitment, and further indicate that intact SCFs are transient complexes within the cell. This operational characteristics of the SCF ubiquitination machinery provides enormous flexibility for the core SCF to assemble with a large and diversified family of F-box-containing proteins or their engineered functional derivatives to target degradation of cellular proteins.

FIG. 8 shows that a genetically engineered SCF$^{Cdc4p}$ complex efficiently targets degradation of the papillomavirus E2 transcriptional regulator in the yeast model system. INVSc1 cells expressing pADH-Cdc4p$^{F/WD}$-E1C and ptetO$^R$-EE-E2 or ptetO$^R$-EE-E2(E39A) were growing to logarithmic phase respectively. The decay of EE-E2 or EE-E2(E39A) were determined by promoter shut-off with the addition of 10 ug/ml deoxycycline. 10 ml of culture were withdrawn at the indicated time points for preparing protein extracts. EE-E2 or EE-E2(E39A) were detected by immunoprecipitation from 200 ug of extracts followed by immunoblotting using the anti-EE monoclonal antibody (Babco).

Targeted Degradation of the Retinoblastoma Tumor Suppressor in Mammalian Cells h-βTrCP, was recently identified that targets CD4 for degradation in the presence of the HIV1 viral protein Vpu (Margottin et al., 1998). CD4 proteolysis requires the F-box region of h-βTrCP that interacts with human Skp 1, suggesting that an analogous human SCF machinery operates in the degradation of h-βTrCP substrates (Margottin et al., 1998). Indirect immunofluorescence studies indicated that h-βTrCP was localized both in the nucleus and cytoplasm (FIG. 9), suggesting the possibilities that h-βTrCP can be engineered to target the degradation of mammalian nuclear and cytoplasmic proteins. To demonstrate the efficacy of the engineered SCF system in mammalian cells to degrade stable cellular proteins, we studied whether expression of an engineered βTrCP-E7N hybrid is capable of mediating proteolysis of the physiologically stable pRB protein in mammalian cells. βTrCP-E7N and βTrCP-E7N(ΔDLYC) hybrids were constructed in pcDNA3 vector (Invitrogen) and were expressed under the control of the CMV promoter respectively. βTrCP-E7N efficiently interacts with pRB, whereas neither and βTrCP-E7N (ΔDLYC) nor βTrCP itself was capable of associating with pRB in the in vitro binding assays (FIG. 10A). The decay of an exogenous HA-tagged pRB protein was then examined in human osteosarcoma Saos-2 cells lacking a functional pRb. As shown in FIG. 10B, pRB was rapidly degraded in Saos-2 cells expressing βTrCP-E7N, but not βTrCP-E7N (ΔDLYC). These results demonstrate that the SCF ubiquitin-proteolytic machinery operates similarly both in yeast and in mammals, and that the F-box-containing ubiquitin-protein ligases can be genetically engineered towards degradation of any cellular proteins of interest.

FIG. 9 βTrCP is an unstable protein localized both in the nucleus and in cytoplasm of Hela cells. (A) Human βTrCP is a short-lived protein. The human osteosarcoma Saos-2 cells were transiently transfected with Flag-tagged βTrCP expression plasmid. The decay of F-βTrCP over time were determined by pulse-chase analysis by $^{35}$S-Express labeling and immunoprecipitation with the anti-Flag M2 monoclonal antibody at the indicated chase times. (B) Hela cells plated on glass coverslips were transfected with Flag-tagged βTrCP (F-TrCP) or control untagged βTrCP. Cellular distribution of the F-TrCP was assayed by indirect immunofluorescence using the anti-Flag M2 monoclonal antibody.

FIG. 10 Degradation of pRB by the engineered βTrCP. (A) The engineered F-TrCP-E7N ubiquitin-protein ligase can interact with pRB. In vitro translated (IVT), $^{35}$S-labeled pRB was mixed with similarly labeled IVTs of βTrCP (lane1), F-βTrCP (lane 2), F-TrCP-E7N (lane 3) and F-TrCP-E7N (ΔDLYC) (lane 4) for 1 hour at 4° C. Complexes were then immunoprecipitated using the anti-Flag M2 monoclonal antibody and subjected to SDS PAGE electrophoresis. Lanes 5–9 represent 50% of the input $^{35}$S-labeled proteins used in the co-immunoprecipitation analysis. (B) The engineered F-TrCP-E7N ubiquitin-protein ligase can degrade transfected pRB. SAOS-2 cells were transiently transfected with the indicated amounts of HA-pRB and F-TrCP-E7N or F-TrCP-E7N(ΔDLYC). HA-pRB protein was determined from 200 ug of cell extracts by western blotting using the AB-5 anti-pRB monoclonal antibody. (C) F-TrCP-E7N blocks pRB induced growth arrest in SAOS-2 cells. SAOS-2 cells were transfected with 1.5 ug of pBabe-puro and 5.0 ug of each of the indicated plasmids. Transfected cells were subjected to puromycin selection for 7 to 10 days, and the percentage of flat cells were determined as previously described (Tienmann and Hinds (1998) EMBO J 17: 1040–52). The graph shown was the average from two independent experiments.

Targeted Degradation of Endogenous p107 in Mammalian Cells

A critical step for the application of the engineered proteolysis system is to target the degradation of endogenous proteins. We therefore tested whether βTrCP-E7N could target the proteolysis of p107, a pocket protein related to pRB and also capable of binding HPV16 E7. The cervical carcinoma C33A cells lacking wt pRB, which can be transfected at high efficiency (60% to 70%), were used in this experiment to study whether endogenous p107 could be degraded by the engineered βTrCP-E7N (Dyson et al. (1992) J Virol 66: 6893–902; Davies et al. (1993) J Virol 67: 2521–8). In this set of experiments, the C33A cells were co-transfected with CMV-CD19, and transfected cells were selected by immunomagnetic selection of those cells expressing CD19. As shown in FIG. 11A, the steady-state levels of p107 were dramatically decreased in βTrCP-E7N expressing cells, but were not affected in C33A cells expressing the control βTrCP-E7N (ΔDLYC) protein unable to bind p107. The CD19 negative Saos-2 cells, which did not receive transfected F-βTrCP-E7N or βTrCP-E7N (ΔDLYC), contain the same levels of p107 (data not shown).

To further improve the efficiency for the delivery of the engineered ubiquitin-protein ligase, we constructed adenovirus expressing F-βTrCP-E7N or F-βTrCP-E7N (ΔDLYC) to infect exponentially growing C33A cells (He et al. (1998) Proc Natl Acad Sci U S A 95:2509–14). Twenty-four hours post-infection, 100% of C33A cells were infected by the viruses, as determined by the expression of green fluorescence protein (GFP) from the adenovirus vector (He et al. (1998) Proc Natl Acad Sci USA 95:2509–14). As shown in FIG. 11B, expression of F-βTrCP-E7N completely eliminated the endogenous p107 in C33A cells, whereas expression of F-βTrCP-E7N (ΔDLYC) or the control virus has no effect on the cellular p107 protein levels. Collectively, these results demonstrated that by engineering an F-box-containing ubiquitin-protein ligase, the cellular SCF machinery could be redirected to deplete specific cellular proteins through the SCF-mediated ubiquitination machinery.

FIG. 11 shows that expression of the engineered F-TrCP-E7N ubiquitin-protein ligase can target degradation of the endogenous p107 in C33A cells. (A) C33A cells were transiently transfected with 3 ug of pCMVCD19 expression plasmid and the pCDNA3 vector alone, or the indicated amounts of pCDNA-F-TrCP-E7N or pCDNA-F-TrCP-E7N (ΔDLYC). Following transfection, cells were subjected to immunomagnetic selection by the anti-CD19 monoclonal antibody and the Dynabeads coated with Rat anti-Mouse IgG1. Extracts (200 ug) of CD19 positive cells were examined for the levels of the endogenous p107 using anti-p107 polyclonal antibody (Santa Cruze). The endogenous actin levels are indicated as an internal loading control. (B) C33A cells were mock infected, or infected with either control adenovirus (C), or adenoviruses expressing F-TrCP-E7N or F-TrCP-E7N (ΔDLYC) for 20 hours to analyze the levels of endogenous p107 as described in (A).

Experimental Procedures

Yeast Strains and Plasmids.

The S. cerevisiae strains used for half life determination and in vivo ubiquitination studies were gifts from Drs. D. Finley, S Elledge and S. Reed and were shown as follows: KY130 (Mat a, ura3-52, leu2-Δl, gcn4-Δ, ade8::GCN4), KY203 (Mat a, ura3-52, leu2-Δl, gcn4-Δ ade8::GCN4, cdc34-2), YY371 (Mat a, ura3, leu2-3, 112, his3-11), YY374(Mat a, ura3, leu2-3, 112, his3-11, prel-1, pre4-1), Y81 (Mat a, can1-100, ade2-1, his3-11, -15, leu2-3, -112, trpl-1. ura3-1), Y553 (Mat α, can1-100, ade2-1, his3-11, -15, leu2-3, -112, trpl-1. ura3-1, skpl-11) or cdc28-4 (Mat a, ura3, leu2, adel, trpl, arg4, his2, cdc28-4). SJ1012-4 (Mat a, leu2-3, -112, ura3-52, lys2, adel, his7, cdc4-5) is a gift of Drs. B. Byers and B. Jenson. INVSc1 (Mat α, his3Δ1, leu2, trpl-289, ura3-52) was purchased from Invitrogen. Flag-tagged Cdc4p and Skp1p, or HA-tagged Cdc53p and Sic1p were generated by PCR for cloning into the pYES2 vector (Invitrogen). F-Cdc4p, F-Skp1p and HA-Cdc53p were functional since they could complement the temperature sensitive mutants of cdc4-3, skpl-11 and cdc53-1. SIC1-HA was previously shown to be able to substitute for the chromosomal SIC] (Schwob et al. (1994) Cell 79: 233-44). Flag-tagged Cdc4p carrying the Gly 300 to Asp alteration, or a deletion of the entire F-box, were constructed by PCR-directed mutagenesis and were cloned into the pYES2 vector. Individual Cdc4p segments encompassing the F-box, the WD repeats or both the F-box and the WD repeats were generated by PCR and were cloned into pLDSG5 vector to make fusions to LacZ (Bachmair et al. (1986) Science 234: 179–86). PCR fragments with ubiquitin or Myc-Ub encompassed by the CUP1 promoter and the CYCI terminator sequences (Ellison and Hochstrasser (1991) J Biol Chem 266: 5966–76) were cloned into the pRS425 vector for coexpression with HA-Grr1p$^{\Delta N}$ in Y81 cells. All PCR products described above were verified by automated sequencing. Information on details of the plasmid construction are available upon request.

Protein Stability

Promoter shut-off, pulse-chase analysis, immunoprecipitation and immunoblotting were carried out as described (Bachmair et al. (1986) Science 234: 179–86; Visintin et al. (1997) Science 278: 460–3). For half-life studies by promote shut-off, exponentially growing KY130 or Y81 cells carrying either F-Cdc4p, HA-Cdc53p, Flag-Skp1p, Sic1p-HA, F-Cdc4p(G300D), FCdc4p(ΔF) or various Cdc4p segments/β-Gal fusions under the control of the GAL1-10 promoter, were induced to express the individual proteins for 1 hour by adding 2% galactose to the raffinose containing media. Cells were then transferred to glucose-containing medium containing 1 mg/ml cyclohexamide to repress transcription and translation, respectively (Visintin et al. (1997) Science 278: 460–3). Aliquots from the cell culture were withdrawn at the indicated time intervals, protein extracts were prepared and 100 ug of each extract was used for immunoblotting. To determine Cdc4p stability at different cell cycle stages, KY130 cells carrying GAL-F-Cdc4p were arrested by α-factor (3 ug/ml) in GI phase, hydroxyurea (10 mg/ml) in S phase or nocodazole (15 ug/ml) in M phase in raffinose-containing medium. After 3.5 hours, 2% galactose was added to induce synthesis of F-Cdc4p for 45 minutes. Cells were then washed into fresh medium containing 2% glucose and the half life of F-Cdc4p in G1, S or M phase synchronized cells was determined by immunoprecipitation and visualized by immunoblotting using the anti-Flag M2 antibody (Visintin et al. (1997) Science 278: 460–3). For pulse-chase analysis, exponentially growing KY130 cells or Y81 cells expressing HA-Grr1p$^{\Delta N}$ were pulse-labeled with $^{35}$S-Methionine for 15 minutes followed by chasing in cold fresh medium containing 0.15% L-Cys/0.2% L-Met/50 mM (NH4)$_2$SO$_4$. Portions were withdrawn at the indicated time intervals and analyzed by immunoprecipitation to determine the half lives of the endogenous Cdc4p, Skp1p, or HA-Grr1p$^{\Delta N}$. To assess Cdc4p degradation in YY374, cdc34-2, skpl-11 and cdc28-4 ts mutants, cells carrying the galactose inducible F-Cdc4p plasmid were grown at 25° C. to mid-log phase. Half of each culture was allowed to continue growing at 25° C. and the other half was shifted to 37° C. for 1 to 3 hours. 2% galactose was then added to induce F-Cdc4p expression in each culture 1 hour prior to promoter shut-off to determine the half-life of F-Cdc4p at the non-restrictive (25° C.) or restrictive temperatures (37° C.). As a control, the turn over rate of F-Cdc4p was also determined at 37° C. in the respective isogenic wild type cells (data not shown).

In Vivo Ubiquitination

Exponentially growing INVSc1 cells expressing an untagged Cdc4p (pYES2) and Myc-Ub (YEP105), under the control of the GAL1-10 and CUP1 promoters respectively, were carried out with induction media containing 2% calactose and 100 mM CuSO$_4$ for 3 hours (Ellison and Hochstrasser (1991) J Biol Chem 266: 21150–7). Yeast cells were lysed by vortexing with glass beads n NP-40 lysis buffer (150 mM NaCl, 1.0% NP-40, 50 mM Tris (pH 8.0)), and Cdc4p was immunoprecipitated from 1 mg of each extract adjusted to RIPA buffer condition (150 mM NaCl, 1.0% NP-40, 0.5% DOC, 0.1% SDS, 50 mM Tris (pH 8.0)) using 2 ug of affinity purified anti-Cdc4p polyclonal antibody (Harlow (1988) Antibodies, a laboratory manual (Cold Spring Harbor: Cold Spring Harbor Laboratories). The ubiquitinated Cdc4p species was detected by immunoblotting using the anti-Cdc4p or 9E10 antibodies. Y81 cells carrying the constitutively expressed HA-Grr1p$^{\Delta N}$ were induced for 3 hours by 100 mM CuSO$_4$ to express Ub (YEP96) or Myc-Ub (YEP 105) for detection of ubiquitinated Grr1p.

Yeast Strains, Cell Culture and Plasmids

S. cerevisiae INVSc1 (Invitrogen) and Y81 cells (gifts of S. Elledge) were used to assess the in vivo degradation of the papillomavirus E2 or pRB by the engineered Cdc4p ubiquitin-protein ligases. The human osteosarcoma Saos-2 cell was a gift of Drs. David Thomas and Philip Hinds. The galactose inducible pRB expression plasmid p2202TRB was a gift of Dr. Robert Weinberg (Hatakeyama et al. (1994) Genes Dev. 8: 1759–71). The engineered Cdc4p derivatives designed for targeting pRB degradation were constructed as follows: Cdc4p$^{F/WD}$-LTP and Cdc4p$^{F/WD}$-LTP(FGSK) cDNAs were generated by PCR using the 5' primer 5'-GCG-GATCCACCATGGATAAMAAAGAGGGAC-CTAATAAC-3' (SEQ ID No. 30) that hybridizes to CDC4 corresponding to residues 270 to 277 with a BamHI site and the ATG translation initiation codon at the 5' end, and the 3' primer encoding sequences of either the Cdc4p C-terminus (residues –779) in frame fused to the pRB binding domain of the SV40 large T antigen (residues 103–115), or the same primer carrying point mutations of the LFCSE (SEQ ID No. 47) motif that abolishes its interaction with pRB (DeCaprio et al. (1989) Cell 58:1085–95; Dyson et al. (1989) Science 243: 934–7; Figge et al. (1993) Protein Sci 2: 155–64; Munger et al. (1989) EMBO J 8: 4099–105); Yang et al. (1995) Nucleic Acids Res 23: 1152–6). The sequences of these two 3' primers carrying the NotI site and a translation stop codon are 5'-GCGCGGCCGCCTACTCATCATCAC-TAGATGGCAMCTTCTGAGCAAAACAG CCCTCTGG TATTATAGTTGTCCTCGT-3' (SEQ ID No. 31) and 5'-CGCGGCCGCCTACTCATCATCACTAG ATG-GCAMTTGAGCCAAAGTTTTCTCTGGTAT-TATAGTTGTCCTCGT-3' (SEQ ID No. 32). The resulting PCR fragments encoding Cdc4p$^{F/WD}$-LTP or Cdc4p$^{F/WD}$-LTP(FGSK) hybrids were digested with BamHI and NotI, and were subsequently cloned into the pYES2 vector (Invitrogen) for expression in Y81 cells under the control of the GAL1,10 promoter. The Cdc4p$^{F/WD}$-E7N or Cdc4p$^{F/WD}$-E7N(DLYC) hybrid constructs were obtained by a two-step PCR approach as described in detail (Dieffenbach, 1995). The first PCR reactions for making individual Cdc4p$^{F/WD}$-E7N or E7N(DLYC) DNA fragments were conducted using pYES-F-CDC4 (this work), pGST-E7(2–35) or pGST-E7 (2–35)(DLYC) plasmids as templates (Gifts of Dr. K. Munger). The sequences for the primer sets used are as follows: 5'-GCWATCCACCATGGATAATITAAAGAGG-GACCTAATAAC-3' (SEQ ID No. 33) (5'-extreme) and 5'-GTAGGTGTATCTCCATGTGGTATrATAGTrGTCC-3' (SEQ ID No. 34) for Cdc4p$^{F/WD}$, 5'-GGACAAC-TATAATACCACATGGAGATACACCTAC-3' (SEQ ID No. 35) and 5'-GCCTCGAGTCACTCCTCCTCTGAGCTGTC-3' (SEQ ID No. 36) (3'-extreme) for E7N or E7N(DLYC), respectively. The second step PCR reactions were conducted using the same 5'- and 3' extreme primers to ligate Cdc4p$^{F/WD}$/E7N or Cdc4p$^{F/WD}$/E7N(DLYC) PCR fragments together. The resulting hybrid Cdc4p$^{F/WD}$-E7N or Cdc4p$^{F/WD}$-E7N(DLYC) DNA fragments were digested with BamHI and XhoI which were introduced by the 5'- and 3'-extreme primers, respectively, and were cloned into the p426-ADH plasmid (ATCC) for constitutive expression in Y81 cells under the control of the ADH promoter. Cdc4p$^{F/WD}$-E1C were constructed similarly by the two-step PCR approach using primer pairs 5'-GCGGATCCACCATG-GATAAMAAAGAGGGAC CTAATAAC-3' (SEQ ID No. 37) (5'-extreme)-3' and 5'-CCTATCACATCTATATTTTAT-TGGTATTA TAGTTGTC-3' (SEQ ID No. 38) for Cdc4p$^{F/WD}$, and 5'-GACAACTATAATACCAATAAAATATAG ATGTGATAGG-3' (SEQ ID No.39) and 5'-GCCTCGAGT-CATAATGTGTTAGTATTTTGTCCTG-3' (SEQ ID No. 40) for E1C. The resulting Cdc4p$^{F/WD}$-EIC fragment was cloned into the BamHI/XhoI sites of p426-ADH vector. EE-tagged HPV16-E2 and HPV16-E2(E39A) were generated by PCR using primers 5'-GCGGATCCACCATGGAGGAAGAA-GAGTATATGCCCA TGGAGGAGACTCTT TGC-CAACGTTTTAAATGTG-3' (SEQ ID No. 41) and 5'-GCGCGGCCGCTCATATAGACATAAATCCA GTA-GAC-3' (SEQ ID No. 42), and the resulting PCR fragments were cloned into the single copy plasmid pCM185 for expression under the control of the tetracycline-repressible (tetO$^R$) promoter in S. cerevisiae.

βTrCp-E7N and βTrCP-E7N(DLYC) were also constructed by the two step PCR approach with primer pairs 5'-GCGGATCCGCCACCATGGACTACAAGGACGAC GATGACAAAGATGACCCGGCCGAGGCGGTGCTG-3' (SEQ ID No. 43) and 5'-GTAGGTGT ATCTCCATGTCTG-GAGATGTAGGTGTATG-3' (SEQ ID No. 44) for PTRCP, 5'-CATACACCTA CATCTCCAGACATGGAGATACAC-CTAC-3' (SEQ ID No. 45) and 5'GCGCGGCCGCT-CACTCCTCCTCTGAGCTGTC-3' (SEQ ID No. 46) primer sets for E7N or E7N(DLYC). The final PCR fragments were cloned into the BamHI/NotI sites of pcDNA3 (Invitrogen). The cloned PCR fragments described above were sequenced by the BCMP core facility at Harvard Medical School. Expression of the engineered Cdc4p hybrids in Y81 cells were confirmed by immunoblotting using the anti-Cdc4p polyclonal antibody.

Immunofluorescence Staining

The cellular distribution of βTRCP was analyzed by indirect immunofluorescence. Hela cells grown on glass coverslips were transfected with F-TrCP, βTRCP or pCDNA3 vector using the FuGENE transfection reagent. 36 hours post transfection, cells were washed with PBS and fixed in 3% paraformaldehyde for 10 minutes at room temperature. Cells were then washed in blocking buffer (0.2% Fish Skin Gelatin, 0.02% Triton-100 in PBS) and hybridized with the anti-Flag monoclonal antibody (3 ug/ul) (Kodak) at 1:500 dilution in blocking buffer for 30 minutes. After washing 3 times with blocking buffer, cells were hybridized with 1:500 dilution of Cy3-conjugated goat anti-mouse IgG (Jackson Immunoresearch Inc.) for 30 minutes, washed twice in blocking buffer, once in PBS, and mounted on microscope slides for visualization.

Interaction of pRB with the Engineered Ubiquitin-Protein Ligases

Interaction of pRB and the pRB binding peptides for engineering Cdc4p-derived ubiquitin-protein ligases were demonstrated previously by in vitro binding and by the two hybrid interaction assay in yeast cells (Yang et al. (1995) Nucleic Acids Res 23: 1152–6 (K. Munger, personal communications). To verify the interaction between pRB and the engineered F-TrCP-E7(N), pRB and the individual F-box/WD40 repeats-containing βTrCP derivatives were synthesized in vitro in the TNT rabbit reticulocyte lysates in the presence of $^{35}$S-methionine. 10 ul of each radiolabeled proteins, βTrCP, Flag-tagged βTRCP (F-TrCP), F-TrCP-E7(N) and F-TrCP-E7(N)(ΔDLYC) (lanes 1–4) were mixed with 10 ul of $^{35}$S-labeled pRB individually for co-immunoprecipitation with 1 ug of the anti-Flag (M2) monoclonal antibody (Kodak) in NP40 lysis buffer (250 mM NaCl, 0.1% Nonidet P-40, 50 mM Tris-HCl, 5 mM EDTA, 1 mM dithiothreitol, 0.01% phenylmethylsulfonyl fluoride, 1 ug each of aprotinin and leupeptin) as described in detail (Harlow (1988) Antibodies, a laboratory manual (Cold Spring Harbor: Cold Spring Harbor Laboratories), and were electrophorized on a 7.5% SDS PAGE gel.

Engineered SCF System in Yeast and Mammalian Cells

To evaluate pRB stability in *S. cerevisiae*, Y81 cells containing the pRB expressing plasmid p2202TRB under the control of the GAL1,10 promoter were grown to log phase in raffinose-containing medium, and were induced for 1 hour by addition of 2% galactose. Cells were washed into glucose-containing medium in the presence of 1 mg/ml cyclohexamide to repress pRB transcription and translation respectively. Aliquots of cells were collected at the indicated time points following promoter shut-off, extracts were prepared by vortexing in glass beads containing NP-40 lysis buffer, and 100 ug of each extracts were analyzed by immunoblotting using the Ab-5 anti-pRB monoclonal antibody (CALBIOCHEM). pRB half life was determined similarly by promoter shut-off in Y81 cells constitutively expressing the engineered Cdc4p derivatives, Cdc4p$^{F/WD}$-E7N or Cdc4p$^{F/WD}$E7N(ΔDLYC), under the control of the alcohol dehydrogenase (ADH) promoter. The steady-state levels of pRB was also determined from 100 ug of Y81 extracts induced for the indicated hours to express Cdc4p$^{F/WD}$-LTP or the mutant Cdc4p$^{F/WD}$-LTP(FGSK) hybrid by immunoblotting using the Ab-5 anti-pRB monoclonal antibody (CALBIOCHEM). The half lives of EE-E2 or EE-E2(E39A) were similarly determined in Cdc4p$^{F/WD}$-E1C expressing INVSc1 cells by promoter shut-off in the presence of 10 ug/ml deoxycycline, a metabolically stable tetracycline derivative. The decay of EE-E2 or EE-E2(E39A) over time were determined by immunoprecipitation followed by immunoblotting using the anti-EE monoclonal antibody (Babco).

To demonstrate the efficacy of the engineered ubiquitin system in mammalian cells, the human osteosarcoma Saos-2 cells lacking endogenous pRb were co-transfected with 5 ug each of HA-tagged pRB and F-TrCP-E7(N) (lanes 1–3), or with 5 ug each of HA-pRB and F-TrCP-E7(N)(ΔDLYC) (lanes 4–6) using the FuGENE transfection reagent, respectively. 36 hours after transfection, cells were starved for 1 hour in DMEM media without L-Met and L-Cys, pulse labeled for 1 hour with the $^{35}$S-Express labeling mix, and then chased with fresh DMEM media containing 15% fetal calf serum at times 0, 3 hours and 6 hours. Cell lysates were prepared in NP-40 lysis buffer and 200 ug of each extracts were subjected to immunoprecipitation by the 12CA5 monoclonal antibody.

6. POLYPEPTIDE AND NUCLEIC ACID COMPOSITIONS

F-Box Polypeptides and F-Box Encoding Nucleic Acids

The F-box protein Cdc4p is encoded by a nucleic acid sequence corresponding to nucleotides 7558 to 9897 of GenBank Accession No. D31600 (SEQ ID No. 1) as shown below, and which encodes the F-box protein corresponding to GenBank Accession No. BAA06495 (SEQ ID No. 2) as shown below.

```
                                                           SEQ ID No. 1
  1  ggatccgtgt cgtaactgcg ttccgtacac cttaaaatga actttccagc aggtgcacca
 61  tcttccaatc cattgaaaaa tcttactgat tcttcgacct cctcctggct taagtttgtc
121  tccaaatgaa tatatagcag ccaaatcaat atgtttgatc tatcctttgg ctcgtatttc
181  gaatagtcca gtatatcaaa taatgttgtt gcataagctg cttttgattc ttgtttttca
241  ttttccgctt ccgtttcttt tacttcattc tgttcatcta ccatatcttg ctcctgagct
301  ttcgattcga cttccacata cttggaaaga aacctcttgt caattaggcc ggaattatca
361  catatgctaa acaacatatt aataatgtta aatttgttaa cggtgtccac ttcaccatca
421  ttttggtcga ccttttttgta agtctccatc aatgagagtt gctcattgcc ccacggcaga
481  tttttcagaa tagatttcag tctaggtgta tcctgcaaaa gtttcggatc attggcatgt
541  aattgtaaaa ctggcacgga gtgaaaagtt ctcaattgcg atgtcatttc taaataaaaa
601  tttatagtgg tgttcaacct accaatgttg accaataacg ctaaaacaca agtagaaaat
661  gctacttgtt ggtctaataa tagtttatct ctgagaattt tggaacattt gatagaagtg
721  gctattgtca acacatacaa ttgtgcgaac gtcaatttat cgttaaatac aaatgtcctt
```

-continued

```
 781 gcatcgtact ctttgtcggt cacgttgatt gataatttat cgccatcgat attaatgggt
 841 acaatagagt tcttgtatag gggtttttaga acattagtga agatttgcct cttgtccatc
 901 aacagttctt gcatgaaact gaactgaatg tcctttctat tgaatggctc gccgtcaggt
 961 ttcttcaaat gacgattgta tttactggca ttgctttctt tgggtttcct tctaacagtg
1021 ttagttgtca ctggccccgt tgccgtactt gctcctgttg cttcaggcac tgtagaaggt
1081 tcgaagttga gcaagatgtt ggtattttct tcttcacttt gcgtggagtc atcatcattt
1141 ttatcgtcga tttcaatctc gtgtataact ggaatgcttt ttgtagtcac agtctcggtc
1201 tctgattgaa tggagcttgg ggatgcttct tcttgtgatc ccgattttac agattgcatt
1261 ggagaatctg cttttgtttc gtcagaattg tcttctcgta gttggaaagt atcatgaatt
1321 ggatcgtata ctctcttccc catctttaat tagagtgtcg cctttattta gctttcgatt
1381 ttacttagtt aatcatgaac tgtttccaat accatatcag cattcattgg gcgttcttta
1441 cttacttgta ccgttaccgc attcgagggt aacctgtttt tcgttgtaca cgatatgcta
1501 cagaattgtc ttaatatggg ctaagaaaaa aaaagtctg attatttctg atactgcaaa
1561 atatatactg gcttggttaa gaaaagtgtt gctttagttc ctttacatca agagtcgtta
1621 aattgttttg tgtcataaca gtagtggtct tttgagacat caatcgactc tcaggttttc
1681 cttctgttca tcttcttgtt ttcggtaaag gtcagccagc atatttcaat tctctctttt
1741 ttgaaataac attatgtaat ctttcaatcc tttctatcca acgtctgcta ataatttat
1801 tcaaatgaca tgtagaccag aaaatcgaac gttggataat ttttcatcct gaatcatgtt
1861 ggtctcaact agagcaattt tttcacgtcc tctgacacaa aactcgataa actgtcgcat
1921 cagtttaaaa aaatatgtac gtgtataata actgaattta aaaggatagt aaataatttt
1981 tgcattttat ggaatgtcaa aatactaata agtcgcaaat atagctatca aataccataa
2041 tttagctact tatagaaaga tgcccaaatc ccgaccaaaa aggaccattg cgtcttcctc
2101 gtcagttttt tatggaagtt caccttccca aaatgatggc tacatcaaag taatggaact
2161 cgtatcacac attgtcattg aaataaatca ttcacctacc gcaacaacga atgaaacgag
2221 aaagcagaat aatccggagc tgaaagtgaa agaaccagtt tgtaacctca agaagtggga
2281 aaataacact aactttatat tggaagatca tacgaagaat aaaacaaaac tttctagcac
2341 agataggata cgtaagtggt ttagaagaca tatattaaag gaagagatcg aaatcctttc
2401 ccatggaaaa caattgagta gtattgatga ggattattgc ccttcaaatg ttcttgtagg
2461 atgttcaaga gatctaaata aactcagatc atttcaaaat ttttaggaat ataaaatttc
2521 tcagtaagaa aaagaagatg aatgcgttta tagtatttta agttgttcaa tagaatatct
2581 tcaatatgtt catatgtgga ctaaagaag attttggtat atgtctataa atttattgtt
2641 ggtaaacgcc attaagcagc tttccaagaa tatgttatca ttgaggagaa gtacgaaaac
2701 tgattatgca cgattaggaa aaattctgca aggagtatta aaaaatggcc ttcgagaaga
2761 aatgaaatct ctttcgatga gcaatggtct tatggataat ttgatagaca tatgaaaaag
2821 tcaaaagttt ttttggccat atgcagtaaa aacttaccct tcaaattgca aaaccattag
2881 ttttattata ttttttttt tttctttcat tgaagtatac acgaaatccc atacgcaaat
2941 aaacagtcgt tgtatcatca atttcggctg tctggatggc gactacgaga ggaagcttgc
3001 ttgccatgat aggaccaatc tcaattttta attttcatt aactagctaa ttttctataa
3061 tgctctaagt ttccttttc gttttgtttc tttatagtga tgatgctgtt attgtgacgc
3121 tatcaaatca tatactgtca tcaatcctca tctcatcggc tccggaacgc gttgaatatg
```

-continued

```
3181  ttgttaaaca agctctttat agctagctat agtagaaaag gaaggaaaga agtctaatcg
3241  ctgtattatc gactgacaag ggttgtcagt tgccttcttt tattttttgt actcccctga
3301  atcgagcgga tgtatttttt aacaaagtat tcagaattgt ttttgtataa tcaaaatttg
3361  tcgacgctaa gaaaatgacg gacgtcgtaa ttccgctact aggttttgtg tgctcatcga
3421  tatttgacac ctattttcga cactttttaag gttatatact ttgtttcgga tgtggggtac
3481  actcagttga ctgattatga agatatggc gtagccgttg ggttagggtt attacacaga
3541  aatgaattat accagtgaaa ttattctctt tatgtttgtt cctacatgtt ttccaatcag
3601  aaggaattgt tatataagga cacaagaaat gtgttggtac gctctgcgcc tcaatgacgg
3661  tttatctatc taaaactatt tctttctcgt aataaaaata caataaataa ttaataataa
3721  tatagttgat cgatataaca aaaaaataac agcgaggatg gttagttcaa gtgtttccat
3781  tttggggact agcgccaagg catccacttc tctaagtaga aaggatgaaa ttaaactaac
3841  ccctgaaaca agggaagcta gcttggacat tccatacaaa cccattattg catactggac
3901  ggtgatgggt ctctgtctga tgattgcctt tggtggattc attttggtt gggatacagg
3961  aaccatttca gggtttatta accaaacaga tttcaagaga aggtttggtg agttacaaag
4021  ggacggcagt tttcaactat cagatgtcag gacagggcta attgtcggta tcttcaacat
4081  aggttgtgct ttaggtggcc taacgctggg acgcctgggc gatatttatg ggcgtaaaat
4141  cggcttaatg tgtgttatac tggtgtatgt tgttggtatc gtgatccaga ttgcttcctc
4201  tgacaaatgg tatcaatatt ttattggtag aattgtttct ggaatgggtg ttggaggtgt
4261  tgctgtgctg tcgccaactt tgatctcaga aatttcccca aagcacctaa gaggcacttg
4321  tgtctctttt taccagctaa tgattaccct tggaattttc ttgggctact gtaccaatta
4381  tggtacaaag aaatattcaa attcaataca gtggcgggtt cccttgggtt tgtgttttgc
4441  gtgggcaatc tttatggtga ttggaatggt tatggttccg gaatcgccca gatatttagt
4501  agaaaaggt aagtatgaag aagctagaag gtctttggcc aaatcaaaca aggtcacagt
4561  tactgatcca ggcgttgttt ttgagtttga tactatagtt gcaaatatgg aattagaaag
4621  ggctgttgga aatgccagtt ggcacgaact cttctcaaat aaaggagcaa ttctaccaag
4681  ggtaataatg ggaatcgtta tccagtcact gcaacagctt actggctgta attattttt
4741  ctactacggc acgaccattt tcaatgctgt tggaatgcaa gactctttcg agacttccat
4801  tgtccttggg gctgttaatt ttgcttctac atttgttgca ctatacattg tggataaatt
4861  tgggcgtcga aaatgtttat tgtgggggtc tgcctcgatg gcaatttgtt tcgtcatatt
4921  cgccaccgtt ggcgtcacta gattatggcc acaagggaaa gaccaacctt cttcgcaaag
4981  tgctggtaat gttatgatcg tttttacttg tttcttcatt ttctcttttg ccattacttg
5041  ggctcctatc gcctatgtca ttgtggcaga aacttatcca ttaagagtta aaaatcgtgc
5101  catggccatt gcggttggtg cgaactggat gtggggttc ttgattggat ttttcacacc
5161  ctttatcact agatccatag gattttctta tggctatgtt tcatggggtt gcttaatctt
5221  ttcgtacttc tacgttttct tctttgtttg cgaaacaaag ggattaactc tggaggaagt
5281  taatgaaatg tacgaagaaa gaataaagcc atggaagtcc ggaggttgga ttcccagttc
5341  tagaagaaca ccacaaccaa caagcagtac accattagtt attgttgata gtaaataatt
5401  tctaaatatt cttgtactct ggtaaacaga aataacaaca gataatggat tgatgctta
5461  cttctatttc atggagattg gttttatata atagccttta ttaatggcgt cacaaattga
5521  aaaaaaaatt aaaaaaaata agacggacac atttgcgacg ccggtgaata aatgcatata
```

-continued

```
5581  agtagtttat aagctagcta ctactcagaa ataatttcaa aaaaaaaaag aagtgggcac
5641  tttaaaatga agattagcta tagtaaatta ctgtagtata acaactacct gctatctttc
5701  tgaaaaaatc aggcaatgta aggtcaaact tgtaccatcg acatatataa tgttttgaga
5761  tataagtaac tagagaccag tttatacagg atcttacctc tttttaccgt tatgaaagct
5821  ttattactgc gttgttagta aacacacata ttattttcgg gtagtcctgt cgatgttcca
5881  aggctttgca tttatcattg tttccgcttc atcggtggta ttagttagtg tatctgtatg
5941  tgaagtatgt ggataggtgc ttctattatt ggaacaaaac accttaaacg cgcactaggt
6001  tataggaaag ggtccattat tcaaagaacg gcttattgaa aagtatgttg taaagctcgg
6061  tcatatcgcg catagccacg ataaggcgtg gtgctgcttc atagattgag aggcgcagtc
6121  aatacacaac cataccggta gtttgataaa tgatactatc attccggaag ctctctagta
6181  agctgtaggt ggcatatacg gtatctatca tctagtaata gctattgatt tttttctcga
6241  ctatgctata tgtgttgtga tggttcactt agaagtgaaa aagtagcaat aaattagaca
6301  gacagaagta attgaagcta cattcaacaa catggctaag taaaaaagcg tagaatatca
6361  tgatgggttt ttttatcttt taattgcttt ctatgtagta taatggaccg atctttgcaa
6421  gtatatatct gtatgtatcc atatttagat ggcagcaagc aatatagatt tgatgagctt
6481  atatcatttt atcgtccttg tccaaaaagt cttgataaca ttaaaagtca ctaccgtcaa
6541  atccatcatc aaatccgccg tcgaacccac cagcatcatc aaatccgccg tcggacccac
6601  cagcatcatc accgtagtaa ttgttctcga caacgacagt gtctggtccg tcatagttgt
6661  ggtcgtcaaa tgcgtgttct agcatagctc cacctaacaa acccgcacca acaccaagta
6721  aaccacccat catggcaccg ccgtgtccac taccttaact ggtgcttggc gcagttccat
6781  agtatgcttg ctgtggtgct gctgctggca taggggcttg ttgaggatag taacgctgct
6841  gttgagggta ttgagggtac tgaggctgtt gaggctgata gtaacgaggt tgctgtgctt
6901  gggccctgc ttgcacttgc ggtgttgatt gagaagaata aggtggagga gcctggtctg
6961  cctgttgacg agaactcttc tcattgttaa cacctggtgg aggacctttg ggtcttggcc
7021  atgttgttcc ccttggtggt tcccactgag agctgttcgt agataaatct acataatacc
7081  aagtctggta ttcatcatca aaaacagcct tccagccaga aggcacttga ggaggattac
7141  ttttactttg agccattact ttaaaatgtt ttgggttttt ttatcgactc tcttgtagtg
7201  agtgataaaa gcaattcaga aagagtcttt tgattatcat gactaaagta aactttttct
7261  tccagctgcc ggctcggtca ggtggacgaa acaaaaaagc ctgttgaaat aatactgaat
7321  acgttaaaac gtcacagcgc ttgtatatct tgtgagagaa aggctattac cactgttata
7381  tgaatataga ttgctcaaca aagcgtgtct ttttctgtgt gcttaaaata tagtgtcttt
7441  tttgggaaaa aaacgtttat ttacagtatt ctcttcttct tctcctcatt caacttgttg
7501  cggttcgaag aaaattacgc ataaagaatc aaagaaaggc aaaaattacg ctgtacgatg
7561  gggtcgtttc ccttagctga gtttccatta cgtgatatcc ctgttcctta tagctaccgt
7621  gtgtctggcg gtatagcttc ctcaggtagt gttactgcgc ttgttactgc cgctggcact
7681  catcgaaact cgtccacggc taagacagtt gagacagaag acggcgaaga agatatcgat
7741  gagtatcaga ggaaaagagc agctggttct ggcgaatcca ctcctgaacg cagtgatttc
7801  aaaagggtaa aacatgataa tcacaaaacc ctccatccag ttaacttaca gaacaccggt
7861  gcagcgtctg tggataatga cggtctgcac aatttaacag atatatccaa cgatgcagaa
7921  aaacttttga tgtctgtgga tgatggttct gccgcacctt ctacattgag tgtaaacatg
```

-continued

```
 7981 ggagtggcat ctcataatgt tgctgctccc actaccgtca atgcggcaac aataactggc
 8041 agtgatgtta gtaacaatgt taatagtgct actattaaca atcctatgga ggaaggagcg
 8101 ctgccgttat cacccactgc ttcctctcca ggtaccacaa ctcctttagc taaaactacg
 8161 aaaactatca acaacaataa taatatcgcc gatttgatag aatccaaaga ttctataatc
 8221 tcccctgaat acctttctga tgagattttc agcgcaataa acaataatct ccctcacgca
 8281 tacttcaaaa atttattatt tagattagtt gccaacatgg ataggagtga actatccgac
 8341 ttggggactt taatcaagga taatttaaag agggacctaa taacgtcttt gccttttgaa
 8401 ataagtttga aaattttcaa ttatttgcaa ttcgaggata ttataaattc ccttggggtc
 8461 tcccaaaatt ggaacaaaat aattagaaaa tctacatcgt tgtggaaaaa acttctgata
 8521 tcggaaaatt ttgtgagccc aaagggtttt aattctctca atctcaaact ctcccaaaaa
 8581 tacccaaaac tctcacaaca agatcgcctt agattatctt ttctggagaa tatattcatt
 8641 ttaaaaaatt ggtacaatcc caagtttgta ccacaaagga ccacgttaag aggccatatg
 8701 acgagtgtta ttacgtgctt gcaatttgaa gataattatg tcattacggg ggctgatgac
 8761 aaaatgatca gagtttatga ttcgataaac aagaaatttc ttctacaact atcaggtcat
 8821 gatggtgggg tttgggcatt gaagtatgcc catggcggta ttttagtcag cggttctaca
 8881 gacagaacgg tgcgagtttg ggatattaag aaaggttgtt gtacccatgt gtttaaaggt
 8941 cataactcta cggtgaggtg cctagatata gtagaatata aaatatcaa gtacattgtt
 9001 actggttcga gagataacac tttgcacgtt tggaaattgc caaggagtc ctccgttcct
 9061 gatcatgggg aagaacatga ttatccatta gtctttcata cccctgagga gaacccatat
 9121 tttgttggtg ttttaagagg acatatggca tctgtaagaa ctgtctcagg ccacggtaat
 9181 attgtcgtta gtggctccta tgataataca ctgattgtgt gggatgttgc gcaaatgaaa
 9241 tgtttgtata ttttaagtgg acatacggat cgtatttatt cgacaatcta cgatcatgaa
 9301 agaaaaaggt gcatctctgc cagtatggat accactatta gaatttggga tttggaaaat
 9361 atatggaata atggagaatg ttcctacgca acaaattcag catcgccatg cgccaaaata
 9421 cttggtgcta tgtacacttt gcagggtcat acagctttgg tcggtttatt aagattatcc
 9481 gacaaatttt tggtcagtgc cgctgcagac ggttcaataa ggggttggga cgcaaacgac
 9541 tactctagaa aatttttccta ccatcatacc aatttgagtg caattaccac attttatgta
 9601 tcggataata ttttggtgag tggatcggaa aatcagttca acatctataa tctacggagt
 9661 gggaaattgg tccacgcaaa tattctaaaa gatgctgatc agatttggtc ggttaatttt
 9721 aagggcaaaa cacttgttgc agcagttgaa aaagatggac agagcttttt agaaattctg
 9781 gatttcagca aagcttcaaa aattaactac gttagcaatc ccgtaaactc ctcgtcgtcg
 9841 tctttggaat ccatttctac ttctttgggt ctaacgagga caactataat accatgacct
 9901 ttcccagaga ataagcattg actcatactt agataatata gcttaataag tagttatata
 9961 atcagtaaaa aagtacaata acaacttcgt acattttatt gagtataaac tgcagctaaa
10021 ctgcctggat gtgtcaattt taattgtgtt tacaaaaagg gtgccgttta ttaattaatg
10081 tttcttccct gaaaatatgg aaagtacaag tttttagttg agaagggttt aagaaagttt
10141 tgaaatgat ctaaaaaat ataaagcaa tcaagaaat aaaagctgga aaaatgcgta
10201 ataaccgaag tgactaaaat ttctttacgc gccaaataag aaatcgatgc tcttgaaagt
10261 agcaaccatt ttttaaataa tatattcctg atggttcttg gcccaagagt tttcttgaac
10321 ttttaacgtt aagaagttga ttctgctgat tttttcaag ttatcaagcg ttatgttttg
```

-continued

```
10381  aaacatctgt tccgttttca gtttttcaaa aagatcgata ttctcttgag aattaggaag
10441  ttctacgctc aacctcccgt gggcagaaga aatacaaaag ctaatacaat tgtgttagaa
10501  taaagttcta atattatcta attagtagta ttcatgttac tagtatatta tcacatgata
10561  tttctcaaat tggacaatgt aaataatgag tgtttttatg acacaatctt tatcgttaga
10621  tgtttcaacg ttccaaggct tggttctatc gctcttctct tcaaattgta atcgtttgtc
10681  atgataaaca cgtacgggaa aaaaaaaaa agtatcaata acgcgtaaag tgaatagagt
10741  attggattct ataagaccga agacgctcat atcacatctc ataaaatcac ttaaagcaag
10801  catccagagg ctattgataa aaagcaggca caaggagacg caatgggacg tttagttggc
10861  ttagaactaa gtaatttcaa gtcctataga ggcgttacca aggtaggatt cggcgagtcg
10921  aatttcacaa gtattatcgg tcctaacgga tctggtaaat cgaatatgat ggatgctatc
10981  tcattcgtac tcggtgtgcg gagtaatcat ttgaggtcaa acatcttgaa agatttaatc
11041  tatagaggtg ttctaaacga tgagaatagt gacgattatg ataacgaggg cgctgcctct
11101  tcgaacccac aatccgcata cgtgaaggca ttttatcaaa aaggtaacaa actggtggag
11161  ctgatgagga taatttccag aaacggtgac actagttata aaattgatgg aaaaactgtc
11221  tcctataagg actattctat atttcttgag aacgaaaata ttcttatcaa agccaaaaat
11281  tttctagtgt tccagggtga tgttgagcaa attgcagcac aatctcccgt agaattatca
11341  agaatgtttg aagaagtatc aggttctatc caatacaaaa aggagtatga agagttgaag
11401  gaaaagattg agaaattaag caaatctgca accgaatcta taaaaaatag gagaaggatc
11461  catggagaat tgaagacata taagaaggt atcaataaga acgaggagta taggaaacaa
11521  ttggacaaaa aaaatgaatt acagaagttc caggctctat ggcagttata tcatttagag
11581  caacaaaaag aggagctaac ggacaagctg tccgcattaa actctgaaat atcgtctta
11641  aagggaaaaa taataacga gatgaaatca ttacaacgct caaaatcttc ctttgttaaa
11701  gaaagcgcag taatttctaa gcaaaaaagt aaattagatt atatcttcaa ggataaggaa
11761  aaattagtct cggatttacg gctcataaag gttcctcaac aggcagcagg gaagcgaatt
11821  tcccatatag aaaaaagaat cgaaagttta cagaaagatc ttcaaagaca gaagacttat
11881  gtggagagat ttgaaacaca actaaaagtg gtgaccagat caaaggaagc ttttgaagag
11941  gaaatcaaac aatctgctag aaactatgac aaattcaagc taaatgaaaa tgatttaaag
12001  acatataatt gcttacatga aaaatatctg actgaaggtg ggtcaatcct agaagaaaaa
12061  attgccgttt tgaacaacga taagcgagaa atccaagagg aattggagag attcaacaaa
12121  agggcagata tttctaaaag aaggataacg gaggagcttt ctataacagg agaaaaattg
12181  gacacgcaat taaacgattt aagagtttct ttgaatgaga aaaacgcccc tcatactgaa
12241  cgtttgcacg agctgaaaaa attacaatct gatattgaat ctgctaataa tcaagaatac
12301  gacttaaatt tcaagttgag ggaaacgttg gttaagatcg atgacttgag tgctaatcaa
12361  agagaaacaa tgaaagaaag aaaactaaga gaaatatag caatgttgaa aagattcttc
12421  cccggagtaa aaggtcttgt tcatgatctt tgtcacccaa aaaggagaa atatggcttg
12481  gcagtgtcta ccatcttagg taagaacttt gattccgtca ttgtagaaaa tttaaccgta
12541  gctcaagaat gcattgcatt tttgaagaag caacgtgcgg gcactgcatc tttcatacca
12601  ctagacacaa ttgagacaga gttacctaca ttatcattgc ctgactcaca agactatatt
12661  ttatcaatta atgctattga ctacgagccg gaatatgaaa aagcgatgca atatgtgtgt
12721  ggcgattcca tcatatgtaa tacgttgaat attgctaaag atctgaaatg gaaaaagggc
```

-continued

```
12781  ataagaggca aattggttac aattgaaggt gctttgatcc acaaggccgg tttgatgaca
12841  ggtggtatat caggagatgc caataatagg tgggataaag aagaatatca aagcttaatg
12901  tctttaaaag acaaattact aatccaaatc gatgaacttt ccaacggtca acgctctaat
12961  tcaatcagag caagagaagt tgaaaatagt gtttcactat tgaactcgga catagcaaat
13021  ttgagaactc aagtaacaca acaaaaacgc tccttggatg aaaatcgttt agagattaag
13081  taccataatg acttgataga gaaagaaatt caaccgaaga taactgaact aaagaagaag
13141  ctagatgatt tagaaaatac taaagataat ttagtgaaag agaaggaggc tttacaaaat
13201  aatattttca aagaattcac tagtaaaatt ggctttacaa tcaaagaata tgaaaatcat
13261  tccggtgaat tgatgagaca acaatctaaa gaattacagc agttacaaaa acaaattttg
13321  accgttgaaa ataagttgca gtttgagaca gacagactaa gtactactca aagaagatat
13381  gaaaaggcgc aaaaggattt agagaatgct caagttgaaa tgaagtcttt ggaagaacag
13441  gaatatgcaa tagaaatgaa atcggatcca atagagtcta aattggaaga acacaaaaat
13501  cacttagatg agttacagaa gaaatttgta acgaagcaaa gtgaattaaa ttccagcgaa
13561  gatattctag aggacatgaa cagcaactta caagtcttaa aaagggaaag agacggtata
13621  aaggaagata ttgaaaagtt tgatttagag agagtaacag cgttaaagaa ttgtaaaatt
13681  tctaatataa atatacctat atcatctgaa acaacgatag atgatttacc aatatcttcc
13741  actgataatg aagcaattac aatttccaac agtatcgata taaactataa aggactacct
13801  aaaaaataca aagaaaacaa taccgattcg gcaaggaagg agctggagca gaagattcat
13861  gaagtggagg aaatattgaa cgagttgcag cccaatgcaa gagctttgga gagatacgac
13921  gaggcggaag gaaggtttga agtgattaat aacgaaacag aacaactaaa ggccgaagaa
13981  aagaaaatat taaccagtt cctaaaaatt aagaaaaaaa gaaaggaact gttcgaaaag
14041  acatttgatt atgtgagcga ccatttagac gcaatctaca gggaacttac taaaaatccc
14101  aactccaatg tggaattggc cggtggtaac gcttctttaa ccatagaaga cgaagatgaa
14161  ccgttcaatg cgggaatcaa atatcatgcc actccgcctc ttaaaagatt caaagacatg
14221  gaatatcttt ctggtggtga aaaaaccgta gctgcattag ctctattatt tgctattaat
14281  tcctaccagc ctagtccctt cttcgtgctg gacgaagtgg acgcagccct agacattact
14341  aacgtccaga gaattgctgc ctatataaga aggcaccgta atccagatct ccaattcatt
14401  gtcatttcat tgaagaacac catgtttgaa aaatctgacg ctctcgttgg ggtttacaga
14461  cagcaacaag aaaactcgtc gaagatcata actttggact tgagcaatta cgcagaataa
14521  tctatgaaac caacctctgc tataacccgt caaataacta ataatatcta tataggtcaa
14581  ctagctagtg caatatcata gtaacaataa tattaataac gtcacttttt ttccagggta
14641  acccaattgt ggtgggtggc ggccgaggta tcccttagaa aagaattttt taagttcttt
14701  ctcatctctt accagtggag aagtacacga tatttgcaaa gtctgtcatc agggcttgat
14761  aataaagctg cattagatct tagcaaaaac tacgagaaga acattgaata ttgtagctgt
14821  atttgcatac ataaacttta tcattgttcg ttagctagct ttgcacatta ttttttcgat
14881  ttgttaccgc caatgaccgc taacaatgac gatgatatca aatcacccat tcccattact
14941  aacaagacct tatcccaatt gaagcgcttt gagagaagtc caggaaggcc cagttcttct
15001  cagggcgaga taaaacgtaa aaagtctagg ctatatgccg cagacggaag accacattct
15061  ccgctaagag caaggtctgc taccccaacg ctacaggacc aaaaactgtt caatggcatg
15121  gattccactt cccttttgaa tgaaaggcta cagcattata cgctggatta tgttagtgac
```

-continued

```
15181  agggcccagc atatgaagaa tatatatgac ccatcatctc gctggttcag cagatccgtg
15241  aggcctgaat ttcctattga agagttctta ccatataaga ctgaaagtca tgaagatcaa
15301  gcgaaatact tgtgccatgt cttagttaat ctttatattg cgatcagctc attagatata
15361  caaggtttga tttctatttc cagtaaagat ctggctgatt taagaaaga agtggatgat
15421  ttagctctta aaaccgatct tttcaggtta tctaacaaca cagcggagaa tgacttactt
15481  ggtaacgata ttgctgatta tgacgatgcg gaaggcctgg aggacgaatt ggatgaatac
15541  ttcgacttag caggccccga ctttaatgct accggaaaaa tcacagctaa atcagctact
15601  attgtgaatg taaaccattg gactaatgag ctcaaaaatt gtctacattt tgattttcca
15661  gtagctttaa gaaagtcgct agcgacagtt tattattatt tgtctcttgt tcagggccaa
15721  aaggtgtata gacaaatgca tgtcgatatg ttcgaaagat tagtaagcct tgacgatgat
15781  aggacaaatt tcactgaact gttgcaaaaa caaggtcttt tgctagatca tcaaatcatg
15841  ctcaatttcc tgtgcgaatt tctaccttat ccagatcccg actatgctcg ttatgaatta
15901  tcatcaaagg aagatttaca gttatttaga ttacttttga agcatgcaca taatgcaaaa
15961  ccattttttcg ataagtcaaa ggaaagtttg ttagttgata cgatgaattt tctgttgtct
16021  agtcttgcac catctactat gatggctgtc atgcctatcg ttacatccgt tgtgccctat
16081  cattatcata tccattctaa gatcatcgat tatttcccgt tttgctatag catctggagc
16141  tcagtcagcg caaacgtggc catcgacact cacatgtatg attttgttgg gtcaatttcc
16201  aaagacgttc ataataagat tttgagtagc gagcatgaaa aggatgtagt tggagtggag
16261  tttggagaat tcgggatttt tactgatgat caaatgactt ttatgttcaa taggttacaa
16321  ggccatctta gaacagacgg tcaaatacat tcgtattccc gcacagtgaa gccttttgtt
16381  tatgctataa acggatcaaa aaaagatagg ttttttgaaa aacttgtaag tttagccaaa
16441  gcaatcgaaa catttatcca tccctctaat aatgggtttt ggaccaagcc aaatgctaaa
16501  ttcgttcatg catttataaa gtcttaccac ggaagggtca aatatgaaga agatatttgt
16561  gctaggggcg tcacaaatgg gatatgttta acttcttttt gtcacgaaga gatagttgaa
16621  atattcttaa atattatcag tctgggttca cagaataaaa atcctgatat tgcgaactat
16681  tacatctctt gtttcgcata tctgttagag ctggatcctt caaatgcata tttaatttat
16741  gacaaaatac tgatagattt gtacgatacg ctggctgacc aatttatcaa ttcgagacac
16801  agaatcattt cctctttgaa acaatttaca agagtaattc ggtttattgt gatggataag
16861  ctatatcgcg tgcacataac aaacgtcctt tcgatgctgg tctccaaact tgatatgaac
16921  gatactaatt tgacaagcaa cctcatcaac ggtattgtat ctatagccgc tttcattcct
16981  atccaagacc tcactgggga ggacgattat atatcgtttg aatcggatac tcttcccttta
17041  gttcaacaac atttttatca tattaagtgt ggcgaaagtt caaagacctt ccgagttgat
17101  gatgaactgt taaataacgc tttcaaagct tccactacag ttttttcaaag tatgctaaaa
17161  gtatacgtag aaaaaatttt ccaattggtt gatgtagact tagaggactc tttggttact
17221  aaaataaacc aaacaactat gattttacaa gagtctatgg acgataaaat atttaattat
17281  tttgcttctt tattacagag aaacttctgg agtaatgact ccttcaagga aaaggatcca
17341  aactatgaat tagttactat cccactagcg gctttagtaa gaaggaataa tggtttgagt
17401  aaagagttgg tcagaactct tttattccat atcaaagaac aaatcaaaag aggcgccggg
17461  tctgtaagaa gtacttcaga gattcaacag agggatgtta agttagtttt atacttaact
17521  gcactaaatg atgtcttaag gcaatgtcat gaatctctat ggagtatag cgatgagttg
```

-continued

```
17581  ataacattca tgaaatattt atacgacaac gtcactaacc cgccattgga tgttatcaca
17641  tctattgtta ttcacagtgc tttagcaact ctatgtacaa ccgaaataac tgattgtcgt
17701  ctattcccag aggactctaa gattccggaa aaagacagat ggggaggact acagttcgat
17761  cctcgaagat tgataaaca gcatttgagt tttcagtggc acgtaccttc tagtgacgag
17821  ataactttat ccataagcat tctagaaagc ctttccgaat actgtattaa caacgtagaa
17881  gaactgatga agctccaag acatgattcc gaatatggcg atatgataca aaaatatgtt
17941  ttagttatga cacatacgct ttccgggtca agtttacttt tgatccaga tttaacaaa
18001  tataggacgc aatcaaactt atcatacaga gagaaactga ttttattaaa gaatatacgc
18061  gaaataatt gtgaccctca agaactggat attgatattg aacaaattcg ttctggcaag
18121  gatgatgaag actatattga gagtaaggac attgaagcag ggctgaatgc aggagtttcc
18181  gatgttgtgc agttaagaga tgagtttccg gatgaattaa ttgttgatga agaagtagtg
18241  tctgagatgc catctggtgt aaatacccct atcgcgggga cgcatggcac ggacaattca
18301  gctatgagtt cggatctagc tttcagggat ttagatattt acacctgtaa ttattacttc
18361  ggaaatacca ctgaggagaa gttacaaaac ccacaatatt tacaagtcca cagagttaga
18421  gcgcgcattg gacatttctt tcacaaactc tatgttttt tatctacaaa cttcgaaaac
18481  aacaccaaca tgttccaaat tctattgcac ggattgaaag tttggttcac agatctggga
18541  caagaaacgg tcttcaatga agacccaaat gccttcattg acgttgattt cctagaaaac
18601  gttcaatctc tctcacacgt aaatgagccc ttcacgagaa ccaatttgc aatcagagca
18661  aacagtttgc accagagtag agttctatta cattcaacaa atagaaaagc ttccaagctg
18721  gaaaacctat tgttagttga catcatacag ttagcgacat cccttatcc tgatatttat
18781  aaaccagcac agggaacttt ggtacactgt atgaaacaat tagttgggtc atatggcgta
18841  gtcatcaata aaattattcc atcattagag aaagcgatta aggatcatga ttatatgaaa
18901  atccaagtta ttttaaatgt tttgttaatt aagaaaatcc ataggaagct tatgacggat
18961  tataaagaca tcggcagatt gatatttctg cttattgaat gttgtcgtgt gaatgaatta
19021  gagattggta tgtatgcaga taaaatctta actgacatag tgattgggat caagattcct
19081  tctagtgtat gtgtcatttc cgatcaagct ttcttacctt tagcacctcc tgatggtact
19141  attaatttgc aagttgaagc ggtaaagctt gccaaaaaga aaaagcgtga gtactacctc
19201  tctctgttag tggatttgca ggacaaactt ttagacaaat tagataatga aaaagatatg
19261  gggtggaaga taagaatgtt cattttacgt tttgttacac aaatccaatc gaacctcgaa
19321  agcaaacccg ataaaagagc agtattttca ataatctccc aaatctccac aaaacatccc
19381  gaaatcatac atttggttgt aaagtcattg ttgtcgacgt gcaacaagat aatatctctc
19441  tctgactatg aatatgacat caccagggcc tataagaatg aattcaatcc atcatttgtg
19501  gaaatactgg acacttcgac cacaagcttc cctaaaacgt ttactgaaga atgaataac
19561  tttgataacc ccaagtattt tatcgatttg agggcgtatg tagggtggct atgttgggga
19621  aggcttatgt acgtcatgtc gccgaaagct ttaaagctca atttacgtga gaatgaactg
19681  gaagtcctca agacagctgg tcatctattg acaagagaat tcctgagaga tgttacaatg
19741  aatttagtcc aagataatga aactaggggt gttttagta gtggtaacgt gtcattttc
19801  tctttagtaa tccttttgat atcatctggt ttctgcgaac tgaatatgtc ggatctcttt
19861  gagctatgtg aatcctacta taacaaagac gataaggctt cgatgatcat gtctgtcgag
19921  atagtggctg gcttagtttg cgggagtaag tttatgtcag tctctgactt ggacaaacgt
```

-continued

```
19981 gacactttta tcgaaaactt cctagccaaa tgtttagatt atgagttgaa ccatgacgca
20041 tttgaaattt ggagcacctt ggcatggtgg ttgcctgcag tcgttgattt aagaaggtct
20101 aaaacttttt tttgccattt tatcaacgcc gatggcatgt ttgaccgtga atctgatgca
20161 gccacacatc aaacctccaa aatttacatg ctaagaagta tcttgatgag catggaattt
20221 agagcccag atgttggtaa gctatttgat gagttggtat ttgatcaccc atacgatcag
20281 gttcgccagc tgtcgctaaa ctattgacga ccttagttca aaatcaaagt aatccgtcaa
20341 tttcagatcc aaccacatta ttagaagcag aacggaatga tcc
```

```
                                                          SEQ ID No. 2
  1 mgsfplaefp lrdipvpysy rvsggiassg svtalvtaag thrnsstakt vetedgeedi
 61 deyqrkraag sgestpersd fkrvkhdnhk tlhpvnlqnt gaasvdndgl hnltdisnda
121 ekllmsvddg saapstlsvn mgvashnvaa pttvnaatit gsdvsnnvns atinnpmeeg
181 alplsptass pgtttplakt tktinnnnni adlieskdsi ispeylsdei fsainnnlph
241 ayfknllfrl vanmdrsels dlgtlikdnl krdlitslpf eislkifnyl qfediinslg
301 vsqnwnkiir kstslwkkll isenfvspkg fnslnlklsq kypklsqqdr lrlsflenif
361 ilknwynpkf vpqrttlrgh mtsvitclqf ednyvitgad dkmirvydsi nkkfllqlsg
421 hdggvwalky ahggilvsgs tdrtvrvwdi kkgccthvfk ghnstvrcld iveyknikyi
481 vtgsrdntlh vwklpkessv pdhgeehdyp lvfhtpeenp yfvgvlrghm asvrtvsghg
541 nivvsgsydn tlivwdvaqm kclyilsght driystiydh erkrcisasm dttiriwdle
601 niwnngecsy atnsaspcak ilgamytlqg htalvgllrl sdkflvsaaa dgsirgwdan
661 dysrkfsyhh tnlsaittfy vsdnilvsgs enqfniynlr sgklvhanil kdadqiwsvn
721 fkgktlvaav ekdgqsflei ldfskaskin yvsnpvnsss sslesistsl gltrttiip
```

The human F-box protein hβTrCp is encoded by a nucleic acid sequence corresponding to GenBank Accession No. NM_003939 (SEQ ID No. 3) as shown below, and which encodes the F-box protein corresponding to GenBank Accession No. 4502477 (SEQ ID No.4) as shown below.

```
                                                          SEQ ID No.3
  1 tgcgttggct gcggcctggc accaaagggg cggccccggc ggagagcgga cccagtggcc
 61 tcggcgatta tggacccggc cgaggcggtg ctgcaagaga aggcactcaa gtttatgaat
121 tcctcagaga gagaagactg taataatggc gaaccccta ggaagataat accagagaag
181 aattcactta gacagacata caacagctgt gccagactct gcttaaacca agaaacagta
241 tgtttagcaa gcactgctat gaagactgag aattgtgtgg ccaaaacaaa acttgccaat
301 ggcacttcca gtatgattgt gcccaagcaa cggaaactct cagcaagcta tgaaaaggaa
361 aaggaactgt gtgtcaaata ctttgagcag tggtcagagt cagatcaagt ggaatttgtg
421 gaacatctta tatcccaaat gtgtcattac caacatgggc ataaaactc gtatcttaaa
481 cctatgttgc agagagattt cataactgct ctgccagctc ggggattgga tcatatcgct
541 gagaacattc tgtcatacct ggatgccaaa tcactatgtg ctgctgaact tgtgtgcaag
601 gaatggtacc gagtgacctc tgatggcatg ctgtgaaga agcttatcga gagaatggtc
661 aggacagatt ctctgtggag aggcctggca gaacgaagag gatggggaca gtatttattc
721 aaaaacaaac ctcctgacgg gaatgctcct cccaactctt tttatagagc actttatcct
781 aaaattatac aagacattga gacaatagaa tctaattgga gatgtggaag acatagttta
841 cagagaattc actgccgaag tgaaacaagc aaaggagttt actgtttaca gtatgatgat
```

-continued

```
 901 cagaaaatag taagcggcct tcgagacaac acaatcaaga tctgggataa aaacacattg
 961 gaatgcaagc gaattctcac aggccataca ggttcagtcc tctgtctcca gtatgatgag
1021 agagtgatca taacaggatc atcggattcc acggtcagag tgtgggatgt aaatacaggt
1081 gaaatgctaa acacgttgat tcaccattgt gaagcagttc tgcacttgcg tttcaataat
1141 ggcatgatgg tgacctgctc caaagatcgt tccattgctg tatgggatat ggcctcccca
1201 actgacatta ccctccggag ggtgctggtc ggacaccgag ctgctgtcaa tgttgtagac
1261 tttgatgaca agtacattgt ttctgcatct ggggatagaa ctataaaggt atggaacaca
1321 agtacttgtg aatttgtaag gaccttaaat ggacacaaac gaggcattgc ctgtttgcag
1381 tacagggaca ggctggtagt gagtggctca tctgacaaca ctatcagatt atgggacata
1441 gaatgtggtg catgtttacg agtgttagaa ggccatgagg aattggtgcg ttgtattcga
1501 tttgataaca agaggatagt cagtgggggcc tatgatggaa aaattaaagt gtgggatctt
1561 gtggctgctt tggaccccccg tgctcctgca gggacactct gtctacggac ccttgtggag
1621 cattccggaa gagttttttcg actacagttt gatgaattcc agattgtcag tagttcacat
1681 gatgacacaa tcctcatctg ggacttccta aatgatccag ctgcccaagc tgaaccccccc
1741 cgttccccctt ctcgaacata cacctacatc tccagataaa taaccataca ctgacctcat
1801 acttgcccag gacccattaa agttgcggta tttaacgtat ctgccaatac caggatgagc
1861 aacaacagta acaatcaaac tactgcccag tttccctgga ctagccgagg agcagggctt
1921 tgagactcct gttgggacac agttggtctg cagtcggccc aggacggtct actcagcaca
1981 actgactgct tcagtgctgc tatcagaaga tgtcttctat caattgtgaa tgattggaac
2041 ttttaaacct cccctcctct cctcctttca cctctgcacc tagttttttc ccattggttc
2101 cagacaaagg tgacttataa atatatttag tgttttgcca gaaaaaaaaa a
```

```
                                                                  SEQ ID No.4
  1 mdpaeavlqe kalkfmnsse redcnngepp rkiipeknsl rqtynscarl clnqetvcla
 61 stamktencv aktklangts smivpkqrkl sasyekekel cvkyfeqwse sdqvefvehl
121 isqmchyqhg hinsylkpml qrdfitalpa rgldhiaeni lsyldakslc aaelvckewy
181 rvtsdgmlwk kliermvrtd slwrglaerr gwgqylfknk ppdgnappns fyralypkii
241 qdietiesnw rcgrhslqri hcrsetskgv yclqyddqki vsglrdntik iwdkntleck
301 riltghtgsv lclqydervi itgssdstvr vwdvntgeml ntlihhceav lhlrfnngmm
361 vtcskdrsia vwdmasptdi tlrrvlvghr aavnvvdfdd kyivsasgdr tikvwntstc
421 efvrtlnghk rgiaclqyrd rlvvsgssdn tirlwdiecg aclrvleghe elvrcirfdn
481 krivsgaydg kikvwdlvaa ldprapagtl clrtlvehsg rvfrlqfdef qivssshddt
541 iliwdflndp aaqaeppprsp srtytyisr
```

The yeast F-box protein Grr1p is encoded by a nucleic acid sequence corresponding to GenBank Accession No. M59247 (SEQ ID No. 5) as shown below, and which encodes the F-box protein corresponding to GenBank Accession No. AAA34652 (SEQ ID No.6) as shown below.

```
                                                                  SEQ ID No.5
  1 cacgctaatc atgactcaaa taaatccata aagttttata cagttttttaa aaatatcatc
 61 atctattacc cagatgtgtt aatgaaccat tctatagtca tcattactag gctttcatta
121 ctactgaggt tacccgccta tggaccttcc ttggtaaagg aacttgtttt aaaatttgcc
181 ttttaacaaa tttagtgata tgattatcaa aaaaggcgtg gcaaaataca taacaccaaa
```

-continued

```
 241 tttaactgtg cctgtgtgtt actttctttt gtccatactt caccagtttt tcgattttac
 301 acaataattc gttttcattt aatcgttctc ttagaagccc ggttttttgaa tatcaaaatc
 361 gtacttgtgt ccaactagca gggaagccca aaaattaagg cattgcattt aagcttacac
 421 ctgcgtgaaa tcttgaaatt tctcattgat ttcggcacaa taattatcat tggtagtgag
 481 gctaaacagt ttgcggtttc ctttatacta agaaggtcta aatggatca ggataacaac
 541 aaccacaatg acagcaatag gctgcaccca cctgatatac atccaaattt gggccctcaa
 601 ttgtggctga atagtagcgg tgattttgac gacaacaaca acaacaacaa caacaacaac
 661 aataataata gcacaagacc acaaatgcca tcacgaacta gagaaacggc aacttcggaa
 721 agaaatgcaa gtgaggttag ggatgcaacg ctaaataata tctttaggtt cgatagtatt
 781 caacgggaaa cgcttttgcc aaccaacaac ggacaaccgc taaatcaaaa cttttcgctg
 841 acatttcaac cacaacagca aacaaatgcg ctgaacggga ttgacataaa cactgtgaac
 901 acaaacctta tgaatggtgt caatgttcaa atagatcaac ttaatcgatt gttaccgaac
 961 ctaccagagg aagaacggaa gcaaatccac gaattcaagc taatagtggg caaaaaaatc
1021 caagagtttc tggttgttat agagaaacgt agaaaaaaaa tactgaacga aattgagcta
1081 gacaacctta aactaaagga gctacgtatt gataactccc cacaagcaat tagttatttg
1141 cataaattac aaagaatgag gcttagggcg ctagagacag aaaacatgga aattagaaat
1201 ttaaggctaa aaatattaac aattatagaa gagtacaaaa agtcattata tgcatactgc
1261 cattccaagc taagaggtca acaagtgaaa aatccaacag ataatttcat catttggata
1321 aactccatag atactactga atcatctgac ttgaaagaag ggctacaaga tctttcgaga
1381 tattcaaggc agttcataaa taatgtgctt tcgaatccat caaatcaaaa catatgtacg
1441 agtgtcaccc gaagatcacc tgtgtttgcc ctaaacatgc taccctcgga aatattacac
1501 ttaatattag ataaacttaa ccaaaaatat gatattgtaa aattccttac cgtttccaaa
1561 ctctgggctg aaataattgt gaagatactt tattacagac cgcacatcaa caaaaagagt
1621 caattagact tgttttttaag gactatgaag ttaacttctg aagaaactgt attcaactat
1681 cgtttaatga tcaaaagatt aaatttttca tttgttggtg actacatgca cgatacagag
1741 cttaactatt ttgtcggatg taagaatttg gagcgactaa ctttagtatt ttgcaagcat
1801 ataaccagtg ttccaatatc ggctgttttg agaggatgta aatttctcca aagtgtggat
1861 atcactggaa taagagacgt ttccgatgac gtatttgata ccttagcgac atattgtccc
1921 agagtacagg gcttttatgt tcctcaggca aggaatgtaa cattcgattc actgcggaat
1981 ttcatagtcc attccccgat gttgaaaaga ataaaaatca cagcaaacaa taacatgaat
2041 gacgaattag tagaactatt agccaacaaa tgcccttttgc ttgtagaggt cgatataaca
2101 ttaagtccaa atgtcactga ttctagtttg ttaaaactcc tcactaggtt agttcagctg
2161 agggaattca gaataactca taatacgaat attacggata atcttttcca ggagctttct
2221 aaagtagttg acgatatgcc ctctttaaga ttgattgatc tttctggatg tgaaaatatt
2281 acagataaaa ctatagaaag tatagtcaat ttagccccta aattacgtaa tgttttttcta
2341 ggcaagtgta gccgaattac agatgcatcg ttgttccaat tatcgaagct gggcaaaaac
2401 ttgcaaacag tgcattttgg gcactgtttc aatataactg ataacggggt aagagcactc
2461 tttcattcat gtacaagaat acagtatgtg gactttgcgt gctgtacgaa tttaaccaat
2521 agaactcttt atgaactagc agacttacca aaattaaaga gaattggcct tgtcaaatgt
2581 acgcaaatga ctgacgaggg tttgttgaat atggtttcct tgcgaggccg aaatgatact
```

-continued

```
2641 ttagaaaggg tacatttatc ttactgttct aatttaacaa tatatccgat atatgagctt
2701 ctaatgtctt gcccaaggct ctcacatttg tctttgactg ctgttccgtc atttttacgc
2761 cccgatataa cgatgtattg caggcctgca ccctcagact ttagtgaaaa tcaacgtcaa
2821 atattctgcg tattttcagg gaaaggtgtt cataaacttc gccattattt agtaaattta
2881 acgtcgcccg cttttggacc acatgtcgat gtaaatgatg ttttgacaaa atatattaga
2941 tccaagaatt tgatatttaa cggtgaaaca cttgaagatg ctcttaggag aatcataact
3001 gatttaaatc aagattccgc tgcaattata gctgctacag gattaaatca aatcaacggt
3061 ctaaataacg attttctttt ccagaatatc aattttgaac gaatagatga agtattcagt
3121 tggtatctca atactttga tggcattagg atgagctcgg aggaagttaa ctcactatta
3181 ttgcaagtaa acaagacgtt ttgtgaagat ccatttagtg atgtggacga tgatcaagat
3241 tatgtcgtag cacctggtgt aaaccgggaa attaacagtg aaatgtgtca tattgttaga
3301 aaattccatg agttaaatga tcatattgat gatttcgagg tgaatgttgc tagtttggta
3361 agagttcagt ttcagtttac tggttttttta cttcatgaaa tgactcaaac ctatatgcaa
3421 atgattgaat taaacagaca aatttgttta gtacaaaaaa cggttcagga atcgggcaac
3481 atagattacc aaaaagggct tttaatatgg cgacttttat tcattgacaa attcattatg
3541 gtggttcaga agtacaagct ctccaccgtt gttttgagac tatatttaaa agataacata
3601 acattgttaa ccagacaaag agaactatta atagcccacc aaagatcagc atggaataac
3661 aataatgaca atgacgccaa ccggaacgcc aacaacatag tgaatattgt atcggatgct
3721 ggggcaaacg atacaagtaa caatgaaact aacaatggta atgatgacaa tgaaacagaa
3781 aatccaaatt tctggcgtca gtttggcaat agaatgcaaa tatcacctga ccagatgagg
3841 aatctccaaa tgggacttcg taatcagaac atggttagga acaataacaa caacacaatt
3901 gacgaatcaa tgcctgacac tgccattgat tctcaaatgg atgaagcatc aggaacgccc
3961 gatgaagata tgttataatt gtatttcatt gaatacttac tgtcctacta cacctttatt
4021 ttcaaaatcc cacttttctt acttatttac atataaatac ataatgcatt cactttgaaa
4081 cttttttgcct tagcatgtat acgctataga cttgcggtat caacgaatat acgtaacgtt
4141 gtcacgtcca cagaagatgc tatgtcaaca gttccctgca gatatctgCg atgcggcgaa
4201 acattctata cacagtttca aaactacaaa aaatacaaac ctttagcctg tttatcaaat
4261 tagttagcta taaaatgccc attttcttag caatatcgat caattgattg tcatcttcca
4321 aagtttcaat aaaatttgtg gcagtatagt aatcccttct caatatgtcc aatttcttat
4381 cacagtcatc tataaattcg cgcttaatag attgcacttt taggttcacc caattgttga
4441 atgtcatgat ccaactcttc tgcaggattt
```

```
                                                              SEQ ID No.6
  1 mdqdnnnhnd snrlhppdih pnlgpqlwln ssgdfddnnn nnnnnnnnns trpqmpsrtr
 61 etatsernas evrdatlnni frfdsiqret llptnngqpl nqnfsltfqp qqqtnalngi
121 dintvntnlm ngvnvqidql nrllpnlpee erkqihefkl ivgkkiqefl vviekrrkki
181 lneieldnlk lkelridnsp qaisylhklq rmrlralete nmeirnlrlk iltiieeykk
241 slyaychskl rgqqvenptd nfiiwinsid ttessdlkeg lqdlsrysrq finnvlsnps
301 nqnictsvtr rspvfalnml pseilhlild klnqkydivk fltvsklwae iivkilyyrp
361 hinkksqldl flrtmkltse etvfnyrlmi krlnfsfvgd ymhdtelnyf vgcknlerlt
421 lvfckhitsv pisavlrgck flqsvditgi rdvsddvfdt latycprvgg fyvpqarnvt
```

-continued

```
 481 fdslrnfivh spmlkrikit annnmndelv ellankcpll vevditlspn vtdssllkll
 541 trlvqlrefr ithntnitdn lfqelskvvd dmpslrlidl sgcenitdkt iesivnlapk
 601 lrnvflgkcs ritdaslfql sklgknlqtv hfghcfnitd ngvralfhsc triqyvdfac
 661 ctnltnrtly eladlpklkr iglvkctqmt degllnmvsl rgrndtlerv hlsycsnlti
 721 ypiyellmsc prlshlslta vpsflrpdit mycrpapsdf senqrqifcv fsgkgvhklr
 781 hylvnltspa fgphvdvndv ltkyirsknl ifngetleda lrriitdlnq dsaaiiaatg
 841 lnqinglnnd flfqninfer idevfswyln tfdgirmsse evnslllqvn ktfcedpfsd
 901 vdddqdyvva pgvnreinse mchivrkfhe lndhiddfev nvaslvrvqf qftgfllhem
 961 tqtymqmiel nrqiclvqkt vqesgnidyq kglliwrllf idkfimvvqk yklstvvlrl
1021 ylkdnitllt rqrelliahq rsawnnnndn danrnanniv nivsdagand tsnnetnngn
1081 ddnetenpnf wrqfgnrmqi spdqmrnlqm glrnqnmvrn nnnntidesm pdtaidsqmd
1141 easgtpdedm l
```

The yeast F-box protein Met30p is encoded by a nucleic acid sequence corresponding to nucleotides 3742 to 5664 of GenBank Accession Nos. Z46861 and Z47047 (SEQ ID No. 7) as shown below, and which encodes the F-box protein corresponding to GenBank Accession No. CAA86905 (SEQ ID No.8) as shown below.

```
                                                                  SEQ ID No.7
   1 tttcttgttg cttcaacgga ttatcttaaa aaaatctatc atatttcaaa atataaattc
  61 ttatttttac aaagaagata tagattatgc ataatattat tttgttacat ttttttttctt
 121 ttacttttta ttttcttttc tttgtacttc ctcaaataag catctttagc aggttaacaa
 181 tagcaaatat catgtccagc ccaaatcaca taatactttc cacttcactt tcactatctg
 241 tttcgggaga cctatcatcc acggtattga cagttggtct ttggaaatca gttgcatgtg
 301 cccaaggaat ggatctcgaa atgttctcaa cacggagga ccttcttctg aaagtcccac
 361 ggtaagcggg cataggttcg gcaaaactgt gaggattatt gtcatgtgaa ggcgtgatag
 421 gtatgtcgtt aagtgatgaa aaggcttttg aacccaaatc actactatcc atagaatcat
 481 caccgacctg cgcaattgga taaggcagag gagcgtcacc ggtaaccctg aataggtgaa
 541 cattggcaac atgttcattt tcgactctga agatgatcca aacgaatctt cttaaaacct
 601 ccaaagggc caatataaac gacgtcacag cactctgctg aattgtttga ggagcaattg
 661 cgtatacaat ccactcaaat ctaatgagga tacccaaat catagcaaag taataaacta
 721 acttcctact gaatgaataa ctgccgtttt cccaattttt tttaccagct aaatacaagt
 781 cgtctcttag caaccaattg taagaagtag tattgtgagc aaaggaccaa tccataacta
 841 aatcccaggc ggaagtaagg atcgaattca acgtagcgca cacgataaaa ggggttctcc
 901 tttgttcaga acggtctgac aatctgtaag cacaaagtgt ggcattatac gctataccca
 961 aagtgtattt cgccgcgttc aaaagatgag ggaaccaatc accggaatca gcaaatcttc
1021 gtaaacattg catgaatctc caataacttg gtaaacatga taaacaccc attgctctgg
1081 aatgtgaaga gccacataga ttgttgggcg tatgagagta aacacagaag aacatggcaa
1141 tatcggcaat agaatacgtc aacgaacaaa taatatctcc caaaagaaa tcaccaaact
1201 caacagggaa aaaccagac atcatcagtc taataagagt aaccaccagc cattttctag
1261 tgtgtacaac tttgtcccaa tatggaatta gaccagaggg acataaaaat aagaaagaca
1321 caataccaat atataaaaag cctaagggtg tgagcttctc caaagcgaaa cttaacatgg
1381 aacagaccgc acaaggtact atgaagaatg tcaagaaata caacttgagc ggaattttac
```

-continued

```
1441  tcgtggcaaa atcattgttg aaaaattgcg taccattctt ggattgaatc tcacccagca
1501  taataaatct ataattaatc ccggttctat gccagataaa acaattaaca agaaagagaa
1561  acgcgatcaa caaaaccatg taccaaccac cccacagtgg gaacagaatc ttgtgcgtaa
1621  atgacgtttc ttcagagcta atgcccaaat acaaagtgta agtgatcaaa gtcattgaca
1681  cacctatgcc cagcccgaca accagcatct gcacaatcga tctgttgttt ctatgaacca
1741  tttgttcgga gatagagtac tgaatggtca atttcttcaa cttatgggta ttgtgcttcc
1801  tgtccttagg cgaattggtc aacgcagtgg tgaaccactc ggtgatctgc gtttccaacc
1861  aagtgatggg ctctttgtct ctttgggcgg aagagagctc cgaagtgggg ttggttgcg
1921  aactggttat ttgttgcatc ttctgtgcca ccaactgcac gttggcatcc gcgtgcttga
1981  aaagggtgta gtgggtcctg gcgtacgaca tgaacgtggt cagctctctt gtgtgacacg
2041  ttttgtcgaa tttcttgacc attttacgga acccggtgac gttgatatcc cggaacgatt
2101  tgaccaattg caagtacaga tagtactcga ttatagcgtt gcttaacaag tttctagcct
2161  gggttgtcgt catagtctcc agaaagaag cgccaaaagc aaacgtctcg cggcctcttg
2221  aggacgcatc ctgtctcaag tcctgtagca gagaaaatcc acgtttgggc cacgatggca
2281  gcagcctatt gtccttaaga actttctgac agtacgctag cagcgacaaa cgcggcttct
2341  tggcctcttt ggtgcagggc attgacccat acataacaga ccggctatcg ctgtcgatgc
2401  tattgaccct ggagtcagaa cgaccagcaa gccctgccgc atatagactc gtggacatgt
2461  caacattcga actagaccgg ttcaagttgt cgcgctcata attcttctgc agcgagtaat
2521  agtgcagttg cgactgtaaa acctcaaact tcttgtcgca ctcctttagc aaccaaaggt
2581  aaaactcgtt acacttactc aactggaacg agatcaacca gtcttcaatg aagtcagcaa
2641  cgaactccct ctgcaaagca gaatagtcct tcttgaacgc aggtccggag cgatagtctc
2701  cgtcgctgcg acttttgccg ggctctctct gctgaaatgc agtctggtat accgacacag
2761  agggcatcca gctccggtag gagctggatt gctcttcttC ggcatccagc ttctccttgt
2821  agcggcgaag cttcttcttg ccgaccttat aatcaatata tttgtccctc cattccggga
2881  tggcagactc ggttagatgg tcagcaaact tcatctgata cggtgctatg gtaaagccct
2941  tccattgctg ccaactgaat taaaaaaaa aaaaaaataa ctaccaacca tcaaatcaaa
3001  caaacaaaa caaaaaagca aaggagaaaa cccatcttgt acatgtacag tcccaaactg
3061  ttgcgaaacc gtgcgatgat gttcatggaa cttgcgtcaa ataaaaccgc atcccgtccc
3121  acgtgacaaa cggcacccaa aatccgttct agaaatgcct cacacccaca ccgatgatgg
3181  gcttccgact cgatgactac caacacatag ccagccgcag cggctggcag catgtgcatg
3241  ataatgataa gtgatgatga atgatggtga taacgatttt gaacaaatgg ctgcagcgat
3301  agcaactaag gggatggaaa gacagatctg ggagagataa ctgcagggtg tggcacggca
3361  acacaaggct attgtattgc actaaacggg caagaagcca tgatgtgcgt ctgtatccca
3421  aaaaaaaac taatggattg gcgcgtgtac tatatatatt catatgtcgt gtgtttgtat
3481  atgtgtggga gtgattgtgc gtgtatatgt gtgttggcgt gtgtggtaca atgtgtgtgt
3541  tttaatgtag aaatgaggtt gtagcacgtg atcgggaagc cacagtttgc gcggagatat
3601  tttatttttt ttcatcagcg taagaagaaa gcaaccttgc agtctgtatc gtaagagaag
3661  actgcagtta aagaagttta gagaagaggc ttgagtatcg gtaaagggggt gtgtgtttgg
3721  tgatttataa aggagaaggg catgaggaga gagaggcaaa ggatgatgag tttcgaggac
3781  aaggacaagg acgaccttga caatagtaat agtaataaca gcagtgaaat gacagatacg
```

-continued

```
3841  gcgatgatgc caccattaaa gagattgctt attacgggca gtagcgatga tttggcacaa
3901  ggatcatcgg gtaagaagaa gatgacgatg gcgacgaggt cgccatcgtc atcacccgat
3961  ttggcgacaa acgacagcgg cactagggta cagccattgc cagaatataa cttcaccaag
4021  ttctgctatc ggcataaccc ggacattcag ttctcaccaa ctcatacagc gtgctacaag
4081  caggatttga acgaacgca agagattaat gctaatatcg cgaagctacc cctgcaggag
4141  caatccgaca tccaccacat tatctcgaag tacagcaatt ccaatgacaa gatacggaag
4201  ctgattctgg atgggatcct atcgacgagt tgcttcccac agctttccta catttcgtca
4261  ctcgttacac acatgatcaa gatcgacttc atcagcattc tgccgcagga gctgtcgctg
4321  aagatcttga gttatctgga ttgccaatct ctttgcaacg ccacgagagt gtgccgcaag
4381  tggcagaagc tcgcggatga cgacagggta tggtaccaca tgtgcgagca gcacatagac
4441  aggaaatgtc ccaactgtgg ctgggggctg cctcttttgc acatgaaacg tgcgcggata
4501  caacagaata gtacaggatc tagcagcaac gcagatatcc agacgcaaac tacgcgacct
4561  tggaaagtca tctacagaga acggttcaaa gtggagtcaa actggagaaa gggccactgc
4621  aggattcagg aattcaaggg ccacatggat ggtgtgttaa cgctccagtt taactacagg
4681  cttttgttca caggctcgta cgactccacc ataggtatat gggacttatt cacggggaag
4741  ctaatacgaa ggctcagcgg ccattcggac ggcgtcaaga cattatattt tgacgataga
4801  aagctgatta cgggctcgct cgacaagacg atccgtgttt ggaactacat aaccggtgaa
4861  tgcatttcca cgtatcgagg ccactcggat agcgttctga gcgtagattc ataccagaag
4921  gttatcgttt ccggcagtgc tgacaagacg gtcaaggtat ggcacgtgga gtccaggaca
4981  tgctacacct tgagaggcca cacggaatgg gttaattgcg tcaaattgca tccgaaaagc
5041  ttttcatgtt ttagttgcag tgacgatacc acaatccgaa tgtgggatat caggaccaat
5101  tcatgcctaa aagtgttcag gggtcatgta gggcaggtgc aaaagatcat accgcttacc
5161  attaaggatg tagagaatct agccaccgac aacacttctg atggcagctc tccgcaggat
5221  gacccaacaa tgactgatgg tgcagacgaa tcagacacac cgtcgaacga gcaagaaact
5281  gtcttagatg aaaacatacc ttatccaaca catctactat cttgcggact ggataacaca
5341  atcaaactat gggacgtcaa accggtaaa tgcataagaa cacagtttgg gcacgtggaa
5401  ggtgtttggg acatcgccgc tgacaacttc agaattataa gtggttctca cgacggaagc
5461  attaaggtct gggacttgca aagcgggaag tgtatgcaca cgttcaacgg tcgaagacta
5521  caaagagaaa ctcagcacac acaaacacaa tccttgggtg ataaagtcgc ccctatcgct
5581  tgtgtttgta ttggagattc agaatgcttt agtggtgatg aatttggtg cgtaaaaatg
5641  tacaaattcg atctcaatga ttaggacctg tgtgtggtct tttcttggtc aaaaacatcc
5701  gtagtacctc gaatatatat gcttacatat ataatgaaaa atacataata gcattttaca
5761  tttatttat ttccaggaaa aaaataaatc gctagcgtat cactagcctt ttccatcttc
5821  agtttttttc cttcctcttt ttcgtctcga taaaactctt gaccattaga tgctattact
5881  ccccacgga gcccttccca cgctaagggg gatgtcaagg gggggactga agataaagct
5941  tattatattg acggcgatga tgaagagggc gtacgcataa aatgtcgtac aagatccata
6001  atctgcaata ttgttccctc aacagtacta ataatccaa agggcgaagg tactttatta
6061  tataaacgcg cacggccatt gtatataaag gcgattacat aatagaatac ttatcgattc
6121  cgtaatcctt gaaatataga atatacataa aatagacaag aacccaacag ttgaggcgcc
6181  agctttggta atagcttaat aataaataaa aaagataat atagctagct agtattattg
```

-continued

```
6241 cttttatccg tatggccacc accacgcaac cacaaaatat actgatggat gaacctttaa
6301 atcttcctaa taacagtgcc cacaacaata actatggaaa cataaatgcg aatataagaa
6361 cttttgctgg tatgagcatg cacatgcacc ctgccaggct gaactctctg gagtttttgc
6421 acaagcccag gagactatct aatgtaaaac tgcacagatt acctcaggac gagcttcaaa
6481 gaaatacgga catgaataag ggaatgtatt ttaatgggaa acaagttcat gcccatcacc
6541 cgtttataaa ttctggagcg aactttaacg cacatcatca agacgtcagt aaattaggcg
6601 aggaggaaga cgaaatctct cctctatcac atgataattt ccagtatgaa tccgaggaaa
6661 atggtaatcc ttcacctccc atttacaaga aatctggaga actggttaag agttcattaa
6721 aaagaagatc caagtcccta cccattactc ccaaatctat attcaacaaa actggctcta
6781 agagtaaaca tgtcaattta gatcatgtag atactaggct attgcaaaga agtaaaagtg
6841 tccatttcga tcgtgtttta ccaataaagc tgttcaatga aaatgagaaa cccatagatg
6901 ttggcaaaca aatggttcaa caagatgttc tgaatttcaa gcataagcct tgacgagac
6961 taagtgccct taatggcggt agtgatagcg tacctataga agatttacta tctgaaaaca
7021 accaaaacga atatggagat acatggctac aaaacccgaa gggtgtattc ctatttggta
7081 caaattctaa taatcgtaga aataaaaaaa agaagtttaa actaagtgac gatgacagtg
7141 atattgaaaa tgacaatgat agtgacgacg ctataaaccg tttagtaagg caacaagaca
7201 aagaccaagc tcatcttgcg cacgggttga agaatttgtt aataaacgat gacgacgatt
7261 atttagaaac aagaacaaat tctgctaaat caggagccaa cttgtttatt ggaaactcta
7321 aaagaattgt tggtctttac aacaagaact ttccaatatt aagtgacagg aaccgtaaga
7381 gtttaaaact taacatattt ctgaatcttt cccgtggaag gcccgttttt ttgcaagaaa
7441 ttacgctact aactggcttc cacaacatgg ttataattgg caagtctttt gtgaaaaaca
7501 tatactttga taagaagatt atcgtaagat atacatggga tgcatggaga acttttcatg
7561 aatcagaatg cgtgtatttt tctaatgcca atggcatctt accaggaagc aatatggata
7621 tttttaagtt ctccattgat gatatacaca atccaaatga taagatagc aatatatcac
7681 aattggagtt ttgtattcaa tacttaactt ggggcgttga tcgttctagg aaggaatatt
7741 gggacaataa tgattcggca aactataaaa ttgacgtggt aacgaatgaa acgaggacag
7801 ggcccacaac agacgtcaat gataactacg agatgaaaca tagtcttttc agaaacccat
7861 tccattaaag aaaaaaacaa aaactaatag tattgttta catatacaaa agaaaaaaaa
7921 aagataagaa tacgtacttt ctattttat ttgaaggtca tttctttat ataaataat
7981 atactggaat gatgttcttt ttgttgcttt ctatatttgc tttcttttt tactttttat
8041 tcaactccag acgttcttaa ataactcgtt atcatccaat gaaatgttag aactggaatt
8101 tgaattcata ctattattat ttgtagcggt aattccagtg ttcacgaatg gtgacggagt
8161 attacaaggc tgaggtgtcg tggaagtgaa aaatgagttc tggctttgag tctgggcaga
8221 aggttttgag tataaagata aaatggattt tttcaaatcg ttcctttgcc caaattcacc
8281 gactctgttg ccagtcttgg tattagcagc acctatgctt gttgcagaac tagttacact
8341 tgtattagat gtagtcttag aaagcgatga aacctgtagg tttaataagc tcgtattact
8401 ccttgaggtg cttaataagt gggaaggtgg ttgtgtttgc gtcttttgta atgaatttga
8461 gctctggtcc aatcttgcat tcgaagcagg caacgaatga ttcgcagacg gcttatgcag
8521 aactggttca gtagaatcat ttaaccttc aatactggag aggtcaccaa tccacttctt
8581 atattcatat ttattcttga tgaaattttg taaactgctc gtatcagtga ttttcctctg
```

-continued

```
 8641 tttcaattca tcagccaaag tagcttcgta gtatgagtta gctcttaaat tgttttttgaa
 8701 ctgtatcagt ttcaccaaat gttcttcctt ccatgtatcc agatcaacag atttcacttt
 8761 cgaaatgtgc gttcccaatg atctatgtat accagcacat ttaatgcaaa tgaaaacacc
 8821 aagtgaccag gaagcccagc gtggatgtag ttgcgcctta cagtcggcac aatgactgtt
 8881 tcctggatcg cgtaaaagag cacttaatgc cttcttgact gggactgacg tcgacatcgc
 8941 ttgtaaattg ccccacgttc tatgctcctt tgtacagttg aagcaagtat taccttact
 9001 tttgttacta ttagtaccga tcttatacgt attatcgagt cgaaaatcgt ccagcacgaa
 9061 atatggaaac ggtgcgttta ggtgactaaa ctaaatagcg tatatattat atatgttcca
 9121 atctatatat atatatatgg cactctgtta cagttcctta tcttaaaaca caaacacctg
 9181 gtcttccatc ttggaaagcg gtttggaacg tctgaacccc aagtccacgg tacttcttct
 9241 aactgaggca accatggctg gaggaccaca gatcaaaatt tgaacgttgt ccattgtagc
 9301 agcgggcaag tgttccttga tgacatcctt ggtaatgtat cctacaccac cagtccagtc
 9361 ttcacggtca ggagagtcta agtagtaaac tatcttaaat tgggaaggct tcatggccac
 9421 caacgcttcc agttccttct tcaacagaat atcctcctca tggacgttcc caaagactag
 9481 agagaccttg gtagtgtcgt gagggtccat ggcaatagct ttcatgatct gatacatggg
 9541 cgcaatacca gtaccaccag caatcatccc tagatgggaa cggcagtttc tctcataatg
 9601 atagttccca cgagggccct tgatctggat cgagtcacct atcttcaact ctccaatcat
 9661 cttagaaacg ttacctgtgg ggtaagactt cactagtaat tcaaagtttc ccttttgtatc
 9721 tccatccaac gatgtgggcg tatacgatct ggtaatatcc ttaccattga tattggcctt
 9781 aattacgata tgctgaccaa ttggtaaacc gagtacgtcg tcagcatgag gtagcccgaa
 9841 cttgtacatc gaagtattat gcgttaagat ggttttttca accagcggaa atgattggaa
 9901 gtcattcctt tgggatcca gcacaggctt ggtcttcggt ccgataatga acttgaagag
 9961 caaaggcacg accacgatca cgatgaccac cacaagcttt tgagcatcaa tagccatctt
10021 cgattgctta attgattgag tctcttgttg aagagccagt tgaatgcata ctttcaacac
10081 tttttttttct cgttcatttt ttcgccttat ataataagaa tatttataca tatgtagata
10141 atttaaagaa gtagaaagag cccttaatgg taccgcttta cgaggaaatt tagcactgtt
10201 acttttttgga gagtagtgca gtcttagaag ggcctttgag cttgatgtac acgtccgtgc
10261 cccagccaag taaactttga acgtcaatct tgcccccaaa cagttctagg tacgtcttgc
10321 acattggtag accaaagccc atgccggaga cgttgttgat ttgctcgccg ggcagatctg
10381 tagactcaga gtcagctgat tgttgggtat tgtagagta agagtagttg aacatgaggg
10441 cctctacctc gggcgtgatc ccaccaccat ggtcccgtat ccgtaagtac agctcgtcat
10501 cgtctggctt taaaagattg atctctatgg gcatatgttc cttttccaaga gctatctgag
10561 cttcaaaagc gttcttgaat acctctgtca taatatactc cagaatgggc ggaatgcacg
10621 tgaatgtgat gtcttgtgat ggcgggtgaa ttaggaccgg ggtccgctga gtgttgaact
10681 tcacaaagca tatatcattg acataatcag aaacgtgctt gatcaattgt gctatgggga
10741 ggtcccggtg caagattcca atcatccttt tgttcgtgtc acctttgttc tgtgccatca
10801 acgacaaata gtgcgtcaca agcagcttca tcgtgattct ctccttcagg tggaagttca
10861 agaactgcga aatttgaaac tttgggtaac acgattggat ttcctgaaga ccttttgcca
10921 ataccacaat ggcgtcctcg tggtcgtcca gcagttctgt gaacttggcc tgtatcttgg
10981 gaggattgtg caactcgtac gggtatgcga ttgatagcaa cgtttgcaag cttttcaaat
```

-continued

```
11041  acaaagagtt ggttctctca atatgagggt tgattaccgc attatacggt agcctctgaa
11101  tggcattaag ccgtttacac gtcaatgaaa gcaacaggtt gattgtcttg atcgtcagca
11161  tgtactcctc cttcttggtc agcggcggcc tgtattgcag gaaatactcg tagtttaggg
11221  gcgcaattgg tttactagcg tagtcctgta tcagcagctc aatgttcgac ctaatcttgt
11281  aatgctggtc gaacgacagt tgcgacagca gctcgtgtga gggtcgctgg cgatgtgccc
11341  agcgcattcc cccacatttc catgaacgca taatcttcca catactaccg tgaaggcgtc
11401  ttgataccac gtcttccagt tatggtcttg actcaccaat gttctcagtt taatgttgtt
11461  tgcttcatac tggcagacat tttcccttat taccgtgaga agcgagcggt ggattaatcg
11521  ggatgtcaaa acaagaaaaa ttgcaacctt cttcacctat aacctatatg atttgtaggc
11581  agaggagtgg aataagcaac aaatcatagt catcaatgtc gtttaatgcc ttcgccagct
11641  ctttgagcaa gaaattacag gaaatatcca caagtgtttc cgaaaaaacc caggaattgc
11701  ccagtttggc gcaatccacc caaagaatgg tccaggaacg tttgggccag gtgacggaca
11761  tctcccaatt gccaagagag tacacagagc tggaagataa ggttgacacc atcaaactga
11821  tttacaacca cttcttgggt gtaactgcta tctacgaaaa cggatcgtac gattaccta
11881  aatacatcaa cgaatccgtc aacgagtttt caagaagcgt ggcttccaag ttgacagagt
11941  tgactcatgc tacatctgcg tctgaggcac aaaacatctt agttgctcca ggccccatca
12001  aagaacccaa gacgttgaac tacgccctca gtaaagtggc tttgaactcc agtgaatgtt
12061  tgaacaagat gttccccacc gaggaacaac ccttggcttc ggcactcttg caattcagtg
12121  atgtgcaggc taagattgct caagctagaa ttcaacaaga taccttgatt caaaccaaat
12181  tcaataaaaa tttgagggaa aggctctctt ttgagatcgg taaggccgat aagtgccgca
12241  aggatgtcca ttccatgaga ttaagatatg acgtggcaag aactaacttg gcaaacaaca
12301  agaagccaga aaaggaagct tccttgagag tccaaatgga gactttggaa gaccagtttg
12361  ctcaagtcac tgaagacgct actgtgtgct tgcaggaggt tatttctcac gctaacttca
12421  gtgaagattt gaaggaattg gccaaggctc aagctgagta ttttgaaacc tcggctggcc
12481  taatgaaaga gttcctatcc aactcatttg cggaagagcc ggaagcaaag cctgaggttg
12541  cagaagaaga aaagccacag acagctatct ctatgaatga cgaagacgac gcttaatagc
12601  cgccctgttc ttgtctttct ctctccttct ctatatatat atatttactt aatacaatat
12661  catattctct agtgtcgtac gaatattatc atttatttgc tggcttttgt agtgagtata
12721  tttttttgtag agaaaatata attactggaa gagaaaaagc tactgaaaaa aatttcgtaa
12781  cagtcaccaa agggcaaagt gagcaaccca aaaatggacg ctactcaacc gcaatacgaa
12841  ctatccgtag taacacaatg cctaaagtct gccattgacg tcatccaatg gttgattcct
12901  actattacta agttcagcca atcacacccg ttagttttcc aactattgtt tattttcttc
12961  acattttatg tcttttacaa gttgttgatg aacttcatta ctctggtcaa aagattcctg
13021  tatttgacgt tggtagtaac atgtatcggt atttatatgc gtggttcgca gcagtttttg
13081  actgtggacc tgttgaattt ctacaatttc gtcatgtcaa atagatacta cgcatttaaa
13141  atttatactc tgtttattaa tgccctggaa agagaaatca acactgttta tcatttggcg
13201  cagatgaaaa tggaacagtt gcttaaatag agcgaaacgc ctctgcttac tcggaacatc
13261  ttaaagtaat tacatatctt aatttctaaa tattcatata gataaagaac gttttttttg
13321  ctagattcct cccctagtca ctatcaaata ttgagctatt tttggtgact tgtgttttcc
13381  aaattattca ttacaattgt gacttgattt ctgaagtttt aagaaaaatt gcaaactaag
```

-continued

```
13441  ttattacaag cgatttatcc ggtcgcgatt gaagaactga aaacaacagc agcagcattg 13501  taccaagaat cccaagatgc tcaggtgtgc ggtcaagaag tttgcatatt ttgccacctt 13561  cctcactatc gtcgctaata tttacatcta tacttatcca tctttccatc cagaacagtg 13621  ttcatggaac tgctctaaca agaacgcacc actacagaaa gatttgactt ttgtggacaa 13681  agtgaagaat tacttcagtg atgttcgaga gcaatggcat ggtagccatg cctctgcagg 13741  taacgatgag gatattcata ttttggcctt cggtgatcct cagattaaag gcatctggcc 13801  aaagacgcca tatgtgtccc gattagatac atacggtaat gactactatc ttggtcacat 13861  ctatgatatg atgcagcaga gactgaagcc tcaggtggtg actgttatgg gtgatctttt 13921  ctccagtcaa tggatcggtg attccgaatt ccataataga acgaaaaggt atattagcag 13981  aattttcaaa agagacccaa cttctattga aaatatcaaa caacagaacc tcgatgagaa 14041  aggtcaatat aaggcgaatt ggcctgaatg gggagaccgt tttaatgaga ttttagacaa 14101  tgtcaaggaa aacgaggctg ataatcaaga actttctttt gggtttggtt atgaaaatat 14161  ccactcatgg aatccagact tggaagactt tttaatcatc aacatcacag gtaatcatga 14221  tgtaggttac tcaggcgacg cgacttatca acatatgaca aggttccacg accttttcgg 14281  taaggacaac tattggattg aatacgaaac caacactacc catccttgga gaattgtagt 14341  gttgaatgat cttttactag aaggtcccgc tttacaacca gaatttgttg aagctacttg 14401  gatctttttta aaccaactaa atgaacgtaa attcaatggt agtactgttt tgttgacgca 14461  tgttccattt tacaagcgtg aagggttatg cgttgatggc ccagacacta ggtattatcc 14521  agatgcccat gccccagaat catataaatc tgggcttttg agatcccaaa atcatttgag 14581  tgaatccgtt tcaaatcaag ttttgaatat gatatttgaa atgggaagc caggtatcat 14641  attaactggt catgaccatg agggctgtga aacagtttat aataaaaaat ctacatctac 14701  ttgggaagcg actaaaaata tcgaaagtga cgttttcgtt aaagaaatca cagttaagtc 14761  tatgatgggt gaatttaatg ggaatactgg tttggttaca ggacacttca acacagattc 14821  aatgacttgg gagtggactt tcagtttatg cccattcgct attcaacatg tttggtggtt 14881  cgctaaagtg tccctgctcg tcaccatatt cacttggtcc tcgctactat ttgtctaaac 14941  aaaaaagagt aaagaagata aaactcctgt atagagattt atattaaatg tatgtatata 15001  tatgcatata ctgctcttca aattgcttat gttttataaa cattgacatc ggggttccac 15061  acatcaagat aatcattata ataccttaga ttgtaaaatg tttacttact actttaaaat 15121  aactataaat aaaattaaaa atcaaattaa aaatcaaatt atactgccat tagcactgat 15181  ttttgttgtt tttgttttaa agggatgcac atttttttttt tttatgttat tatcatacac 15241  taattttttcc ctgtttcaat tgtttcaaga gctgcttgcc gtgagaaatt tcttgttttt 15301  gttgttctaa agttacatta ctctgatcat taacattgtt attgtcaaca ctcacatcac 15361  ggacctcaga cgctgtatct accggtggct gcaaaatga ataatccagt ctgaagttaa 15421  ttttatcaat tactgtccaa tcgtccagtt taaaaatttt gtaatcacca acttcgcaaa 15481  tttcattaaa aaacttgacc tcaccttgtc ttaaaaacca cattgtacca tcctttgaaa 15541  ctttccaatc cctctcattt agaatcttgt atgcaatctc cctttctaaa ggagtaatag 15601  caaaataata gttataaaat aacgaaaaca tttctaaagt tctgaaattt tctagaattt 15661  tggcataaat tgacgatgaa tcttctttca gcctttcgga gcctataata atatcacgca 15721  acgaacaacg cataacgtcc cactgttgag tagatctgaa tgcatccaag ggagatggtg 15781  gattaactcc ttgcggtact tcgaccagcc tggaaatttc acacatatca cgagacctttt
```

-continued

```
15841  tgtacgttat tttcgattca atttgactat tatagagttc agaactcatt atgaattctt
15901  gcacaccact tggtagaagt aaagtttcaa aatcacttac aaattctttt ttgatttcat
15961  ttgtcttagc ttctctttgt tccaagctta aatatttcgg tgtgcttggt tgttcttctt
16021  cctctggctc cgtctctgaa tccctatccg attcaaaatc gtcatcgaat actccaaaag
16081  ttggcacttg caatttattt ctttcttctg gtgactcttc ctccttctgc tccataacct
16141  tcttagttgt gttctcaggc ccattttggt ttaccgtagt tgcaacttca tgttcagact
16201  ttggatttgt cgccaaggaa actaaaggat gatgtgagga gctcatattt ctatagaagg
16261  cctgattgtt ttgatgcaca gcagccgccc cagcagccaa aacagcagcg gccgttgctg
16321  ctgaagatga tgcgccggta ttgtcaggtt gtaaagacaa agatgaagta gataacttag
16381  gtgtattcaa cgcactacca atcctgctgt tagcgttgga tgatgttgta gtagcagcag
16441  cagttgttgg agtctttgtt gaggtattgg atatggtgga cgatgcagaa gtgactttc
16501  tatccttttc taccgcttgt gatgcagcaa cggcccattt taattcacca gcaggttttg
16561  ctggaagagt agcaggtttc aatgtagtgg caccagtaat accgtttgga gtttgatgaa
16621  tatgtgtatg tacatttgtt ggagtttctg gtgtagctga acttggtgat ttttgcaatg
16681  acggaagcaa attatcagca ctgctcctgg gactctttat agaagtttta acagcctctt
16741  caggctttgt tgcattatgg ataggggaag atgaaggact tctttccgtt tcttttgaag
16801  catcagcaac gggaatgaca ggtgacggcg tagaagaggg accagcaacg ggtatagctg
16861  cacctgttgc attttttgcc gcaagtttag cagccttttt ggcttctctt tccaattttc
16921  tttgctcctt tttagaaagt tttgatatgt cctgcagaga ttcattagca tccgatgtat
16981  tgttatcttc agcattttgt gaagcaaaat actgggccac ctcatgagca atggcttcgt
17041  tactctgtaa attcaaaccg tcataaatag tttcatcctc tacgaaatct ggatcctgat
17101  ttgactccac gaagtaattt atatcgtcct gcacgttttt aacatcttgg gggtccaatt
17161  cctcattggc taacaatctc aaggctaact ccatctgctg ttgatgccac ctatacctcg
17221  cttgaaaacg cttatattgt tccttttttt catcatttgt cgtagatgac gttttcttct
17281  ttttattaag aagtaaaagc ttgtcaattt ccacttgtag ggaatcgtat tgccttcca
17341  gctcatcgat catttgggaa aggtactcag atatatctct cctttccctt tcttgcgggt
17401  ctaaagtctc tgattttttc aggctaatat tagagtatgc ttttctttg gacgccttct
17461  ctacagcctt atacttttcc atcgctattt ctacagacct tctgtaatct agaagagaat
17521  ctttatcttt aatatcgggt gagctttgcc atgattttat ctgttccctt agcctttgca
17581  gcttttgac ttctctttt aaatccgact ctagcttgtc cttttgggaa ggattgtttg
17641  tgcatgattc atgtctttcg taatagctat tgaagatttc taaaccttcg ttaattttt
17701  taaagaccct atcgacctcc tgctgtaatt ttctatgagc catgtcgatc gactaaacat
17761  acaatgaatc ttcaaaaatc taaatttgaa aatgaataaa taatgtgct gtagataata
17821  gcttttgatt ttttgtcttg acacaatgag acttctcgtt aaagtcaaac caaaggaga
17881  tgaacaaaag aaagttcgaa atatcaacaa aatgctttaa aaaatgtaga agcaaagtta
17941  ttaataactt tacaagcgcc ttagtcagtt tattgatctg taggtcagta ggttttagag
18001  attacgcaca gatgaaagtg aattaagcta ctattacata aaatcaaggt atctttcaca
18061  agtttttcac tcagcgaaaa ttgcgagacc gctcgtggaa ggtgacgata atacgatact
18121  tacaacttta atattataaa tataagcatg tggtggaaca atatagtcag gcaaactgct
18181  aaaagtcccc acttataaac agtgtgtaaa aagtacgttt gttttgctc cttatccttt
```

-continued

```
18241 atttggcgtt ttgacagtga agacaatgcc gctaccgatg cgttggttat attaattcct
18301 cgattaatta taccatattt ttgaatgtcc agtgcaaatg aagaatttgt attcgtaact
18361 tcgtatgtcg gtaggaaata ctgacccagg aactcattaa ttgaatcgct gcctaacaga
18421 ggctcaacct gcaggtctat cccctgccaa ttttgagaac tctcattaag atattttca
18481 aactgagtgt ttgtgtcgtt aacccaaaga tttaggatgt ccgttgattg cactttcaaa
18541 ttggggtcag tttgaaggct taaatttgct gtaatgaact tttcattcac ttccatttgg
18601 aaattttcac acaataatga tacgctgtca ttaatgaaac cctctatcgt agttgttata
18661 tttccatctg tccaaacttc cctttgtat agcgaaggtc ccgctctttt gtggaatgta
18721 ggcaaactgg gtacttcaaa gtttgttaat cgcgtcacta tctgccaatg aattaataac
18781 atcaaaaaac caaacagcca caggtgagcc ccatttgaga ttatccacca gttacagtaa
18841 aatagttttg attttttgac tttttgtca tcgattttt ctggttctct tttaaatatt
18901 ttttgattga taagctttgt taattggtag ggaattggat aaagtgtact gagattcaga
18961 gtagtaatta agcttttcaa aactttgttg tatttagtaa aattggtttg tcctgtcagg
19021 ccattaattt gggacataac caggtttact tgctgatttt ccagctgaaa cagaattctt
19081 tcgattgcca tgagcaaaat cacaaatgca aagtacatga ctgtgaaaat tattgtcatt
19141 ctcttacatt tacggaaaac gtgatttttt actgcactta gtacactgtt ttcctcgcta
19201 tttgttttca gagaccgttt aattattgaa gtagacgatg taacctcggt actccccca
19261 gataaaatgg aaatttcatt ctgtaagttt gcagtaaagt tcctttcaa ctgaagccag
19321 tcagtggaat ttcgtagaaa attcaaactt aaggtactag aggtatctaa ttgagtagaa
19381 aagtcagtga tagtgccatt gaagttctgc aatgatttca atttccttga gtagttccca
19441 aaaatactgt caaacatgga gtaatttaac agtaggtttg atgccatttg tgaaatggaa
19501 tccttatcaa tggtcattgc gtcttctgat atttcattcc atgtgtcatt tatcagctgt
19561 gatttagtga gtagttcgtt aaaaattgta ttgtttacct caagaacttc cttaatcaat
19621 tcagttcca aacttatttg gtcgttgata agtttttgtt tattatccag tatgtcgtct
19681 gtgtatgact tgaattttc ttgcatatcc gtacctaccg tagattcaat actccgtagt
19741 ttgctttcga aatactgatc aattgtatta tcaatgaatg ttttatttaa agagtaactg
19801 ttggcagaat atatggcatg ctgtgttgtg actgctgtca ttgtggccgt tgttgtggcc
19861 gttgttgtgg ctgtcgctgt agcagttgaa atagatgcaa aggttgagac ggtatcattt
19921 cgtttgacct gtgcgtgaga catttttgcc attgtaatgt caatgactga aaaggaaccc
19981 caaatagtta aaataacaga agtaaagaat atcagtaata gaggatggaa aatacaacta
20041 aaaaacctct gtggaagtga taaaggttta attatgtgta cattgttcat ctttgccgta
20101 ctcttagttt tatcgaaaag tggtgtagat tttcagctac ttaagccatg ttagtgttct
20161 agtttttgc tttacatgtt atataaaggg ccaagatagc atatgtaaat gttttattac
20221 tgggctgaaa catttttaaa acattttca ataatgtgct gttataaccg tacaaggacg
20281 gttataattc tgaattaaaa tgctgcaccg aatgaaaata ccaatgttct tccaaaccta
20341 ttggcgaaaa ttaagataag ctgtcgcctc tataatcaag aataatctca actattataa
20401 atattattcc cagaagttga aattgtgaca catttgagta atatccacctt acacggaaca
20461 tagttgcccc cttctccgaa attgctgaca atgataatcg gggattcaat gacaatgaca
20521 atgaaggcaa aagatttca tattgtactc ttgttttttg agttatcact ttcaagtacc
20581 ttcttgttaa cagaaataga accgctatag aggttatcgt gtatacgtat ctgttggtgt
```

-continued

```
20641  ttctaaatca aaaactcgct tttaaagcag tctttcaatt ggaagattca aaaggatcta
20701  aaaagatcta aagtagtaaa gaaaaaagta taagcccaca ccttttttggt aggataatgt
20761  ttactggtca ggagtatcat tccgtagact ctaattccaa caagcaaaaa gacaacaata
20821  aacgtggtat tgatgacaca tcaaagatct tgaataataa gataccgcac tctgttagtg
20881  atacttctgc cgccgccacc accacttcta ctatgaacaa ttctgcttta agtagatcct
20941  tagatcctac tgacataaac tatagcacaa atatggctgg tgtggttgac caaatacatg
21001  attatactac ttccaataga aattctttaa ccccacaata ttctattgca gctggaaacg
21061  tcaattcgca tgatcgggtt gttaaaccca gcgccaattc aaactatcag caggctgcat
21121  accttcgaca acagcaacag caggatcagc gacaacagtc accctctatg aaaactgaag
21181  aggaatccca actctacggt gatattctga tgaattctgg tgtcgtacag gatatgcatc
21241  agaatctggc cactcataca aatctgagcc aactgtcgtc tacccgtaag tccgctccga
21301  atgattctac tacagccccg actaatgcgt ccaacatcgc caatacggct tctgtgaaca
21361  agcagatgta tttcatgaac atgaatatga ataacaaccc acatgccttg aacgatccat
21421  ccatcctgga aacattgtcg ccatttttc aacctttttgg tgttgatgta gcacatttac
21481  ctatgacgaa tccaccaatt ttccaaagtt ctttgcctgg atgcgatgag ccaattagaa
21541  gaagaagaat atcaatctct aacggtcaaa taagccagct aggcgaagat attgaaactt
21601  tggaaaacct gcacaacaca cagccgcccc cgatgcccaa ttttcacaat tataatggtc
21661  tgagccaaac taggaatgta tcaaacaagc cggtcttcaa ccaagcagtg ccggttagta
21721  gtattccaca atacaatgca aaaaagtta ttaatcccac gaaggactcc gcattgggtg
21781  atcagagcgt tatttactcg aaaagtcagc agcgaaattt tgtaaacgcg ccatcaaaga
21841  atactccagc ggagagtata agtgatttgg aaggcatgac gacgtttgcg ccaactactg
21901  gaggtgaaaa taggggcaaa tctgcactta gggaatctca ctctaatcct agcttcactc
21961  caaaatctca aggatctcat ttaaatttag cggcgaacac acagggaaat ccaatccctg
22021  gtactacggc atggaagaga gcaagattgt tagaaagaaa tcgaattgca gcttcgaaat
22081  gtagacaaag gaaaaaggtt gcgcagctgc agctccaaaa ggaatttaac gaaattaaag
22141  acgagaatag aattttactg aaaaagttaa attactatga aaaactaatc tctaaattca
22201  agaaattctc caaaattcat ttacgtgaac atgaaaaact aataaagac tcagataata
22261  atgttaatgg cactaatagt agcaacaaaa atgaaagcat gactgtggat tcattaaaga
22321  tcattgaaga acttttaatg atcgattcag acgttacaga agtggataaa gatactggta
22381  agatcatagc catcaagcac gagccatact ctcaacgttt cggaagcgat actgacgatg
22441  acgatataga tctcaagccc gtagaaggtg gtaaggatcc agacaaccaa tcattaccca
22501  attctgaaaa gataaaataa caaagttttg gtgagcacaa cggtgtttca ttcaagaatg
22561  ataaggacaa ctatatatgt aatatacgtg tataaatact cgagctgcat cctttcttt
22621  ctgccgttat tatttcgttt agttactaca tttatggtat aaattacctt taagacatta
22681  ttattttgca tgtatgaaat ttgctcgtgt caacccctta gtcctccttg cctctgttgt
22741  atggaggaag ccctttaaac ctgtatttag ttttttaaat ctattagaat taagtacaat
22801  tgtacagatg gtaaaaaaaa gtaatcgtta tatcgtttgt cagtgatttt ttttttttta
22861  tttcattcat tatttattc ttattttttca atttgttccc ttattgggc aaaccacggg
22921  tgtcccatcg cttccttagc agttaatctt tcttgatgat catatctcaa aagattgtca
22981  ataaggtcaa taatttcatc gttgccgctt aaatgtttat taccatcatt gatgaatcta
```

-continued

```
23041  tgccaaggct ttctgatgta ttggtccata tcgtaaaatt ctctcggtaa ggtaatttca
23101  tacttcaaca ggtatttctc aaaatcgctt gtaccaagta ctttgacgat cttgacaagc
23161  tggtctgtgt tactcgttcc atggaaaaat ggctctcttt taaagatcat agaagccaac
23221  attgtcccaa acgaccacaa gtctaaagaa taatcataca ttctgtagtc aactagtagt
23281  tcaggaccct taaaaaacct cgacgcaaca cgaacattgt attccatatt aacatgataa
23341  aattcagcaa gcccccaatc tatcaatcgc aatttttat tcttatgatc aatcattacg
23401  ttatgaggtt taacatctct atgcattatt cccattgaat gacaatagtc taaggccttt
23461  aataactcaa acatataaaa cctaatttcg agatcggtta atttagggta agaatacgg
23521  aagtccacat tatctacgta ttcgaagacc aaagccggag tttttgagat gggatccttt
23581  attatatcaa atagatgaat tatgtttgca tgaccattgt gtggctgatc aaagatatag
23641  ggcctgatga attttaaaac gtcctccttt tgatttgtgt aatattgatc tttttgaaat
23701  ggcaaagtcg ttggaggcac ttttttcgtta gacaaatccg ttaagatttt gatttctctc
23761  ttgatcttct tcttttttaac tggtttcaac atcttaataa caattttaac tttagagtct
23821  aatttgacac cttggaaaac ctcggagtat tttcctcgcc caactttatt ttcaatttca
23881  tagtccttg tatttgtgga ccaatcaatt acagtatttt cataatccca atattcctcg
23941  gttctttgtt tattgatatt cgtataaaca cgagcctctg accataccot gcatttcata
24001  gttcgaatca aatattcctt ctacaacccc ctattttgt ctgtatattt gacttcttaa
24061  gtccctattc agaaaactcc tagtaggtaa ttgcaataca ccgagtatca acagtatatg
24121  aagtccctta atccgtttta ctacaggact gcgaggttcg tctaattgct actgaaattt
24181  tccaagcgtt ggtcatattt ttgatttttc gctttttctt cagtgttcgt tccgagtgat
24241  ttttgatagc gcttttctac cacttagtgc tgctgtatgt atttatatga tataccagcg
24301  atacatgtaa atatttctat aaagactgta aacctctgat tacctctgcc tgtgcgtctt
24361  tattcgcttc ctcagcagag gaagcaatgg ctgcgttctt tgtttggtgg aagatatctc
24421  ttgtcttttc gaaataaaca gtttccaata gatttctcat ctgagactca atgtcctcaa
24481  ttaaggaacc caaattagcg acatgtgatg tgaaaataac atctaatgga cgggacatat
24541  caatagcgat gtcctttcg gtctgtcttg tcaggttccc ggataacatc atatgagaat
24601  tctggtcagt ttttgttttg tccaagtgca gaatgattgt agtggtgact ctatagttga
24661  aactgtcggg agaagaagga gatgttgtaa cttcaaaaac atggatactg tcccaattac
24721  tgtgatctga ttggtttttt ttgaaaagca ctaccctgc aaaatcgtgc ccattgaaat
24781  cttcttcatt gaggtcccag aggtacacgc tggagatacc gccttcataa tagagatctc
24841  tgtaaacgtc gaaagagtca ttggctaaga tctccaattt tcttaaaggg gctgagggaa
24901  aggggctgtc ttgtagatcc tttggggata gttctgggta ataagtgttc gaccaaggcg
24961  atctgaacga atcaatatca cgattatagt cgcagcataa gtactcccgg tttgaatcgg
25021  cggaatcttt ctgtgtggat aggggaacgt ctactgaaga tagtaaatct tgtgccaaat
25081  ttggttgtaa ttcgatcaag ttgtttagat tctcctgtaa cgtggtagga tttagcctcc
25141  taagaagatc taaagcagca tcgaattgag catcagacat acggtggtg attgtagagt
25201  tggagagagt ttttgtatgt cacttgattg aacagttctc ctttatttgt tacaaatgct
25261  ctcattttta cgttttccgt ggtgaaaaaa aaaaaaaaaa atgaacatat atacatgtag
25321  taacagcagt agtagatgaa gaatttagag tttaaacagg taacataacg ctataaggga
25381  aaggaaagtg gagatgttat acattatatt tacgtagacg ttgaaggaag aagaaagaaa
```

```
25441  aagggaacag aagaagaaga aaaagagaaa ggaaattcat gtggatttaa gatcgcttcc
25501  cctttttact taatgtcttg taggatcatt gagctttaat acgtctactg caggacccag
25561  taaacgttga aaaccacttt tccccaatgt ggcaacttg gttctctttg tagcagtcac
25621  agtggcctgt ctgggcaaat cgtttagcaa ggccacttca ccgaaataat catggtcttt
25681  cagtttattt atgacacctt ggcccttctt agagacgtcc acagctccgt actcaattaa
25741  ataaaagttc tccccttgat caccctcgcg aatgattgtt tcacccggct ggtagatctt
25801  ggtatccagt gcatcggcaa gtttggcacg tcgtacgta gtcaaactct tcaaaactgg
25861  catgctcttc aaaagatcgt catacatgag tctcttcttg aaagagctgc caaaagtat
25921  ttttctgaag gtgagcctgt ctagagccca caacaaacag tcggaggttg ctacaacggt
25981  ggcagcacga gggctgttgt acataagagc aagttccccg aaactggagc ctggcccgga
26041  agagttgacc ttgttgtcgt tgacgtagaa gtcaacagta ccctttcga cgacatagaa
26101  gtagtcccct tggtcacctt gcttgattat cgtagcacct ttggggacgg acttctcctc
26161  cagacaattt atgaccagcc ttttgagtc ggaatccagc ttgttgaaca gaaagttatt
26221  acggatcgat ttttccagtc tttgcaattg ctgctcggac ttttccttat agtgatctgg
26281  agtccaatcg tcaaaattgt ttggttgtaa ggtctcacca ctaacagaag tacgcctttg
26341  ggcgttgaag tgcattggga gtggaggagt tgatgtcttt tctctagtat gctgttgttc
26401  ttcctgtgct tgctggtgag tgtcctgttc gtgcgggtct aaattaaacc cactttaaa
26461  cacgttggag tgtgggtcct cgttcacaaa gggggatttg aacataacac tcgatctgga
26521  tcttgattga gattgagctg attgaggtct ggaaaatgac tcctctggtt ccggaaatag
26581  aacaatgttc tttgccttaa attcaggctc cctggccttg aggaacgctc tctgttgttc
26641  cagccttta ttgaaatagt tggcggagaa ctgaagaaag tcggacggat tagcggcgtt
26701  gatttcgttc tggaacagtt gcaattcggc ttgcgattcc ttgggcaaag aagataccat
26761  cgtttattct tactgttgtc ttttgaaaat aatctgcttg ttgtaaatga tcttcctatt
26821  tatgtatgcg tgaaatgcgt gtaatggatg tgatgatagc gatcgcttga cttagtcgag
26881  gaaagcgtaa agtgtccctt tttctctttc ccttttccct gtttgttcaa attttctctt
26941  ttctaccttc ctcttcgttt tgctccttgc cagcaaaacg aggaaggaca agaattttgg
27001  agagcggcgg cgcggcgcca taataaatgc acttgagcaa atgcaataag ttcagcttat
27061  ggcttctgca acaaagaaga ggtcggaatc cgagcacagt ataatcaata tattatcagg
27121  cagaacaaaa gtggcgggta taacacgaag aaagaaggaa gggtggtgat tgggtgcttt
27181  gttttttcc gctcgtcgtg gtggcatgcg cttttttttt cttgggtgaa gattagccgc
27241  cgaagtcgta tgctcctctt ttgagcgttt tgaaagatag aaaaagctg agtaagtaaa
27301  atcgtcggcg gctaatctga aaagtatata aagtccttta tattttccac tcgtattctt
27361  ttccctcctc cttttttttt ttactttctc acgtatggct tgtttcattt attatcagat
27421  cagtaatcac gtgccgtgtc gttagaaatg acatttggtt ctttgccttc tttgtccttt
27481  ttctatcttc ctactaagag aaactattat acaatacaat aagagaacat cgtgaaacaa
27541  cataaagat atcacgtcat cagagagaga taaaacatca caaccaatta cattacagtg
27601  tattcgtttc ttcttagaga gagaaataaa gagcgggata aaggacact acacagtata
27661  ccccatacc aggtgcaata atacacgtat atctatgttt attgcacatc aaaccccaca
27721  tatatgtctg ccagaaaacg caagtttaat agtctcaaac cgctagacac cttgaacagc
27781  tctcgtgcca gctctccaag gtcctctgct tctctaccgc ccaaaagata taacactttt
```

-continued

```
27841  cgtaaggatc cgaaaatcgt tgatcatcta aacaatgctt ctacaaagga tttcttacca
27901  gttttgagta tgaacagcga gagtaagagg cagatcgaat tgtcggataa tgatgttgat
27961  aataatgatg aaggtgaagg cgtcaacagt ggctgttcag atcaagattt tgaacctttg
28021  caaagctctc ctttgaaaag acactcatca ctcaaaagca cttccaatgg tcttttgttc
28081  caaatgtcta ataatctggg gaatggttca ccggaaccgg cagtagcgag cacttctcca
28141  aatggctcaa ttatttccac taaactaaat ttgaacggcc aattttcttg cgttgattcg
28201  aaaacattgc gaatttatcg gcataaagca ccatgcataa tgacttttgt ctcagatcat
28261  aatcatccga aattttcatt gtattttcaa caatcggtga tctacaattc acaagttaat
28321  ctgcttgatg atgttgaatt gataatttta gataagaaga actcttttat ggctataatt
28381  ttaaaagatc tgaaaaaggt caagatgata ctagacgtga ataactcttc aatcaacatt
28441  aacacgaaca tcttgatatg gtccactgca agctccgctt caaataaaaa aataaagtct
28501  attaaaagat tcctgttgat gtcatattct tcgtcgataa aagtcgaaat tttagatcat
28561  aaagagcaga ttttggaaag actaaaacat ctgattcatc ctatttcttc gtcatcacct
28621  tcattgaaca tggaaagggc aataaactcc actaaaaatg cattcgactc tttaagactt
28681  aaaaaaacta aactttctac taatgatgat gaaagtccgc aaattcatac tcatttctta
28741  tcaaacaaac ctcatggttt gcaatcctta acaaaaagga ctcgtattgc cagccttggg
28801  aaaaaagagc attcaatatc tgttccaaaa tcgaatattt caccctcaga tttctacaac
28861  actaacggga cagaaacttt acaatcccac gcagtttcac aactaagacg ttcaaataga
28921  tttaaagatg tttcggatcc agcaaactca aattcaaatt cagaatttga tgatgcaact
28981  acggaatttg aaacaccaga actgttttaaa cctagcctct gttacaaatt caacgatggt
29041  tcaagctata ctataacaaa tcaagatttc aagtgtcttt tcaataagga ttgggttaat
29101  gatagcattt tggattttt tacaaaattt tacattgaat catctattga aaagtcaatt
29161  atcaaaagag agcaagttca cttaatgtcc tctttttttt acacgaaact aattagtaat
29221  ccagcagatt attattctaa tgtaaaaaag tgggttaaca atactgattt gttttctaaa
29281  aagtacgttg ttataccaat taacataagt tatcattggt ttagttgcat tataacaaac
29341  ttggatgcga tcttggattt tcatcaaaac aaagataaaa acgatgccat caactccgat
29401  gagatttcta taaataatcc tctggttaat attttgactt tcgactcgtt gaggcaaact
29461  cattcaagag aaattgatcc aataaaagaa tttctcatat cctatgcact tgataaatat
29521  tcaattcaac tggataaaac acaaatcaaa atgaaaacgt gtccagttcc acaacaacct
29581  aatatgagcg attgtggtgt tcatgttatt ttgaatatta gaaaattttt tgaaaatccg
29641  gtggaaacaa ttgatgtatg gaagaattct aagattaaaa gtaagcactt caccgcaaaa
29701  atgattaata aatattttga taaaatgaaa agaaatagtg cgagaaagaa tttaaggcat
29761  actctaaaac tcttacaact caattacatc agctatctga aaaagaaaa tttatatgaa
29821  gaagttatgc aaatggagga gaaaaaaagc accaatatca acaataatga aaattacgac
29881  gatgacgatg aagaaattca aatcattgaa aatatagatc aaagcagtaa agataataac
29941  gcgcagttaa cctcggaacc tccctgctca cgatcatcca gtatttcaac aacagaaaga
30001  gagccgacag agttgcataa ttccgtagta cgacagccca ccggtgaaat aataactgat
30061  aatgaagatc ccgttcgcgc tgcttctcca gaaacagcat ccgtttctcc tcccatacgt
30121  cacaatattt taagagttc atctcctttc atatcagaaa gtgcgaatga aactgaacaa
30181  gaagaatttta cgtcaccata cttttggaagg ccgtctttaa agacgagggc taagcagttt
```

-continued

```
30241 gaaggcgttt cgtcaccaat aaaaaacgat caagccctgt catccaccca tgatattatg
30301 atgccgtcgc ctaaacctaa aaggatttac ccaagcaaaa aaatcccaca actttcctcg
30361 catgttcaat ctctatcgac tgattctatg gaacgccaat ctagtcccaa taataccaac
30421 attgtaattt cagatacaga acaagattcg aggttaggag tgaattctga agtaaaaat
30481 actagtggta ttgttaacag ggatgactcg gacgtcaatt taattggtag ttcactacct
30541 aatgtagcgg aaaaaaatca tgacaacact caggaaagta atggtaataa tgacagtctt
30601 ggtaaaatac ttcaaaatgt tgacaaagaa ctgaacgaaa agttggttga tattgatgat
30661 gtggcattta gtagtccaac taggggtatt ccaagaacca gcgcgacaag caagggatca
30721 aatgcacaac ttctctctaa ttatggagat gaaaataacc agtctcaaga ttctgtttgg
30781 gatgagggca gagataatcc tatactcttg gaagatgaag acccttgaaa gcactcgcac
30841 gcatagtttt atattttta ttcttttcct ctttattttt atttttttaa cattctcgca
30901 taataatagt aacagcaata aaataactag taatatacat actcacataa ataggcatat
30961 tttttatttt gttctttcgt attcagaatg gtaaatttt ctaatgaaat gttttacaaa
31021 aattttttt ctataattct aacaataaga aataaaacag tggaaaaaca tataacttaa
31081 tgtagatata tatatgtaaa tatgctagca ttcattttaa atgtaaggaa gaaaacgcct
31141 ttaactttca tctggtaaat tttctaaagc tctacccta gtgtaaacct cgtcttttac
31201 attctgtaca gtacttttga accattgaat gaacagcaca gttgcttgga aaaagaacgt
31261 aaatgactct aatgctatca gtagtccgaa ataaatatct tgcatccttg tccatgttgg
31321 gaatgattcg ttaagcgata aagtgaaact cctggatcca tggctaatat cgataatctg
31381 ctttgtagaa acatcacgta aaaatactaa ggataaaata ataatcggca agacgtaaat
31441 taccatgtgc aggaaacctt gtttaaacag ttccaaagcc attgttttca agaagttcaa
31501 tttactagta tttctgtttc tgaaaaatag tttcaatgac ttatatccgg ttccgaaatt
31561 gaccattgac gaaatgatcc aaacgacgaa taacaaactc tcgtcatatt taaaccattt
31621 ggaattacca atagtgtatg aagaattgcc aaacactctg atggtgagat aattgtaaca
31681 ggctagtata ccatcggtta agacgaccca cgaaaccata gttctaataa ccgcaatcat
31741 gatagctata aacaccatca ggttatactt caccaacata ctatcaaata tactgttaaa
31801 gatggccatg aaaattcctt gaccctcttc cacattattg atattattaa caggggcatt
31861 gttgatatct ctctctggta tatcgtgttc cacttcctct acttcgtttt cgtcaacggc
31921 atgttcatcg agagtgtttt ggccttctgt aaaatgaaga atatccttag caatcttgga
31981 taaacaaaca gatccgacac agacataata aatgttcaaa taggagtagc taatgtcaga
32041 gagttccttc catgcaacat agaccttatt tctttcacct aacaatagct ttacgactgg
32101 aagaaagccg aaactacaaa caaagtttat taaagcttga ctaataaatg taacaccaag
32161 cattaaaatg gaagcaaata accaaaccag gccaagcaat gtcatatagc gtaaacggaa
32221 atctggaggg acgtaaacga tataatattg atcatattcc gtgttttgtt cgtctaaata
32281 accaaattca ccagcagcac gtttgtttct ctctttaatt cttttccaaat ctaatggttt
32341 caacagctta tcatcctttg taacggggac aaacattgtt tgtacataat ttctggatac
32401 tatatcagaa gaaggaacac gcattaaaac gccatcgggg acaaaataag catgaacgtc
32461 acgaacttgc ccaaacaatt cttctgcttg ttctagagtc tttggtttag tgaaaagttc
32521 ttggtttgac cattctgcat tcttggcagc aatgtacttg taaaacaaat tgcggtaaac
32581 aatatggcct ctctctgttg gggtatcttt acctaagata aaggatgata aacgtaattt
```

-continued

```
32641 tcttgaacat aacttaaaaa ttgttttcca atacctttcc aataagggtt taacgtaaga
32701 gctagactcc aggatcctct tcgtaaaata taaagttagc aaaattgtat tgaacttcca
32761 tgaaataatt gatgttggtt tataagcttc aggaacggat aataagttcg atttgagcat
32821 gaatgggaaa aaaattctag tatggaagcc aaaacctaag acaataaaaa tcgcataaat
32881 aaacatggat aagcaaagcc ttgataattg aatactcatc ggatgaatta aactatcatg
32941 caagatctta atattaggat cttctggaga tctgataaag aatagaacac ctggtctaat
33001 gatattttc ctaatcattc cgatatattt ggcaaaccaa tacatgtaga gagtaccaat
33061 cgtccagtat acgaaaaggg aaaatggagg ccatattgcg catattgaag gaacccaaag
33121 catccgacta ttggatgcca ggattgggca aaataatgag aaatctagca ttacaccagc
33181 tagaatgggg aatccagcca attcgatgaa aaataaagtg aacaccttga aagtgcattt
33241 gagtgcaaat aaaatctgga aaatcagcct tctagtaggg ttgctcattc cgttctcacg
33301 gccataaccc ctcgagacaa gattggatga agcacaaacg atactgactg aggttagata
33361 cgtcgttaaa gcaggtaaag ctctgatgaa aattgagtgc ttcatggtgt tttcagtgta
33421 gccgttgtaa agataaatga tgtcatgaat taagtggtct gaaatccaac tcatcgcgac
33481 atctacttta gggaccagtt tcgtcagccc attgtaagct atatgagcgc cagacaagta
33541 gtaaagatgg cacaacccac gcaaaataac cttaaatata ccaaaataaa ttttcaacaa
33601 accgaaccca ataaaagttg gaaacaaata ggaaattgcc aggtatattg cggtgaaaac
33661 tacggcaatt atgaaataag caatgacatt caacaatttc aatttgagat ttatcactag
33721 agggccttgt ccttgatcgt ctgggttagc ctgtgctggt ggcacaccaa cagctgcgcc
33781 aaagtcttgt tcgtcttgat cgacatttcc agctctgttt tgggcaggtg gtgggatgaa
33841 aaccggagcg ttgggcctgt ttattgcgtt ctgttgagca gcgattaggt catcaaattc
33901 attttgcgca cgacgatttg cccacatgtc aatcggattg ggctctatat gatc
```

SEQ ID No.8

```
  1 mrrerqrmms fedkdkddld nsnsnnssem tdtammpplk rllitgssdd laqgssgkkk
 61 mtmatrspss spdlatndsg trvqplpeyn ftkfcyrhnp diqfspthta cykqdlkrtq
121 einaniaklp lqeqsdihhi iskysnsndk irklildgil stscfpqlsy isslvthmik
181 idfisilpqe lslkilsyld cqslcnatrv crkwqkladd drvwyhmceq hidrkcpncg
241 wglpllhmkr ariqqnstgs ssnadiqtqt trpwkviyre rfkvesnwrk ghcriqefkg
301 hmdgvltlqf nyrllftgsy dstigiwdlf tgklirrlsg hsdgvktlyf ddrklitgsl
361 dktirvwnyi tgecistyrg hsdsvlsvds yqkvivsgsa dktvkvwhve srtcytlrgh
421 tewvncvklh pksfscfscs ddttirmwdi rtnsclkvfr ghvgqvqkii pltikdvenl
481 atdntsdgss pqddptmtdg adesdtpsne qetvldenip ypthllscgl dntiklwdvk
541 tgkcirtqfg hvegvwdiaa dnfriisgsh dgsikvwdlq sgkcmhtfng rrlqretqht
601 qtqslgdkva piacvcigds ecfsgdefgc vkmykfdlnd
```

The fission yeast F-box protein Pop2 encodes a novel F-box/WD-repeat protein involved in the proteolysis of the Cdc2p inhibitor Rum1p and the replication initiator Cdc18p and is encoded by a nucleic acid sequence corresponding to GenBank Accession No. AF038867 (SEQ ID No. 9) as shown below, and which encodes the F-box protein corresponding to GenBank Accession No. AAB95480 (SEQ ID No.10) as shown below.

SEQ ID No.9

```
  1 atgtcactct ctaggtgtcc aactgacaat tcgtcctccc gtataaattc ctctgttcct
 61 ttaataaata gcagcagccc tgctacacct ccagaatcat ttgatcctca agtatttcct
```

-continued

```
 121 tcttcactta ttcatgggga taacctgctt cctcaagatg atcaaattgc atcggatcct
 181 cgctcagaat caaatagttg taatggcaat acgagttctt ccctgccgtg cactgattcg
 241 tatcagtacc cattaaagca ttcttgtacg ccttcttttc ttcgaaagtt taatgaaagt
 301 atagagaatg tctcttataa atgcttagac cactcaccgc cagatagtgt tcctggcgat
 361 ttttccattt cccttgttcc tcaaaggaat tttctatatt ctcattcttc tcttccacct
 421 aaaattatat caattgatag aaacaatcga attaagttag ataatagcat ttcatctaac
 481 tccgacaatt tccctccttc tccgaaagtc gacacatcaa acactgtttc acctggtagt
 541 aaacctatct ctgaggatct tgaagattta aacttacagt caattgttca aacttttgag
 601 gatcttccag aaggaattca atcttatgcg ttttttcaac tactccgttc gtgcaatcgg
 661 caatcgatgc gttattattg aatgaatgc gagccgcttc taaaaaaga tactttca
 721 aatcttcctt tttccattgt tcagtctata ttattaaatc tggatataca ttcttttctt
 781 tcttgccgtc ttgtttcgcc tacttggaat agaatacttg atgtgcatac ttcatactgg
 841 aaacacatgt ttagtttatt tggctttcaa atcaatgaaa atgactggaa atatgctaat
 901 ccaaacttaa atcgtccacc ttttttgcac aacgaccaaa tctcagatga ctattttccg
 961 gaaattttca aaagacattt tctcaataga aaacgatggt tatttccttc gatacctcca
1021 agtcatctat cttttcccat tcatgttcca aactttatga taacttcttt actacttcat
1081 aaagacagaa taatcaccac ttcgggatct ggaacaattc aaattcataa tgctattacc
1141 ggtgttttag aagctcgatt agagggtcat aaagaaggtg tttgggctgt caaaatacat
1201 gagaatacac ttgtatctgg ttcgatcgat aaaactgttc gcgtttggaa catagagaaa
1261 gctaaatgta cgcacatatt taggggacat atttccatca tcagatgctt agagatctta
1321 gttccgagtc gtcttattcg ccatggagtt gaaattgttg aaccagatca accgtacatt
1381 gtcagcggct ctcgggatca tacacttcgg gtttggaagc ttccaaaaaa cacggatcct
1441 ccttatcttc cagataatac aaactctatt gaccgttggg agaagaaccc gtattttgta
1501 catactttga taggacatac agactctgta cgaactatat ccggctatgg tgatatactt
1561 gtgagtggga gttatgattc ttcaattcgc atttggagag tttcaacagg ggaatgtctt
1621 taccatctgc ggggtcatag tcttcgtata tatagtgttt tatatgaacc agaaaggaat
1681 atttgcataa gcggtagcat ggataagtcc attagggttt gggatttatc gacagggact
1741 tgtaaatatg tgcttgaagg ccatgatgcc tttgttacgc ttcttaatgt attccagaat
1801 aggttgatat caggttctgc tgactccaca attagaatat gggatttgaa tactgggaaa
1861 ccattaatgg ttttgccgtc taattcaggc tacattagta gctttgtgtc agatgaacac
1921 aaaattatta gtggtaatga tggttctgta aagttatggg atgttaggac tggaaagctg
1981 ttacgttttc tattaacaga cctcacaaaa atatggcatg tcgattttga tgctatgcgt
2041 tgtgtggctg cagtgcagcg tgatgatcaa gcatatttgg aagttattaa tttttccgga
2101 tcaagaccgt ag
```

SEQ ID No.10

```
  1 mslsrcptdn sssrinssvp linsssspatp pesfdpqvfp sslihgdnll pqddqiasdp
 61 rsesnscngn tssslpctds yqyplkhsct psflrkfnes ienvsykcld hsppdsvpgd
121 fsislvpqrn flyshsslpp kiisidrnnr ikldnsissn sdnfppspkv dtsntvspgs
181 kpisedledl nlqsivqtfe dlpegiqsya ffqllrscnr qsmrlllnec epllkkdils
241 nlpfsivqsi llnldihsfl scrlvsptwn rildvhtsyw khmfslfgfq inendwkyan
```

-continued

```
301 pnlnrppflh ndqisddyfp eifkrhflnr krwlfpsipp shlsfpihvp nfmitslllh 361 kdriittsgs gtiqihnait gvlearlegh kegvwavkih entlvsgsid ktvrvwniek 421 akcthifrgh isiircleil vpsrlirhgv eivepdqpyi vsgsrdhtlr vwklpkntdp 481 pylpdntnsi drweknpyfv htlightdsv rtisgygdil vsgsydssir iwrvstgecl 541 yhlrghslri ysvlyepern icisgsmdks irvwdlstgt ckyvleghda fvtllnvfqn 601 rlisgsadst iriwdlntgk plmvlpsnsg yissfvsdeh kiisgndgsv klwdvrtgkl 661 lrflltdltk iwhvdfdamr cvaavqrddq aylevinfag srp
```

The murine F-box protein FWD1p involved in ubiquitin-dependent degradation of IkappaBalpha and is encoded by a nucleic acid sequence corresponding to GenBank Accession No. AF081887 (SEQ ID No. 11) as shown below, and which encodes the F-box protein corresponding to GenBank Accession No. AAD17755 (SEQ ID No.12) as shown below.

SEQ ID No.11

```
   1 gaattcggca cgaggcggag ctgcgttggc tgcggcctgg cacgaaaggg gcggccccgg 61 cggagagcag acccagtagt ccggggcgatt atggacccgg cagaggcggt gctgcaggag 121 aaagcgctta agtttatgaa ttcctcagag agagaagact gtaataatgg cgaaccccct 181 aggaagataa taccagagaa gaattcactt agacagactt acaacagctg tgccaggctt 241 tgcataaacc aagagacagt atgtctaaca agcactgcta tgaagactga aaattgtgtg 301 gccaaagcca aacttgccaa tggcacttcc agcatgattg tgcccaagca gcggaaactc 361 tcagcaagct atgagaagga aaggagctg tgtgtcaagt attttgagca gtggtcagag 421 tctgatcaag tggaatttgt agaacacctt atatcccaaa tgtgtcacta ccagcatggg 481 cacatcaact cctacctaaa acctatgctg cagagggatt tcataactgc actgccagca 541 cggggtctgg accacatcgc tgagaacatt ctgtcatact tggacgccaa gtcactgtgt 601 gctgctgagc tcgtgtgcaa ggaatggtac cgcgtgacgt cggacggcat gctgtggaaa 661 aagctcatcg agaggatggt caggacggac tctctgtggc gaggcctggc agagcgcaga 721 ggctggggac agtacttatt caaaaacaaa cctcctgatg agaacgctcc tcccaactcc 781 ttttatagag cgctttatcc taaaatcata caagacattg agacaataga gtccaattgg 841 agatgtgggc gacatagttt acagagaatc cactgccgga gtgaaacaag taaagggggtt 901 tactgtttac agtacgacga ccagaagata gtcagcggcc ttcgagacaa caccatcaag 961 atctgggata aaagcacact ggaatgcaag cggattctca cgggccacac gggctccgtc 1021 ctgtgtctgc agtacgatga gagggtgatc atcacaggct cctcagactc caccgtcaga 1081 gtgtgggatg taaatgcagg tgagatgcta aacacattga ttcaccactg tgaagccgtt 1141 ctgcacctgc gcttcaataa tggcatgatg gtgacctgtt ccaaagaccg ttccatcgct 1201 gtgtgggata tggcttcccc aactgacatc accctcagga gggtgctggt gggacaccga 1261 gctgcggtca atgttgtaga ctttgatgac aagtacatcg tttctgcctc tggagataga 1321 accataaagg tgtggaacac aagtacctgt gaattcgtaa ggaccctaaa tgggcacaag 1381 cgtggcatcg cctgtttgca gtacagagac aggctggtgg tgagcggctc ctctgacaac 1441 accatcaggc tgtgggacat agagtgtgga gcatgcctgc gagtgttgga gggccatgag 1501 gagttggtac gctgcattcg atttgataac aaaaggatag tgagcggagc ctatgatggg 1561 aaaattaaag tgtgggatct tatggctgct ttggacccgc gtgctccagc agggactctc 1621 tgtctgcgga cacttgtgga gcattctgga gagttttcc gcctccagtt tgatgaattc 1681 cagattgtca gtagttcaca tgatgacaca attctcatct gggacttcct gaatgatcca
```

-continued

```
1741 gctgctcacg ctgaaccgcc ccgctcccct tctcggacat acacctacat ctccagataa
1801 ataacccaac actggcctca taattgccca ggattcgtta atgttgcagt atttaacaga
1861 cctgccaaga ccaggatgaa caacaatcaa actcctaccc ggattcccgg acggatgagc
1921 gaggagcagg gctttgagac tcctgttggg acacagtcgg tcagcagccg accaggacgg
1981 cctgctcggc accggctgcc tcagtgctgc tatcagaaga tgtctttatc ttgtgtgaat
2041 gattggaact tccaagcctc cctcccttc ccttcccctt cctccctgca cctgtttccc
2101 tcccattggg ttccagacaa agatgactta taaatatatt tagtgttttg cctaaaaaaa
2161 aaaaaaaaaa aaaaa
```

```
                                                          SEQ ID No.12
  1 mdpaeavlqe kalkfmnsse redcnngepp rkiipeknsl rqtynscarl cinqetvclt
 61 stamktencv akaklangts smivpkqrkl sasyekekel cvkyfeqwse sdgvefvehl
121 isqmchyqhg hinsylkpml qrdfitalpa rgldhiaeni lsyldakslc aaelvckewy
181 rvtsdgmlwk kliermvrtd slwrglaerr gwgqylfknk ppdenappns fyralypkii
241 qdietiesnw rcgrhslqri hcrsetskgv yclqyddqki vsglrdntik iwdkstleck
301 riltghtgsv lclqydervi itgssdstvr vwdvnageml ntlihhceav lhlrfnngmm
361 vtcskdrsia vwdmasptdi tlrrvlvghr aavnvvdfdd kyivsasgdr tikvwntstc
421 efvrtlnghk rgiaclqyrd rlvvsgssdn tirlwdiecg aclrvleghe elvrcirfdn
481 krivsgaydg kikvwdlmaa ldprapagtl clrtlvehsg rvfrlqfdef qivssshddt
541 iliwdflndp aahaepprsp srtytyisr
```

Other exemplary polypeptides and nucleic acids for use in the invention include:

Exemplary SCF subunit-encoding genes and their encoded polypeptides include Skp1p (GenBank Accession No. U61764) which encodes Skp1p (GenBank Accession No. AAC49492); and the murine SCF complex protein cul-1 (encoded by the nucleic acid of GenBank Accession No. AF083216 which encodes the cul-1 polypeptide of GenBank Accession No. AAD16038).

EQUIVALENTS

Those skilled in the art will recognize, or be able to ascertain using no more than routine experimentation, many equivalents of the specific embodiments of the invention described herein. Such equivalents are intended to be encompassed by the following claims.

---

We claim:

1. A method for targeting a target polypeptide for ubiquitin-dependent proteolysis in an isolated mammalian cell, comprising:

expressing in an isolated mammalian cell a hybrid polypeptide that comprises (i) an F-box that is encoded by a nucleotide sequence that is at least 95% identical to SEQ ID NO: 48, and (ii) a target polypeptide interaction domain that binds to the target polypeptide, wherein the F-box recruits the hybrid polypeptide to a Skp1/Cul 1/F-box protein (SCF) ubiquitin ligase complex, thereby targeting the target polypeptide for ubiquitin-dependent proteolysis in the mammalian cell.

2. The method of claim 1, wherein said ubiquitin-dependent proteolysis is by the proteasome.

3. The method of claim 1, wherein the target polypeptide interaction domain is selected from the group consisting of a papillomavirus E7 polypeptide, and an SV40 LTP polypeptide.

4. The method of claim 1, wherein the target polypeptide is selected from the group consisting of a retinoblastoma polypeptide, a p107 polypeptide, IκB, Sic1, Cln2, a papillomavirus E2 polypeptide and beta-catenin.

5. The method of claim 1, wherein the hybrid polypeptide further comprises a WD domain consisting essentially of an amino acid sequence selected from the group consisting of amino acids 260–293 of SEQ ID NO: 4; amino acids 305–333 of SEQ ID NO: 4; amino acids 345–373 of SEQ ID NO: 4; amino acids 388–416 of SEQ ID NO: 4; amino acids 428–456 of SEQ ID NO: 4; amino acids 468–497 of SEQ ID NO: 4 and amino acids 518–546 of SEQ ID NO: 4.

6. The method of claim 1, wherein the mammalian cell is a human cell.

7. A method for targeting a target polypeptide for ubiquitin-dependent proteolysis in an isolated mammalian cell, comprising:
expressing in an isolated mammalian cell a hybrid polypeptide that comprises (i) an F-box that is encoded by a nucleic acid that hybridizes under stringent hybridization conditions including a wash step with 0.2×SSC at 65° C. to a nucleic acid consisting of SEQ ID NO: 48, and (ii) a target polypeptide interaction domain that binds to the target polypeptide, wherein the F-box recruits the hybrid polypeptide to an SCF ubiquitin ligase complex, thereby targeting the target polypeptide for ubiquitin-dependent proteolysis in the mammalian cell.

8. The method of claim 1, wherein the F-box is encoded by a nucleotide sequence that is at least 98% identical to SEQ ID NO: 48.

9. The method of claim 8, wherein the F-box is encoded by a nucleotide sequence that is at least 99% identical to SEQ ID NO: 48.

10. The method of claim 9, wherein the F-box is encoded by the nucleotide sequence of SEQ ID NO: 48.

11. The method of claim 1, wherein the mammalian cell is a murine cell.

12. The method of claim 7, wherein the mammalian cell is a human cell.

13. The method of claim 7, wherein the mammalian cell is a murine cell.

* * * * *

SEQUENCE LISTING

```
<160> NUMBER OF SEQ ID NOS: 49

<210> SEQ ID NO 1
<211> LENGTH: 20383
<212> TYPE: DNA
<213> ORGANISM: Saccharomyces cerevisiae

<400> SEQUENCE: 1
ggatccgtgt cgtaactgcg ttccgtacac cttaaaatga actttccagc aggtgcacca      60
tcttccaatc cattgaaaaa tcttactgat tcttcgacct cctcctggct taagtttgtc     120
tccaaatgaa tatatagcag ccaaatcaat atgtttgatc tatcctttgg ctcgtatttc     180
gaatagtcca gtatatcaaa taatgttgtt gcataagctg cttttgattc ttgtttttca     240
ttttccgctt ccgtttcttt tacttcattc tgttcatcta ccatatcttg ctcctgagct     300
ttcgattcga cttccacata cttggaaaga aacctcttgt caattaggcc ggaattatca     360
catatgctaa acaacatatt aataatgtta aatttgttaa cggtgtccac ttcaccatca     420
```

-continued

```
ttttggtcga cctttttgta agtctccatc aatgagagtt gctcattgcc ccacggcaga    480
tttttcagaa tagatttcag tctaggtgta tcctgcaaaa gtttcggatc attggcatgt    540
aattgtaaaa ctggcacgga gtgaaaagtt ctcaattgcg atgtcatttc taaataaaaa    600
tttatagtgg tgttcaacct accaatgttg accaataacg ctaaaacaca agtagaaaat    660
gctacttgtt ggtctaataa tagtttatct ctgagaattt tggaacattt gataagtg      720 gctattgtca acacatacaa ttgtgcgaac gtcaatttat cgttaaatac aaatgtcctt    780
gcatcgtact ctttgtcggt cacgttgatt gataatttat cgccatcgat attaatgggt    840
acaatagagt tcttgtatag gggttttaga acattagtga agatttgcct cttgtccatc    900
aacagttctt gcatgaaact gaactgaatg tcctttctat tgaatggctc gccgtcaggt    960
ttcttcaaat gacgattgta tttactggca ttgctttctt tgggtttcct tctaacagtg    1020
ttagttgtca ctggccccgt tgccgtactt gctcctgttg cttcaggcac tgtagaaggt    1080
tcgaagttga gcaagatgtt ggtatttct tcttcacttt gcgtggagtc atcatcattt     1140
ttatcgtcga tttcaatctc gtgtataact ggaatgcttt ttgtagtcac agtctcggtc   1200
tctgattgaa tggagcttgg ggatgcttct tcttgtgatc ccgattttac agattgcatt   1260
ggagaatctg ctttttgttc gtcagaattg tcttctcgta gttggaaagt atcatgaatt   1320
ggatcgtata ctctcttccc catctttaat tagagtgtcg cctttattta gctttcgatt    1380
ttacttagtt aatcatgaac tgtttccaat accatatcag cattcattgg gcgttcttta   1440
cttacttgta ccgttaccgc attcgagggt aacctgtttt tcgttgtaca cgatatgcta   1500
cagaattgtc ttaatatggg ctaagaaaaa aaaagtctg attatttctg atactgcaaa    1560
atatatactg gcttggttaa gaaaagtgtt gctttagttc ctttacatca agagtcgtta   1620
aattgttttg tgtcataaca gtagtggtct tttgagacat caatcgactc tcaggttttc   1680
cttctgttca tcttcttgtt ttcggtaaag gtcagccagc atatttcaat tctctctttt    1740
ttgaaataac attatgtaat ctttcaatcc tttctatcca acgtctgcta ataatttat    1800 tcaaatgaca tgtagaccag aaaatcgaac gttggataat ttttcatcct gaatcatgtt   1860
ggtctcaact agagcaattt tttcacgtcc tctgacacaa aactcgataa actgtcgcat   1920
cagtttaaaa aaatatgtac gtgtataata actgaattta aaaggatagt aaataatttt   1980
tgcattttat ggaatgtcaa aatactaata agtcgcaaat atagctatca ataccataa    2040 tttagctact tatagaaaga tgcccaaatc ccgaccaaaa aggaccattg cgtcttcctc   2100
gtcagttttt tatggaagtt caccttcca aaatgatggc tacatcaaag taatggaact    2160
cgtatcacac attgtcattg aaataaatca ttcacctacc gcaacaacgg atgaaacgag   2220
aaagcagaat aatccggagc tgaaagtgaa agaaccagtt tgtaacctca agaagtggga   2280
aaataacact aactttatat tggaagatca tacgaagaat aaaacaaaac tttctagcac   2340
agataggata cgtaagtggt ttagaagaca tatattaaag gaagagatcg aaatcctttc   2400
ccatggaaaa caattgagta gtattgatga ggattattgc ccttcaaatg ttcttgtagg   2460
atgttcaaga gatctaaata aactcagatc atttcaaaat ttttaggaat ataaatttc    2520 tcagtaagaa aaagaagatg aatgcgttta gtattttta agttgttcaa tagaatatct   2580
tcaatatgtt catatgtgga ctaaaagaag attttggtat atgtctataa atttattgtt   2640
ggtaaacgcc attaagcagc tttccaagaa tatgttatca ttgaggagaa gtacgaaaac   2700
tgattatgca cgattaggaa aaattctgca aggagtatta aaaaatggcc ttcgagaaga   2760
```

```
aatgaaatct ctttcgatga gcaatggtct tatggataat ttgatagaca tatgaaaaag   2820
tcaaaagttt ttttggccat atgcagtaaa aacttaccct tcaaattgca aaaccattag   2880
ttttattata tttttttttt tttctttcat tgaagtatac acgaaatccc atacgcaaat   2940
aaacagtcgt tgtatcatca atttcggctg tctggatggc gactacgaga ggaagcttgc   3000
ttgccatgat aggaccaatc tcaattttta attttcatt aactagctaa ttttctataa    3060
tgctctaagt ttcctttttc gttttgtttc tttatagtga tgatgctgtt attgtgacgc   3120
tatcaaatca tatactgtca tcaatcctca tctcatcggc tccggaacgc gttgaatatg   3180
ttgttaaaca agctctttat agctagctat agtagaaaag gaaggaaaga agtctaatcg   3240
ctgtattatc gactgacaag ggttgtcagt tgccttcttt tatttttgt actcccctga    3300 atcgagcgga tgtatttttt aacaaagtat tcagaattgt ttttgtataa tcaaatttg    3360 tcgacgctaa gaaaatgacg gacgtcgtaa ttccgctact aggttttgtg tgctcatcga   3420
tatttgacac ctattttcga cacttttaag gttatatact ttgtttcgga tgtgggtac    3480 actcagttga ctgattatga agatatggc gtagccgttg ggttagggtt attacacaga    3540
aatgaattat accagtgaaa ttattctctt tatgtttgtt cctacatgtt ttccaatcag   3600
aaggaattgt tatataagga cacaagaaat gtgttggtac gctctgcgcc tcaatgacgg   3660
tttatctatc taaaactatt tctttctcgt aataaaaata caataaataa ttaataataa   3720
tatagttgat cgatataaca aaaaataac agcgaggatg gttagttcaa gtgtttccat    3780 tttgggact agcgccaagg catccacttc tctaagtaga aaggatgaaa ttaaactaac    3840
ccctgaaaca agggaagcta gcttggacat tccatacaaa cccattattg catactggac   3900
ggtgatgggc tctgtctga tgattgcctt tggtggattc attttttggtt gggatacagg    3960 aaccatttca gggtttatta accaaacaga tttcaagaga aggtttggtg agttacaaag   4020
ggacggcagt tttcaactat cagatgtcag gacagggcta attgtcggta tcttcaacat   4080
aggttgtgct ttaggtggcc taacgctggg acgcctgggc gatatttatg ggcgtaaaat   4140
cggcttaatg tgtgttatac tggtgtatgt tgttggtatc gtgatccaga ttgcttcctc   4200
tgacaaatgg tatcaatatt ttattggtag aattgtttct ggaatgggtg ttggaggtgt   4260
tgctgtgctg tcgccaactt tgatctcaga aatttcccca aagcacctaa gaggcacttg   4320
tgtctctttt taccagctaa tgattaccct tggaattttc ttgggctact gtaccaatta   4380
tggtacaaag aaatattcaa attcaataca gtggcgggtt cccttgggtt tgtgttttgc   4440
gtgggcaatc tttatggtga ttggaatggt tatggttccg gaatcgccca gatatttagt   4500
agaaaaaggt aagtatgaag aagctagaag gtctttggcc aaatcaaaca aggtcacagt   4560
tactgatcca ggcgttgttt ttgagtttga tactatagtt gcaaatatgg aattagaaag   4620
ggctgttgga aatgccagtt ggcacgaact cttctcaaat aaaggagcaa ttctaccaag   4680
ggtaataatg ggaatcgtta tccagtcact gcaacagctt actggctgta attatttttt   4740
ctactacggc acgaccattt tcaatgctgt tggaatgcaa gactctttcg agacttccat   4800
tgtccttggg gctgttaatt ttgcttctac atttgttgca ctatacattg tggataaatt   4860
tgggcgtcga aaatgtttat tgtgggggtc tgcctcgatg gcaatttgtt tcgtcatatt   4920
cgccaccgtt ggcgtcacta gattatggcc acaaggaaa gaccaacctt cttcgcaaag    4980
tgctggtaat gttatgatcg tttttacttg tttcttcatt ttctcttttg ccattacttg   5040
ggctcctatc gcctatgtca ttgtggcaga aacttatcca ttaagagtta aaaatcgtgc   5100
catggccatt gcggttggtg cgaactggat gtgggtttc ttgattggat ttttcacacc    5160
```

-continued

```
ctttatcact agatccatag gattttctta tggctatgtt ttcatgggtt gcttaatctt   5220
ttcgtacttc tacgttttct tctttgtttg cgaaacaaag ggattaactc tggaggaagt   5280
taatgaaatg tacgaagaaa gaataaagcc atggaagtcc ggaggttgga ttcccagttc   5340
tagaagaaca ccacaaccaa caagcagtac accattagtt attgttgata gtaaataatt   5400
tctaaatatt cttgtactct ggtaaacaga ataacaaca gataatggat tgatgcttta    5460
cttctatttc atggagattg gttttatata atagccttta ttaatggcgt cacaaattga   5520
aaaaaaaatt aaaaaaaata agacggacac atttgcgacg ccggtgaata aatgcatata   5580
agtagtttat aagctagcta ctactcagaa ataatttcaa aaaaaaaaag aagtgggcac   5640
tttaaaatga agattagcta tagtaaatta ctgtagtata caactacct gctatctttc    5700
tgaaaaaatc aggcaatgta aggtcaaact tgtaccatcg acatatataa tgttttgaga   5760
tataagtaac tagagaccag tttatacagg atcttacctc tttttaccgt tatgaaagct   5820
ttattactgc gttgttagta aacacacata ttattttcgg gtagtcctgt cgatgttcca   5880
aggctttgca tttatcattg tttccgcttc atcggtggta ttagttagtg tatctgtatg   5940
tgaagtatgt ggataggtgc ttctattatt ggaacaaaac accttaaacg cgcactaggt   6000
tataggaaag ggtccattat tcaaagaacg gcttattgaa aagtatgttg taaagctcgg   6060
tcatatcgcg catagccacg ataaggcgtg gtgctgcttc atagattgag aggcgcagtc   6120
aatacacaac cataccggta gtttgataaa tgatactatc attccggaag ctctctagta   6180
agctgtaggt ggcatatacg gtatctatca tctagtaata gctattgatt ttttttctcga  6240
ctatgctata tgtgttgtga tggttcactt agaagtgaaa aagtagcaat aaattagaca   6300
gacagaagta attgaagcta cattcaacaa catggctaag taaaaaagcg tagaatatca   6360
tgatgggttt ttttatcttt taattgcttt ctatgtagta taatggaccg atctttgcaa   6420
gtatatatct gtatgtatcc atatttagat ggcagcaagc aatatagatt tgatgagctt   6480
atatcatttt atcgtccttg tccaaaaagt cttgataaca ttaaaagtca ctaccgtcaa   6540
atccatcatc aaatccgccg tcgaacccac cagcatcatc aaatccgccg tcggacccac   6600
cagcatcatc accgtagtaa ttgttctcga caacgacagt gtctggtccg tcatagttgt   6660
ggtcgtcaaa tgcgtgttct agcatagctc cacctaacaa acccgcacca acaccaagta   6720
aaccacccat catggcaccg ccgtgtccac tacctttact ggtgcttggc gcagttccat   6780
agtatgcttg ctgtggtgct gctgctggca taggggcttg ttgaggatag taacgctgct   6840
gttgagggta ttgagggtac tgaggctgtt gaggctgata gtaacgaggt tgctgtgctt   6900
gggcccctgc ttgcacttgc ggtgttgatt gagaagaata aggtggagga gcctggtctg   6960
cctgttgacg agaactcttc tcattgttaa cacctggtgg aggacctttg ggtcttggcc   7020
atgttgttcc ccttggtggt tcccactgag agctgttcgt agataaatct acataatacc   7080
aagtctggta ttcatcatca aaaacagcct tccagccaga aggcacttga ggaggattac   7140
ttttactttg agccattact ttaaaatgtt tgggttttt ttatcgactc tcttgtagtg    7200
agtgataaaa gcaattcaga aagagtcttt tgattatcat gactaaagta aactttttct   7260
tccagctgcc ggctcggtca ggtggacgaa acaaaaaagc ctgttgaaat aatactgaat   7320
acgttaaaac gtcacagcgc ttgtatatct tgtgagagaa aggctattac cactgttata   7380
tgaatataga ttgctcaaca aagcgtgtct ttttctgtgt gcttaaaata tagtgtcttt   7440
tttgggaaaa aaacgtttat ttacagtatt ctcttcttct tctcctcatt caacttgttg   7500
```

```
cggttcgaag aaaattacgc ataaagaatc aaagaaaggc aaaaattacg ctgtacgatg   7560
gggtcgtttc ccttagctga gtttccatta cgtgatatcc ctgttcctta tagctaccgt   7620
gtgtctggcg gtatagcttc ctcaggtagt gttactgcgc ttgttactgc cgctggcact   7680
catcgaaact cgtccacggc taagacagtt gagacagaag acggcgaaga agatatcgat   7740
gagtatcaga ggaaaagagc agctggttct ggcgaatcca ctcctgaacg cagtgatttc   7800
aaaagggtaa aacatgataa tcacaaaacc ctccatccag ttaacttaca gaacaccggt   7860
gcagcgtctg tggataatga cggtctgcac aatttaacag atatatccaa cgatgcagaa   7920
aaacttttga tgtctgtgga tgatggttct gccgcacctt ctacattgag tgtaaacatg   7980
ggagtggcat ctcataatgt tgctgctccc actaccgtca atgcggcaac aataactggc   8040
agtgatgtta gtaacaatgt taatagtgct actattaaca atcctatgga ggaaggagcg   8100
ctgccgttat cacccactgc ttcctctcca ggtaccacaa ctcctttagc taaaactacg   8160
aaaactatca acaacaataa taatatcgcc gatttgatag aatccaaaga ttctataatc   8220
tcccctgaat acctttctga tgagattttc agcgcaataa acaataatct ccctcacgca   8280
tacttcaaaa atttattatt tagattagtt gccaacatgg ataggagtga actatccgac   8340
ttggggactt taatcaagga taatttaaag agggacctaa taacgtcttt gccttttgaa   8400
ataagtttga aaattttcaa ttatttgcaa ttcgaggata ttataaattc ccttggggtc   8460
tcccaaaatt ggaacaaaat aattagaaaa tctacatcgt tgtggaaaaa acttctgata   8520
tcggaaaatt ttgtgagccc aaagggtttt aattctctca atctcaaact ctcccaaaaa   8580
tacccaaaac tctcacaaca agatcgcctt agattatctt ttctggagaa tatattcatt   8640
ttaaaaaatt ggtacaatcc caagtttgta ccacaaagga ccacgttaag aggccatatg   8700
acgagtgtta ttacgtgctt gcaatttgaa gataattatg tcattacggg ggctgatgac   8760
aaaatgatca gagtttatga ttcgataaac aagaaatttc ttctacaact atcaggtcat   8820
gatggtgggg tttgggcatt gaagtatgcc catggcggta ttttagtcag cggttctaca   8880
gacagaacgg tgcgagtttg ggatattaag aaaggttgtt gtacccatgt gtttaaaggt   8940
cataactcta cggtgaggtg cctagatata gtagaatata aaaatatcaa gtacattgtt   9000 actggtcga gagataacac tttgcacgtt tggaaattgc ccaaggagtc ctccgttcct   9060
gatcatgggg aagaacatga ttatccatta gtctttcata cccctgagga gaacccatat   9120
tttgttggtg ttttaagagg acatatggca tctgtaagaa ctgtctcagg ccacggtaat   9180
attgtcgtta gtggctccta tgataataca ctgattgtgt gggatgttgc gcaaatgaaa   9240
tgtttgtata ttttaagtgg acatacggat cgtatttatt cgacaatcta cgatcatgaa   9300
agaaaaaggt gcatctctgc cagtatggat accactatta gaatttggga tttggaaaat   9360
atatggaata atggagaatg ttcctacgca acaaattcag catcgccatg cgccaaaata   9420
cttggtgcta tgtacacttt gcagggtcat acagcttttgg tcgtttatt aagattatcc   9480 gacaaatttt tggtcagtgc cgctgcagac ggttcaataa ggggttggga cgcaaacgac   9540
tactctagaa aatttcccta ccatcatacc aatttgagtg caattaccac attttatgta   9600
tcggataata ttttggtgag tggatcggaa aatcagttca acatctataa tctacggagt   9660
gggaaattgg tccacgcaaa tattctaaaa gatgctgatc agatttggtc ggttaatttt   9720
aagggcaaaa cacttgttgc agcagttgaa aaagatggac agagcttttt agaaattctg   9780
gatttcagca agcttcaaa aattaactac gttagcaatc ccgtaaactc ctcgtcgtcg   9840
tctttggaat ccatttctac ttctttgggt ctaacgagga caactataat accatgacct   9900
```

```
ttcccagaga ataagcattg actcatactt agataatata gcttaataag tagttatata   9960
atcagtaaaa aagtacaata acaacttcgt acattttatt gagtataaac tgcagctaaa  10020
ctgcctggat gtgtcaattt taattgtgtt tacaaaaagg gtgccgttta ttaattaatg  10080
tttcttccct gaaaatatgg aaagtacaag ttttttagttg agaagggttt aagaaagttt  10140
tgaaaatgat ctaaaaaaat ataaaagcaa tcaaagaaat aaaagctgga aaaatgcgta  10200
ataaccgaag tgactaaaat ttctttacgc gccaaataag aaatcgatgc tcttgaaagt  10260
agcaaccatt ttttaaataa tatattcctg atggttcttg gcccaagagt tttcttgaac  10320
ttttaacgtt aagaagttga ttctgctgat ttttttcaag ttatcaagcg ttatgttttg  10380
aaacatctgt tccgttttca gtttttcaaa aagatcgata ttctcttgag aattaggaag  10440
ttctacgctc aacctcccgt gggcagaaga aatacaaaag ctaatacaat tgtgttagaa  10500
taagttcta atattatcta attagtagta ttcatgttac tagtatatta tcacatgata  10560
tttctcaaat tggacaatgt aaataatgag tgttttatg acacaatctt tatcgttaga  10620
tgtttcaacg ttccaaggct tggttctatc gctcttctct tcaaattgta atcgtttgtc  10680
atgataaaca cgtacgggaa aaaaaaaaa agtatcaata acgcgtaaag tgaatagagt  10740
attggattct ataagaccga agacgctcat atcacatctc ataaaatcac ttaaagcaag  10800
catccagagg ctattgataa aaagcaggca caaggagacg caatgggacg tttagttggc  10860
ttagaactaa gtaatttcaa gtcctataga ggcgttacca aggtaggatt cggcgagtcg  10920
aatttcacaa gtattatcgg tcctaacgga tctggtaaat cgaatatgat ggatgctatc  10980
tcattcgtac tcggtgtgcg gagtaatcat ttgaggtcaa acatcttgaa agatttaatc  11040
tatagaggtg ttctaaacga tgagaatagt gacgattatg ataacgaggg cgctgcctct  11100
tcgaacccac aatccgcata cgtgaaggca ttttatcaaa aaggtaacaa actggtggag  11160
ctgatgagga taatttccag aaacggtgac actagtata aaattgatgg aaaaactgtc  11220
tcctataagg actattctat atttcttgag aacgaaaata ttcttatcaa agccaaaaat  11280
tttctagtgt tccagggtga tgttgagcaa attgcagcac aatctcccgt agaattatca  11340
agaatgtttg aagaagtatc aggttctatc caatacaaaa aggagtatga agagttgaag  11400
gaaaagattg agaaattaag caaatctgca accgaatcta taaaaaatag gagaaggatc  11460
catggagaat tgaagacata taagaaggt atcaataaga acgaggagta taggaaacaa  11520
ttggacaaaa aaaatgaatt acagaagttc caggctctat gcagttata tcatttagag  11580
caacaaaaag aggagctaac ggacaagctg tccgcattaa actctgaaat atcgtcttta  11640
aagggaaaaa taaataacga gatgaaatca ttacaacgct caaaatcttc ctttgttaaa  11700
gaaagcgcag taatttctaa gcaaaaaagt aaattagatt atatcttcaa ggataaggaa  11760
aaattagtct cggatttacg gctcataaag gttcctcaac aggcagcagg gaagcgaatt  11820
tcccatatag aaaaaagaat cgaaagtttta cagaaagatc ttcaaagaca gaagacttat  11880
gtggagagat ttgaaacaca actaaaagtg gtgaccagat caaggaagc ttttgaagag  11940
gaaatcaaac aatctgctag aaactatgac aaattcaagc taaatgaaaa tgatttaaag  12000
acatataatt gcttcatga aaaatatctg actgaaggtg ggtcaatcct agaagaaaaa  12060
attgccgttt tgaacaacga taagcgagaa atccaagagg aattggagag attcaacaaa  12120
agggcagata tttctaaaag aaggataacg gaggagcttt ctataacagg agaaaaattg  12180
gacacgcaat taaacgattt aagagtttct ttgaatgaga aaaacgccct tcatactgaa  12240
```

```
cgtttgcacg agctgaaaaa attacaatct gatattgaat ctgctaataa tcaagaatac    12300
gacttaaatt tcaagttgag ggaaacgttg gttaagatcg atgacttgag tgctaatcaa    12360
agagaaacaa tgaaagaaag aaaactaaga gaaatatag caatgttgaa aagattcttc     12420
cccggagtaa aaggtcttgt tcatgatctt tgtcacccaa aaaaggagaa atatggcttg    12480
gcagtgtcta ccatcttagg taagaacttt gattccgtca ttgtagaaaa tttaaccgta    12540
gctcaagaat gcattgcatt tttgaagaag caacgtgcgg gcactgcatc tttcatacca    12600
ctagacacaa ttgagacaga gttacctaca ttatcattgc ctgactcaca agactatatt    12660
ttatcaatta atgctattga ctacgagccg aatatgaaa aagcgatgca atatgtgtgt     12720
ggcgattcca tcatatgtaa tacgttgaat attgctaaag atctgaaatg gaaaagggc     12780 ataagaggca aattggttac aattgaaggt gctttgatcc acaaggccgg tttgatgaca    12840
ggtggtatat caggagatgc caataatagg tgggataaag aagaatatca aagcttaatg    12900
tctttaaaag acaaattact aatccaaatc gatgaacttt ccaacggtca acgtctaat    12960 tcaatcagag caagagaagt tgaaaatagt gtttcactat tgaactcgga catagcaaat    13020
ttgagaactc aagtaacaca acaaaaacgc tccttggatg aaaatcgttt agagattaag    13080
taccataatg acttgataga gaaagaaatt caaccgaaga taactgaact aaagaagaag    13140
ctagatgatt tagaaaatac taaagataat ttagtgaaag agaaggaggc tttacaaaat    13200 aatatttca aagaattcac tagtaaaatt ggctttacaa tcaaagaata tgaaaatcat     13260
tccggtgaat tgatgagaca acaatctaaa gaattacagc agttacaaaa acaaattttg    13320
accgttgaaa ataagttgca gtttgagaca gacagactaa gtactactca aagaagatat    13380
gaaaaggcgc aaaaggattt agagaatgct caagttgaaa tgaagtcttt ggaagaacag    13440
gaatatgcaa tagaaatgaa aatcggatca atagagtcta aattggaaga acacaaaaat    13500
cacttagatg agttacagaa gaaatttgta acgaagcaaa gtgaattaaa ttccagcgaa    13560
gatattctag aggacatgaa cagcaactta caagtcttaa aaagggaaag agacggtata    13620
aaggaagata ttgaaaagtt tgatttagag agagtaacag cgttaaagaa ttgtaaaatt    13680
tctaatataa atatacctat atcatctgaa acaacgatag atgatttacc aatatcttcc    13740
actgataatg aagcaattac aatttccaac agtatcgata taaactataa aggactacct    13800
aaaaaataca aagaaaacaa taccgattcg gcaaggaagg agctggagca gaagattcat    13860
gaagtggagg aaatattgaa cgagttgcag cccaatgcaa gagctttgga gagatacgac    13920
gaggcggaag gaaggtttga agtgattaat aacgaaacag aacaactaaa ggccgaagaa    13980
aagaaaatat taaccagtt cctaaaaatt aagaaaaaa gaaaggaact gttcgaaaag    14040
acatttgatt atgtgagcga ccatttagac gcaatctaca gggaacttac taaaaatccc    14100
aactccaatg tggaattggc cggtggtaac gcttctttaa ccatagaaga cgaagatgaa    14160
ccgttcaatg cgggaatcaa atatcatgcc actccgcctc ttaaaagatt caaagacatg    14220
gaatatcttt ctggtggtga aaaaccgta gctgcattag ctctattatt tgctattaat     14280
tcctaccagc ctagtccctt cttcgtgctg gacgaagtgg acgcagccct agacattact    14340
aacgtccaga gaattgctgc ctatataaga aggcaccgta atccagatct ccaattcatt    14400
gtcatttcat tgaagaacac catgtttgaa aaatctgacg ctctcgttgg ggtttacaga    14460
cagcaacaag aaaactcgtc gaagatcata actttggact tgagcaatta cgcagaataa    14520
tctatgaaac caacctctgc tataacccgt caaataacta ataatatcta tataggtcaa    14580
ctagctagtg caatatcata gtaacaataa tattaataac gtcacttttt ttccagggta    14640
```

```
acccaattgt ggtgggtggc ggccgaggta tcccttagaa aagaattttt taagttcttt    14700
ctcatctctt accagtggag aagtacacga tatttgcaaa gtctgtcatc agggcttgat    14760
aataaagctg cattagatct tagcaaaaac tacgagaaga acattgaata ttgtagctgt    14820
atttgcatac ataaacttta tcattgttcg ttagctagct ttgcacatta attttttcgat   14880 ttgttaccgc caatgaccgc taacaatgac gatgatatca aatcacccat tcccattact    14940
aacaagacct tatcccaatt gaagcgcttt gagagaagtc caggaaggcc cagttcttct    15000
cagggcgaga taaacgtaa aaagtctagg ctatatgccg cagacggaag accacattct     15060
ccgctaagag caaggtctgc taccccaacg ctacaggacc aaaaactgtt caatggcatg    15120
gattccactt ccctttttgaa tgaaaggcta cagcattata cgctggatta tgttagtgac   15180
agggcccagc atatgaagaa tatatatgac ccatcatctc gctggttcag cagatccgtg    15240
aggcctgaat ttcctattga agagttctta ccatataaga ctgaaagtca tgaagatcaa    15300
gcgaaatact tgtgccatgt cttagttaat ctttatattg cgatcagctc attagatata    15360
caaggtttga tttctatttc cagtaaagat ctggctgatt taaagaaaga agtggatgat    15420
ttagctctta aaaccgatct tttcaggtta tctaacaaca cagcggagaa tgacttactt    15480
ggtaacgata ttgctgatta tgacgatgcg gaaggcctgg aggacgaatt ggatgaatac    15540
ttcgacttag caggccccga ctttaatgct accggaaaaa tcacagctaa atcagctact    15600
attgtgaatg taaaccattg gactaatgag ctcaaaaatt gtctacattt tgattttcca    15660
gtagctttaa gaaagtcgct agcgacagtt tattattatt tgtctcttgt tcagggccaa    15720
aaggtgtata gacaaatgca tgtcgatatg ttcgaaagat tagtaagcct tgacgatgat    15780
aggacaaatt tcactgaact gttgcaaaaa caaggtcttt tgctagatca tcaaatcatg    15840
ctcaatttcc tgtgcgaatt tctaccttat ccagatcccg actatgctcg ttatgaatta    15900
tcatcaaagg aagatttaca gttatttaga ttacttttga agcatgcaca taatgcaaaa    15960 ccattttttcg ataagtcaaa ggaaagtttg ttagttgata cgatgaattt tctgttgtct   16020
agtcttgcac catctactat gatggctgtc atgcctatcg ttacatccgt tgtgccctat    16080
cattatcata tccattctaa gatcatcgat tatttcccgt tttgctatag catctggagc    16140
tcagtcagcg caaacgtggc catcgacact cacatgtatg attttgttgg gtcaatttcc    16200
aaagacgttc ataataagat tttgagtagc gagcatgaaa aggatgtagt tggagtggag    16260
tttggagaat tcgggatttt tactgatgat caaatgactt ttatgttcaa taggttacaa    16320
ggccatctta gaacagacgg tcaaatacat tcgtattccc gcacagtgaa gccttttgtt    16380
tatgctataa acggatcaaa aaaagatagg tttttttgaaa aacttgtaag tttagccaaa   16440
gcaatcgaaa catttatcca tccctctaat aatgggtttt ggaccaagcc aaatgctaaa    16500
ttcgttcatg catttataaa gtcttaccac ggaagggtca aatatgaaga agatatttgt    16560
gctaggggcg tcacaaatgg gatatgttta acttcttttt gtcacgaaga gatagttgaa    16620
atattcttaa atattatcag tctggggttca cagaataaaa atcctgatat tgcgaactat   16680
tacatctctt gtttcgcata tctgttagag ctggatcctt caaatgcata tttaatttat    16740
gacaaaatac tgatagattt gtacgatacg ctggctgacc aatttatcaa ttcgagacac    16800
agaatcattt cctctttgaa acaatttaca agagtaattc ggtttattgt gatggataag    16860
ctatatcgcg tgcacataac aaacgtcctt tcgatgctgg tctccaaact tgatatgaac    16920
gatactaatt tgacaagcaa cctcatcaac ggtattgtat ctatagccgc tttcattcct    16980
```

```
atccaagacc tcactgggga ggacgattat atatcgtttg aatcggatac tcttccttta   17040
gttcaacaac atttttatca tattaagtgt ggcgaaagtt caaagacctt ccgagttgat   17100
gatgaactgt taaataacgc tttcaaagct tccactacag tttttcaaag tatgctaaaa   17160
gtatacgtag aaaaaatttt ccaattggtt gatgtagact tagaggactc tttggttact   17220
aaaataaacc aaacaactat gattttacaa gagtctatgg acgataaaat atttaattat   17280
tttgcttctt tattacagag aaacttctgg agtaatgact ccttcaagga aaaggatcca   17340
aactatgaat tagttactat cccactagcg gctttagtaa aaggaataa tggtttgagt    17400
aaagagttgg tcagaactct tttattccat atcaaagaac aaatcaaaag aggcgccggg   17460
tctgtaagaa gtacttcaga gattcaacag agggatgtta agttagtttt atacttaact   17520
gcactaaatg atgtcttaag gcaatgtcat gaatctctat tggagtatag cgatgagttg   17580
ataacattca tgaaatattt atacgacaac gtcactaacc cgccattgga tgttatcaca   17640
tctattgtta ttcacagtgc tttagcaact ctatgtacaa ccgaaataac tgattgtcgt   17700
ctattcccag aggactctaa gattccggaa aaagacagat ggggaggact acagttcgat   17760
cctcgaagat ttgataaaca gcatttgagt tttcagtggc acgtaccttc tagtgacgag   17820
ataactttat ccataagcat tctagaaagc cttccgaat  actgtattaa caacgtagaa   17880
gaactgatga aagctccaag acatgattcc gaatatggcg atatgataca aaatatgtt   17940
ttagttatga cacatacgct ttccgggtca gtttactttt tgatccaga ttttaacaaa    18000
tataggacgc aatcaaactt atcatacaga gagaaactga ttttattaaa gaatatacgc   18060
gaaaataatt gtgaccctca agaactggat attgatattg aacaaattcg ttctggcaag   18120
gatgatgaag actatattga gagtaaggac attgaagcag ggctgaatgc aggagttttcc  18180
gatgttgtgc agttaagaga tgagtttccg gatgaattaa ttgttgatga agaagtagtg   18240
tctgagatgc catctggtgt aaatacccct atcgcgggga cgcatggcac ggacaattca   18300
gctatgagtt cggatctagc tttcagggat ttagatattt acacctgtaa ttattacttc   18360
ggaaatacca ctgaggagaa gttacaaaac ccacaatatt tacaagtcca cagagttaga   18420
gcgcgcattg gacatttctt tcacaaactc tatgtttttt tatctacaaa cttcgaaaac   18480
aacaccaaca tgttccaaat tctattgcac ggattgaaag tttggttcac agatctggga   18540
caagaaacgg tcttcaatga agacccaaat gccttcattg acgttgattt cctagaaaac   18600
gttcaatctc tctcacacgt aaatgagccc ttcacgagaa ccaattttgc aatcagagca   18660
aacagtttgc accagagtag agttctatta cattcaacaa atagaaaagc ttccaagctg   18720
gaaaacctat tgttagttga catcatacag ttagcgacat ccctttatcc tgatatttat   18780
aaaccagcac agggaacttt ggtacactgt atgaaacaat tagttgggtc atatggcgta   18840
gtcatcaata aaattattcc atcattagag aaagcgatta aggatcatga ttatatgaaa   18900
atccaagtta tttaaatgt tttgttaatt aagaaaatcc ataggaagct tatgacggat    18960
tataaagaca tcggcagatt gatatttctg cttattgaat gttgtcgtgt gaatgaatta   19020
gagattggta tgtatgcaga taaatcttaa actgacatag tgattgggat caagattcct   19080
tctagtgtat gtgtcatttc cgatcaagct ttcttacctt tagcacctcc tgatggtact   19140
attaatttgc aagttgaagc ggtaaagctt gccaaaaaga aaaagcgtga gtactacctc   19200
tctctgttag tggatttgca ggacaaactt ttagacaaat tagataatga aaagatatg    19260
gggtggaaga taagaatgtt cattttacgt tttgttacac aaatccaatc gaacctcgaa   19320
agcaaacccg ataaaagagc agtattttca ataatctccc aaatctccac aaaacatccc   19380
```

-continued

```
gaaatcatac atttggttgt aaagtcattg ttgtcgacgt gcaacaagat aatatctctc    19440
tctgactatg aatatgacat caccagggcc tataagaatg aattcaatcc atcatttgtg    19500
gaaatactgg acacttcgac cacaagcttc cctaaaacgt ttactgaaga atgaataac     19560 tttgataacc ccaagtattt tatcgatttg agggcgtatg tagggtggct atgttgggga    19620
aggcttatgt acgtcatgtc gccgaaagct ttaaagctca atttacgtga gaatgaactg    19680
gaagtcctca agacagctgg tcatctattg acaagagaat tcctgagaga tgttacaatg    19740
aatttagtcc aagataatga aactaggggt gtttttagta gtggtaacgt gtcatttttc    19800
tctttagtaa tccttttgat atcatctggt ttctgcgaac tgaatatgtc ggatctcttt    19860
gagctatgtg aatcctacta taacaaagac gataaggctt cgatgatcat gtctgtcgag    19920
atagtggctg gcttagtttg cgggagtaag tttatgtcag tctctgactt ggacaaacgt    19980 gacacttta  tcgaaaactt cctagccaaa tgtttagatt atgagttgaa ccatgacgca    20040
tttgaaattt ggagcacctt ggcatggtgg ttgcctgcag tcgttgattt aagaaggtct    20100
aaaacttttt tttgccattt tatcaacgcc gatggcatgt ttgaccgtga atctgatgca    20160
gccacacatc aaacctccaa aatttacatg ctaagaagta tcttgatgag catggaattt    20220
agagccccag atgttggtaa gctatttgat gagttggtat ttgatcaccc atacgatcag    20280
gttcgccagc tgtcgctaaa ctattgacga ccttagttca aaatcaaagt aatccgtcaa    20340
tttcagatcc aaccacatta ttagaagcag aacggaatga tcc                      20383
```

<210> SEQ ID NO 2
<211> LENGTH: 779
<212> TYPE: PRT
<213> ORGANISM: Saccharomyces cerevisiae

<400> SEQUENCE: 2

```
Met Gly Ser Phe Pro Leu Ala Glu Phe Pro Leu Arg Asp Ile Pro Val
  1               5                  10                  15

Pro Tyr Ser Tyr Arg Val Ser Gly Gly Ile Ala Ser Ser Gly Ser Val
                 20                  25                  30

Thr Ala Leu Val Thr Ala Ala Gly Thr His Arg Asn Ser Ser Thr Ala
             35                  40                  45

Lys Thr Val Glu Thr Glu Asp Gly Glu Glu Asp Ile Asp Glu Tyr Gln
         50                  55                  60

Arg Lys Arg Ala Ala Gly Ser Gly Glu Ser Thr Pro Glu Arg Ser Asp
 65                  70                  75                  80

Phe Lys Arg Val Lys His Asp Asn His Lys Thr Leu His Pro Val Asn
                 85                  90                  95

Leu Gln Asn Thr Gly Ala Ala Ser Val Asp Asn Asp Gly Leu His Asn
            100                 105                 110

Leu Thr Asp Ile Ser Asn Asp Ala Glu Lys Leu Leu Met Ser Val Asp
        115                 120                 125

Asp Gly Ser Ala Ala Pro Ser Thr Leu Ser Val Asn Met Gly Val Ala
    130                 135                 140

Ser His Asn Val Ala Ala Pro Thr Thr Val Asn Ala Ala Thr Ile Thr
145                 150                 155                 160

Gly Ser Asp Val Ser Asn Asn Val Asn Ser Ala Thr Ile Asn Asn Pro
                165                 170                 175

Met Glu Glu Gly Ala Leu Pro Leu Ser Pro Thr Ala Ser Ser Pro Gly
            180                 185                 190
```

-continued

```
Thr Thr Thr Pro Leu Ala Lys Thr Lys Thr Ile Asn Asn Asn
        195                 200                 205

Asn Ile Ala Asp Leu Ile Glu Ser Lys Asp Ser Ile Ile Ser Pro Glu
        210                 215                 220

Tyr Leu Ser Asp Glu Ile Phe Ser Ala Ile Asn Asn Asn Leu Pro His
225                 230                 235                 240

Ala Tyr Phe Lys Asn Leu Leu Phe Arg Leu Val Ala Asn Met Asp Arg
                245                 250                 255

Ser Glu Leu Ser Asp Leu Gly Thr Leu Ile Lys Asp Asn Leu Lys Arg
                260                 265                 270

Asp Leu Ile Thr Ser Leu Pro Phe Glu Ile Ser Leu Lys Ile Phe Asn
                275                 280                 285

Tyr Leu Gln Phe Glu Asp Ile Ile Asn Ser Leu Gly Val Ser Gln Asn
        290                 295                 300

Trp Asn Lys Ile Ile Arg Lys Ser Thr Ser Leu Trp Lys Lys Leu Leu
305                 310                 315                 320

Ile Ser Glu Asn Phe Val Ser Pro Lys Gly Phe Asn Ser Leu Asn Leu
                325                 330                 335

Lys Leu Ser Gln Lys Tyr Pro Lys Leu Ser Gln Gln Asp Arg Leu Arg
                340                 345                 350

Leu Ser Phe Leu Glu Asn Ile Phe Ile Leu Lys Asn Trp Tyr Asn Pro
                355                 360                 365

Lys Phe Val Pro Gln Arg Thr Thr Leu Arg Gly His Met Thr Ser Val
        370                 375                 380

Ile Thr Cys Leu Gln Phe Glu Asp Asn Tyr Val Ile Thr Gly Ala Asp
385                 390                 395                 400

Asp Lys Met Ile Arg Val Tyr Asp Ser Ile Asn Lys Lys Phe Leu Leu
                405                 410                 415

Gln Leu Ser Gly His Asp Gly Gly Val Trp Ala Leu Lys Tyr Ala His
                420                 425                 430

Gly Gly Ile Leu Val Ser Gly Ser Thr Asp Arg Thr Val Arg Val Trp
        435                 440                 445

Asp Ile Lys Lys Gly Cys Cys Thr His Val Phe Lys Gly His Asn Ser
        450                 455                 460

Thr Val Arg Cys Leu Asp Ile Val Glu Tyr Lys Asn Ile Lys Tyr Ile
465                 470                 475                 480

Val Thr Gly Ser Arg Asp Asn Thr Leu His Val Trp Lys Leu Pro Lys
                485                 490                 495

Glu Ser Ser Val Pro Asp His Gly Glu His Asp Tyr Pro Leu Val
                500                 505                 510

Phe His Thr Pro Glu Glu Asn Pro Tyr Phe Val Gly Val Leu Arg Gly
        515                 520                 525

His Met Ala Ser Val Arg Thr Val Ser Gly His Gly Asn Ile Val Val
        530                 535                 540

Ser Gly Ser Tyr Asp Asn Thr Leu Ile Val Trp Asp Val Ala Gln Met
545                 550                 555                 560

Lys Cys Leu Tyr Ile Leu Ser Gly His Thr Asp Arg Ile Tyr Ser Thr
                565                 570                 575

Ile Tyr Asp His Glu Arg Lys Arg Cys Ile Ser Ala Ser Met Asp Thr
                580                 585                 590

Thr Ile Arg Ile Trp Asp Leu Glu Asn Ile Trp Asn Asn Gly Glu Cys
        595                 600                 605

Ser Tyr Ala Thr Asn Ser Ala Ser Pro Cys Ala Lys Ile Leu Gly Ala
```

```
              610                 615                 620
Met Tyr Thr Leu Gln Gly His Thr Ala Leu Val Gly Leu Leu Arg Leu
625                 630                 635                 640

Ser Asp Lys Phe Leu Val Ser Ala Ala Asp Gly Ser Ile Arg Gly
                645                 650                 655

Trp Asp Ala Asn Asp Tyr Ser Arg Lys Phe Ser Tyr His His Thr Asn
                660                 665                 670

Leu Ser Ala Ile Thr Thr Phe Tyr Val Ser Asp Asn Ile Leu Val Ser
                675                 680                 685

Gly Ser Glu Asn Gln Phe Asn Ile Tyr Asn Leu Arg Ser Gly Lys Leu
690                 695                 700

Val His Ala Asn Ile Leu Lys Asp Ala Asp Gln Ile Trp Ser Val Asn
705                 710                 715                 720

Phe Lys Gly Lys Thr Leu Val Ala Ala Val Glu Lys Asp Gly Gln Ser
                725                 730                 735

Phe Leu Glu Ile Leu Asp Phe Ser Lys Ala Ser Lys Ile Asn Tyr Val
                740                 745                 750

Ser Asn Pro Val Asn Ser Ser Ser Ser Leu Glu Ser Ile Ser Thr
                755                 760                 765

Ser Leu Gly Leu Thr Arg Thr Thr Ile Ile Pro
770                 775
```

<210> SEQ ID NO 3
<211> LENGTH: 2151
<212> TYPE: DNA
<213> ORGANISM: Homo sapiens

<400> SEQUENCE: 3

```
tgcgttggct gcggcctggc accaaagggg cggccccggc ggagagcgga cccagtggcc      60
tcggcgatta tggaccccgg cgaggcggtg ctgcaagaga aggcactcaa gtttatgaat     120
tcctcagaga gagaagactg taataatggc gaaccccta ggaagataat accagagaag     180
aattcactta gacagacata caacagctgt gccagactct gcttaaacca agaaacagta     240
tgtttagcaa gcactgctat gaagactgag aattgtgtgg ccaaaacaaa acttgccaat     300
ggcacttcca gtatgattgt gcccaagcaa cggaaactct cagcaagcta tgaaaaggaa     360
aaggaactgt gtgtcaaata cttttgagcag tggtcagagt cagatcaagt ggaatttgtg     420
gaacatctta tcccaaat gtgtcattac caacatgggc acataaactc gtatcttaaa       480
cctatgttgc agagagattt cataactgct ctgccagctc ggggattgga tcatatcgct     540
gagaacattc tgtcatacct ggatgccaaa tcactatgtg ctgctgaact tgtgtgcaag     600
gaatggtacc gagtgacctc tgatggcatg ctgtggaaga agcttatcga gagaatggtc     660
aggacagatt ctctgtggag aggcctggca gaacgaagag gatggggaca gtatttattc     720
aaaaacaaac ctcctgacgg aatgctcct cccaactctt tttatagagc actttatcct      780
aaaattatac aagacattga acaatagaa tctaattgga gatgtggaag acatagttta      840
cagagaattc actgccgaag tgaaacaagc aaaggagttt actgtttaca gtatgatgat     900
cagaaaatag taagcggcct tcgagacaac acaatcaaga tctgggataa aaacacattg     960
gaatgcaagc gaattctcac aggccataca ggttcagtcc tctgtctcca gtatgatgag    1020
agagtgatca taacaggatc atcggattcc acggtcagag tgtgggatgt aaatacaggt    1080
gaaatgctaa acacgttgat tcaccattgt gaagcagttc tgcacttgcg tttcaataat    1140
ggcatgatgg tgacctgctc caaagatcgt tccattgctg tatgggatat ggcctcccca    1200
```

-continued

```
actgacatta ccctccggag ggtgctggtc ggacaccgag ctgctgtcaa tgttgtagac    1260
tttgatgaca agtacattgt ttctgcatct ggggatagaa ctataaaggt atggaacaca    1320
agtacttgtg aatttgtaag gaccttaaat ggacacaaac gaggcattgc ctgtttgcag    1380
tacagggaca ggctggtagt gagtggctca tctgacaaca ctatcagatt atgggacata    1440
gaatgtggtg catgtttacg agtgttagaa ggccatgagg aattggtgcg ttgtattcga    1500
tttgataaca agaggatagt cagtggggcc tatgatggaa aaattaaagt gtgggatctt    1560
gtggctgctt tggaccccg tgctcctgca gggacactct gtctacggac ccttgtggag    1620
cattccggaa gagttttcg actacagttt gatgaattcc agattgtcag tagttcacat    1680
gatgacacaa tcctcatctg ggacttccta aatgatccag ctgcccaagc tgaaccccc    1740 cgttccctt ctcgaacata cacctacatc tccagataaa taaccataca ctgacctcat    1800
acttgcccag gacccattaa agttgcggta tttaacgtat ctgccaatac caggatgagc    1860
aacaacagta acaatcaaac tactgcccag tttccctgga ctagccgagg agcagggctt    1920
tgagactcct gttgggacac agttggtctg cagtcggccc aggacggtct actcagcaca    1980
actgactgct tcagtgctgc tatcagaaga tgtcttctat caattgtgaa tgattggaac    2040
ttttaaacct cccctcctct cctcctttca cctctgcacc tagttttttc ccattggttc    2100
cagacaaagg tgacttataa atatatttag tgttttgcca gaaaaaaaaa a            2151
```

<210> SEQ ID NO 4
<211> LENGTH: 569
<212> TYPE: PRT
<213> ORGANISM: Homo sapiens

<400> SEQUENCE: 4

```
Met Asp Pro Ala Glu Ala Val Leu Gln Glu Lys Ala Leu Lys Phe Met
  1               5                  10                  15

Asn Ser Ser Glu Arg Glu Asp Cys Asn Asn Gly Glu Pro Pro Arg Lys
             20                  25                  30

Ile Ile Pro Glu Lys Asn Ser Leu Arg Gln Thr Tyr Asn Ser Cys Ala
         35                  40                  45

Arg Leu Cys Leu Asn Gln Glu Thr Val Cys Leu Ala Ser Thr Ala Met
     50                  55                  60

Lys Thr Glu Asn Cys Val Ala Lys Thr Lys Leu Ala Asn Gly Thr Ser
 65                  70                  75                  80

Ser Met Ile Val Pro Lys Gln Arg Lys Leu Ser Ala Ser Tyr Glu Lys
                 85                  90                  95

Glu Lys Glu Leu Cys Val Lys Tyr Phe Glu Gln Trp Ser Glu Ser Asp
            100                 105                 110

Gln Val Glu Phe Val Glu His Leu Ile Ser Gln Met Cys His Tyr Gln
        115                 120                 125

His Gly His Ile Asn Ser Tyr Leu Lys Pro Met Leu Gln Arg Asp Phe
    130                 135                 140

Ile Thr Ala Leu Pro Ala Arg Gly Leu Asp His Ile Ala Glu Asn Ile
145                 150                 155                 160

Leu Ser Tyr Leu Asp Ala Lys Ser Leu Cys Ala Ala Glu Leu Val Cys
                165                 170                 175

Lys Glu Trp Tyr Arg Val Thr Ser Asp Gly Met Leu Trp Lys Lys Leu
            180                 185                 190

Ile Glu Arg Met Val Arg Thr Asp Ser Leu Trp Arg Gly Leu Ala Glu
        195                 200                 205
```

-continued

```
Arg Arg Gly Trp Gly Gln Tyr Leu Phe Lys Asn Lys Pro Pro Asp Gly
    210                 215                 220
Asn Ala Pro Pro Asn Ser Phe Tyr Arg Ala Leu Tyr Pro Lys Ile Ile
225                 230                 235                 240
Gln Asp Ile Glu Thr Ile Glu Ser Asn Trp Arg Cys Gly Arg His Ser
                245                 250                 255
Leu Gln Arg Ile His Cys Arg Ser Glu Thr Ser Lys Gly Val Tyr Cys
            260                 265                 270
Leu Gln Tyr Asp Asp Gln Lys Ile Val Ser Gly Leu Arg Asp Asn Thr
        275                 280                 285
Ile Lys Ile Trp Asp Lys Asn Thr Leu Glu Cys Lys Arg Ile Leu Thr
    290                 295                 300
Gly His Thr Gly Ser Val Leu Cys Leu Gln Tyr Asp Glu Arg Val Ile
305                 310                 315                 320
Ile Thr Gly Ser Ser Asp Ser Thr Val Arg Val Trp Asp Val Asn Thr
                325                 330                 335
Gly Glu Met Leu Asn Thr Leu Ile His His Cys Glu Ala Val Leu His
            340                 345                 350
Leu Arg Phe Asn Asn Gly Met Met Val Thr Cys Ser Lys Asp Arg Ser
        355                 360                 365
Ile Ala Val Trp Asp Met Ala Ser Pro Thr Asp Ile Thr Leu Arg Arg
    370                 375                 380
Val Leu Val Gly His Arg Ala Ala Val Asn Val Val Asp Phe Asp Asp
385                 390                 395                 400
Lys Tyr Ile Val Ser Ala Ser Gly Asp Arg Thr Ile Lys Val Trp Asn
                405                 410                 415
Thr Ser Thr Cys Glu Phe Val Arg Thr Leu Asn Gly His Lys Arg Gly
            420                 425                 430
Ile Ala Cys Leu Gln Tyr Arg Asp Arg Leu Val Val Ser Gly Ser Ser
        435                 440                 445
Asp Asn Thr Ile Arg Leu Trp Asp Ile Glu Cys Gly Ala Cys Leu Arg
450                 455                 460
Val Leu Glu Gly His Glu Glu Leu Val Arg Cys Ile Arg Phe Asp Asn
465                 470                 475                 480
Lys Arg Ile Val Ser Gly Ala Tyr Asp Gly Lys Ile Lys Val Trp Asp
                485                 490                 495
Leu Val Ala Ala Leu Asp Pro Arg Ala Pro Ala Gly Thr Leu Cys Leu
            500                 505                 510
Arg Thr Leu Val Glu His Ser Gly Arg Val Phe Arg Leu Gln Phe Asp
        515                 520                 525
Glu Phe Gln Ile Val Ser Ser His Asp Asp Thr Ile Leu Ile Trp
    530                 535                 540
Asp Phe Leu Asn Asp Pro Ala Ala Gln Ala Glu Pro Pro Arg Ser Pro
545                 550                 555                 560
Ser Arg Thr Tyr Thr Tyr Ile Ser Arg
                565
```

<210> SEQ ID NO 5
<211> LENGTH: 4470
<212> TYPE: DNA
<213> ORGANISM: Saccharomyces cerevisiae

<400> SEQUENCE: 5
cacgctaatc atgactcaaa taaatccata aagttttata cagttttta aaatatcatc    60

-continued

| | | | | |
|---|---|---|---|---|
| atctattacc | cagatgtgtt | aatgaaccat | tctatagtca | tcattactag | gctttcatta | 120 |
| ctactgaggt | tacccgccta | tggaccttcc | ttggtaaagg | aacttgtttt | aaaatttgcc | 180 |
| ttttaacaaa | tttagtgata | tgattatcaa | aaaaggcgtg | gcaaaataca | taacaccaaa | 240 |
| tttaactgtg | cctgtgtgtt | actttctttt | gtccatactt | caccagtttt | tcgattttac | 300 |
| acaataattc | gttttcattt | aatcgttctc | ttagaagccc | ggttttgaa | tatcaaaatc | 360 |
| gtacttgtgt | ccaactagca | gggaagccca | aaaattaagg | cattgcattt | aagcttacac | 420 |
| ctgcgtgaaa | tcttgaaatt | tctcattgat | tccggcacaa | taattatcat | tggtagtgag | 480 |
| gctaaacagt | ttgcggtttc | ctttatacta | agaaggtcta | aatggatca | ggataacaac | 540 |
| aaccacaatg | acagcaatag | gctgcaccca | cctgatatac | atccaaattt | gggccctcaa | 600 |
| ttgtggctga | atagtagcgg | tgattttgac | gacaacaaca | acaacaacaa | caacaacaac | 660 |
| aataataata | gcacaagacc | acaaatgcca | tcacgaacta | gagaaacggc | aacttcggaa | 720 |
| agaaatgcaa | gtgaggttag | ggatgcaacg | ctaaataata | tctttaggtt | cgatagtatt | 780 |
| caacggaaa | cgcttttgcc | aaccaacaac | ggacaaccgc | taaatcaaaa | ctttcgctg | 840 |
| acatttcaac | cacaacagca | aacaaatgcg | ctgaacggga | ttgacataaa | cactgtgaac | 900 |
| acaaccttta | tgaatggtgt | caatgttcaa | atagatcaac | ttaatcgatt | gttaccgaac | 960 |
| ctaccagagg | aagaacggaa | gcaaatccac | gaattcaagc | taatagtggg | caaaaaaatc | 1020 |
| caagagtttc | tggttgttat | agagaaacgt | agaaaaaaaa | tactgaacga | aattgagcta | 1080 |
| gacaaccttta | aactaaagga | gctacgtatt | gataactccc | cacaagcaat | tagttatttg | 1140 |
| cataaattac | aaagaatgag | gcttagggcg | ctagagacag | aaaacatgga | aattagaaat | 1200 |
| ttaaggctaa | aaatattaac | aattatagaa | gagtacaaaa | agtcattata | tgcatactgc | 1260 |
| cattccaagc | taagaggtca | acaagtggaa | aatccaacag | ataatttcat | catttggata | 1320 |
| aactccatag | atactactga | atcatctgac | ttgaaagaag | gctacaaga | tctttcgaga | 1380 |
| tattcaaggc | agttcataaa | taatgtgctt | tcgaatccat | caaatcaaaa | catatgtacg | 1440 |
| agtgtcaccc | gaagatcacc | tgtgtttgcc | ctaaacatgc | taccctcgga | aatattacac | 1500 |
| ttaatattag | ataaacttaa | ccaaaaatat | gatattgtaa | aattccttac | cgtttccaaa | 1560 |
| ctctgggctg | aaataattgt | gaagatactt | tattacagac | cgcacatcaa | caaaagagt | 1620 |
| caattagact | tgtttttaag | gactatgaag | ttaacttctg | aagaaactgt | attcaactat | 1680 |
| cgttaatga | tcaaaagatt | aaatttttca | tttgttggtg | actacatgca | cgatacagag | 1740 |
| cttaactatt | ttgtcggatg | taagaatttg | gagcgactaa | ctttagtatt | ttgcaagcat | 1800 |
| ataaccagtg | ttccaatatc | ggctgttttg | agaggatgta | aatttctcca | aagtgtggat | 1860 |
| atcactggaa | taagagacgt | ttccgatgac | gtatttgata | ccttagcgac | atattgtccc | 1920 |
| agagtacagg | gcttttatgt | tcctcaggca | aggaatgtaa | cattcgattc | actgcggaat | 1980 |
| ttcatagtcc | attccccgat | gttgaaaaga | ataaaaatca | cagcaaacaa | taacatgaat | 2040 |
| gacgaattag | tagaactatt | agccaacaaa | tgcccttttgc | ttgtagaggt | cgatataaca | 2100 |
| ttaagtccaa | atgtcactga | ttctagtttg | ttaaaactcc | tcactaggtt | agttcagctg | 2160 |
| agggaattca | gaataactca | taatacgaat | attacggata | atcttttcca | ggagctttct | 2220 |
| aaagtagttg | acgatatgcc | ctcttttaaga | ttgattgatc | tttctggatg | tgaaaatatt | 2280 |
| acagataaaa | ctagagaaag | tatagtcaat | ttagccccta | aattacgtaa | tgttttctta | 2340 |
| ggcaagtgta | gccgaattac | agatgcatcg | ttgttccaat | tatcgaagct | gggcaaaaac | 2400 |

-continued

| | |
|---|---|
| ttgcaaacag tgcatttttgg gcactgtttc aatataactg ataacggggt aagagcactc | 2460 |
| tttcattcat gtacaagaat acagtatgtg gactttgcgt gctgtacgaa tttaaccaat | 2520 |
| agaactcttt atgaactagc agacttacca aaattaaaga gaattggcct tgtcaaatgt | 2580 |
| acgcaaatga ctgacgaggg tttgttgaat atggtttcct tgcgaggccg aaatgatact | 2640 |
| ttagaaaggg tacatttatc ttactgttct aatttaacaa tatatccgat atatgagctt | 2700 |
| ctaatgtctt gcccaaggct ctcacatttg tctttgactg ctgttccgtc attttttacgc | 2760 |
| cccgatataa cgatgtattg caggcctgca ccctcagact ttagtgaaaa tcaacgtcaa | 2820 |
| atattctgcg tattttcagg gaaaggtgtt cataaacttc gccattattt agtaaattta | 2880 |
| acgtcgcccg cttttggacc acatgtcgat gtaaatgatg ttttgacaaa atatattaga | 2940 |
| tccaagaatt tgatatttaa cggtgaaaca cttgaagatg ctcttaggag aatcataact | 3000 |
| gatttaaatc aagattccgc tgcaattata gctgctacag gattaaatca aatcaacggt | 3060 |
| ctaaataacg attttctttt ccagaatatc aattttgaac gaatagatga agtattcagt | 3120 |
| tggtatctca atacttttga tggcattagg atgagctcgg aggaagttaa ctcactatta | 3180 |
| ttgcaagtaa acaagacgtt ttgtgaagat ccatttagtg atgtggacga tgatcaagat | 3240 |
| tatgtcgtag cacctggtgt aaaccgggaa attaacagtg aaatgtgtca tattgttaga | 3300 |
| aaattccatg agttaaatga tcatattgat gatttcgagg tgaatgttgc tagtttggta | 3360 |
| agagttcagt ttcagtttac tggttttttta cttcatgaaa tgactcaaac ctatatgcaa | 3420 |
| atgattgaat taaacagaca aatttgttta gtacaaaaaa cggttcagga atcgggcaac | 3480 |
| atagattacc aaaaagggct tttaatatgg cgacttttat tcattgacaa attcattatg | 3540 |
| gtggttcaga agtacaagct ctccaccgtt gtttttgagac tatatttaaa agataacata | 3600 |
| acattgttaa ccagacaaag agaactatta atagcccacc aaagatcagc atggaataac | 3660 |
| aataatgaca atgacgccaa ccggaacgcc aacaacatag tgaatattgt atcggatgct | 3720 |
| gggggcaaacg atacaagtaa caatgaaact aacaatggta atgatgacaa tgaaacagaa | 3780 |
| aatccaaatt tctggcgtca gtttggcaat agaatgcaaa tatcacctga ccagatgagg | 3840 |
| aatctccaaa tgggacttcg taatcagaac atggttagga caataacaa caacacaatt | 3900 |
| gacgaatcaa tgcctgacac tgccattgat tctcaaatgg atgaagcatc aggaacgccc | 3960 |
| gatgaagata tgttataatt gtatttcatt gaatacttac tgtcctacta cacctttatt | 4020 |
| ttcaaaatcc cacttttctt acttatttac atataaatac ataatgcatt cacttttgaaa | 4080 |
| cttttttgcct tagcatgtat acgctataga cttgcggtat caacgaatat acgtaacgtt | 4140 |
| gtcacgtcca cagaagatgc tatgtcaaca gttccctgca gatatctgcg atgcggcgaa | 4200 |
| acattctata cacagtttca aaactacaaa aaatacaaac ctttagcctg tttatcaaat | 4260 |
| tagttagcta taaatgccc attttcttag caatatcgat caattgattg tcatcttcca | 4320 |
| aagtttcaat aaaatttgtg gcagtatagt aatcccttct caatatgtcc aatttcttat | 4380 |
| cacagtcatc tataaattcg cgcttaatag attgcacttt taggttcacc caattgttga | 4440 |
| atgtcatgat ccaactcttc tgcaggattt | 4470 |

<210> SEQ ID NO 6
<211> LENGTH: 1151
<212> TYPE: PRT
<213> ORGANISM: Saccharomyces cerevisiae

<400> SEQUENCE: 6

Met Asp Gln Asp Asn Asn Asn His Asn Asp Ser Asn Arg Leu His Pro

-continued

```
  1               5                  10                 15
Pro Asp Ile His Pro Asn Leu Gly Pro Gln Leu Trp Leu Asn Ser Ser
                 20                 25                 30
Gly Asp Phe Asp Asn Asn Asn Asn Asn Asn Asn Asn Asn Asn Asn Asn
                 35                 40                 45
Asn Ser Thr Arg Pro Gln Met Pro Ser Arg Thr Arg Glu Thr Ala Thr
                 50                 55                 60
Ser Glu Arg Asn Ala Ser Glu Val Arg Asp Ala Thr Leu Asn Asn Ile
 65                  70                 75                 80
Phe Arg Phe Asp Ser Ile Gln Arg Glu Thr Leu Leu Pro Thr Asn Asn
                 85                 90                 95
Gly Gln Pro Leu Asn Gln Asn Phe Ser Leu Thr Phe Gln Pro Gln Gln
                100                105                110
Gln Thr Asn Ala Leu Asn Gly Ile Asp Ile Asn Thr Val Asn Thr Asn
                115                120                125
Leu Met Asn Gly Val Asn Val Gln Ile Asp Gln Leu Asn Arg Leu Leu
                130                135                140
Pro Asn Leu Pro Glu Glu Arg Lys Gln Ile His Glu Phe Lys Leu
145                150                155                160
Ile Val Gly Lys Lys Ile Gln Glu Phe Leu Val Val Ile Glu Lys Arg
                165                170                175
Arg Lys Lys Ile Leu Asn Glu Ile Glu Leu Asp Asn Leu Lys Leu Lys
                180                185                190
Glu Leu Arg Ile Asp Asn Ser Pro Gln Ala Ile Ser Tyr Leu His Lys
                195                200                205
Leu Gln Arg Met Arg Leu Arg Ala Leu Glu Thr Glu Asn Met Glu Ile
                210                215                220
Arg Asn Leu Arg Leu Lys Ile Leu Thr Ile Ile Glu Glu Tyr Lys Lys
225                230                235                240
Ser Leu Tyr Ala Tyr Cys His Ser Lys Leu Arg Gly Gln Gln Val Glu
                245                250                255
Asn Pro Thr Asp Asn Phe Ile Ile Trp Ile Asn Ser Ile Asp Thr Thr
                260                265                270
Glu Ser Ser Asp Leu Lys Glu Gly Leu Gln Asp Leu Ser Arg Tyr Ser
                275                280                285
Arg Gln Phe Ile Asn Asn Val Leu Ser Asn Pro Ser Asn Gln Asn Ile
                290                295                300
Cys Thr Ser Val Thr Arg Arg Ser Pro Val Phe Ala Leu Asn Met Leu
305                310                315                320
Pro Ser Glu Ile Leu His Leu Ile Leu Asp Lys Leu Asn Gln Lys Tyr
                325                330                335
Asp Ile Val Lys Phe Leu Thr Val Ser Lys Leu Trp Ala Glu Ile Ile
                340                345                350
Val Lys Ile Leu Tyr Tyr Arg Pro His Ile Asn Lys Lys Ser Gln Leu
                355                360                365
Asp Leu Phe Leu Arg Thr Met Lys Leu Thr Ser Glu Glu Thr Val Phe
                370                375                380
Asn Tyr Arg Leu Met Ile Lys Arg Leu Asn Phe Ser Phe Val Gly Asp
385                390                395                400
Tyr Met His Asp Thr Glu Leu Asn Tyr Phe Val Gly Cys Lys Asn Leu
                405                410                415
Glu Arg Leu Thr Leu Val Phe Cys Lys His Ile Thr Ser Val Pro Ile
                420                425                430
```

```
Ser Ala Val Leu Arg Gly Cys Lys Phe Leu Gln Ser Val Asp Ile Thr
        435                 440                 445
Gly Ile Arg Asp Val Ser Asp Val Phe Asp Thr Leu Ala Thr Tyr
    450                 455                 460
Cys Pro Arg Val Gln Gly Phe Tyr Val Pro Gln Ala Arg Asn Val Thr
465                 470                 475                 480
Phe Asp Ser Leu Arg Asn Phe Ile Val His Ser Pro Met Leu Lys Arg
                485                 490                 495
Ile Lys Ile Thr Ala Asn Asn Met Asn Asp Glu Leu Val Glu Leu
            500                 505                 510
Leu Ala Asn Lys Cys Pro Leu Leu Val Glu Val Asp Ile Thr Leu Ser
        515                 520                 525
Pro Asn Val Thr Asp Ser Ser Leu Leu Lys Leu Leu Thr Arg Leu Val
        530                 535                 540
Gln Leu Arg Glu Phe Arg Ile Thr His Asn Thr Asn Ile Thr Asp Asn
545                 550                 555                 560
Leu Phe Gln Glu Leu Ser Lys Val Val Asp Asp Met Pro Ser Leu Arg
                565                 570                 575
Leu Ile Asp Leu Ser Gly Cys Glu Asn Ile Thr Asp Lys Thr Ile Glu
                580                 585                 590
Ser Ile Val Asn Leu Ala Pro Lys Leu Arg Asn Val Phe Leu Gly Lys
            595                 600                 605
Cys Ser Arg Ile Thr Asp Ala Ser Leu Phe Gln Leu Ser Lys Leu Gly
        610                 615                 620
Lys Asn Leu Gln Thr Val His Phe Gly His Cys Phe Asn Ile Thr Asp
625                 630                 635                 640
Asn Gly Val Arg Ala Leu Phe His Ser Cys Thr Arg Ile Gln Tyr Val
                645                 650                 655
Asp Phe Ala Cys Cys Thr Asn Leu Thr Asn Arg Thr Leu Tyr Glu Leu
                660                 665                 670
Ala Asp Leu Pro Lys Leu Lys Arg Ile Gly Leu Val Lys Cys Thr Gln
            675                 680                 685
Met Thr Asp Glu Gly Leu Leu Asn Met Val Ser Leu Arg Gly Arg Asn
690                 695                 700
Asp Thr Leu Glu Arg Val His Leu Ser Tyr Cys Ser Asn Leu Thr Ile
705                 710                 715                 720
Tyr Pro Ile Tyr Glu Leu Leu Met Ser Cys Pro Arg Leu Ser His Leu
                725                 730                 735
Ser Leu Thr Ala Val Pro Ser Phe Leu Arg Pro Asp Ile Thr Met Tyr
            740                 745                 750
Cys Arg Pro Ala Pro Ser Asp Phe Ser Glu Asn Gln Arg Gln Ile Phe
        755                 760                 765
Cys Val Phe Ser Gly Lys Gly Val His Lys Leu Arg His Tyr Leu Val
        770                 775                 780
Asn Leu Thr Ser Pro Ala Phe Gly Pro His Val Asp Val Asn Asp Val
785                 790                 795                 800
Leu Thr Lys Tyr Ile Arg Ser Lys Asn Leu Ile Phe Asn Gly Glu Thr
                805                 810                 815
Leu Glu Asp Ala Leu Arg Arg Ile Ile Thr Asp Leu Asn Gln Asp Ser
            820                 825                 830
Ala Ala Ile Ile Ala Ala Thr Gly Leu Asn Gln Ile Asn Gly Leu Asn
        835                 840                 845
```

```
Asn Asp Phe Leu Phe Gln Asn Ile Asn Phe Glu Arg Ile Asp Glu Val
    850                 855                 860

Phe Ser Trp Tyr Leu Asn Thr Phe Asp Gly Ile Arg Met Ser Ser Glu
865                 870                 875                 880

Glu Val Asn Ser Leu Leu Leu Gln Val Asn Lys Thr Phe Cys Glu Asp
                885                 890                 895

Pro Phe Ser Asp Val Asp Asp Gln Asp Tyr Val Val Ala Pro Gly
            900                 905                 910

Val Asn Arg Glu Ile Asn Ser Glu Met Cys His Ile Val Arg Lys Phe
        915                 920                 925

His Glu Leu Asn Asp His Ile Asp Asp Phe Glu Val Asn Val Ala Ser
    930                 935                 940

Leu Val Arg Val Gln Phe Gln Phe Thr Gly Phe Leu Leu His Glu Met
945                 950                 955                 960

Thr Gln Thr Tyr Met Gln Met Ile Glu Leu Asn Arg Gln Ile Cys Leu
                965                 970                 975

Val Gln Lys Thr Val Gln Glu Ser Gly Asn Ile Asp Tyr Gln Lys Gly
            980                 985                 990

Leu Leu Ile Trp Arg Leu Leu Phe Ile Asp Lys Phe Ile Met Val Val
        995                 1000                1005

Gln Lys Tyr Lys Leu Ser Thr Val Val Leu Arg Leu Tyr Leu Lys Asp
    1010                1015                1020

Asn Ile Thr Leu Leu Thr Arg Gln Arg Glu Leu Leu Ile Ala His Gln
1025                1030                1035                1040

Arg Ser Ala Trp Asn Asn Asn Asp Asn Asp Ala Asn Arg Asn Ala
                1045                1050                1055

Asn Asn Ile Val Asn Ile Val Ser Asp Ala Gly Ala Asn Asp Thr Ser
            1060                1065                1070

Asn Asn Glu Thr Asn Asn Gly Asn Asp Asp Asn Glu Thr Glu Asn Pro
        1075                1080                1085

Asn Phe Trp Arg Gln Phe Gly Asn Arg Met Gln Ile Ser Pro Asp Gln
    1090                1095                1100

Met Arg Asn Leu Gln Met Gly Leu Arg Asn Gln Asn Met Val Arg Asn
1105                1110                1115                1120

Asn Asn Asn Asn Thr Ile Asp Glu Ser Met Pro Asp Thr Ala Ile Asp
                1125                1130                1135

Ser Gln Met Asp Glu Ala Ser Gly Thr Pro Asp Glu Asp Met Leu
            1140                1145                1150

<210> SEQ ID NO 7
<211> LENGTH: 33954
<212> TYPE: DNA
<213> ORGANISM: Saccharomyces cerevisiae

<400> SEQUENCE: 7
tttcttgttg cttcaacgga ttatcttaaa aaatctatc  atatttcaaa atataaattc       60 ttattttttac aaagaagata tagattatgc ataatattat tttgttacat tttttttctt    120
ttacttttta ttttcttttc tttgtacttc ctcaaataag catctttagc aggttaacaa     180
tagcaaatat catgtccagc ccaaatcaca taatactttc cacttcactt tcactatctg     240
tttcgggaga cctatcatcc acggtattga cagttggtct ttggaaatca gttgcatgtg     300
cccaaggaat ggatctcgaa atgttctcaa acacggagga ccttcttctg aaagtcccac     360
ggtaagcggg cataggttcg gcaaaactgt gaggattatt gtcatgtgaa ggcgtgatag     420
```

```
gtatgtcgtt aagtgatgaa aaggcttttg aacccaaatc actactatcc atagaatcat    480
caccgacctg cgcaattgga taaggcagag gagcgtcacc ggtaaccctg aataggtgaa    540
cattggcaac atgttcattt tcgactctga agatgatcca aacgaatctt cttaaaacct    600
ccaaaagggc caatataaac gacgtcacag cactctgctg aattgtttga ggagcaattg    660
cgtatacaat ccactcaaat ctaatgagga tatcccaaat catagcaaag taataaaacta   720 acttcctact gaatgaataa ctgccgtttt cccaattttt tttaccagct aaatacaagt    780
cgtctcttag caaccaattg taagaagtag tattgtgagc aaaggaccaa tccataacta    840
aatcccaggc ggaagtaagg atcgaattca acgtagcgca cacgataaaa ggggttctcc    900
tttgttcaga acggtctgac aatctgtaag cacaaagtgt ggcattatac gctataccca    960
aagtgtattt cgccgcgttc aaaagatgag ggaaccaatc accggaatca gcaaatcttc   1020
gtaaacattg catgaatctc caataacttg gtaaacatga taaaacaccc attgctctgg   1080
aatgtgaaga gccacataga ttgttgggcg tatgagagta acacagaag aacatggcaa    1140 tatcggcaat agaatacgtc aacgaacaaa taatatctcc caaaagaaa tcaccaaact    1200 caacagggaa aaaccagac atcatcagtc taataagagt aaccaccagc cattttctag   1260
tgtgtacaac tttgtcccaa tatggaatta gaccagaggg acataaaaat aagaaagaca   1320
caataccaat atataaaaag cctaagggtg tgagcttctc caaagcgaaa cttaacatgg   1380
aacagaccgc acaaggtact atgaagaatg tcaagaaata caacttgagc ggaattttac   1440
tcgtggcaaa atcattgttg aaaaattgcg taccattctt ggattgaatc tcacccagca   1500
taataaatct ataattaatc ccggttctat gccagataaa acaattaaca agaaagagaa   1560
acgcgatcaa caaaaccatg taccaaccac cccacagtgg gaacagaatc ttgtgcgtaa   1620
atgacgtttc ttcagagcta atgcccaaat acaaagtgta agtgatcaaa gtcattgaca   1680
cacctatgcc cagcccgaca accagcatct gcacaatcga tctgttgttt ctatgaacca   1740
tttgttcgga gatagagtac tgaatggtca atttcttcaa cttatgggta ttgtgcttcc   1800
tgtccttagg cgaattggtc aacgcagtgg tgaaccactc ggtgatctgc gtttccaacc   1860
aagtgatggg ctcttttgtct ctttgggcgg aagagagctc cgaagtgggt gttggttgcg   1920
aactggttat ttgttgcatc ttctgtgcca ccaactgcac gttggcatcc gcgtgcttga   1980
aaagggtgta gtgggtcctg gcgtacgaca tgaacgtggt cagctctctt gtgtgacacg   2040
ttttgtcgaa tttcttgacc attttacgga acccggtgac gttgatatcc cggaacgatt   2100
tgaccaattg caagtacaga tagtactcga ttatagcgtt gcttaacaag tttctagcct   2160
gggttgtcgt catagtctcc agaaaagaag cgccaaaagc aaacgtctcg cggcctcttg   2220
aggacgcatc ctgtctcaag tcctgtagca gagaaaatcc acgtttgggc cacgatggca   2280
gcagcctatt gtccttaaga actttctgac agtacgctag cagcgacaaa cgcggcttct   2340
tggcctcttt ggtgcaggc attgacccat acataacaga ccggctatcg ctgtcgatgc   2400
tattgaccct ggagtcagaa cgaccagcaa gccctgccgc atatagactc gtggacatgt   2460
caacattcga actagaccgg ttcaagttgt cgcgctcata attcttctgc agcgagtaat   2520
agtgcagttg cgactgtaaa acctcaaact tcttgtcgca ctcctttagc aaccaaaggt   2580
aaaactcgtt acacttactc aactggaacg agatcaacca gtcttcaatg aagtcagcaa   2640
cgaactccct ctgcaaagca gaatagtcct tcttgaacgc aggtccggag cgatagtctc   2700
cgtcgctgcg acttttgccg ggctctctct gctgaaatgc agtctggtat accgacacag   2760
agggcatcca gctccggtag gagctggatt gctcttcttc ggcatccagc ttctccttgt   2820
```

```
agcggcgaag cttcttcttg ccgaccttat aatcaatata tttgtccctc cattccggga   2880
tggcagactc ggttagatgg tcagcaaact tcatctgata cggtgctatg gtaaagccct   2940
tccattgctg ccaactgaat taaaaaaaaa aaaaaaataa ctaccaacca tcaaatcaaa   3000
caaaacaaaa caaaaaagca aggagaaaa cccatcttgt acatgtacag tcccaaactg    3060
ttgcgaaacc gtgcgatgat gttcatggaa cttgcgtcaa ataaaaccgc atcccgtccc   3120
acgtgacaaa cggcacccaa aatccgttct agaaatgcct cacacccaca ccgatgatgg   3180
gcttccgact cgatgactac caacacatag ccagccgcag cggctggcag catgtgcatg   3240
ataatgataa gtgatgatga atgatggtga taacgatttt gaacaaatgg ctgcagcgat   3300
agcaactaag gggatggaaa gacagatctg ggagagataa ctgcagggtg tggcacggca   3360
acacaaggct attgtattgc actaaacggg caagaagcca tgatgtgcgt ctgtatccca   3420
aaaaaaaaac taatggattg gcgcgtgtac tatatatatt catatgtcgt gtgtttgtat   3480
atgtgtggga gtgattgtgc gtgtatatgt gtgttggcgt gtgtggtaca atgtgtgtgt   3540
tttaatgtag aaatgaggtt gtagcacgtg atcgggaagc cacagtttgc gcggagatat   3600
tttatttttt ttcatcagcg taagaagaaa gcaaccttgc agtctgtatc gtaagagaag   3660
actgcagtta aagaagttta gagaagaggc ttgagtatcg gtaaaggggt gtgtgttttgg  3720 tgatttataa aggagaaggg catgaggaga gagaggcaaa ggatgatgag tttcgaggac   3780
aaggacaagg acgaccttga caatagtaat agtaataaca gcagtgaaat gacagatacg   3840
gcgatgatgc caccattaaa gagattgctt attacgggca gtagcgatga tttggcacaa   3900
ggatcatcgg gtaagaagaa gatgacgatg gcgacgaggt cgccatcgtc atcacccgat   3960
ttggcgacaa acgacagcgg cactagggta cagccattgc cagaatataa cttcaccaag   4020
ttctgctatc ggcataaccc ggacattcag ttctcaccaa ctcatacagc gtgctacaag   4080
caggatttga aacgaacgca agagattaat gctaatatcg cgaagctacc cctgcaggag   4140
caatccgaca tccaccacat tatctcgaag tacagcaatt ccaatgacaa gatacggaag   4200
ctgattctgg atgggatcct atcgacgagt tgcttcccac agctttccta catttcgtca   4260
ctcgttacac acatgatcaa gatcgacttc atcagcattc tgccgcagga gctgtcgctg   4320
aagatcttga gttatctgga ttgccaatct ctttgcaacg ccacgagagt gtgccgcaag   4380
tggcagaagc tcgcggatga cgacagggta tggtaccaca tgtgcgagca gcacatagac   4440
aggaaatgtc ccaactgtgg ctgggggctg cctcttttgc acatgaaacg tgcgcggata   4500
caacagaata gtacaggatc tagcagcaac gcagatatcc agacgcaaac tacgcgacct   4560
tggaaagtca tctacagaga acggttcaaa gtggagtcaa actggagaaa gggccactgc   4620
aggattcagg aattcaaggg ccacatggat ggtgtgttaa cgctccagtt taactacagg   4680
cttttgttca caggctcgta cgactccacc ataggtatat gggacttatt cacggggaag   4740
ctaatacgaa ggctcagcgg ccattcggac ggcgtcaaga cattatattt tgacgataga   4800
aagctgatta cgggctcgct cgacaagacg atccgtgttt ggaactacat aaccggtgaa   4860
tgcatttcca cgtatcgagg ccactcggat agcgttctga gcgtagattc ataccagaag   4920
gttatcgttt ccggcagtgc tgacaagacg gtcaaggtat ggcacgtgga gtccaggaca   4980
tgctacacct tgagaggcca cacggaatgg gttaattgcg tcaaattgca tccgaaaagc   5040
ttttcatgtt ttagttgcag tgacgatacc acaatccgaa tgtgggatat caggaccaat   5100
tcatgcctaa aagtgttcag gggtcatgta gggcaggtgc aaaagatcat accgcttacc   5160
```

-continued

| | | | | |
|---|---|---|---|---|
| attaaggatg | tagagaatct | agccaccgac | aacacttctg | atggcagctc | tccgcaggat | 5220 |
| gacccaacaa | tgactgatgg | tgcagacgaa | tcagacacac | cgtcgaacga | gcaagaaact | 5280 |
| gtcttagatg | aaaacatacc | ttatccaaca | catctactat | cttgcggact | ggataacaca | 5340 |
| atcaaactat | gggacgtcaa | aaccggtaaa | tgcataagaa | cacagtttgg | gcacgtggaa | 5400 |
| ggtgtttggg | acatcgccgc | tgacaacttc | agaattataa | gtggttctca | cgacggaagc | 5460 |
| attaaggtct | gggacttgca | aagcgggaag | tgtatgcaca | cgttcaacgg | tcgaagacta | 5520 |
| caaagagaaa | ctcagcacac | acaaacacaa | tccttgggtg | ataaagtcgc | ccctatcgct | 5580 |
| tgtgtttgta | ttggagattc | agaatgcttt | agtggtgatg | aatttgggtg | cgtaaaaatg | 5640 |
| tacaaattcg | atctcaatga | ttaggacctg | tgtgtggtct | tttcttggtc | aaaaacatcc | 5700 |
| gtagtacctc | gaatatatat | gcttacatat | ataatgaaaa | atacataata | gcattttaca | 5760 |
| tttatttat | ttccaggaaa | aaaataaatc | gctagcgtat | cactagccctt | ttccatcttc | 5820 |
| agttttttc | cttcctcttt | ttcgtctcga | taaaactctt | gaccattaga | tgctattact | 5880 |
| cccccacgga | gcccttccca | cgctaagggg | gatgtcaagg | ggggactga | agataaagct | 5940 |
| tattatattg | acggcgatga | tgaagagggc | gtacgcataa | aatgtcgtac | aagatccata | 6000 |
| atctgcaata | ttgttccctc | aacagtacta | ataaatccaa | agggcgaagg | tactttatta | 6060 |
| tataaacgcg | cacggccatt | gtatataaag | gcgattacta | aatagaatac | ttatcgattc | 6120 |
| cgtaatcctt | gaaatataga | atatacataa | aatagacaag | aacccaacag | ttgaggcgcc | 6180 |
| agctttggta | atagcttaat | aataaataaa | aaagataat | atagctagct | agtattattg | 6240 |
| cttttatccg | tatgccacc | accacgcaac | cacaaaatat | actgatggat | gaacctttaa | 6300 |
| atcttcctaa | taacagtgcc | cacaacaata | actatgaaaa | cataaatgcg | aatataagaa | 6360 |
| cttttgctgg | tatgagcatg | cacatgcacc | ctgccaggct | gaactctctg | gagttttgc | 6420 |
| acaagcccag | gagactatct | aatgtaaaac | tgcacagatt | acctcaggac | gagcttcaaa | 6480 |
| gaaatacgga | catgaataag | ggaatgtatt | ttaatgggaa | acaagttcat | gcccatcacc | 6540 |
| cgtttataaa | ttctggagcg | aactttaacg | cacatcatca | agacgtcagt | aaattaggcg | 6600 |
| aggaggaaga | cgaaatctct | cctctatcac | atgataattt | ccagtatgaa | tccgaggaaa | 6660 |
| atggtaatcc | ttcacctccc | atttacaaga | aatctggaga | actggttaag | agttcattaa | 6720 |
| aaagaagatc | caagtcccta | cccattactc | ccaaatctat | attcaacaaa | actggctcta | 6780 |
| agagtaaaca | tgtcaattta | gatcatgtag | atactaggct | attgcaaaga | agtaaaagtg | 6840 |
| tccatttcga | tcgtgtttta | ccaataaagc | tgttcaatga | aaatgagaaa | cccatagatg | 6900 |
| ttggcaaaca | aatggttcaa | caagatgttc | tgaatttcaa | gcataagcct | ttgacgagac | 6960 |
| taagtgccct | taatggcggt | agtgatagcg | tacctataga | agatttacta | tctgaaaaca | 7020 |
| accaaaacga | atatgagat | acatggctac | aaaacccgaa | gggtgtattc | ctatttggta | 7080 |
| caaattctaa | taatcgtaga | aataaaaaaa | agaagtttaa | actaagtgac | gatgacagtg | 7140 |
| atattgaaaa | tgacaatgat | agtgacgacg | ctataaaccg | tttagtaagg | caacaagaca | 7200 |
| aagaccaagc | tcatcttgcg | cacgggttga | agaatttgtt | aataaacgat | gacgacgatt | 7260 |
| atttagaaac | aagaacaaat | tctgctaaat | caggagccaa | cttgtttatt | ggaaactcta | 7320 |
| aaagaattgt | tggtctttac | aacaagaact | ttccaatatt | aagtgacagg | aaccgtaaga | 7380 |
| gtttaaaact | taacatattt | ctgaatcttt | cccgtggaag | gcccgttttt | ttgcaagaaa | 7440 |
| ttacgctact | aactggcttc | cacaacatgg | ttataattgg | caaagtcttt | gtgaaaaaca | 7500 |
| tatactttga | taagaagatt | atcgtaagat | atacatggga | tgcatggaga | acttttcatg | 7560 |

```
aatcagaatg cgtgtatttt tctaatgcca atggcatctt accaggaagc aatatggata   7620
tttttaagtt ctccattgat gatatacaca atccaaatga taaagatagc aatatatcac   7680
aattggagtt ttgtattcaa tacttaactt ggggcgttga tcgttctagg aaggaatatt   7740
gggacaataa tgattcggca aactataaaa ttgacgtggt aacgaatgaa acgaggacag   7800
ggcccacaac agacgtcaat gataactacg agatgaaaca tagtcttttc agaaacccat   7860
tccattaaag aaaaaaacaa aaactaatag tattgtttta catatacaaa agaaaaaaaa   7920
aagataagaa tacgtacttt ctatttttat ttgaaggtca ttttctttat ataaaataat   7980
atactggaat gatgttcttt ttgttgcttt ctatatttgc tttcttttttt actttttat   8040
tcaactccag acgttcttaa ataactcgtt atcatccaat gaaatgttag aactggaatt   8100
tgaattcata ctattattat ttgtagcggt aattccagtg ttcacgaatg gtgacggagt   8160
attacaaggc tgaggtgtcg tggaagtgaa aaatgagttc tggctttgag tctgggcaga   8220
aggttttgag tataaagata aatggatttt ttcaaatcg ttcctttgcc caaattcacc    8280
gactctgttg ccagtcttgg tattagcagc acctatgctt gttgcagaac tagttacact   8340
tgtattagat gtagtcttag aaagcgatga aacctgtagg tttaataagc tcgtattact   8400
ccttgaggtg cttaataagt gggaaggtgg ttgtgtttgc gtcttttgta atgaatttga   8460
gctctggtcc aatcttgcat tcgaagcagg caacgaatga ttcgcagacg gcttatgcag   8520
aactggttca gtagaatcat ttaacccttc aatactggag aggtcaccaa tccacttctt   8580
atattcatat ttattcttga tgaaattttg taaactgctc gtatcagtga ttttcctctg   8640
tttcaattca tcagccaaag tagcttcgta gtatgagtta gctcttaaat tgttttttgaa   8700
ctgtatcagt ttcaccaaat gttcttcctt ccatgtatcc agatcaacag atttcacttt   8760
cgaaatgtgc gttcccaatg atctatgtat accagcacat ttaatgcaaa tgaaaacacc   8820
aagtgaccag gaagcccagc gtggatgtag ttgcgcctta cagtcggcac aatgactgtt   8880
tcctggatcg cgtaaaagag cacttaatgc cttcttgact gggactgacg tcgacatcgc   8940
ttgtaaattg ccccacgttc tatgctcctt tgtacagttg aagcaagtat tacctttact   9000
tttgttacta ttagtaccga tcttatacgt attatcgagt cgaaaatcgt ccagcacgaa   9060
atatggaaac ggtgcgttta ggtgactaaa ctaaatagcg tatatattat atatgttcca   9120
atctatatat atatatatgg cactctgtta cagttcctta tcttaaaaca caaacacctg   9180
gtcttccatc ttggaaagcg gtttggaacg tctgaacccc aagtccacgg tacttcttct   9240
aactgaggca accatggctg gaggaccaca gatcaaaatt tgaacgttgt ccattgtagc   9300
agcgggcaag tgttccttga tgacatcctt ggtaatgtat cctacaccac cagtccagtc   9360
ttcacggtca ggagagtcta agtagtaaac tatcttaaat tgggaaggct tcatggccac   9420
caacgcttcc agttccttct tcaacagaat atcctcctca tggacgttcc caaagactag   9480
agagaccttg gtagtgtcgt gagggtccat ggcaatagct ttcatgatct gatacatggg   9540
cgcaatacca gtaccaccag caatcatccc tagatgggaa cggcagtttc tctcataatg   9600
atagttccca cgagggccct tgatctggat cgagtcacct atcttcaact ctccaatcat   9660
cttagaaacg ttacctgtgg ggtaagactt cactagtaat tcaaagtttc cctttgtatc   9720
tccatccaac gatgtgggcg tatacgatct ggtaatatcc ttaccattga tattggcctt   9780
aattacgata tgctgaccaa ttggtaaacc gagtacgtcg tcagcatgag gtagcccgaa   9840
cttgtacatc gaagtattat gcgttaagat ggttttttca accagcggaa atgattggaa   9900
```

```
gtcattcctt tgggatcca gcacaggctt ggtcttcggt ccgataatga acttgaagag    9960
caaaggcacg accacgatca cgatgaccac cacaagcttt tgagcatcaa tagccatctt  10020
cgattgctta attgattgag tctcttgttg aagagccagt tgaatgcata ctttcaacac  10080
ttttttttct cgttcatttt ttcgccttat ataataagaa tatttataca tatgtagata  10140
atttaaagaa gtagaaagag cccttaatgg taccgcttta cgaggaaatt tagcactgtt  10200 acttttttgga gagtagtgca gtcttagaag ggcctttgag cttgatgtac acgtccgtgc  10260
cccagccaag taaactttga acgtcaatct tgcccccaaa cagttctagg tacgtcttgc  10320
acattggtag accaaagccc atgccggaga cgttgttgat ttgctcgccg ggcagatctg  10380
tagactcaga gtcagctgat tgttgggtat gtgtagagta agagtagttg aacatgaggg  10440
cctctacctc gggcgtgatc ccaccaccat ggtcccgtat ccgtaagtac agctcgtcat  10500
cgtctggctt taaaagattg atctctatgg gcatatgttc ctttccaaga gctatctgag  10560
cttcaaaagc gttcttgaat acctctgtca taatatactc cagaatgggc ggaatgcacg  10620
tgaatgtgat gtcttgtgat ggcgggtgaa ttaggaccgg ggtccgctga gtgttgaact  10680
tcacaaagca tatatcattg acataatcag aaacgtgctt gatcaattgt gctatgggga  10740
ggtcccggtg caagattcca atcatccttt tgttcgtgtc acctttgttc tgtgccatca  10800
acgacaaata gtgcgtcaca agcagcttca tcgtgattct ctccttcagg tggaagttca  10860
agaactgcga aatttgaaac tttgggtaac acgattggat ttcctgaaga ccttttgcca  10920
ataccacaat ggcgtcctcg tggtcgtcca gcagttctgt gaacttggcc tgtatcttgg  10980
gaggattgtg caactcgtac gggtatgcga ttgatagcaa cgtttgcaag cttttcaaat  11040
acaaagagtt ggttctctca atatgagggt tgattaccgc attatacggt agcctctgaa  11100
tggcattaag ccgtttacac gtcaatgaaa gcaacaggtt gattgtcttg atcgtcagca  11160
tgtactcctc cttcttggtc agcggcggcc tgtattgcag gaaatactcg tagtttaggg  11220
gcgcaattgg tttactagcg tagtcctgta tcagcagctc aatgttcgac ctaatcttgt  11280
aatgctggtc gaacgacagt tgcgacagca gctcgtgtga gggtcgctgg cgatgtgccc  11340
agcgcattcc cccacatttc catgaacgca taatcttcca catactaccg tgaaggcgtc  11400
ttgataccac gtcttccagt tatggtcttg actcaccaat gttctcagtt taatgttgtt  11460
tgcttcatac tggcagacat tttcccttat taccgtgaga agcgagcggt ggattaatcg  11520
ggatgtcaaa aacaagaaaa ttgcaacctt cttcacctat aacctatatg atttgtaggc  11580
agaggagtgg aataagcaac aaatcatagt catcaatgtc gtttaatgcc ttcgccagct  11640
ctttgagcaa gaaattacag gaaatatcca caagtgtttc cgaaaaaacc caggaattgc  11700
ccagtttggc gcaatccacc caagaatgg tccaggaacg tttgggccag gtgacggaca  11760
tctcccaatt gccaagagag tacacagagc tggaagataa ggttgacacc atcaaactga  11820
tttacaacca cttcttgggt gtaactgcta tctacgaaaa cggatcgtac gattacccta  11880
aatacatcaa cgaatccgtc aacgagtttt caagaagcgt ggcttccaag ttgacagagt  11940
tgactcatgc tacatctgcg tctgaggcac aaaacatctt agttgctcca ggccccatca  12000
aagaacccaa gacgttgaac tacgccctca gtaaagtggc tttgaactcc agtgaatgtt  12060
tgaacaagat gttccccacc gaggaacaac ccttggcttc ggcactcttg caattcagtg  12120
atgtgcaggc taagattgct caagctagaa ttcaacaaga taccttgatt caaaccaaat  12180
tcaataaaaa tttgagggaa aggctctctt ttgagatcgg taaggccgat aagtgccgca  12240
aggatgtcca ttccatgaga ttaagatatg acgtggcaag aactaacttg gcaaacaaca  12300
```

```
agaagccaga aaaggaagct tccttgagag tccaaatgga gactttggaa gaccagtttg    12360
ctcaagtcac tgaagacgct actgtgtgct tgcaggaggt tatttctcac gctaacttca    12420
gtgaagattt gaaggaattg gccaaggctc aagctgagta ttttgaaacc tcggctggcc    12480
taatgaaaga gttcctatcc aactcatttg cggaagagcc ggaagcaaag cctgaggttg    12540
cagaagaaga aaagccacag acagctatct ctatgaatga cgaagacgac gcttaatagc    12600
cgccctgttc ttgtctttct ctctccttct ctatatatat atatttactt aatacaatat    12660
catattctct agtgtcgtac gaatattatc atttatttgc tggcttttgt agtgagtata    12720 tttttttgtag agaaaatata attactggaa gagaaaaagc tactgaaaaa aatttcgtaa   12780
cagtcaccaa agggcaaagt gagcaaccca aaaatggacg ctactcaacc gcaatacgaa    12840
ctatccgtag taacacaatg cctaaagtct gccattgacg tcatccaatg gttgattcct    12900
actattacta agttcagcca atcacacccg ttagttttcc aactattgtt tattttcttc    12960 acatttatg tcttttacaa gttgttgatg aacttcatta ctctggtcaa aagattcctg     13020
tatttgacgt tggtagtaac atgtatcggt atttatatgc gtggttcgca gcagttttg    13080 actgtggacc tgttgaattt ctacaatttc gtcatgtcaa atagatacta cgcatttaaa    13140
atttatactc tgtttattaa tgccctggaa agagaaatca acactgttta tcatttggcg    13200
cagatgaaaa tggaacagtt gcttaaatag agcgaaacgc ctctgcttac tcggaacatc    13260
ttaaagtaat tacatatctt aatttctaaa tattcatata gataaagaac gttttttttg    13320
ctagattcct cccctagtca ctatcaaata ttgagctatt tttggtgact tgtgttttcc    13380
aaattattca ttacaattgt gacttgattt ctgaagtttt aagaaaaatt gcaaactaag    13440
ttattacaag cgatttatcc ggtcgcgatt gaagaactga aaacaacagc agcagcattg    13500
taccaagaat cccaagatgc tcaggtgtgc ggtcaagaag tttgcatatt ttgccaccttt   13560 cctcactatc gtcgctaata tttacatcta tacttatcca tctttccatc cagaacagtg    13620
ttcatggaac tgctctaaca agaacgcacc actacagaaa gatttgactt ttgtggacaa    13680
agtgaagaat tacttcagtg atgttcgaga gcaatggcat ggtagccatg cctctgcagg    13740
taacgatgag gatattcata ttttggcctt cggtgatcct cagattaaag gcatctggcc    13800
aaagacgcca tatgtgtccc gattagatac atacggtaat gactactatc ttggtcacat    13860
ctatgatatg atgcagcaga gactgaagcc tcaggtggtg actgttatgg gtgatctttt    13920
ctccagtcaa tggatcggtg attccgaatt ccataataga acgaaaaggt atattagcag    13980
aattttcaaa agagacccaa cttctattga aaatatcaaa caacagaacc tcgatgagaa    14040
aggtcaatat aaggcgaatt ggcctgaatg gggagaccgt tttaatgaga ttttagcaaa    14100
tgtcaaggaa aacgaggctg ataatcaaga actttctttt gggtttggtt atgaaaatat    14160
ccactcatgg aatccagact tggaagactt tttaatcatc aacatcacag gtaatcatga    14220
tgtaggttac tcaggcgacg cgacttatca acatatgaca aggttccacg accttttcgg    14280
taaggacaac tattggattg aatacgaaac caacactacc catccttgga gaattgtagt    14340
gttgaatgat cttttactag aaggtcccgc tttacaacca gaatttgttg aagctacttg    14400
gatcttttta aaccaactaa atgaacgtaa attcaatggt agtactgttt tgttgacgca    14460
tgttccattt tacaagcgtg aagggttatg cgttgatggc ccagacacta ggtattatcc    14520
agatgcccat gccccagaat catataaatc tgggcttttg agatcccaaa atcatttgag    14580
tgaatccgtt tcaaatcaag ttttgaatat gatatttgaa aatgggaagc caggtatcat    14640
```

```
attaactggt catgaccatg agggctgtga aacagtttat aataaaaaat ctacatctac    14700
ttgggaagcg actaaaaata tcgaaagtga cgttttcgtt aaagaaatca cagttaagtc    14760
tatgatgggt gaatttaatg ggaatactgg tttggttaca ggacacttca acacagattc    14820
aatgacttgg gagtggactt tcagtttatg cccattcgct attcaacatg tttggtggtt    14880
cgctaaagtg tccctgctcg tcaccatatt cacttggtcc tcgctactat ttgtctaaac    14940 aaaaagagt  aaagaagata aaactcctgt atagagattt atattaaatg tatgtatata    15000
tatgcatata ctgctcttca aattgcttat gttttataaa cattgacatc ggggttccac    15060
acatcaagat aatcattata ataccttaga ttgtaaaatg tttacttact actttaaaat    15120
aactataaat aaaattaaaa atcaaattaa aaatcaaatt atactgccat tagcactgat    15180
ttttgttgtt tttgttttaa agggatgcac attttttttt tttatgttat tatcatacac    15240 taattttttcc ctgtttcaat tgtttcaaga gctgcttgcc gtgagaaatt tcttgttttt    15300
gttgttctaa agttacatta ctctgatcat taacattgtt attgtcaaca ctcacatcac    15360
ggacctcaga cgctgtatct accggtggct gcaaaaatga ataatccagt ctgaagttaa    15420
ttttatcaat tactgtccaa tcgtccagtt taaaaatttt gtaatcacca acttcgcaaa    15480
tttcattaaa aaacttgacc tcaccttgtc ttaaaaacca cattgtacca tcctttgaaa    15540 cttttccaatc cctctcattt agaatcttgt atgcaatctc cctttctaaa ggagtaatag    15600
caaaataata gttataaaat aacgaaaaca tttctaaagt tctgaaattt tctagaattt    15660
tggcataaat tgacgatgaa tcttcttttca gcctttcgga gcctataata atatcacgca    15720
acgaacaacg cataacgtcc cactgttgag tagatctgaa tgcatccaag ggagatggtg    15780
gattaactcc ttgcggtact tcgaccagcc tggaaatttc acacatatca cgagacccttt   15840 tgtacgttat tttcgattca atttgactat tatagagttc agaactcatt atgaattctt    15900
gcacaccact tggtagaagt aaagtttcaa aatcacttac aaattctttt ttgatttcat    15960
ttgtcttagc ttctctttgt tccaagctta aatatttcgg tgtgcttggt tgttcttctt    16020
cctctggctc cgtctctgaa tccctatccg attcaaaatc gtcatcgaat actccaaaag    16080
ttggcacttg caatttattt cttttcttctg gtgactcttc ctccttctgc tccataacct    16140
tcttagttgt gttctcaggc ccattttggt ttaccgtagt tgcaacttca tgttcagact    16200
ttggatttgt cgccaaggaa actaaaggat gatgtgagga gctcatattt ctatagaagg    16260
cctgattgtt ttgatgcaca gcagccgccc cagcagccaa aacagcagcg gccgttgctg    16320
ctgaagatga tgcgccggta ttgtcaggtt gtaaagacaa agatgaagta gataacttag    16380
gtgtattcaa cgcactacca atcctgctgt tagcgttgga tgatgttgta gtagcagcag    16440
cagttgttgg agtctttgtt gaggtattgg atatggtgga cgatgcagaa gtgacttttc    16500
tatccttttc taccgcttgt gatgcagcaa cggcccattt taattcacca gcaggttttg    16560
ctggaagagt agcaggtttc aatgtagtgg caccagtaat accgtttgga gtttgatgaa    16620
tatgtgtatg tacatttgtt ggagtttctg gtgtagctga acttggtgat ttttgcaatg    16680
acggaagcaa attatcagca ctgctcctgg gactctttat agaagtttta acagcctctt    16740
caggctttgt tgcattatgg atagggaag  atgaaggact tctttccgtt tcttttgaag    16800
catcagcaac gggaatgaca ggtgacggcg tagaagaggg accagcaacg ggtatagctg    16860
cacctgttgc attttttgcc gcaagtttag cagccttttt ggcttctctt tccaattttc    16920
tttgctcctt tttagaaagt tttgatatgt cctgcagaga ttcattagca tccgatgtat    16980
tgttatcttc agcattttgt gaagcaaaat actgggccac ctcatgagca atggcttcgt    17040
```

```
tactctgtaa attcaaaccg tcataaatag tttcatcctc tacgaaatct ggatcctgat    17100
ttgactccac gaagtaattt atatcgtcct gcacgttttt aacatcttgg gggtccaatt    17160
cctcattggc taacaatctc aaggctaact ccatctgctg ttgatgccac ctatacctcg    17220
cttgaaaacg cttatattgt tccttttttt catcatttgt cgtagatgac gttttcttct    17280
ttttattaag aagtaaaagc ttgtcaattt ccacttgtag ggaatcgtat tgcctttcca    17340
gctcatcgat catttgggaa aggtactcag atatatctct cctttcccctt tcttgcgggt    17400
ctaaagtctc tgattttttc aggctaatat tagagtatgc tttttctttg gacgccttct    17460
ctacagcctt atacttttcc atcgctattt ctacagacct tctgtaatct agaagagaat    17520
ctttatcttt aatatcgggt gagctttgcc atgattttat ctgttcccctt agcctttgca    17580
gcttttttgac ttctcttttt aaatccgact ctagcttgtc cttttgggaa ggattgtttg    17640
tgcatgattc atgtctttcg taatagctat tgaagatttc taaaccttcg ttaattttt    17700
taaagaccct atcgacctcc tgctgtaatt ttctatgagc catgtcgatc gactaaacat    17760
acaatgaatc ttcaaaaatc taaatttgaa aatgaataaa taatgtgct gtagataata    17820
gcttttgatt ttttgtcttg acacaatgag acttctcgtt aaagtcaaac caaaaggaga    17880
tgaacaaaag aaagttcgaa atatcaacaa aatgctttaa aaaatgtaga agcaaagtta    17940
ttaataactt tacaagcgcc ttagtcagtt tattgatctg taggtcagta ggttttagag    18000
attacgcaca gatgaaagtg aattaagcta ctattacata aaatcaaggt atctttcaca    18060
agttttttcac tcagcgaaaa ttgcgagacc gctcgtggaa ggtgacgata atacgatact    18120
tacaacttta atattataaa tataagcatg tggtggaaca atatagtcag gcaaactgct    18180
aaaagtcccc acttataaac agtgtgtaaa aagtacgttt gttttttgctc cttatccttt    18240
atttggcgtt ttgacagtga agacaatgcc gctaccgatg cgttggttat attaattcct    18300
cgattaatta taccatattt ttgaatgtcc agtgcaaatg aagaatttgt attcgtaact    18360
tcgtatgtcg gtaggaaata ctgacccagg aactcattaa ttgaatcgct gcctaacaga    18420
ggctcaacct gcaggtctat cccctgccaa ttttgagaac tctcattaag atattttca    18480
aactgagtgt ttgtgtcgtt aacccaaaga tttaggatgt ccgttgattg cactttcaaa    18540
ttggggtcag tttgaaggct taaatttgct gtaatgaact tttcattcac ttccatttgg    18600
aaatttttcac acaataatga tacgctgtca ttaatgaaac cctctatcgt agttgttata    18660
tttccatctg tccaaacttc ccttttgtat agcgaaggtc ccgctctttt gtggaatgta    18720
ggcaaactgg gtacttcaaa gtttgttaat cgcgtcacta tctgccaatg aattaataac    18780
atcaaaaaac caaacagcca caggtgagcc ccatttgaga ttatccacca gttacagtaa    18840
aatagttttg atttttttgac ttttttgtca tcgattttt ctggttctct tttaaatatt    18900
ttttgattga taagctttgt taattggtag ggaattggat aaagtgtact gagattcaga    18960
gtagtaatta agcttttcaa aactttgttg tatttagtaa aattggtttg tcctgtcagg    19020
ccattaattt gggacataac caggtttact tgctgatttt ccagctgaaa cagaattctt    19080
tcgattgcca tgagcaaaat cacaaatgca aagtacatga ctgtgaaaat tattgtcatt    19140
ctcttacatt tacggaaaac gtgatttttt actgcactta gtacactgtt ttcctcgcta    19200
tttgttttca gagaccgttt aattattgaa gtagacgatg taacctcggt actccccca    19260
gataaaatgg aaatttcatt ctgtaagttt gcagtaaagt tccttttcaa ctgaagccag    19320
tcagtggaat ttcgtagaaa attcaaactt aaggtactag aggtatctaa ttgagtagaa    19380
```

```
aagtcagtga tagtgccatt gaagttctgc aatgatttca atttccttga gtagttccca   19440
aaaatactgt caaacatgga gtaatttaac agtaggtttg atgccatttg tgaaatggaa   19500
tccttatcaa tggtcattgc gtcttctgat atttcattcc atgtgtcatt tatcagctgt   19560
gatttagtga gtagttcgtt aaaaattgta ttgtttacct caagaacttc cttaatcaat   19620
tcagtttcca aacttatttg gtcgttgata agttttttgtt tattatccag tatgtcgtct   19680
gtgtatgact tgaattttttc ttgcatatcc gtacctaccg tagattcaat actccgtagt   19740 ttgcttttcga aatactgatc aattgtatta tcaatgaatg ttttatttaa agagtaactg   19800
ttggcagaat atatggcatg ctgtgttgtg actgctgtca ttgtggccgt tgttgtggcc   19860
gttgttgtgg ctgtcgctgt agcagttgaa atagatgcaa aggttgagac ggtatcattt   19920
cgtttgacct gtgcgtgaga cattttttgcc attgtaatgt caatgactga aaaggaaccc   19980
caaatagtta aaataacaga agtaaagaat atcagtaata gaggatggaa aatacaacta   20040 aaaacctct gtggaagtga taaaggttta attatgtgta cattgttcat ctttgccgta   20100
ctcttagttt tatcgaaaag tggtgtagat tttcagctac ttaagccatg ttagtgttct   20160
agttttttgc tttacatgtt atataaaggg ccaagatagc atatgtaaat gttttattac   20220
tgggctgaaa cattttttaaa acattttttca ataatgtgct gttataaccg tacaaggacg   20280
gttataattc tgaattaaaa tgctgcaccg aatgaaaata ccaatgttct tccaaaccta   20340
ttggcgaaaa ttaagataag ctgtcgcctc tataatcaag aataatctca actattataa   20400
atattattcc cagaagttga aattgtgaca catttgagta atatcacctt acacggaaca   20460
tagttgcccc cttctccgaa attgctgaca atgataatcg gggattcaat gacaatgaca   20520
atgaaggcaa aagattttca tattgtactc ttgtttttttg agttatcact ttcaagtacc   20580
ttcttgttaa cagaaataga accgctatag aggttatcgt gtatacgtat ctgttggtgt   20640
ttctaaatca aaaactcgct tttaaagcag tcttttcaatt ggaagattca aaaggatcta   20700
aaaagatcta aagtagtaaa gaaaaaagta taagcccaca cctttttggt aggataatgt   20760
ttactggtca ggagtatcat tccgtagact ctaattccaa caagcaaaaa gacaacaata   20820
aacgtggtat tgatgacaca tcaaagatct tgaataataa gataccgcac tctgttagtg   20880
atacttctgc cgccgccacc accacttcta ctatgaacaa ttctgcttta agtagatcct   20940
tagatcctac tgacataaac tatagcacaa atatggctgg tgtggttgac caaatacatg   21000
attatactac ttccaataga aattctttaa ccccacaata ttctattgca gctggaaacg   21060
tcaattcgca tgatcgggtt gttaaaccca gcgccaattc aaactatcag caggctgcat   21120
accttcgaca acagcaacag caggatcagc gacaacagtc accctctatg aaaactgaag   21180
aggaatccca actctacggt gatattctga tgaattctgg tgtcgtacag gatatgcatc   21240
agaatctggc cactcataca aatctgagcc aactgtcgtc tacccgtaag tccgctccga   21300
atgattctac tacagccccg actaatgcgt ccaacatcgc caatacggct tctgtgaaca   21360
agcagatgta tttcatgaac atgaatatga ataacaaccc acatgccttg aacgatccat   21420
ccatcctgga aacattgtcg ccatttttttc aaccttttgg tgttgatgta gcacatttac   21480
ctatgacgaa tccaccaatt ttccaaagtt ctttgcctgg atgcgatgag ccaattagaa   21540
gaagaagaat atcaatctct aacggtcaaa taagccagct aggcgaagat attgaaactt   21600
tggaaaacct gcacaacaca cagccgcccc cgatgcccaa ttttcacaat tataatggtc   21660
tgagccaaac taggaatgta tcaaacaagc cggtcttcaa ccaagcagtg ccggttagta   21720
gtattccaca atacaatgca aaaaaagtta ttaatcccac gaaggactcc gcattgggtg   21780
```

```
atcagagcgt tatttactcg aaaagtcagc agcgaaattt tgtaaacgcg ccatcaaaga    21840
atactccagc ggagagtata agtgatttgg aaggcatgac gacgtttgcg ccaactactg    21900
gaggtgaaaa tagggggcaaa tctgcactta gggaatctca ctctaatcct agcttcactc   21960
caaaatctca aggatctcat ttaaatttag cggcgaacac acagggaaat ccaatccctg    22020
gtactacggc atggaagaga gcaagattgt tagaaagaaa tcgaattgca gcttcgaaat    22080
gtagacaaag gaaaaaggtt gcgcagctgc agctccaaaa ggaatttaac gaaattaaag    22140
acgagaatag aattttactg aaaaagttaa attactatga aaaactaatc tctaaattca    22200
agaaattctc caaaattcat ttacgtgaac atgaaaaact aaataaagac tcagataata    22260
atgttaatgg cactaatagt agcaacaaaa atgaaagcat gactgtggat tcattaaaga    22320
tcattgaaga actttaatg atcgattcag acgttacaga agtggataaa gatactggta     22380
agatcatagc catcaagcac gagccatact ctcaacgttt cggaagcgat actgacgatg    22440
acgatataga tctcaagccc gtagaaggtg gtaaggatcc agacaaccaa tcattaccca    22500
attctgaaaa gataaaataa caaagttttg gtgagcacaa cggtgtttca ttcaagaatg    22560
ataaggacaa ctatatatgt aatatacgtg tataaatact cgagctgcat cctttctttt    22620
ctgccgttat tatttcgttt agttactaca tttatggtat aaattacctt taagacatta    22680
ttatttgtca tgtatgaaat ttgctcgtgt caaccccta gtcctccttg cctctgttgt     22740
atggaggaag ccctttaaac ctgtatttag tttttttaaat ctattagaat taagtacaat   22800
tgtacagatg gtaaaaaaaa gtaatcgtta tatcgtttgt cagtgatttt ttttttttta   22860
tttcattcat tatttatttc ttattttttca atttgttccc ttattggggc aaaccacggg   22920
tgtcccatcg cttccttagc agttaatctt tcttgatgat catatctcaa aagattgtca   22980
ataaggtcaa taatttcatc gttgccgctt aaatgtttat taccatcatt gatgaatcta   23040
tgccaaggct ttctgatgta ttggtccata tcgtaaaatt ctctcggtaa ggtaattca    23100
tacttcaaca ggtatttctc aaaatcgctt gtaccaagta ctttgacgat cttgacaagc   23160
tggtctgtgt tactcgttcc atggaaaaat ggctctcttt taaagatcat agaagccaac   23220
attgtcccaa acgaccacaa gtctaaagaa taatcataca ttctgtagtc aactagtagt   23280
tcaggacct taaaaaacct cgacgcaaca cgaaacattgt attccatatt aacatgataa   23340
aattcagcaa gcccccaatc tatcaatcgc aattttttat tcttatgatc aatcattacg   23400
ttatgaggtt taacatctct atgcattatt cccattgaat gacaatagtc taaggccttt    23460
aataactcaa acatataaaa cctaatttcg agatcggtta atttagggta aagaatacgg    23520
aagtccacat tatctacgta ttcgaagacc aaagccggag ttttttgagat gggatccttt    23580
attatatcaa atagatgaat tatgtttgca tgaccattgt gtggctgatc aaagatatag    23640
ggcctgatga attttaaaac gtcctccttt tgatttgtgt aatattgatc tttttgaaat    23700
ggcaaagtcg ttggaggcac tttttcgtta gacaaatccg ttaagatttt gatttctctc    23760
ttgatcttct tctttttaac tggtttcaac atcttaataa caattttaac tttagagtct   23820
aatttgacac cttggaaaac ctcggagtat tttcctcgcc caactttatt ttcaatttca    23880
tagtcctttg tatttgtgga ccaatcaatt acagtatttt cataatccca atattcctcg   23940
gttctttgtt tattgatatt cgtataaaca cgagcctctg accatacccct gcatttcata   24000
gttcgaatca atattccctt ctacaaccccc ctatttttgt ctgtatattt gacttcttaa  24060
gtccctattc agaaaactcc tagtaggtaa ttgcaataca ccgagtatca acagtatatg    24120
```

```
aagtcccttg atccgtttta ctacaggact gcgaggttcg tctaattgct actgaaattt    24180
tccaagcgtt ggtcatattt ttgattttc gcttttctt cagtgttcgt tccgagtgat    24240
ttttgatagc gcttttctac cacttagtgc tgctgtatgt atttatatga tataccagcg    24300
atacatgtaa atatttctat aaagactgta aacctctgat tacctctgcc tgtgcgtctt    24360
tattcgcttc ctcagcagag gaagcaatgg ctgcgttctt tgtttggtgg aagatatctc    24420
ttgtcttttc gaaataaaca gtttccaata gatttctcat ctgagactca atgtcctcaa    24480
ttaaggaacc caaattagcg acatgtgatg tgaaaataac atctaatgga cgggacatat    24540
caatagcgat gtccttttcg gtctgtcttg tcaggttccc ggataacatc atatgagaat    24600
tctggtcagt ttttgttttg tccaagtgca gaatgattgt agtggtgact ctatagttga    24660
aactgtcggg agaagaagga gatgttgtaa cttcaaaaac atggatactg tcccaattac    24720
tgtgatctga ttggttttt ttgaaaagca ctaccctgc aaaatcgtgc ccattgaaat    24780
cttcttcatt gaggtcccag aggtacacgc tggagatacc gccttcataa tagagatctc    24840
tgtaaacgtc gaaagagtca ttggctaaga tctccaattt tcttaaaggg gctgagggaa    24900
aggggctgtc ttgtagatcc tttggggata gttctgggta ataagtgttc gaccaaggcg    24960
atctgaacga atcaatatca cgattatagt cgcagcataa gtactcccgg tttgaatcgg    25020
cggaatcttt ctgtgtggat aggggaacgt ctactgaaga tagtaaatct tgtgccaaat    25080
ttggttgtaa ttcgatcaag ttgtttagat tctcctgtaa cgtggtagga tttagcctcc    25140
taagaagatc taaagcagca tcgaattgag catcagacat tacggtggtg attgtagagt    25200
tggagagagt ttttgtatgt cacttgattg aacagttctc ctttatttgt tacaaatgct    25260
ctcatttta cgttttccgt ggtgaaaaaa aaaaaaaaa atgaacatat atacatgtag    25320
taacagcagt agtagatgaa gaatttagag tttaaacagg taacataacg ctataaggga    25380
aaggaaagtg gagatgttat acattatatt tacgtagacg ttgaaggaag aagaaagaaa    25440
aagggaacag aagaagaaga aaaagagaaa ggaaattcat gtggatttaa gatcgcttcc    25500
ccttttact taatgtcttg taggatcatt gagctttaat acgtctactg caggacccag    25560
taaacgttga aaaccacttt tccccaatgt ggcaactttg gttctctttg tagcagtcac    25620
agtggcctgt ctgggcaaat cgtttagcaa ggccacttca ccgaaataat catggtcttt    25680
cagtttattt atgacacctt ggcccttctt agagacgtcc acagctccgt actcaattaa    25740
ataaagttc tccccttgat caccctcgcg aatgattgtt tcacccggct ggtagatctt    25800
ggtatccagt gcatcggcaa gtttggcacg gtcgtacgta gtcaaactct tcaaaactgg    25860
catgctcttc aaaagatcgt catacatgag tctcttcttg aaagagctgc caaaagtat    25920
ttttctgaag gtgagcctgt ctagagccca caacaaacag tcgagggttg ctacaacggt    25980
ggcagcacga gggctgttgt acataagagc aagttccccg aaactggagc ctggcccgga    26040
agagttgacc ttgttgtcgt tgacgtagaa gtcaacagta ccctttcga cgacatagaa    26100
gtagtccct tggtcacctt gcttgattat cgtagcacct ttggggacgg acttctcctc    26160
cagacaattt atgaccagcc ttttgagtc ggaatccagc ttgttgaaca gaaagttatt    26220
acggatcgat ttttccagtc tttgcaattg ctgctcggac ttttccttat agtgatctgg    26280
agtccaatcg tcaaaattgt ttggttgtaa ggtctcacca ctaacagaag tacgcctttg    26340
ggcgttgaag tgcattggga gtggaggagt tgatgtcttt tctctagtat gctgttgttc    26400
ttcctgtgct tgctggtgag tgtcctgttc gtgcgggtct aaattaaacc cacttttaaa    26460
cacgttggag tgtgggtcct cgttcacaaa ggggatttg aacataacac tcgatctgga    26520
```

```
                                                         -continued tcttgattga gattgagctg attgaggtct ggaaaatgac tcctctggtt ccggaaatag    26580
aacaatgttc tttgccttaa attcaggctc cctggccttg aggaacgctc tctgttgttc    26640
cagcctttta ttgaaatagt tggcggagaa ctgaagaaag tcggacggat tagcggcgtt    26700
gatttcgttc tggaacagtt gcaattcggc ttgcgattcc ttgggcaaag aagataccat    26760
cgtttattct tactgttgtc ttttgaaaat aatctgcttg ttgtaaatga tcttcctatt    26820
tatgtatgcg tgaaatgcgt gtaatggatg tgatgatagc gatcgcttga cttagtcgag    26880
gaaagcgtaa agtgtccctt tttctctttc ccttttccct gtttgttcaa attttctctt    26940
ttctaccttc ctcttcgttt tgctccttgc cagcaaaacg aggaaggaca agaattttgg    27000
agagcggcgg cgcggcgcca taataaatgc acttgagcaa atgcaataag ttcagcttat    27060
ggcttctgca acaaagaaga ggtcggaatc cgagcacagt ataatcaata tattatcagg    27120
cagaacaaaa gtggcgggta taacacgaag aaagaaggaa gggtggtgat tgggtgcttt    27180 gttttttttcc gctcgtcgtg gtggcatgcg ctttttttt cttgggtgaa gattagccgc    27240
cgaagtcgta tgctcctctt ttgagcgttt tgaaagatag aaaaaagctg agtaagtaaa    27300
atcgtcggcg gctaatctga aaagtatata aagtccttta tattttccac tcgtattctt    27360
ttccctcctc cttttttttt ttactttctc acgtatggct tgtttcattt attatcagat    27420
cagtaatcac gtgccgtgtc gttagaaatg acatttggtt ctttgccttc tttgtccttt    27480
ttctatcttc ctactaagag aaactattat acaatacaat aagagaacat cgtgaaacaa    27540
cataaaagat atcacgtcat cagagagaga taaaacatca caaccaatta cattacagtg    27600
tattcgtttc ttcttagaga gagaaataaa gagcgggata aaaggacact acacagtata    27660
ccccataccc aggtgcaata atacacgtat atctatgttt attgcacatc aaaccccaca    27720
tatatgtctg ccagaaaacg caagtttaat agtctcaaac cgctagacac cttgaacagc    27780
tctcgtgcca gctctccaag gtcctctgct tctctaccgc ccaaaagata taacactttt    27840
cgtaaggatc cgaaaatcgt tgatcatcta aacaatgctt ctacaaagga tttcttacca    27900
gttttgagta tgaacagcga gagtaagagg cagatcgaat tgtcggataa tgatgttgat    27960
aataatgatg aaggtgaagg cgtcaacagt ggctgttcag atcaagattt tgaacctttg    28020
caaagctctc ctttgaaaag acactcatca ctcaaaagca cttccaatgg tcttttgttc    28080
caaatgtcta ataatctggg gaatggttca ccggaaccgg cagtagcgag cacttctcca    28140
aatggctcaa ttatttccac taaactaaat ttgaacggcc aatttttcttg cgttgattcg    28200 aaaacattgc gaatttatcg gcataaagca ccatgcataa tgacttttgt ctcagatcat    28260
aatcatccga aattttcatt gtattttcaa caatcggtga tctacaattc acaagttaat    28320
ctgcttgatg atgttgaatt gataatttta gataagaaga actcttttat ggctataatt    28380 ttaaagatc tgaaaaggt caagatgata ctagacgtga ataactcttc aatcaacatt    28440
aacacgaaca tcttgatatg gtccactgca agctccgctt caaataaaaa aataaagtct    28500
attaaaagat tcctgttgat gtcatattct tcgtcgataa aagtcgaaat tttagatcat    28560
aaagagcaga ttttggaaag actaaaacat ctgattcatc ctatttcttc gtcatcacct    28620
tcattgaaca tggaaagggc aataaactcc actaaaaatg cattcgactc tttaagactt    28680
aaaaaaacta aactttctac taatgatgat gaaagtccgc aaattcatac tcatttctta    28740
tcaaacaaac ctcatggttt gcaatcctta acaaaaagga ctcgtattgc cagccttggg    28800
aaaaaagagc attcaatatc tgttccaaaa tcgaatattc caccctcaga tttctacaac    28860
```

```
actaacggga cagaaacttt acaatcccac gcagtttcac aactaagacg ttcaaataga   28920
tttaaagatg tttcggatcc agcaaactca aattcaaatt cagaatttga tgatgcaact   28980
acggaatttg aaacaccaga actgtttaaa cctagcctct gttacaaatt caacgatggt   29040
tcaagctata ctataacaaa tcaagatttc aagtgtcttt caataagga ttgggttaat    29100
gatagcattt tggattttt tacaaaattt tacattgaat catctattga aaagtcaatt    29160
atcaaaagag agcaagttca cttaatgtcc tcttttttt acacgaaact aattagtaat    29220
ccagcagatt attattctaa tgtaaaaaag tgggttaaca atactgattt gttttctaaa   29280
aagtacgttg ttataccaat taacataagt tatcattggt ttagttgcat tataacaaac   29340
ttggatgcga tcttggattt tcatcaaaac aaagataaaa acgatgccat caactccgat   29400
gagatttcta taaataatcc tctggttaat attttgactt tcgactcgtt gaggcaaact   29460
cattcaagag aaattgatcc aataaaagaa tttctcatat cctatgcact tgataaatat   29520
tcaattcaac tggataaaac acaaatcaaa atgaaaacgt gtccagttcc acaacaacct   29580
aatatgagcg attgtggtgt tcatgttatt ttgaatatta gaaattttt tgaaaatccg    29640
gtggaaacaa ttgatgtatg gaagaattct aagattaaaa gtaagcactt caccgcaaaa   29700
atgattaata aatattttga taaaaatgaa agaaatagtg cgagaaagaa tttaaggcat   29760
actctaaaac tcttacaact caattacatc agctatctga aaaagaaaaa tttatatgaa   29820
gaagttatgc aaatggagga gaaaaaaagc accaatatca acaataatga aaattacgac   29880
gatgacgatg aagaaattca aatcattgaa aatatagatc aaagcagtaa agataataac   29940
gcgcagttaa cctcggaacc tccctgctca cgatcatcca gtatttcaac aacagaaaga   30000
gagccgacag agttgcataa ttccgtagta cgacagccca ccggtgaaat aataactgat   30060
aatgaagatc ccgttcgcgc tgcttctcca gaaacagcat ccgtttctcc tcccatacgt   30120
cacaatattt taaagagttc atctcctttc atatcagaaa gtgcgaatga aactgaacaa   30180
gaagaattta cgtcaccata ctttggaagg ccgtctttaa agacgagggc taagcagttt   30240
gaaggcgttt cgtcaccaat aaaaaacgat caagccctgt catccaccca tgatattatg   30300
atgccgtcgc ctaaacctaa aaggatttac ccaagcaaaa aaatcccaca actttcctcg   30360
catgttcaat ctctatcgac tgattctatg gaacgccaat ctagtcccaa taataccaac   30420
attgtaattt cagatacaga acaagattcg aggttaggag tgaattctga agtaaaaat    30480
actagtggta ttgttaacag ggatgactcg gacgtcaatt taattggtag ttcactacct   30540
aatgtagcgg aaaaaaatca tgacaacact caggaaagta atggtaataa tgacagtctt   30600
ggtaaaatac ttcaaaatgt tgacaaagaa ctgaacgaaa agttggttga tattgatgat   30660
gtggcattta gtagtccaac tagggtatt ccaagaacca gcgcgacaag caagggatca    30720
aatgcacaac ttctctctaa ttatggagat gaaaataacc agtctcaaga ttctgtttgg   30780
gatgagggca gagataatcc tatactcttg gaagatgaag acccttgaaa gcactcgcac   30840
gcatagtttt atatttttta ttcttttcct ctttatttt attttttaa cattctcgca    30900
taataatagt aacagcaata aaataactag taatatacat actcacataa ataggcatat   30960
tttttatttt gttctttcgt attcagaatg gtaaattttt ctaatgaaat gttttacaaa   31020
aattttttt ctataattct aacaataaga aataaaacag tggaaaaaca tataacttaa    31080
tgtagatata tatatgtaaa tatgctagca ttcattttaa atgtaaggaa gaaaacgcct   31140
ttaactttca tctggtaaat tttctaaagc tctaccctta gtgtaaacct cgtctttac    31200
attctgtaca gtacttttga accattgaat gaacagcaca gttgcttgga aaagaaacgt   31260
```

```
aaatgactct aatgctatca gtagtccgaa ataaatatct tgcatccttg tccatgttgg    31320
gaatgattcg ttaagcgata aagtgaaact cctggatcca tggctaatat cgataatctg    31380
ctttgtagaa acatcacgta aaaatactaa ggataaaata ataatcggca agacgtaaat    31440
taccatgtgc aggaaaacctt gtttaaacag ttccaaagcc attgttttca agaagttcaa    31500
tttactagta tttctgtttc tgaaaaatag tttcaatgac ttatatccgg ttccgaaatt    31560
gaccattgac gaaatgatcc aaacgacgaa taacaaactc tcgtcatatt taaaccattt    31620
ggaattacca atagtgtatg aagaattgcc aaacactctg atggtgagat aattgtaaca    31680
ggctagtata ccatcggtta agacgaccca cgaaaccata gttctaataa ccgcaatcat    31740
gatagctata aacaccatca ggttatactt caccaacata ctatcaaata tactgttaaa    31800
gatggccatg aaaattcctt gaccctcttc cacattattg atattattaa cagggcatt    31860 gttgatatct ctctctggta tatcgtgttc cacttcctct acttcgtttt cgtcaacggc    31920
atgttcatcg agagtgtttt ggccttctgt aaaatgaaga atatccttag caatcttgga    31980
taaacaaaca gatccgacac agacataata aatgttcaaa taggagtagc taatgtcaga    32040
gagttccttc catgcaacat agaccttatt tctttcacct aacaatagct ttacgactgg    32100
aagaaagccg aaactacaaa caaagtttat taaagcttga ctaataaatg taacaccaag    32160
cattaaaatg gaagcaaata accaaaccag gccaagcaat gtcatatagc gtaaacgaa    32220 atctggaggg acgtaaacga tataatattg atcatattcc gtgttttgtt cgtctaaata    32280
accaaattca ccagcagcac gtttgtttct ctctttaatt cttttccaaat ctaatggtttt    32340 caacagctta tcatcctttg taacggggac aaacattgtt tgtacataat ttctggatac    32400
tatatcagaa gaaggaacac gcattaaaac gccatcgggg acaaaataag catgaacgtc    32460
acgaacttgc ccaaacaatt cttctgcttg ttctagagtc tttggtttag tgaaaagttc    32520
ttggtttgac cattctgcat tcttggcagc aatgtacttg taaacaaat tgcggtaaac    32580 aatatggcct ctctctgttg gggtatcttt acctaagata aaggatgata aacgtaattt    32640
tcttgaacat aacttaaaaa ttgttttcca ataccttttcc aataagggtt taacgtaaga    32700
gctagactcc aggatcctct tcgtaaaata taaagttagc aaaattgtat tgaacttcca    32760
tgaaataatt gatgttggtt tataagcttc aggaacggat aataagttcg atttgagcat    32820
gaatgggaaa aaaattctag tatggaagcc aaaacctaag acaataaaaa tcgcataaat    32880
aaacatggat aagcaaagcc ttgataattg aatactcatc ggatgaatta aactatcatg    32940
caagatctta atattaggat cttctggaga tctgataaag aatagaacac ctggtctaat    33000 gtatttttc ctaatcattc cgatatattt ggcaaaccaa tacatgtaga gagtaccaat    33060
cgtccagtat acgaaaaggg aaaatggagg ccatattgcg catattgaag gaacccaaag    33120
catccgacta ttgatgccca ggattgggca aaataatgag aaatctagca ttacaccagc    33180
tagaatgggg aatccagcca attcgatgaa aaataaagtg aacaccttga aagtgcattt    33240
gagtgcaaat aaaatctgga aaatcagcct tctagtaggg ttgctcattc cgttctcacg    33300
gccataaccc ctcgagacaa gattggatga agcacaaacg atactgactg aggttagata    33360
cgtcgttaaa gcaggtaaag ctctgatgaa aattgagtgc ttcatggtgt tttcagtgta    33420
gccgttgtaa agataaatga tgtcatgaat taagtggtct gaaatccaac tcatcgcgac    33480
atctacttta gggaccagtt tcgtcagccc attgtaagct atatgagcgc agacaagta    33540 gtaaagatgg cacaacccac gcaaaataac cttaaatata ccaaaataaa ttttcaacaa    33600
```

-continued

```
accgaaccca ataaaagttg gaaacaaata ggaaattgcc aggtatattg cggtgaaaac    33660
tacggcaatt atgaaataag caatgacatt caacaatttc aatttgagat ttatcactag    33720
agggccttgt ccttgatcgt ctgggttagc ctgtgctggt ggcacaccaa cagctgcgcc    33780
aaagtcttgt tcgtcttgat cgacatttcc agctctgttt tgggcaggtg gtgggatgaa    33840
aaccggagcg ttgggcctgt ttattgcgtt ctgttgagca gcgattaggt catcaaattc    33900
attttgcgca cgacgatttg cccacatgtc aatcggattg ggctctatat gatc         33954
```

<210> SEQ ID NO 8
<211> LENGTH: 640
<212> TYPE: PRT
<213> ORGANISM: Saccharomyces cerevisiae

<400> SEQUENCE: 8

```
Met Arg Arg Glu Arg Gln Arg Met Met Ser Phe Glu Asp Lys Asp Lys
  1               5                  10                  15

Asp Asp Leu Asp Asn Ser Asn Ser Asn Asn Ser Ser Glu Met Thr Asp
             20                  25                  30

Thr Ala Met Met Pro Pro Leu Lys Arg Leu Leu Ile Thr Gly Ser Ser
         35                  40                  45

Asp Asp Leu Ala Gln Gly Ser Ser Gly Lys Lys Lys Met Thr Met Ala
     50                  55                  60

Thr Arg Ser Pro Ser Ser Ser Pro Asp Leu Ala Thr Asn Asp Ser Gly
 65                  70                  75                  80

Thr Arg Val Gln Pro Leu Pro Glu Tyr Asn Phe Thr Lys Phe Cys Tyr
                 85                  90                  95

Arg His Asn Pro Asp Ile Gln Phe Ser Pro Thr His Thr Ala Cys Tyr
            100                 105                 110

Lys Gln Asp Leu Lys Arg Thr Gln Glu Ile Asn Ala Asn Ile Ala Lys
        115                 120                 125

Leu Pro Leu Gln Glu Gln Ser Asp Ile His His Ile Ile Ser Lys Tyr
    130                 135                 140

Ser Asn Ser Asn Asp Lys Ile Arg Lys Leu Ile Leu Asp Gly Ile Leu
145                 150                 155                 160

Ser Thr Ser Cys Phe Pro Gln Leu Ser Tyr Ile Ser Ser Leu Val Thr
                165                 170                 175

His Met Ile Lys Ile Asp Phe Ile Ser Ile Leu Pro Gln Glu Leu Ser
            180                 185                 190

Leu Lys Ile Leu Ser Tyr Leu Asp Cys Gln Ser Leu Cys Asn Ala Thr
        195                 200                 205

Arg Val Cys Arg Lys Trp Gln Lys Leu Ala Asp Asp Asp Arg Val Trp
    210                 215                 220

Tyr His Met Cys Glu Gln His Ile Asp Arg Lys Cys Pro Asn Cys Gly
225                 230                 235                 240

Trp Gly Leu Pro Leu Leu His Met Lys Arg Ala Arg Ile Gln Gln Asn
                245                 250                 255

Ser Thr Gly Ser Ser Ser Asn Ala Asp Ile Gln Thr Gln Thr Thr Arg
            260                 265                 270

Pro Trp Lys Val Ile Tyr Arg Glu Arg Phe Lys Val Glu Ser Asn Trp
        275                 280                 285

Arg Lys Gly His Cys Arg Ile Gln Glu Phe Lys Gly His Met Asp Gly
    290                 295                 300

Val Leu Thr Leu Gln Phe Asn Tyr Arg Leu Leu Phe Thr Gly Ser Tyr
305                 310                 315                 320
```

-continued

```
Asp Ser Thr Ile Gly Ile Trp Asp Leu Phe Thr Gly Lys Leu Ile Arg
            325                 330                 335
Arg Leu Ser Gly His Ser Asp Gly Val Lys Thr Leu Tyr Phe Asp Asp
        340                 345                 350
Arg Lys Leu Ile Thr Gly Ser Leu Asp Lys Thr Ile Arg Val Trp Asn
    355                 360                 365
Tyr Ile Thr Gly Glu Cys Ile Ser Thr Tyr Arg Gly His Ser Asp Ser
370                 375                 380
Val Leu Ser Val Asp Ser Tyr Gln Lys Val Ile Val Ser Gly Ser Ala
385                 390                 395                 400
Asp Lys Thr Val Lys Val Trp His Val Glu Ser Arg Thr Cys Tyr Thr
                405                 410                 415
Leu Arg Gly His Thr Glu Trp Val Asn Cys Val Lys Leu His Pro Lys
            420                 425                 430
Ser Phe Ser Cys Phe Ser Cys Ser Asp Asp Thr Thr Ile Arg Met Trp
        435                 440                 445
Asp Ile Arg Thr Asn Ser Cys Leu Lys Val Phe Arg Gly His Val Gly
    450                 455                 460
Gln Val Gln Lys Ile Ile Pro Leu Thr Ile Lys Asp Val Glu Asn Leu
465                 470                 475                 480
Ala Thr Asp Asn Thr Ser Asp Gly Ser Ser Pro Gln Asp Asp Pro Thr
                485                 490                 495
Met Thr Asp Gly Ala Asp Glu Ser Asp Thr Pro Ser Asn Glu Gln Glu
            500                 505                 510
Thr Val Leu Asp Glu Asn Ile Pro Tyr Pro Thr His Leu Leu Ser Cys
        515                 520                 525
Gly Leu Asp Asn Thr Ile Lys Leu Trp Asp Val Lys Thr Gly Lys Cys
    530                 535                 540
Ile Arg Thr Gln Phe Gly His Val Glu Gly Val Trp Asp Ile Ala Ala
545                 550                 555                 560
Asp Asn Phe Arg Ile Ile Ser Gly Ser His Asp Gly Ser Ile Lys Val
                565                 570                 575
Trp Asp Leu Gln Ser Gly Lys Cys Met His Thr Phe Asn Gly Arg Arg
            580                 585                 590
Leu Gln Arg Glu Thr Gln His Thr Gln Thr Gln Ser Leu Gly Asp Lys
        595                 600                 605
Val Ala Pro Ile Ala Cys Val Cys Ile Gly Asp Ser Glu Cys Phe Ser
    610                 615                 620
Gly Asp Glu Phe Gly Cys Val Lys Met Tyr Lys Phe Asp Leu Asn Asp
625                 630                 635                 640
```

<210> SEQ ID NO 9
<211> LENGTH: 2112
<212> TYPE: DNA
<213> ORGANISM: Saccharomyces cerevisiae

<400> SEQUENCE: 9

```
atgtcactct ctaggtgtcc aactgacaat tcgtcctccc gtataaattc ctctgttcct      60
ttaataaata gcagcagccc tgctacacct ccagaatcat ttgatcctca agtatttcct     120
tcttcactta ttcatgggga taacctgctt cctcaagatg atcaaattgc atcggatcct     180
cgctcagaat caaatagttg taatggcaat acgagttctt ccctgccgtg cactgattcg     240
tatcagtacc cattaaagca ttcttgtacg ccttctttc ttcgaaagtt taatgaaagt     300
```

-continued

| | |
|---|---|
| atagagaatg tctcttataa atgcttagac cactcaccgc cagatagtgt tcctggcgat | 360 |
| ttttccattt cccttgttcc tcaaaggaat tttctatatt ctcattcttc tcttccacct | 420 |
| aaaattatat caattgatag aaacaatcga attaagttag ataatagcat ttcatctaac | 480 |
| tccgacaatt tccctccttc tccgaaagtc gacacatcaa acactgtttc acctggtagt | 540 |
| aaacctatct ctgaggatct tgaagattta aacttacagt caattgttca aacttttgag | 600 |
| gatcttccag aaggaattca atcttatgcg ttttttcaac tactccgttc gtgcaatcgg | 660 |
| caatcgatgc gtttattatt gaatgaatgc gagccgcttc taaaaaaga tatactttca | 720 |
| aatcttcctt tttccattgt tcagtctata ttattaaatc tggatataca ttcttttctt | 780 |
| tcttgccgtc ttgtttcgcc tacttggaat agaatacttg atgtgcatac ttcatactgg | 840 |
| aaacacatgt ttagtttatt tggctttcaa atcaatgaaa atgactggaa atatgctaat | 900 |
| ccaaacttaa atcgtccacc ttttttgcac aacgaccaaa tctcagatga ctattttccg | 960 |
| gaaattttca aaagacattt tctcaataga aacgatggt tatttccttc gatacctcca | 1020 |
| agtcatctat cttttcccat tcatgttcca aactttatga taacttcttt actacttcat | 1080 |
| aaagacagaa taatcaccac ttcgggatct ggaacaattc aaattcataa tgctattacc | 1140 |
| ggtgttttag aagctcgatt agagggtcat aaagaaggtg tttgggctgt caaaatacat | 1200 |
| gagaatacac ttgtatctgg ttcgatcgat aaaactgttc gcgtttggaa catagagaaa | 1260 |
| gctaaatgta cgcacatatt taggggacat atttccatca tcagatgctt agagatctta | 1320 |
| gttccgagtc gtcttattcg ccatggagtt gaaattgttg aaccagatca accgtacatt | 1380 |
| gtcagcggct ctcgggatca tacacttcgg gtttggaagc ttccaaaaaa cacggatcct | 1440 |
| ccttatcttc cagataatac aaactctatt gaccgttggg agaagaaccc gtattttgta | 1500 |
| catactttga taggacatac agactctgta cgaactatat ccggctatgg tgatatactt | 1560 |
| gtgagtggga gttatgattc ttcaattcgc atttggagag tttcaacagg ggaatgtctt | 1620 |
| taccatctgc ggggtcatag tcttcgtata tatagtgttt tatatgaacc agaaaggaat | 1680 |
| atttgcataa gcggtagcat ggataagtcc attagggttt gggatttatc gacagggact | 1740 |
| tgtaaatatg tgcttgaagg ccatgatgcc tttgttacgc ttcttaatgt attccagaat | 1800 |
| aggttgatat caggttctgc tgactccaca attagaatat gggatttgaa tactgggaaa | 1860 |
| ccattaatgg ttttgccgtc taattcaggc tacattagta gctttgtgtc agatgaacac | 1920 |
| aaaattatta gtggtaatga tggttctgta aagttatggg atgttaggac tggaaagctg | 1980 |
| ttacgttttc tattaacaga cctcacaaaa atatggcatg tcgatttgga tgctatgcgt | 2040 |
| tgtgtggctg cagtgcagcg tgatgatcaa gcatatttgg aagttattaa tttttccgga | 2100 |
| tcaagaccgt ag | 2112 |

<210> SEQ ID NO 10
<211> LENGTH: 703
<212> TYPE: PRT
<213> ORGANISM: Saccharomyces cerevisiae

<400> SEQUENCE: 10

Met Ser Leu Ser Arg Cys Pro Thr Asp Asn Ser Ser Arg Ile Asn
1               5                   10                  15

Ser Ser Val Pro Leu Ile Asn Ser Ser Pro Ala Thr Pro Pro Glu
            20                  25                  30

Ser Phe Asp Pro Gln Val Phe Pro Ser Ser Leu Ile His Gly Asp Asn
            35                  40                  45

-continued

```
Leu Leu Pro Gln Asp Asp Gln Ile Ala Ser Asp Pro Arg Ser Glu Ser
     50                  55                  60

Asn Ser Cys Asn Gly Asn Thr Ser Ser Leu Pro Cys Thr Asp Ser
 65                  70                  75                  80

Tyr Gln Tyr Pro Leu Lys His Ser Cys Thr Pro Ser Phe Leu Arg Lys
                 85                  90                  95

Phe Asn Glu Ser Ile Glu Asn Val Ser Tyr Lys Cys Leu Asp His Ser
                100                 105                 110

Pro Pro Asp Ser Val Pro Gly Asp Phe Ser Ile Ser Leu Val Pro Gln
            115                 120                 125

Arg Asn Phe Leu Tyr Ser His Ser Ser Leu Pro Pro Lys Ile Ile Ser
    130                 135                 140

Ile Asp Arg Asn Arg Ile Lys Leu Asp Asn Ser Ile Ser Ser Asn
145                 150                 155                 160

Ser Asp Asn Phe Pro Pro Ser Pro Lys Val Asp Thr Ser Asn Thr Val
                165                 170                 175

Ser Pro Gly Ser Lys Pro Ile Ser Glu Asp Leu Glu Asp Leu Asn Leu
            180                 185                 190

Gln Ser Ile Val Gln Thr Phe Glu Asp Leu Pro Glu Gly Ile Gln Ser
    195                 200                 205

Tyr Ala Phe Phe Gln Leu Leu Arg Ser Cys Asn Arg Gln Ser Met Arg
    210                 215                 220

Leu Leu Leu Asn Glu Cys Glu Pro Leu Leu Lys Lys Asp Ile Leu Ser
225                 230                 235                 240

Asn Leu Pro Phe Ser Ile Val Gln Ser Ile Leu Leu Asn Leu Asp Ile
                245                 250                 255

His Ser Phe Leu Ser Cys Arg Leu Val Ser Pro Thr Trp Asn Arg Ile
            260                 265                 270

Leu Asp Val His Thr Ser Tyr Trp Lys His Met Phe Ser Leu Phe Gly
    275                 280                 285

Phe Gln Ile Asn Glu Asn Asp Trp Lys Tyr Ala Asn Pro Asn Leu Asn
290                 295                 300

Arg Pro Pro Phe Leu His Asn Asp Gln Ile Ser Asp Asp Tyr Phe Pro
305                 310                 315                 320

Glu Ile Phe Lys Arg His Phe Leu Asn Arg Lys Arg Trp Leu Phe Pro
                325                 330                 335

Ser Ile Pro Pro Ser His Leu Ser Phe Pro Ile His Val Pro Asn Phe
            340                 345                 350

Met Ile Thr Ser Leu Leu Leu His Lys Asp Arg Ile Ile Thr Thr Ser
    355                 360                 365

Gly Ser Gly Thr Ile Gln Ile His Asn Ala Ile Thr Gly Val Leu Glu
    370                 375                 380

Ala Arg Leu Glu Gly His Lys Glu Gly Val Trp Ala Val Lys Ile His
385                 390                 395                 400

Glu Asn Thr Leu Val Ser Gly Ser Ile Asp Lys Thr Val Arg Val Trp
                405                 410                 415

Asn Ile Glu Lys Ala Lys Cys Thr His Ile Phe Arg Gly His Ile Ser
            420                 425                 430

Ile Ile Arg Cys Leu Glu Ile Leu Val Pro Ser Arg Leu Ile Arg His
    435                 440                 445

Gly Val Glu Ile Val Glu Pro Asp Gln Pro Tyr Ile Val Ser Gly Ser
    450                 455                 460

Arg Asp His Thr Leu Arg Val Trp Lys Leu Pro Lys Asn Thr Asp Pro
```

```
                465                 470                 475                 480
Pro Tyr Leu Pro Asp Asn Thr Asn Ser Ile Asp Arg Trp Glu Lys Asn
                485                 490                 495
Pro Tyr Phe Val His Thr Leu Ile Gly His Thr Asp Ser Val Arg Thr
                500                 505                 510
Ile Ser Gly Tyr Gly Asp Ile Leu Val Ser Gly Ser Tyr Asp Ser Ser
                515                 520                 525
Ile Arg Ile Trp Arg Val Ser Thr Gly Glu Cys Leu Tyr His Leu Arg
            530                 535                 540
Gly His Ser Leu Arg Ile Tyr Ser Val Leu Tyr Glu Pro Glu Arg Asn
545                 550                 555                 560
Ile Cys Ile Ser Gly Ser Met Asp Lys Ser Ile Arg Val Trp Asp Leu
                565                 570                 575
Ser Thr Gly Thr Cys Lys Tyr Val Leu Glu Gly His Asp Ala Phe Val
                580                 585                 590
Thr Leu Leu Asn Val Phe Gln Asn Arg Leu Ile Ser Gly Ser Ala Asp
            595                 600                 605
Ser Thr Ile Arg Ile Trp Asp Leu Asn Thr Gly Lys Pro Leu Met Val
        610                 615                 620
Leu Pro Ser Asn Ser Gly Tyr Ile Ser Phe Val Ser Asp Glu His
625                 630                 635                 640
Lys Ile Ile Ser Gly Asn Asp Gly Ser Val Lys Leu Trp Asp Val Arg
                645                 650                 655
Thr Gly Lys Leu Leu Arg Phe Leu Leu Thr Asp Leu Thr Lys Ile Trp
                660                 665                 670
His Val Asp Phe Asp Ala Met Arg Cys Val Ala Ala Val Gln Arg Asp
            675                 680                 685
Asp Gln Ala Tyr Leu Glu Val Ile Asn Phe Ser Gly Ser Arg Pro
        690                 695                 700

<210> SEQ ID NO 11
<211> LENGTH: 2175
<212> TYPE: DNA
<213> ORGANISM: Murine sp.

<400> SEQUENCE: 11
gaattcggca cgaggcggag ctgcgttggc tgcggcctgg cacgaaaggg gcggccccgg      60
cggagagcag acccagtagt ccgggcgatt atggacccgg cagaggcggt gctgcaggag     120
aaagcgctta agtttatgaa ttcctcagag agagaagact gtaataatgg cgaaccccct     180
aggaagataa taccagagaa gaattcactt agacagactt acaacagctg tgccaggctt     240 tgcataaaacc aagagacagt atgtctaaca agcactgcta tgaagactga aaattgtgtg     300
gccaaagcca aacttgccaa tggcacttcc agcatgattg tcccaagca gcggaaactc     360 tcagcaagct atgagaagga aaaggagctg tgtgtcaagt attttgagca gtggtcagag     420
tctgatcaag tggaatttgt agaacaccct atatcccaaa tgtgtcacta ccagcatggg     480
cacatcaact cctacctaaa acctatgctg cagagggatt cataactgc actgccagca     540 cggggtctgg accacatcgc tgagaacatt ctgtcatact ggacgccaa gtcactgtgt     600 gctgctgagc tcgtgtgcaa ggaatggtac cgcgtgacgt cggacggcat gctgtggaaa     660
aagctcatcg agaggatggt caggacggac tctctgtggc gaggcctggc agagcgcaga     720
ggctggggac agtacttatt caaaaacaaa cctcctgatg agaacgctcc tcccaactcc     780 tttttatagag cgctttatcc taaaatcata caagacattg agacaataga gtccaattgg     840
```

```
agatgtgggc gacatagttt acagagaatc cactgccgga gtgaaacaag taaaggggtt      900
tactgtttac agtacgacga ccagaagata gtcagcggcc ttcgagacaa caccatcaag      960
atctgggata aaagcacact ggaatgcaag cggattctca cgggccacac gggctccgtc     1020
ctgtgtctgc agtacgatga gagggtgatc atcacaggct cctcagactc caccgtcaga     1080
gtgtgggatg taaatgcagg tgagatgcta aacacattga ttcaccactg tgaagccgtt     1140
ctgcacctgc gcttcaataa tggcatgatg gtgacctgtt ccaaagaccg ttccatcgct     1200
gtgtgggata tggcttcccc aactgacatc accctcagga gggtgctggt gggacaccga     1260
gctgcggtca atgttgtaga ctttgatgac aagtacatcg tttctgcctc tggagataga     1320
accataaagg tgtggaacac aagtacctgt gaattcgtaa ggaccctaaa tgggcacaag     1380
cgtggcatcg cctgtttgca gtacagagac aggctggtgg tgagcggctc ctctgacaac     1440
accatcaggc tgtgggacat agagtgtgga gcatgcctgc gagtgttgga gggccatgag     1500
gagttggtac gctgcattcg atttgataac aaaaggatag tgagcggagc ctatgatggg     1560
aaaattaaag tgtgggatct tatgctgctg ttggacccgc gtgctccagc agggactctc     1620
tgtctgcgga cacttgtgga gcattctgga agagttttcc gcctccagtt tgatgaattc     1680
cagattgtca gtagttcaca tgatgacaca attctcatct gggacttcct gaatgatcca     1740
gctgctcacg ctgaaccgcc ccgctcccct tctcggacat acacctacat ctccagataa     1800
ataacccaac actggcctca taattgccca ggattcgtta atgttgcagt atttaacaga     1860
cctgccaaga ccaggatgaa caacaatcaa actcctaccc ggattcccgg acggatgagc     1920
gaggagcagg gctttgagac tcctgttggg acacagtcgg tcagcagccg accaggacgg     1980
cctgctcggc accggctgcc tcagtgctgc tatcagaaga tgtctttatc ttgtgtgaat     2040
gattggaact tccaagcctc cctcccttc ccttcccctt cctccctgca cctgtttccc     2100
tcccattggg ttccagacaa agatgactta taaatatatt tagtgttttg cctaaaaaaa     2160
aaaaaaaaaa aaaaa                                                      2175
```

<210> SEQ ID NO 12
<211> LENGTH: 569
<212> TYPE: PRT
<213> ORGANISM: Murine sp.

<400> SEQUENCE: 12

```
Met Asp Pro Ala Glu Ala Val Leu Gln Glu Lys Ala Leu Lys Phe Met
1               5                   10                  15

Asn Ser Ser Glu Arg Glu Asp Cys Asn Asn Gly Glu Pro Pro Arg Lys
            20                  25                  30

Ile Ile Pro Glu Lys Asn Ser Leu Arg Gln Thr Tyr Asn Ser Cys Ala
        35                  40                  45

Arg Leu Cys Ile Asn Gln Glu Thr Val Cys Leu Thr Ser Thr Ala Met
    50                  55                  60

Lys Thr Glu Asn Cys Val Ala Lys Ala Lys Leu Ala Asn Gly Thr Ser
65                  70                  75                  80

Ser Met Ile Val Pro Lys Gln Arg Lys Leu Ser Ala Ser Tyr Glu Lys
                85                  90                  95

Glu Lys Glu Leu Cys Val Lys Tyr Phe Glu Gln Trp Ser Glu Ser Asp
            100                 105                 110

Gln Val Glu Phe Val Glu His Leu Ile Ser Gln Met Cys His Tyr Gln
        115                 120                 125
```

-continued

```
His Gly His Ile Asn Ser Tyr Leu Lys Pro Met Leu Gln Arg Asp Phe
        130                 135                 140
Ile Thr Ala Leu Pro Ala Arg Gly Leu Asp His Ile Ala Glu Asn Ile
145                 150                 155                 160
Leu Ser Tyr Leu Asp Ala Lys Ser Leu Cys Ala Ala Glu Leu Val Cys
                    165                 170                 175
Lys Glu Trp Tyr Arg Val Thr Ser Asp Gly Met Leu Trp Lys Lys Leu
            180                 185                 190
Ile Glu Arg Met Val Arg Thr Asp Ser Leu Trp Arg Gly Leu Ala Glu
        195                 200                 205
Arg Arg Gly Trp Gly Gln Tyr Leu Phe Lys Asn Lys Pro Pro Asp Glu
210                 215                 220
Asn Ala Pro Pro Asn Ser Phe Tyr Arg Ala Leu Tyr Pro Lys Ile Ile
225                 230                 235                 240
Gln Asp Ile Glu Thr Ile Glu Ser Asn Trp Arg Cys Gly Arg His Ser
                    245                 250                 255
Leu Gln Arg Ile His Cys Arg Ser Glu Thr Ser Lys Gly Val Tyr Cys
                260                 265                 270
Leu Gln Tyr Asp Asp Gln Lys Ile Val Ser Gly Leu Arg Asp Asn Thr
            275                 280                 285
Ile Lys Ile Trp Asp Lys Ser Thr Leu Glu Cys Lys Arg Ile Leu Thr
        290                 295                 300
Gly His Thr Gly Ser Val Leu Cys Leu Gln Tyr Asp Glu Arg Val Ile
305                 310                 315                 320
Ile Thr Gly Ser Ser Asp Ser Thr Val Arg Val Trp Asp Val Asn Ala
                    325                 330                 335
Gly Glu Met Leu Asn Thr Leu Ile His His Cys Glu Ala Val Leu His
                340                 345                 350
Leu Arg Phe Asn Asn Gly Met Met Val Thr Cys Ser Lys Asp Arg Ser
            355                 360                 365
Ile Ala Val Trp Asp Met Ala Ser Pro Thr Asp Ile Thr Leu Arg Arg
        370                 375                 380
Val Leu Val Gly His Arg Ala Ala Val Asn Val Val Asp Phe Asp Asp
385                 390                 395                 400
Lys Tyr Ile Val Ser Ala Ser Gly Asp Arg Thr Ile Lys Val Trp Asn
                    405                 410                 415
Thr Ser Thr Cys Glu Phe Val Arg Thr Leu Asn Gly His Lys Arg Gly
                420                 425                 430
Ile Ala Cys Leu Gln Tyr Arg Asp Arg Leu Val Val Ser Gly Ser Ser
            435                 440                 445
Asp Asn Thr Ile Arg Leu Trp Asp Ile Glu Cys Gly Ala Cys Leu Arg
        450                 455                 460
Val Leu Glu Gly His Glu Glu Leu Val Arg Cys Ile Arg Phe Asp Asn
465                 470                 475                 480
Lys Arg Ile Val Ser Gly Ala Tyr Asp Gly Lys Ile Lys Val Trp Asp
                    485                 490                 495
Leu Met Ala Ala Leu Asp Pro Arg Ala Pro Ala Gly Thr Leu Cys Leu
                500                 505                 510
Arg Thr Leu Val Glu His Ser Gly Arg Val Phe Arg Leu Gln Phe Asp
            515                 520                 525
Glu Phe Gln Ile Val Ser Ser His Asp Asp Thr Ile Leu Ile Trp
        530                 535                 540
Asp Phe Leu Asn Asp Pro Ala Ala His Ala Glu Pro Pro Arg Ser Pro
```

```
545             550             555             560
Ser Arg Thr Tyr Thr Tyr Ile Ser Arg
              565

<210> SEQ ID NO 13
<211> LENGTH: 9
<212> TYPE: PRT
<213> ORGANISM: Unknown Organism
<220> FEATURE:
<223> OTHER INFORMATION: Description of Unknown Organism: peptide motif

<400> SEQUENCE: 13

Pro Pro Lys Lys Lys Arg Lys Val Ala
  1               5

<210> SEQ ID NO 14
<211> LENGTH: 32
<212> TYPE: PRT
<213> ORGANISM: Artificial Sequence
<220> FEATURE:
<223> OTHER INFORMATION: Description of Artificial Sequence: formula
      sequence
<220> FEATURE:
<221> NAME/KEY: MOD_RES
<222> LOCATION: (3)...(6)
<223> OTHER INFORMATION: any amino acid
<220> FEATURE:
<221> NAME/KEY: MOD_RES
<222> LOCATION: (7)
<223> OTHER INFORMATION: hydrophobic amino acid
<220> FEATURE:
<221> NAME/KEY: MOD_RES
<222> LOCATION: (8)...(9)
<223> OTHER INFORMATION: any amino acid
<220> FEATURE:
<221> NAME/KEY: MOD_RES
<222> LOCATION: (10)
<223> OTHER INFORMATION: hydrophobic amino acid
<220> FEATURE:
<221> NAME/KEY: MOD_RES
<222> LOCATION: (11)
<223> OTHER INFORMATION: any amino acid
<220> FEATURE:
<221> NAME/KEY: MOD_RES
<222> LOCATION: (12)
<223> OTHER INFORMATION: aromatic amino acid
<220> FEATURE:
<221> NAME/KEY: MOD_RES
<222> LOCATION: (13)
<223> OTHER INFORMATION: any amino acid
<220> FEATURE:
<221> NAME/KEY: MOD_RES
<222> LOCATION: (14)...(16)
<223> OTHER INFORMATION: amino acid which stabilizes a tight polypeptide
      backbone turn such as gly, pro, asp or asn
<220> FEATURE:
<221> NAME/KEY: MOD_RES
<222> LOCATION: (17)
<223> OTHER INFORMATION: polar amino acid
<220> FEATURE:
<221> NAME/KEY: MOD_RES
<222> LOCATION: (18)
<223> OTHER INFORMATION: any amino acid
<220> FEATURE:
<221> NAME/KEY: MOD_RES
<222> LOCATION: (19)...(20)
<223> OTHER INFORMATION: hydrophobic amino acid
<220> FEATURE:
<221> NAME/KEY: MOD_RES
<222> LOCATION: (21)...(24)
<223> OTHER INFORMATION: any amino acid
<220> FEATURE:
<221> NAME/KEY: MOD_RES
<222> LOCATION: (26)...(29)
<223> OTHER INFORMATION: any amino acid
```

```
<220> FEATURE:
<221> NAME/KEY: MOD_RES
<222> LOCATION: (30)
<223> OTHER INFORMATION: hydrophobic
<220> FEATURE:
<223> OTHER INFORMATION: this sequence may also encompass a deletion
      peptide wherein certain positions are absent according to the
      discloure

<400> SEQUENCE: 14

Gly His Xaa Xaa Xaa Xaa Xaa Xaa Xaa Xaa Xaa Xaa Xaa Xaa Xaa
  1               5                  10                  15

Xaa Xaa Xaa Xaa Xaa Xaa Xaa Xaa Asp Xaa Xaa Xaa Xaa Xaa Trp Asp
             20                  25                  30

<210> SEQ ID NO 15
<211> LENGTH: 12
<212> TYPE: PRT
<213> ORGANISM: Unknown Organism
<220> FEATURE:
<223> OTHER INFORMATION: Description of Unknown Organism: EGF-derived
      peptide

<400> SEQUENCE: 15

Cys Met His Ile Glu Ser Leu Asp Ser Tyr Thr Cys
  1               5                  10

<210> SEQ ID NO 16
<211> LENGTH: 12
<212> TYPE: PRT
<213> ORGANISM: Unknown Organism
<220> FEATURE:
<223> OTHER INFORMATION: Description of Unknown Organism: EGF-derived
      peptide

<400> SEQUENCE: 16

Cys Met Tyr Ile Glu Ala Leu Asp Lys Tyr Ala Cys
  1               5                  10

<210> SEQ ID NO 17
<211> LENGTH: 32
<212> TYPE: PRT
<213> ORGANISM: Artificial Sequence
<220> FEATURE:
<223> OTHER INFORMATION: Description of Artificial Sequence: formula
      sequence
<220> FEATURE:
<221> NAME/KEY: MOD_RES
<222> LOCATION: (1)
<223> OTHER INFORMATION: unique amino acid, such as cys or lys
<220> FEATURE:
<221> NAME/KEY: MOD_RES
<222> LOCATION: (2)...(3)
<223> OTHER INFORMATION: amino acid residue selected to modulate the
      affinity of the internalizing peptide for different membranes

<400> SEQUENCE: 17

Xaa Xaa Xaa Glu Ala Ala Leu Ala Glu Ala Leu Ala Glu Ala Leu Ala
  1               5                  10                  15

Glu Ala Leu Ala Glu Ala Leu Ala Glu Ala Leu Glu Ala Leu Ala Ala
             20                  25                  30

<210> SEQ ID NO 18
<211> LENGTH: 8
<212> TYPE: PRT
<213> ORGANISM: Unknown Organism
<220> FEATURE:
<223> OTHER INFORMATION: Description of Unknown Organism: peptide
      substrate for N-myristoyl transferase
```

```
<400> SEQUENCE: 18

Gly Asn Ala Ala Ala Ala Arg Arg
  1               5

<210> SEQ ID NO 19
<211> LENGTH: 10
<212> TYPE: PRT
<213> ORGANISM: Unknown Organism
<220> FEATURE:
<223> OTHER INFORMATION: Description of Unknown Organism: peptide
      derived from laminin

<400> SEQUENCE: 19

Cys Asp Pro Gly Tyr Ile Gly Ser Arg Cys
  1               5                  10

<210> SEQ ID NO 20
<211> LENGTH: 75
<212> TYPE: DNA
<213> ORGANISM: Artificial Sequence
<220> FEATURE:
<223> OTHER INFORMATION: Description of Artificial Sequence: Nde1-EcoR1
      fragment

<400> SEQUENCE: 20
catatgggtg gctgccgtgg cgatatgttc ggttgcggtg ctcctccaaa aaagaagaga      60
aaggtagctg gattc                                                      75

<210> SEQ ID NO 21
<211> LENGTH: 24
<212> TYPE: PRT
<213> ORGANISM: Artificial Sequence
<220> FEATURE:
<223> OTHER INFORMATION: Description of Artificial Sequence: RGD/SV40
      peptide

<400> SEQUENCE: 21

Met Gly Gly Cys Arg Gly Asp Met Phe Gly Cys Gly Ala Pro Pro Lys
  1               5                  10                  15

Lys Lys Arg Lys Val Ala Gly Phe
             20

<210> SEQ ID NO 22
<211> LENGTH: 225
<212> TYPE: DNA
<213> ORGANISM: Artificial Sequence
<220> FEATURE:
<223> OTHER INFORMATION: Description of Artificial Sequence: Nde1-EcoR1
      fragment

<400> SEQUENCE: 22
catatggagc cagtagatcc tagactagag ccctggaagc atccaggaag tcagcctaaa      60
actgcttgta ccaattgcta ttgtaaaaag tgttgctttc attgccaagt ttgtttcata     120
acaaaagccc ttggcatctc ctatggcagg aagaagcgga gacagcgacg aagacctcct     180
caaggcagtc agactcatca gtttctctta agtaagcaag gattc                     225

<210> SEQ ID NO 23
<211> LENGTH: 72
<212> TYPE: PRT
<213> ORGANISM: Artificial Sequence
<220> FEATURE:
<223> OTHER INFORMATION: Description of Artificial Sequence: engineered
      HIV-1 tat
```

<400> SEQUENCE: 23

Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
            20                  25                  30

His Cys Gln Val Cys Phe Ile Thr Lys Ala Leu Gly Ile Ser Tyr Gly
        35                  40                  45

Arg Lys Lys Arg Arg Gln Arg Arg Pro Pro Gln Gly Ser Gln Thr
    50                  55                  60

His Gln Val Ser Leu Ser Lys Gln
65                  70

<210> SEQ ID NO 24
<211> LENGTH: 912
<212> TYPE: DNA
<213> ORGANISM: Artificial Sequence
<220> FEATURE:
<223> OTHER INFORMATION: Description of Artificial Sequence: Nde1-EcoR1
      fragment

<400> SEQUENCE: 24
catatgacct ctcgccgctc cgtgaagtcg ggtccgcggg aggttccgcg cgatgagtac      60
gaggatctgt actacacccc gtcttcaggt atggcgagtc ccgatagtcc gcctgacacc    120
tcccgccgtg gcgccctaca gacacgctcg cgccagaggg gcgaggtccg tttcgtccag    180
tacgacgagt cggattatgc cctctacggg ggctcgtcat ccgaagacga cgaacacccg    240
gaggtccccc ggacgcggcg tcccgttttc ggggcggttt tgtccggccc ggggcctgcg    300
cgggcgcctc cgccacccgc tgggtccgga ggggccggac gcacacccac caccgccccc    360
cgggcccccc gaacccagcg ggtggcgact aaggcccccg cggccccggc ggcggagacc    420
acccgcggca ggaaatcggc ccagccagaa tccgccgcac tcccagacgc ccccgcgtcg    480
acggcgccaa cccgatccaa gacacccgcg caggggctgg ccagaaagct gcactttagc    540
accgcccccc caaaccccga cgcgccatgg acccccgggg tggccggctt taacaagcgc    600
gtcttctgcg ccgcggtcgg gcgcctggcg gccatgcatg cccggatggc ggcggtccag    660
ctctgggaca tgtcgcgtcc gcgcacagac gaagacctca cgaactcct tggcatcacc    720
accatccgcg tgacggtctg cgagggcaaa aacctgcttc agcgcgccaa cgagttggtg    780
aatccagacg tggtgcagga cgtcgacgcg gccacggcga ctcgagggcg ttctgcggcg    840
tcgcgcccca ccgagcgacc tcgagcccca gcccgctccg cttctcgccc cagacggccc    900
gtcgaggaat tc                                                        912

<210> SEQ ID NO 25
<211> LENGTH: 301
<212> TYPE: PRT
<213> ORGANISM: Artificial Sequence
<220> FEATURE:
<223> OTHER INFORMATION: Description of Artificial Sequence: engineered
      HSV-1 VP22

<400> SEQUENCE: 25

Met Thr Ser Arg Arg Ser Val Lys Ser Gly Pro Arg Glu Val Pro Arg
1               5                   10                  15

Asp Glu Tyr Glu Asp Leu Tyr Tyr Thr Pro Ser Ser Gly Met Ala Ser
            20                  25                  30

Pro Asp Ser Pro Pro Asp Thr Ser Arg Arg Gly Ala Leu Gln Thr Arg

```
                35                  40                  45
Ser Arg Gln Arg Gly Glu Val Arg Phe Val Gln Tyr Asp Glu Ser Asp
 50                  55                  60

Tyr Ala Leu Tyr Gly Gly Ser Ser Glu Asp Asp Glu His Pro Glu
 65                  70                  75                  80

Val Pro Arg Thr Arg Pro Val Ser Gly Ala Val Leu Ser Gly Pro
                 85                  90                  95

Gly Pro Ala Arg Ala Pro Pro Pro Ala Gly Ser Gly Gly Ala Gly
                100                 105                 110

Arg Thr Pro Thr Thr Ala Pro Arg Ala Pro Arg Thr Gly Arg Val Ala
                115                 120                 125

Thr Lys Ala Pro Ala Ala Pro Ala Ala Glu Thr Thr Arg Gly Arg Lys
130                 135                 140

Ser Ala Gln Pro Glu Ser Ala Ala Leu Pro Asp Ala Pro Ala Ser Thr
145                 150                 155                 160

Ala Pro Thr Arg Ser Lys Thr Pro Ala Gln Gly Leu Ala Arg Lys Leu
                165                 170                 175

His Phe Ser Thr Ala Pro Pro Asn Pro Asp Ala Pro Trp Thr Pro Arg
                180                 185                 190

Val Ala Gly Phe Asn Lys Arg Val Phe Cys Ala Ala Val Gly Arg Leu
                195                 200                 205

Ala Ala Met His Ala Arg Met Ala Ala Val Gln Leu Trp Asp Met Ser
                210                 215                 220

Arg Pro Arg Thr Asp Glu Asp Leu Asn Glu Leu Leu Gly Ile Thr Thr
225                 230                 235                 240

Ile Arg Val Thr Val Cys Glu Gly Lys Asn Leu Leu Gln Arg Ala Asn
                245                 250                 255

Glu Leu Val Asn Pro Asp Val Val Gln Asp Val Asp Ala Ala Thr Ala
                260                 265                 270

Thr Arg Gly Arg Ser Ala Ala Ser Arg Pro Thr Glu Arg Pro Arg Ala
                275                 280                 285

Pro Ala Arg Ser Ala Ser Arg Pro Arg Arg Pro Val Glu
                290                 295                 300

<210> SEQ ID NO 26
<211> LENGTH: 120
<212> TYPE: DNA
<213> ORGANISM: Artificial Sequence
<220> FEATURE:
<223> OTHER INFORMATION: Description of Artificial Sequence: NdeI-EcoR1
      fragment

<400> SEQUENCE: 26
catatggacg tcgacgcggc cacggcgact cgagggcgtt ctgcggcgtc gcgccccacc        60
gagcgacctc gagccccagc ccgctccgct tctcgcccca cggccccgt cgaggaattc       120

<210> SEQ ID NO 27
<211> LENGTH: 37
<212> TYPE: PRT
<213> ORGANISM: Artificial Sequence
<220> FEATURE:
<223> OTHER INFORMATION: Description of Artificial Sequence: VP22
      (C-terminal domain)

<400> SEQUENCE: 27

Met Asp Val Asp Ala Ala Thr Ala Thr Arg Gly Arg Ser Ala Ala Ser
 1               5                  10                  15
```

```
Arg Pro Thr Glu Arg Pro Arg Ala Pro Ala Arg Ser Ala Ser Arg Pro
            20                  25                  30

Arg Arg Pro Val Glu
        35

<210> SEQ ID NO 28
<211> LENGTH: 16
<212> TYPE: PRT
<213> ORGANISM: Artificial Sequence
<220> FEATURE:
<223> OTHER INFORMATION: Description of Artificial Sequence: synthetic
      or natural linker

<400> SEQUENCE: 28

Gly Gly Gly Ser Gly Gly Gly Ser Gly Gly Gly Ser Gly Gly Gly Ser
 1               5                  10                  15

<210> SEQ ID NO 29
<211> LENGTH: 4
<212> TYPE: PRT
<213> ORGANISM: Unknown Organism
<220> FEATURE:
<223> OTHER INFORMATION: Description of Unknown Organism: tetrapeptide
      isostere

<400> SEQUENCE: 29

Ala Ile Tyr Tyr
 1

<210> SEQ ID NO 30
<211> LENGTH: 38
<212> TYPE: DNA
<213> ORGANISM: Artificial Sequence
<220> FEATURE:
<223> OTHER INFORMATION: Description of Artificial Sequence: primer

<400> SEQUENCE: 30
gcggatccac catggataam aaagagggac ctaataac                            38

<210> SEQ ID NO 31
<211> LENGTH: 76
<212> TYPE: DNA
<213> ORGANISM: Artificial Sequence
<220> FEATURE:
<223> OTHER INFORMATION: Description of Artificial Sequence: primer

<400> SEQUENCE: 31
gcgcggccgc ctactcatca tcactagatg gcamcttctg agcaaaacag ccctctggta    60
ttatagttgt cctcgt                                                   76

<210> SEQ ID NO 32
<211> LENGTH: 72
<212> TYPE: DNA
<213> ORGANISM: Artificial Sequence
<220> FEATURE:
<223> OTHER INFORMATION: Description of Artificial Sequence: primer

<400> SEQUENCE: 32
cgcggccgcc tactcatcat cactagatgg camttgagcc aaagtttttct ctggtattat   60 agttgtcctc gt                                                       72

<210> SEQ ID NO 33
<211> LENGTH: 39
<212> TYPE: DNA
<213> ORGANISM: Artificial Sequence
```

```
<220> FEATURE:
<221> NAME/KEY: modified_base
<222> LOCATION: (20)
<223> OTHER INFORMATION: i
<220> FEATURE:
<223> OTHER INFORMATION: Description of Artificial Sequence: primer

<400> SEQUENCE: 33
gcwatccacc atggataatn taaagaggga cctaataac                       39

<210> SEQ ID NO 34
<211> LENGTH: 34
<212> TYPE: DNA
<213> ORGANISM: Artificial Sequence
<220> FEATURE:
<223> OTHER INFORMATION: Description of Artificial Sequence: primer

<400> SEQUENCE: 34
gtaggtgtat ctccatgtgg tatratagtr gtcc                            34

<210> SEQ ID NO 35
<211> LENGTH: 34
<212> TYPE: DNA
<213> ORGANISM: Artificial Sequence
<220> FEATURE:
<223> OTHER INFORMATION: Description of Artificial Sequence: primer

<400> SEQUENCE: 35
ggacaactat aataccacat ggagatacac ctac                            34

<210> SEQ ID NO 36
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 36
gcctcgagtc actcctcctc tgagctgtc                                  29

<210> SEQ ID NO 37
<211> LENGTH: 38
<212> TYPE: DNA
<213> ORGANISM: Artificial Sequence
<220> FEATURE:
<223> OTHER INFORMATION: Description of Artificial Sequence: primer

<400> SEQUENCE: 37
gcggatccac catggataam aaagagggac ctaataac                        38

<210> SEQ ID NO 38
<211> LENGTH: 37
<212> TYPE: DNA
<213> ORGANISM: Artificial Sequence
<220> FEATURE:
<223> OTHER INFORMATION: Description of Artificial Sequence: primer

<400> SEQUENCE: 38
cctatcacat ctatatttta ttggtattat agttgtc                         37

<210> SEQ ID NO 39
<211> LENGTH: 37
<212> TYPE: DNA
<213> ORGANISM: Artificial Sequence
<220> FEATURE:
<223> OTHER INFORMATION: Description of Artificial Sequence: primer
```

```
<400> SEQUENCE: 39
gacaactata ataccaataa aatatagatg tgatagg                              37

<210> SEQ ID NO 40
<211> LENGTH: 34
<212> TYPE: DNA
<213> ORGANISM: Artificial Sequence
<220> FEATURE:
<223> OTHER INFORMATION: Description of Artificial Sequence: primer

<400> SEQUENCE: 40
gcctcgagtc ataatgtgtt agtattttgt cctg                                 34

<210> SEQ ID NO 41
<211> LENGTH: 69
<212> TYPE: DNA
<213> ORGANISM: Artificial Sequence
<220> FEATURE:
<223> OTHER INFORMATION: Description of Artificial Sequence: primer

<400> SEQUENCE: 41
gcggatccac catggaggaa gaagagtata tgcccatgga ggagactctt tgccaacgtt     60
ttaaatgtg                                                             69

<210> SEQ ID NO 42
<211> LENGTH: 35
<212> TYPE: DNA
<213> ORGANISM: Artificial Sequence
<220> FEATURE:
<223> OTHER INFORMATION: Description of Artificial Sequence: primer

<400> SEQUENCE: 42
gcgcggccgc tcatatagac ataaatccag tagac                                35

<210> SEQ ID NO 43
<211> LENGTH: 65
<212> TYPE: DNA
<213> ORGANISM: Artificial Sequence
<220> FEATURE:
<223> OTHER INFORMATION: Description of Artificial Sequence: primer

<400> SEQUENCE: 43
gcggatccgc caccatggac tacaaggacg acgatgacaa agatgacccg gccgaggcgg     60
tgctg                                                                 65

<210> SEQ ID NO 44
<211> LENGTH: 37
<212> TYPE: DNA
<213> ORGANISM: Artificial Sequence
<220> FEATURE:
<223> OTHER INFORMATION: Description of Artificial Sequence: primer

<400> SEQUENCE: 44
gtaggtgtat ctccatgtct ggagatgtag gtgtatg                              37

<210> SEQ ID NO 45
<211> LENGTH: 37
<212> TYPE: DNA
<213> ORGANISM: Artificial Sequence
<220> FEATURE:
<223> OTHER INFORMATION: Description of Artificial Sequence: primer

<400> SEQUENCE: 45
catacaccta catctccaga catggagata cacctac                              37
```

```
<210> SEQ ID NO 46
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 46
gcgcggccgc tcactcctcc tctgagctgt c                              31

<210> SEQ ID NO 47
<211> LENGTH: 5
<212> TYPE: PRT
<213> ORGANISM: Unknown Organism
<220> FEATURE:
<223> OTHER INFORMATION: Description of Unknown Organism: LFCSE motif

<400> SEQUENCE: 47

Leu Phe Cys Ser Glu
 1               5

<210> SEQ ID NO 48
<211> LENGTH: 135
<212> TYPE: DNA
<213> ORGANISM: Homo sapiens
<220> FEATURE:
<221> NAME/KEY: CDS
<222> LOCATION: (1)..(135)

<400> SEQUENCE: 48 ctg cca gct cgg gga ttg gat cat atc gct gag aac att ctg tca tac      48
Leu Pro Ala Arg Gly Leu Asp His Ile Ala Glu Asn Ile Leu Ser Tyr
 1               5                  10                  15 ctg gat gcc aaa tca cta tgt gct gct gaa ctt gtg tgc aag gaa tgg      96
Leu Asp Ala Lys Ser Leu Cys Ala Ala Glu Leu Val Cys Lys Glu Trp
                20                  25                  30 tac cga gtg acc tct gat ggc atg ctg tgg aag aag ctt                 135
Tyr Arg Val Thr Ser Asp Gly Met Leu Trp Lys Lys Leu
         35                  40                  45

<210> SEQ ID NO 49
<211> LENGTH: 45
<212> TYPE: PRT
<213> ORGANISM: Homo sapiens

<400> SEQUENCE: 49

Leu Pro Ala Arg Gly Leu Asp His Ile Ala Glu Asn Ile Leu Ser Tyr
 1               5                  10                  15

Leu Asp Ala Lys Ser Leu Cys Ala Ala Glu Leu Val Cys Lys Glu Trp
                20                  25                  30

Tyr Arg Val Thr Ser Asp Gly Met Leu Trp Lys Lys Leu
         35                  40                  45
```